(12) United States Patent
Jones et al.

(10) Patent No.: US 11,710,627 B2
(45) Date of Patent: **\*Jul. 25, 2023**

(54) CELL POPULATION ANALYSIS

(71) Applicant: Micromass UK Limited, Wilmslow (GB)

(72) Inventors: Emrys Jones, Manchester (GB); Steven Derek Pringle, Darwen (GB); Keith Richardson, High Peak (GB); James Ian Langridge, Sale (GB); Zoltan Takats, Cambridge (GB)

(73) Assignee: Micromass UK Limited, Wilmslow (GB)

( * ) Notice: Subject to any disclaimer, the term of this patent is extended or adjusted under 35 U.S.C. 154(b) by 12 days.

This patent is subject to a terminal disclaimer.

(21) Appl. No.: 17/558,925

(22) Filed: Dec. 22, 2021

(65) Prior Publication Data

US 2022/0115222 A1    Apr. 14, 2022

Related U.S. Application Data

(63) Continuation of application No. 15/555,694, filed as application No. PCT/GB2016/050603 on Mar. 7, 2016, now Pat. No. 11,239,066.

(30) Foreign Application Priority Data

Mar. 6, 2015  (GB) ........................................ 1503863
Mar. 6, 2015  (GB) ........................................ 1503864
(Continued)

(51) Int. Cl.
*G01N 30/72*   (2006.01)
*H01J 49/04*   (2006.01)
(Continued)

(52) U.S. Cl.
CPC ............ *H01J 49/049* (2013.01); *A61B 1/041* (2013.01); *A61B 1/2736* (2013.01);
(Continued)

(58) Field of Classification Search
None
See application file for complete search history.

(56) References Cited

U.S. PATENT DOCUMENTS 5,015,848 A    5/1991  Bomse et al.
10,867,779 B2  12/2020 Richardson
(Continued)

FOREIGN PATENT DOCUMENTS

CA    2339552 A1    2/2000
CN    1774627 A     5/2006
(Continued)

OTHER PUBLICATIONS

Gonzalez-Dominguez, R., et al. "Development of a metabolomic approach based on urine samples and direct infusion mass spectrometry", Analytical Biochemistry, 465:20-27, Jul. 23, 2014.
(Continued)

*Primary Examiner* — Xiaoyun R Xu
(74) *Attorney, Agent, or Firm* — Goodwin Procter LLP

(57) ABSTRACT

A method of analysis using mass spectrometry and/or ion mobility spectrometry is disclosed comprising: (a) using a first device to generate smoke, aerosol or vapour from a target in vitro or ex vivo cell population; (b) mass analysing and/or ion mobility analysing said smoke, aerosol or vapour, or ions derived therefrom, in order to obtain spectrometric data; and (c) analysing said spectrometric data in order to identify and/or characterise said target cell population or one or more cells and/or compounds present in said target cell population.

17 Claims, 28 Drawing Sheets

(30) Foreign Application Priority Data

| Mar. 6, 2015 | (GB) | 1503867 |
|---|---|---|
| Mar. 6, 2015 | (GB) | 1503876 |
| Mar. 6, 2015 | (GB) | 1503877 |
| Mar. 6, 2015 | (GB) | 1503878 |
| Mar. 6, 2015 | (GB) | 1503879 |
| Sep. 9, 2015 | (GB) | 1516003 |
| Oct. 16, 2015 | (GB) | 1518369 |

(51) Int. Cl.

| A61B 10/02 | (2006.01) |
|---|---|
| A61B 18/00 | (2006.01) |
| A61B 18/14 | (2006.01) |
| A61B 18/20 | (2006.01) |
| G01N 3/00 | (2006.01) |
| G01N 9/00 | (2006.01) |
| G01N 33/68 | (2006.01) |
| H01J 49/00 | (2006.01) |
| H01J 49/06 | (2006.01) |
| H01J 49/16 | (2006.01) |
| G16B 20/50 | (2019.01) |
| G01N 27/623 | (2021.01) |
| A61B 90/13 | (2016.01) |
| A61B 1/04 | (2006.01) |
| A61B 1/273 | (2006.01) |
| A61B 5/00 | (2006.01) |
| A61B 5/01 | (2006.01) |
| A61B 5/0507 | (2021.01) |
| A61B 5/055 | (2006.01) |
| A61B 6/03 | (2006.01) |
| A61B 8/13 | (2006.01) |
| A61B 10/00 | (2006.01) |
| A61B 17/00 | (2006.01) |
| A61B 18/04 | (2006.01) |
| A61B 18/18 | (2006.01) |
| A61F 13/38 | (2006.01) |
| C12Q 1/02 | (2006.01) |
| C12Q 1/04 | (2006.01) |
| C12Q 1/18 | (2006.01) |
| C12Q 1/24 | (2006.01) |
| G01N 1/22 | (2006.01) |
| G01N 27/624 | (2021.01) |
| G01N 33/487 | (2006.01) |
| G01N 33/92 | (2006.01) |
| H01J 49/02 | (2006.01) |
| H01J 49/10 | (2006.01) |
| H01J 49/14 | (2006.01) |
| H01J 49/24 | (2006.01) |
| H01J 49/26 | (2006.01) |
| G16B 20/00 | (2019.01) |
| A61B 17/32 | (2006.01) |
| G16H 10/40 | (2018.01) |
| G16H 15/00 | (2018.01) |
| G16H 50/20 | (2018.01) |
| A61B 1/00 | (2006.01) |
| A61B 1/31 | (2006.01) |
| A61B 5/145 | (2006.01) |

(52) U.S. Cl.
CPC ......... *A61B 5/0066* (2013.01); *A61B 5/0075* (2013.01); *A61B 5/015* (2013.01); *A61B 5/055* (2013.01); *A61B 5/0507* (2013.01); *A61B 6/032* (2013.01); *A61B 6/037* (2013.01); *A61B 8/13* (2013.01); *A61B 10/00* (2013.01); *A61B 10/0041* (2013.01); *A61B 10/0233* (2013.01); *A61B 10/0283* (2013.01); *A61B 17/00* (2013.01); *A61B 18/00* (2013.01); *A61B 18/04* (2013.01); *A61B 18/042* (2013.01); *A61B 18/14* (2013.01); *A61B 18/1445* (2013.01); *A61B 18/1815* (2013.01); *A61B 18/20* (2013.01); *A61B 90/13* (2016.02); *A61F 13/38* (2013.01); *C12Q 1/025* (2013.01); *C12Q 1/04* (2013.01); *C12Q 1/18* (2013.01); *C12Q 1/24* (2013.01); *G01N 1/2202* (2013.01); *G01N 3/00* (2013.01); *G01N 9/00* (2013.01); *G01N 27/623* (2021.01); *G01N 27/624* (2013.01); *G01N 30/724* (2013.01); *G01N 33/487* (2013.01); *G01N 33/6848* (2013.01); *G01N 33/6851* (2013.01); *G01N 33/92* (2013.01); *G16B 20/50* (2019.02); *H01J 49/0004* (2013.01); *H01J 49/0027* (2013.01); *H01J 49/0031* (2013.01); *H01J 49/0036* (2013.01); *H01J 49/025* (2013.01); *H01J 49/044* (2013.01); *H01J 49/0404* (2013.01); *H01J 49/0409* (2013.01); *H01J 49/0422* (2013.01); *H01J 49/0445* (2013.01); *H01J 49/0459* (2013.01); *H01J 49/0463* (2013.01); *H01J 49/0468* (2013.01); *H01J 49/061* (2013.01); *H01J 49/068* (2013.01); *H01J 49/10* (2013.01); *H01J 49/14* (2013.01); *H01J 49/16* (2013.01); *H01J 49/164* (2013.01); *H01J 49/24* (2013.01); *H01J 49/26* (2013.01); *A61B 1/00013* (2013.01); *A61B 1/31* (2013.01); *A61B 5/14542* (2013.01); *A61B 17/320068* (2013.01); *A61B 2010/0083* (2013.01); *A61B 2017/320069* (2017.08); *A61B 2018/00577* (2013.01); *A61B 2018/00589* (2013.01); *A61B 2018/00994* (2013.01); *A61B 2218/002* (2013.01); *A61B 2218/008* (2013.01); *G01N 33/48735* (2013.01); *G01N 2001/2223* (2013.01); *G01N 2333/195* (2013.01); *G01N 2405/00* (2013.01); *G01N 2405/04* (2013.01); *G01N 2405/08* (2013.01); *G01N 2570/00* (2013.01); *G01N 2800/26* (2013.01); *G16B 20/00* (2019.02); *G16H 10/40* (2018.01); *G16H 15/00* (2018.01); *G16H 50/20* (2018.01)

(56) References Cited

U.S. PATENT DOCUMENTS

| 2005/0255606 | A1 | 11/2005 | Ahmed et al. |
|---|---|---|---|
| 2006/0027744 | A1 | 2/2006 | Stults et al. |
| 2006/0038120 | A1 | 2/2006 | Lean et al. |
| 2008/0315087 | A1 | 12/2008 | Wollnik et al. |
| 2011/0012016 | A1 | 1/2011 | Maier et al. |
| 2012/0190055 | A1 | 7/2012 | Cezar et al. |
| 2013/0306856 | A1 | 11/2013 | Trimpin et al. |
| 2014/0127734 | A1 | 5/2014 | Charretier et al. |
| 2020/0144044 | A1 | 5/2020 | Zarrine-Afsar et al. |

FOREIGN PATENT DOCUMENTS

| EP | 1225616 | A2 | 7/2002 |
|---|---|---|---|
| EP | 1530721 | A2 | 5/2005 |
| EP | 1650549 | A2 | 4/2006 |
| EP | 2592420 | A1 | 5/2013 |
| GB | 2278952 | A | 12/1994 |
| GB | 2462190 | A | 2/2010 |
| GB | 2491484 | A | 12/2012 |
| GB | 2507298 | A | 4/2014 |
| JP | 2000149866 | A | 5/2000 |
| JP | 2008249563 | A | 10/2008 |

(56) References Cited

FOREIGN PATENT DOCUMENTS

| | | |
|---|---|---|
| WO | 2009070555 A1 | 6/2009 |
| WO | 2014167828 A1 | 10/2014 |

OTHER PUBLICATIONS

Djidja, M-C., et al., "Novel molecular tumour classification using MALDI-mass spectrometry imaging of tissue micro-array", Analytical and Bioanalytical Chemistry, 397(2): 587-601, Mar. 4, 2010.
Chen, H., et al.,"Neutral desorption sampling coupled to extractive electrospray ionization mass spectrometry for rapid differentiation of biosamples by metabolomic fingerprinting", Journal of Mass Spectrometry, 42(9):1123-1135, Sep. 1, 2007.
Gao, L., et al., "Design and Characterization of a Multisource Hand-Held Tandem Mass Spectrometer", Analytical Chemistry, 80(19):7198-7205, Oct. 1, 2008.
Ouyang, Z., et al., "Handheld Miniature Ion Trap Mass Spectrometers", Analytical Chemistry, 81(7):2421-2425 Apr. 1, 2009.
Chen, H., et al., "Surface desorption atmospheric pressure chemical ionization mass spectrometry for direct ambient sample analysis without toxic chemical contamination", Journal of Mass Spectrometry, 42(8):1045-1056, Jan. 1, 2007.
Cooks, R.G., et al., "Ambient Mass Spectrometry", Science, 311(5767):1566-1570, Mar. 17, 2006.

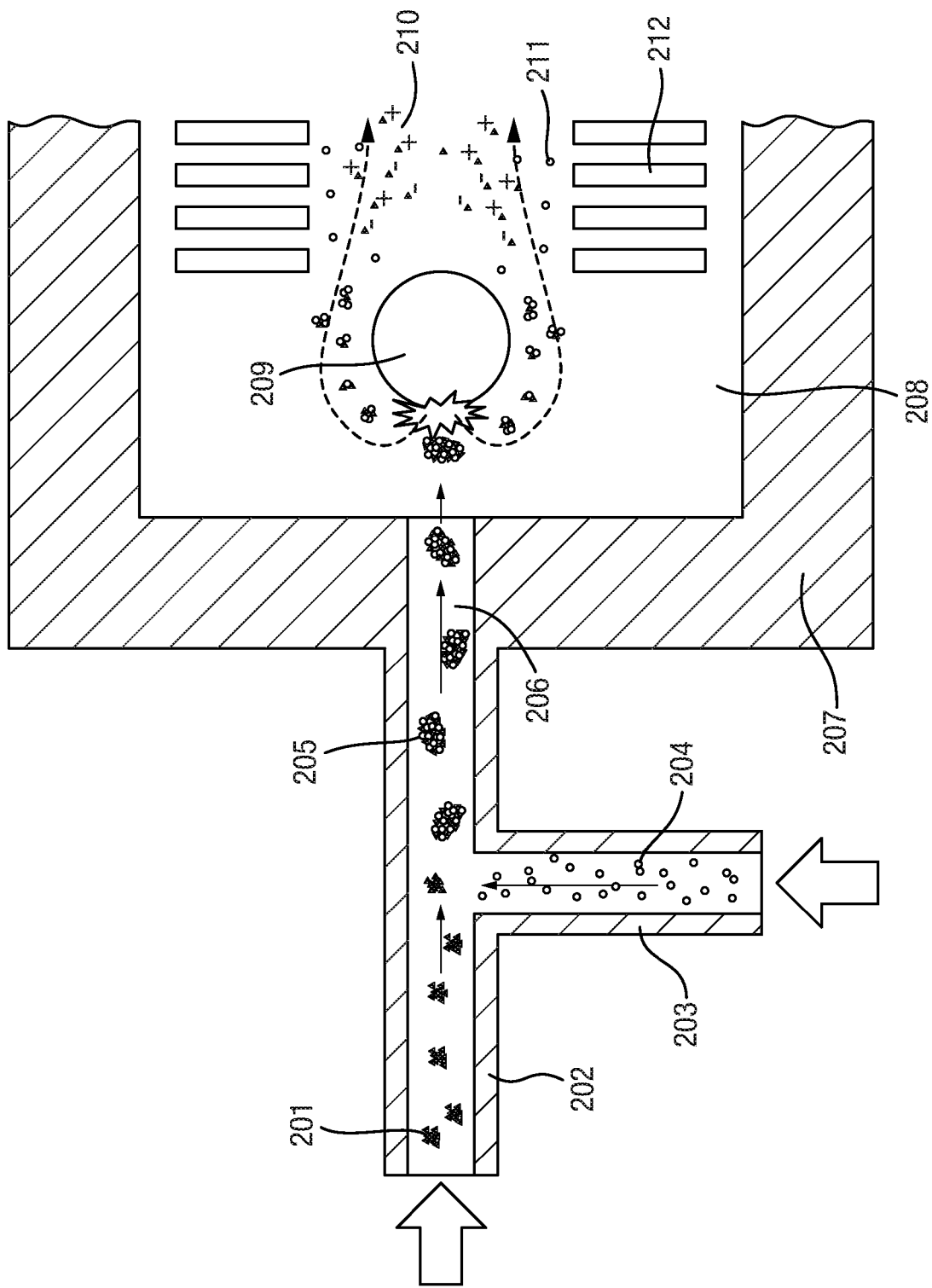

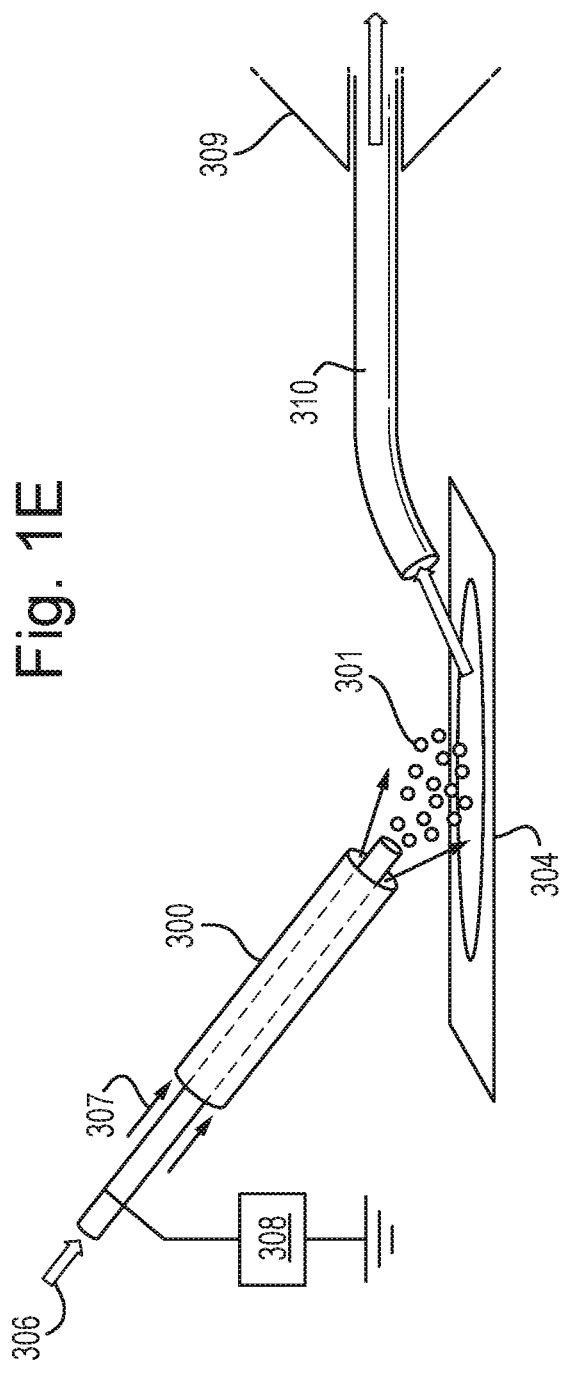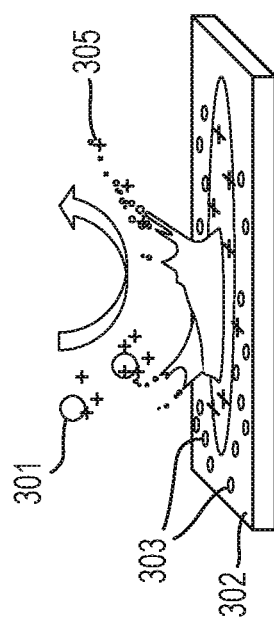

Fig. 4 (Cont.)
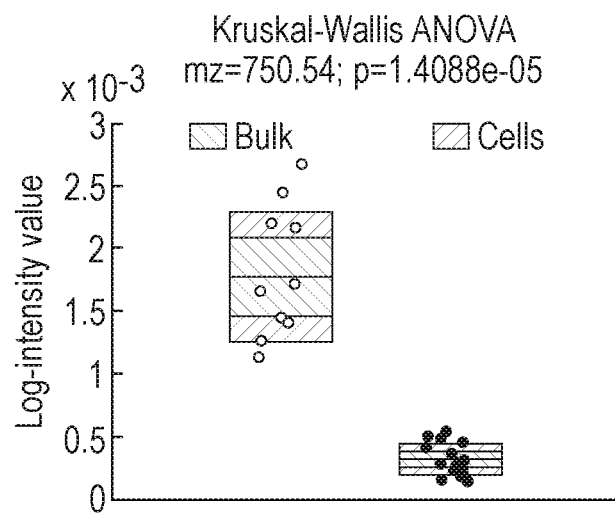
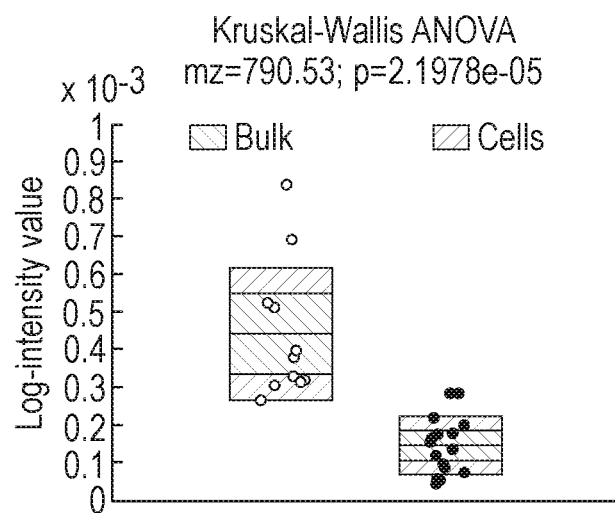
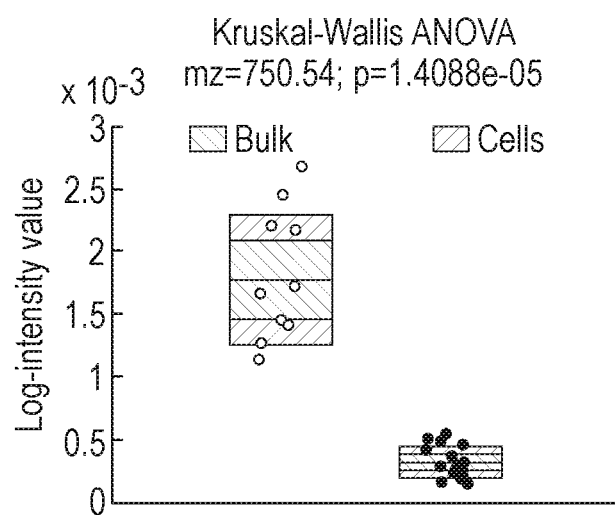

○ HeLa p4 day1    ● MES-SA p8 day1    ✶ SNB-19 p4 day1
▲ HeLa p4 day2    ◇ MES-SA p8 day2    □ SNB-19 p4 day2
▷ HeLa p4 day3    ★ MES-SA p8 day3    + SNB-19 p4 day3
◆ HeLa p6 day1    ▶ MES-SA p10 day1   ■ SNB-19 p6 day1
● HeLa p6 day2    ☆ MES-SA p10 day2   △ SNB-19 p6 day2
⬡ HeLa p6 day3    ◁ MES-SA p10 day3   ◀ SNB-19 p6 day3

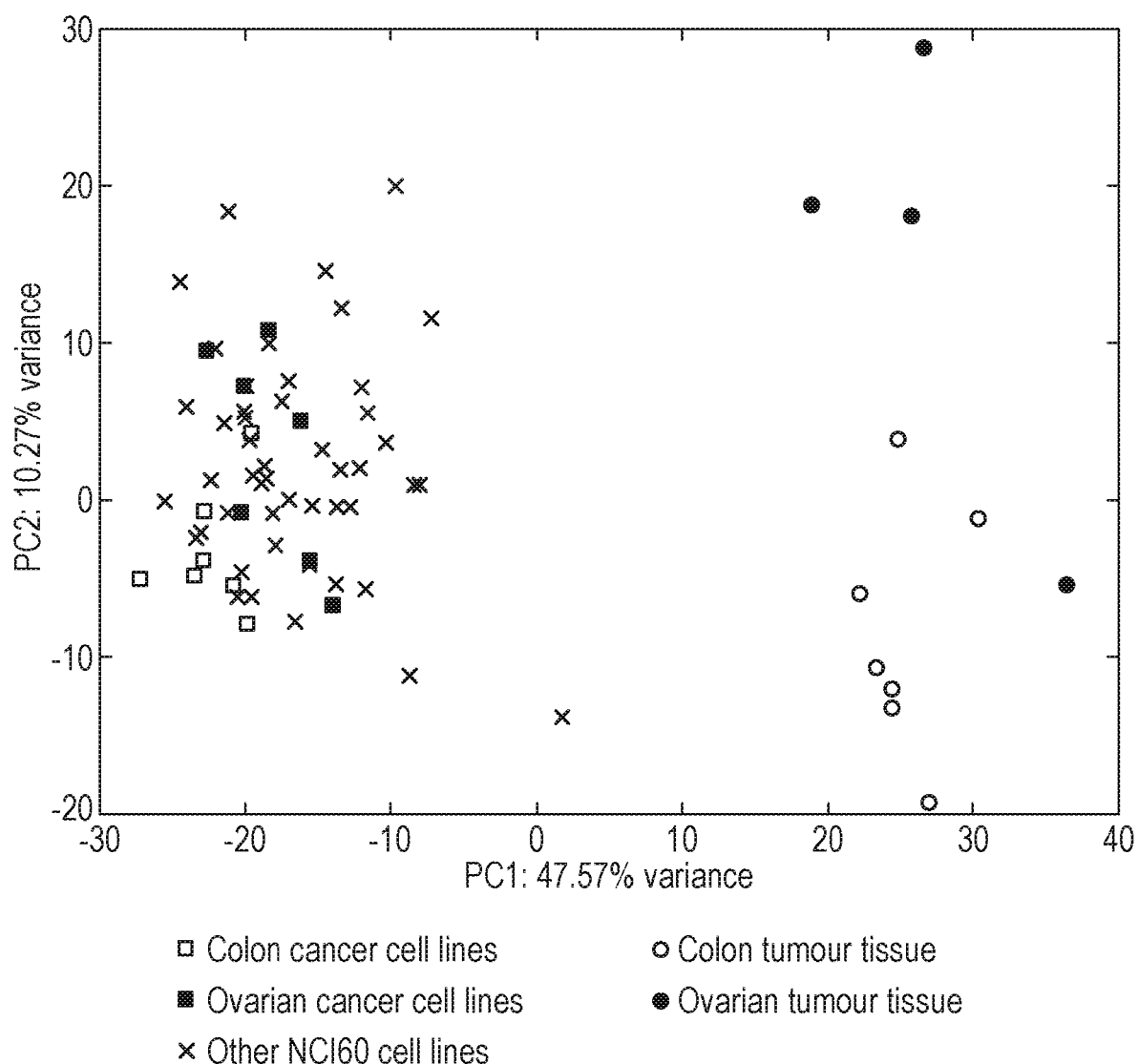

CELL POPULATION ANALYSIS

CROSS-REFERENCE TO RELATED APPLICATIONS

This application is a continuation application of U.S. patent application Ser. No. 15/555,694, filed Sep. 5, 2017, which is the U.S. National Phase of International Application number PCT/GB2016/050603, filed Mar. 7, 2016, which claims priority from and the benefit of United Kingdom patent application No. 1503876.3 filed on 6 Mar. 2015, United Kingdom patent application No. 1503864.9 filed on 6 Mar. 2015, United Kingdom patent application No. 1518369.2 filed on 16 Oct. 2015, United Kingdom patent application No. 1503877.1 filed on 6 Mar. 2015, United Kingdom patent application No. 1503867.2 filed on 6 Mar. 2015, United Kingdom patent application No. 1503863.1 filed on 6 Mar. 2015, United Kingdom patent application No. 1503878.9 filed on 6 Mar. 2015, United Kingdom patent application No. 1503879.7 filed on 6 Mar. 2015 and United Kingdom patent application No. 1516003.9 filed on 9 Sep. 2015. The entire contents of these applications are incorporated herein by reference.

FIELD OF THE INVENTION

The present invention relates generally to mass spectrometers and/or ion mobility spectrometers and in particular to methods of mass analysing and/or ion mobility analysing ex vivo or in vitro cell populations or medium derived therefrom using an ambient ionisation mass spectrometry method such as Rapid Evaporative ionisation Mass Spectrometry ("REIMS") ion source. Particular applications include cell identification, cell characterisation, cellular process analysis, pharmaceutical compound discovery and pharmaceutical compound production.

BACKGROUND

Rapid Evaporative Ionization Mass Spectrometry ("REIMS") is an ambient mass spectrometric method which was recently developed for intra-operative tissue identification. In case of REIMS analysis, biological samples are rapidly heated up via Joule-heating and the resulting aerosol is directly transferred into the mass spectrometer. It was found that electrosurgical tools such as monopolar electroscalpels as used in many open surgeries or the bipolar forceps as commonly applied in brain surgery can serve as ion sources following the REI (rapid evaporation ionization) mechanism. A chemical fingerprint of the sample is recorded by the mass spectrometric analysis of the charged particles carried by the aerosol created during ionization. REIMS profiles mainly display complex phospholipid species originating from the cell membranes and were shown to be highly specific to the histological or histopathological type of the tissues. More recently, the REIMS methodology has been developed to characterize and identify microorganisms including bacteria and fungi with excellent accuracies at species, genus and Gram-level.

REIMS profiles have allowed strain-level differentiation of seven *Escherichia coli* strains with an overall 88% accuracy independent of culturing conditions or the age of colonies. Reference is made to Strittmatter et al. Anal. Chem. 2014, 86, 6555-6562.

A fundamental aim is linking lipidomic profile to phenotype. The traditional technique of choice for lipidomic profiling is liquid chromatography-mass spectrometry (LC-MS). However, even using state of the art ultra-high performance liquid chromatography (UPLC-MS), run-time per sample is still in the range of 10-20 minutes and the analysis requires extensive sample preparation (homogenization, extraction, etc.).

Several mass spectrometric profiling methodologies have been developed in the recent past. Ambient mass spectrometric methods such as the most widely used Desorption Electrospray Ionization Mass Spectrometry (DESI-MS) offer the capabilities to analyze samples in their native state without any significant sample preparation steps. These ambient lipid profiling technologies have recently been deployed in cancer tissue studies to characterize the lipid composition of breast cancer compared to normal breast tissue, the identification of cancer metastasis within lymph nodes, colorectal cancer compared to normal mucosa, and brain cancer among others. A complementary approach for studying the molecular background of histologically specific lipid profiles would involve the use of cell lines, which would address sample availability and standardization of sampling, lift most of the ethical constraints and also allow functional testing including gene silencing or metabolic flux analysis.

Cell lines are a popular means of studying various biochemical and disease processes in vitro. In the case of cancer studies, the cell lines provide a means to study cancer development and progression as well as the investigation of pathobiochemical processes as close to the human body as possible while still allowing free manipulation of experimental parameters.

One of the most extensively characterized cell line collections is the NCI-60 cell line panel compiled by the National Cancer institute as part of the In Vitro Cell Line Screening Project (Robert H. Shoemaker "The NCI60 human tumour cell line anticancer drug screen" Nature Reviews Cancer 6, 813-823, October 2006). The panel comprises 60 human cancerous cell lines from nine different organs of origin, namely leukemia, melanoma, cancers of the lung, colon, brain, ovary, breast, prostate, and kidney.

Data available for these cell lines includes drug sensitivity patterns for more than 100,000 compounds and natural products, global protein and gene expression data and common mutations associated with cancer (Weinstein "Integromic analysis of the NCI-60 cancer cell lines" Breast Dis. 2004; 19:11-22). However, the associated metabolomics and lipidomics data is comparatively sparse. This represents a striking gap in the cancer-related biochemical data.

Complex lipids are the main constituents of cell membranes and play important functional, structural, and metabolic roles by acting as signaling molecules (e.g., PI phosphates, ceramides, lysophosphatidic acids (LPA)) or as precursors for secondary messengers (e.g., inositol triphosphate (IP3)/diacylglycerol (DAG)). Changes in the membrane lipid composition can regulate function and availability of intrinsic membrane proteins and affect cell signaling mechanisms.

Cancers figure among the leading causes of morbidity and mortality worldwide, with approximately 14 million new cases and 8.2 million cancer related deaths in 2012. According to the World Health Organisation, the number of new cases is expected to rise by about 70% over the next 2 decades.

Gastro-intestinal cancers are a leading cause of mortality and account for 23% of cancer-related deaths worldwide. In order to improve outcomes from cancers and other diseases, novel cell characterisation methods are needed in order to facilitate accurate diagnosis.

Rapid evaporative ionization mass spectrometry ("REIMS") is a technology which has recently been developed for the real time identification of tissues during surgical interventions. Coupling of REIMS technology with handheld sampling devices has resulted in iKnife sampling technology, which can provide intra-operative tissue identification with an accuracy of 92-100%.

The iKnife sampling technology allows surgeons to more efficiently resect tumours intra-operatively through minimizing the amount of healthy tissue removed whilst ensuring that all the cancerous tissue is removed.

REIMS analysis of biological tissue has been shown to yield phospholipid profiles showing high histological and histopathological specificity—similar to techniques using Matrix Assisted Laser Desorption Ionisation ("MALDI"), Secondary Ion Mass Spectrometry ("SIMS"), Desorption Electrospray Ionisation ("DESI") imaging, jet desorption ionisation ("JeDI"), laser desorption ionisation ("LDI"), plasma assisted desorption ionization ("PADI"), desorption atmospheric pressure photoionisation ("DAPPI"), and easy ambient sonic-spray ionisation ("EASI"). A mass spectrometric signal is obtained by subjecting the cellular biomass to alternating electric current at radiofrequency which causes localized Joule-heating and the disruption of cells along with desorption of charged and neutral particles. The resulting aerosol or surgical smoke is then transported to a mass spectrometer for on-line mass spectrometric analysis.

The known REIMS technique is typically performed on external tissues or tissues accessed through surgery.

Conventional methods of screening for potential therapeutic agents which interact with cell lines are known.

It is desired to provide improved methods of ambient ionisation mass and/or ion mobility spectrometry and apparatus for performing ambient ionisation mass and/or ion mobility spectrometry.

SUMMARY

The present invention provides a method of analysis using mass and/or ion mobility spectrometry comprising:
  (a) using a first device to generate smoke, aerosol or vapour from a target in vitro or ex vivo cell population and/or medium derived therefrom;
  (b) mass analysing and/or ion mobility analysing said smoke, aerosol or vapour, or ions derived therefrom, in order to obtain spectrometric data; and
  (c) analysing said spectrometric data in order to identify and/or characterise one or more cells and/or compounds present in said target cell population and/or medium derived therefrom.

Optional further details of the invention are provided in the detailed description and in the claims.

Various embodiments are contemplated wherein analyte ions are generated from the target, smoke, aerosol or vapour, e.g., by an ambient ionisation ion source. The analyte ions, or ions derived therefrom, may be subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser such as a quadrupole mass analyser or a Time of Flight mass analyser (or vice versa). Various embodiments also relate to an ion mobility spectrometer and/or mass analyser and a method of ion mobility spectrometry and/or method of mass analysis.

The mass and/or ion mobility spectrometer may obtain data in negative ion mode only, positive ion mode only, or in both positive and negative ion modes. Positive ion mode spectrometric data may be combined or concatenated with negative ion mode spectrometric data. Negative ion mode can provide particularly useful spectra for classifying aerosol, smoke or vapour samples, such as aerosol, smoke or vapour samples from targets comprising lipids.

Ion mobility spectrometric data may be obtained using different ion mobility drift gases, or dopants may be added to the drift gas to induce a change in drift time of one or more species. This data may then be combined or concatenated.

Other embodiments are contemplated wherein the first device for generating aerosol, smoke or vapour from the target may comprise an argon plasma coagulation ("APC") device. An argon plasma coagulation device involves the use of a jet of ionised argon gas (plasma) that is directed through a probe. The probe may be passed through an endoscope. Argon plasma coagulation is essentially a non-contact process as the probe is placed at some distance from the target. Argon gas is emitted from the probe and is then ionized by a high voltage discharge (e.g., 6 kV). High-frequency electric current is then conducted through the jet of gas, resulting in coagulation of the target on the other end of the jet. The depth of coagulation is usually only a few millimetres.

The first device, surgical or electrosurgical tool, device or probe or other sampling device or probe disclosed in any of the aspects or embodiments herein may comprise a non-contact surgical device, such as one or more of a hydrosurgical device, a surgical water jet device, an argon plasma coagulation device, a hybrid argon plasma coagulation device, a water jet device and a laser device.

A non-contact surgical device may be defined as a surgical device arranged and adapted to dissect, fragment, liquefy, aspirate, fulgurate or otherwise disrupt biologic tissue without physically contacting the tissue. Examples include laser devices, hydrosurgical devices, argon plasma coagulation devices and hybrid argon plasma coagulation devices.

As the non-contact device may not make physical contact with the tissue, the procedure may be seen as relatively safe and can be used to treat delicate tissue having low intracellular bonds, such as skin or fat.

BRIEF DESCRIPTION OF THE DRAWINGS

Various embodiments will now be described, by way of example only, and with reference to the accompanying drawings in which:

FIG. 1D shows an interface for ionising aerosol from the target cells and/or medium, and FIGS. 1E-1F show a DESI method for analysing target cells and/or medium;

FIG. 8 shows a 2-dimensional PCA plot of averaged REIMS data collected from the NCI-60 cells (squares) and cancer tissue samples (circles) wherein the tissue of origin is colon or ovarian;

FIG. 9A shows the mass spectral profile for bulk ovarian cancer tissue, FIG. 9B shows a corresponding mass spectral profile for ovarian cancer cell line OVCAR-3, FIG. 9C shows a mass spectral profile for bulk colorectal cancer tissue and FIG. 9D shows a mass spectral profile for colon cancer cell line HCT-15;

DETAILED DESCRIPTION

Figure 1A:
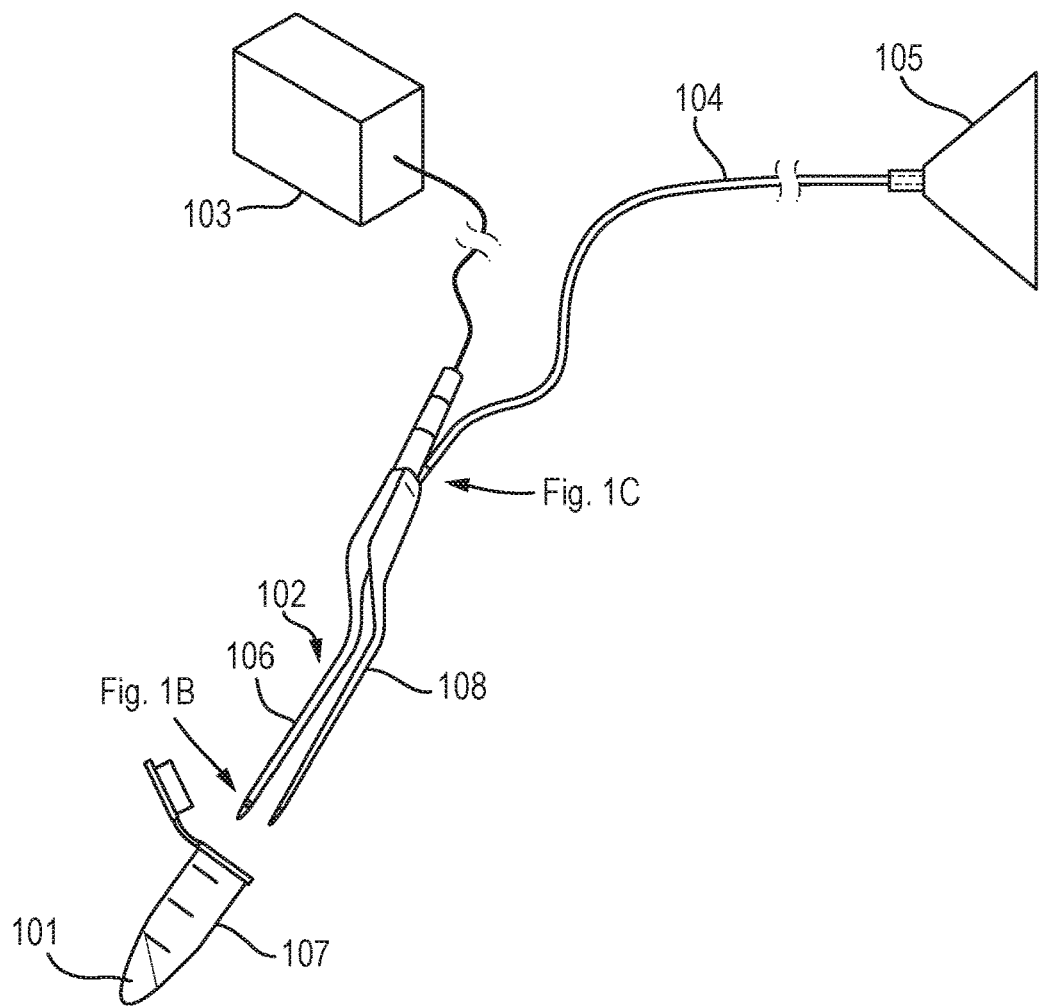
FIGS. 1A-1C show an experimental setup used for REIMS analysis of a cell population and/or medium derived therefrom which may be used in a method provided herein.

Although the present invention has been described with reference to preferred embodiments, it will be understood by those skilled in the art that various changes in form and detail may be made without departing from the scope of the invention as set forth in the accompanying claims.

Mass spectrometry ("MS") based identification techniques such as ambient ionization mass spectrometry are known. Direct ambient ionization mass spectrometry, such as REIMS, has emerged as a technology allowing real-time analysis of targets.

The invention described herein may, for example, be used in or with a real-time, robust characterisation tool which utilises ambient ionisation technologies, such as REIMS.

Various embodiments are described in more detail below which in general relate to generating smoke, aerosol or vapour from a target (details of which are provided elsewhere herein, e.g., an in vitro or ex vivo cell population or target material derived therefrom) using an ambient ionisation ion source. The aerosol, smoke or vapour may then be mixed with a matrix and aspirated into a vacuum chamber of a mass and/or ion mobility spectrometer. The mixture may be caused to impact upon a collision surface causing the aerosol, smoke or vapour to be ionised by impact ionisation which results in the generation of analyte ions. The resulting analyte ions (or fragment or product ions derived from the analyte ions) may then be mass and/or ion mobility analysed and the resulting mass and/or ion mobility spectrometric data may be subjected to multivariate analysis or other mathematical treatment in order to determine one or more properties of the target in real time.

Ambient Ionisation Ion Sources

In any of the methods of the invention a device may be used to generate an aerosol, smoke or vapour from one or more regions of a target (details of which are provided elsewhere herein, e.g., an in vitro or ex vivo cell population). The device may comprise an ambient ionisation ion source which is characterised by the ability to generate analyte aerosol, smoke or vapour from target, optionally with little or no preparation of the target for analysis. By contrast, other types of ionisation ion sources such as Matrix Assisted Laser Desorption Ionisation ("MALDI") ion sources require a matrix or reagent to be added to the sample prior to ionisation.

It will be apparent that the requirement to add a matrix or a reagent directly to a sample may prevent the ability to perform in vivo analysis of tissue and also, more generally, prevents the ability to provide a rapid simple analysis of target material.

Ambient ionisation techniques are particularly useful since they enable a rapid simple analysis of target material to be performed. Whilst there is no requirement to add a matrix or reagent to a sample in order to perform ambient ionization techniques, the method may optionally include a step of adding a matrix or reagent to the target (e.g., directly to the target) prior to analysis. The matrix or reagent may be added to the target, e.g., to lyse the cells of the target or to enhance the signal therefrom during the analysis.

A number of different ambient ionisation techniques are known and are intended to fall within the scope of the present invention. As a matter of historical record, Desorption Electrospray Ionisation ("DESI") was the first ambient ionisation technique to be developed and was disclosed in 2004. Since 2004, a number of other ambient ionisation techniques have been developed. These ambient ionisation techniques differ in their precise ionisation method but they share the same general capability of generating gas-phase ions directly from samples (e.g., without preparation of the sample for analysis). The various ambient ionisation techniques which are intended to fall within the scope of the present invention may not require any sample preparation for the analysis. As a result, the various ambient ionisation techniques enable targets to be analysed without the time, expense and problems associated with adding a matrix or reagent to the target material.

A list of ambient ionisation techniques which are intended to fall within the scope of the present invention are given in the following table:

| Acronym | Ionisation technique |
| --- | --- |
| DESI | Desorption electrospray ionization |
| DeSSI | Desorption sonic spray ionization |
| DAPPI | Desorption atmospheric pressure photoionization |
| EASI | Easy ambient sonic-spray ionization |
| JeDI | Jet desorption electrospray ionization |
| TM-DESI | Transmission mode desorption electrospray ionization |
| LMJ-SSP | Liquid microjunction-surface sampling probe |
| DICE | Desorption ionization by charge exchange |
| Nano-DESI | Nanospray desorption electrospray ionization |
| EADESI | Electrode-assisted desorption electrospray ionization |
| APTDCI | Atmospheric pressure thermal desorption chemical ionization |
| V-EASI | Venturi easy ambient sonic-spray ionization |
| AFAI | Air flow-assisted ionization |
| LESA | Liquid extraction surface analysis |
| PTC-ESI | Pipette tip column electrospray ionization |
| AFADESI | Air flow-assisted desorption electrospray ionization |
| DEFFI | Desorption electro-flow focusing ionization |
| ESTASI | Electrostatic spray ionization |
| PASIT | Plasma-based ambient sampling ionization transmission |
| DAPCI | Desorption atmospheric pressure chemical ionization |
| DART | Direct analysis in real time |
| ASAP | Atmospheric pressure solid analysis probe |
| APTDI | Atmospheric pressure thermal desorption ionization |
| PADI | Plasma assisted desorption ionization |
| DBDI | Dielectric barrier discharge ionization |
| FAPA | Flowing atmospheric pressure afterglow |
| HAPGDI | Helium atmospheric pressure glow discharge ionization |
| APGDDI | Atmospheric pressure glow discharge desorption ionization |
| LTP | Low temperature plasma |
| LS-APGD | Liquid sampling-atmospheric pressure glow discharge |
| MIPDI | Microwave induced plasma desorption ionization |
| MFGDP | Microfabricated glow discharge plasma |
| RoPPI | Robotic plasma probe ionization |
| PLASI | Plasma spray ionization |
| MALDESI | Matrix assisted laser desorption electrospray ionization |
| ELDI | Electrospray laser desorption ionization |
| LDTD | Laser diode thermal desorption |
| LAESI | Laser ablation electrospray ionization |
| CALDI | Charge assisted laser desorption ionization |
| LA-FAPA | Laser ablation flowing atmospheric pressure afterglow |
| LADESI | Laser assisted desorption electrospray ionization |
| LDESI | Laser desorption electrospray ionization |
| LEMS | Laser electrospray mass spectrometry |
| LSI | Laser spray ionization |
| IR-LAMICI | Infrared laser ablation metastable induced chemical ionization |
| LDSPI | Laser desorption spray post-ionization |
| PAMLDI | Plasma assisted multiwavelength laser desorption ionization |
| HALDI | High voltage-assisted laser desorption ionization |
| PALDI | Plasma assisted laser desorption ionization |
| ESSI | Extractive electrospray ionization |
| PESI | Probe electrospray ionization |
| ND-ESSI | Neutral desorption extractive electrospray ionization |
| PS | Paper spray |

| Acronym | Ionisation technique |
| --- | --- |
| DIP-APCI | Direct inlet probe-atmospheric pressure chemical ionization |
| TS | Touch spray |
| Wooden-tip | Wooden-tip electrospray |
| CBS-SPME | Coated blade spray solid phase microextraction |
| TSI | Tissue spray ionization |
| RADIO | Radiofrequency acoustic desorption ionization |
| LIAD-ESI | Laser induced acoustic desorption electrospray ionization |
| SAWN | Surface acoustic wave nebulization |
| UASI | Ultrasonication-assisted spray ionization |
| SPA-nanoESI | Solid probe assisted nanoelectrospray ionization |
| PAUSI | Paper assisted ultrasonic spray ionization |
| DPESI | Direct probe electrospray ionization |
| ESA-Py | Electrospray assisted pyrolysis ionization |
| APPIS | Ambient pressure pyroelectric ion source |
| RASTIR | Remote analyte sampling transport and ionization relay |
| SACI | Surface activated chemical ionization |
| DEMI | Desorption electrospray metastable-induced ionization |
| REIMS | Rapid evaporative ionization mass spectrometry |
| SPAM | Single particle aerosol mass spectrometry |
| TDAMS | Thermal desorption-based ambient mass spectrometry |
| MAII | Matrix assisted inlet ionization |
| SAII | Solvent assisted inlet ionization |
| SwiFERR | Switched ferroelectric plasma ionizer |
| LPTD | Leidenfrost phenomenon assisted thermal desorption |

According to an embodiment the ambient ionisation ion source may comprise a rapid evaporative ionisation mass spectrometry ("REIMS") ion source wherein a RF voltage is applied to one or more electrodes in order to generate smoke, aerosol or vapour by Joule heating.

However, it will be appreciated that other ambient ion sources including those referred to above may also be utilised. For example, according to another embodiment the ambient ionisation ion source may comprise a laser ionisation ion source. According to an embodiment the laser ionisation ion source may comprise a mid-IR laser ablation ion source. For example, there are several lasers which emit radiation close to or at 2.94 µm which corresponds with the peak in the water absorption spectrum. According to various embodiments the ambient ionisation ion source may comprise a laser ablation ion source having a wavelength close to 2.94 µm on the basis of the high absorption coefficient of water at 2.94 µm. According to an embodiment the laser ablation ion source may comprise a Er:YAG laser which emits radiation at 2.94 µm.

Other embodiments are contemplated wherein a mid-infrared optical parametric oscillator ("OPO") may be used to produce a laser ablation ion source having a longer wavelength than 2.94 µm. For example, an Er:YAG pumped ZGP-OPO may be used to produce laser radiation having a wavelength of e.g. 6.1 µm, 6.45 µm or 6.73 µm. In some situations it may be advantageous to use a laser ablation ion source having a shorter or longer wavelength than 2.94 µm since only the surface layers will be ablated and less thermal damage may result. According to an embodiment a Co:MgF$_2$ laser may be used as a laser ablation ion source wherein the laser may be tuned from 1.75-2.5 µm. According to another embodiment an optical parametric oscillator ("OPO") system pumped by a Nd:YAG laser may be used to produce a laser ablation ion source having a wavelength between 2.9-3.1 µm. According to another embodiment a $CO_2$ laser having a wavelength of 10.6 µm may be used to generate the aerosol, smoke or vapour.

According to other embodiments the ambient ionisation ion source may comprise an ultrasonic ablation ion source or a hybrid electrosurgical-ultrasonic ablation source that generates a liquid sample which is then aspirated as an aerosol. The ultrasonic ablation ion source may comprise a focused or unfocussed ultrasound.

According to an embodiment the first device for generating aerosol, smoke or vapour from the target may comprise a tool which utilises an RF voltage, such as a continuous RF waveform. According to other embodiments a radiofrequency system may be used which is arranged to supply pulsed plasma RF energy to a tool. The tool may comprise, for example, a PlasmaBlade®. Pulsed plasma RF tools operate at lower temperatures than conventional electrosurgical tools (e.g. 40-170° C. c.f. 200-350° C.) thereby reducing thermal damage depth.

Pulsed waveforms and duty cycles may be used for both cut and coagulation modes of operation by inducing electrical plasma along the cutting edge(s) of a thin insulated electrode.

According to an embodiment the first device comprises a surgical water/saline jet device such as a resection device, a hybrid of such device with any of the other devices herein, an electrosurgery argon plasma coagulation device, a hybrid argon plasma coagulation and water/saline jet device.

According to an embodiment the first device comprises or forms part of an ambient ion or ionisation source; or said first device generates said aerosol, smoke or vapour from the target and contains ions and/or is subsequently ionised by an ambient ion or ionisation source, or other ionisation source.

Optionally, the first device comprises or forms part of a device, or an ion source, selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source: (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a hybrid CUSA-diathermy device; (xxii) a focused or unfocussed ultrasonic ablation device; (xxiii) a hybrid focused or unfocussed ultrasonic ablation and diathermy device; (xxiv) a microwave resonance device; (xxv) a pulsed plasma RF dissection device; (xxvi) an argon plasma coagulation device; (xxvi) a hybrid pulsed plasma RF dissection and argon plasma coagulation device; (xxvii) a hybrid pulsed plasma RF dissection and JeDI device; (xxviii) a surgical water/saline jet device; (xxix) a hybrid electrosurgery and argon plasma coagulation device; and (xxx) a hybrid argon plasma coagulation and water/saline jet device.

Optionally, the step of using said first device to generate aerosol, smoke or vapour comprises contacting said target with one or more electrodes.

Optionally, said one or more electrodes comprise either: (i) a monopolar device, wherein there is optionally provided a separate return electrode; (ii) a bipolar device; or (iii) a multi-phase RF device, wherein there is optionally provided at least one separate return electrode.

Optionally, said one or more electrodes comprise or forms part of a rapid evaporation ionization mass spectrometry ("REIMS") device.

Optionally, said method further comprises applying an AC or RF voltage to said one or more electrodes in order to generate said aerosol, smoke or vapour.

Optionally, the step of applying said AC or RF voltage to said one or more electrodes further comprises applying one or more pulses of said AC or RF voltage to said one or more electrodes.

Optionally, said step of applying said AC or RF voltage to said one or more electrodes causes heat to be dissipated into said target.

Optionally, said step of using said first device to generate aerosol, smoke or vapour from one or more regions of the target further comprises irradiating the target with a laser.

Optionally, said first device generates aerosol from one or more regions of the target by direct evaporation or vaporisation of target material from said target by Joule heating or diathermy.

Optionally, said step of using said first device to generate aerosol, smoke or vapour from one or more regions of the target further comprises directing ultrasonic energy into said target.

Optionally, said aerosol comprises uncharged aqueous droplets. The droplets may comprise cellular material.

Optionally, at least 50%, 55%, 60%, 65%, 70%, 75%, 80%, 85%, 90% or 95% of the mass or matter generated by said first device and which forms said aerosol may be in the form of droplets.

The first device may be arranged and adapted to generate aerosol wherein the Sauter mean diameter ("SMD", d32) of said aerosol is in a range: (i)<5 µm; (ii) 5-10 µm; (iii) 10-15 µm; (iv) 15-20 µm; (v) 20-25 µm; or (vi) >25 µm.

The aerosol may traverse a flow region with a Reynolds number (Re) in the range: (i)<2000; (ii) 2000-2500; (iii) 2500-3000; (iv) 3000-3500; (v) 3500-4000; or (vi) >4000.

Substantially at the point of generating the aerosol, the aerosol may comprise droplets having a Weber number (We) selected from the group consisting of: (i)<50; (ii) 50-100; (iii) 100-150; (iv) 150-200; (v) 200-250; (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xxi) >1000.

Substantially at the point of generating the aerosol, the aerosol may comprise droplets having a Stokes number (Sk) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) >50.

Substantially at the point of generating the aerosol, the aerosol may comprise droplets having a mean axial velocity selected from the group consisting of: (i)<20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) >150 m/s.

Optionally, said aerosol comprises uncharged aqueous droplets. The droplets may comprise cellular material.

Optionally, the method comprises ionising at least some of said aerosol, smoke or vapour, or analyte therein, so as to generate analyte ions; wherein said analyte ions are analysed to obtain said spectrometric data.

Optionally, the method comprises directing or aspirating at least some of said aerosol, smoke or vapour into a vacuum chamber of a mass and/or ion mobility spectrometer; and/or ionising at least some said aerosol, smoke or vapour, or the analyte therein, within a, or said, vacuum chamber of said spectrometer so as to generate a plurality of analyte ions.

Optionally, the method comprises causing said aerosol, smoke or vapour, or analyte therein, to impact upon a collision surface, optionally located within a, or the, vacuum chamber of said spectrometer, so as to generate the plurality of analyte ions.

Optionally, the collision surface may be heated. The collision surface may be heated to a temperature selected from the group consisting of: (i) about <100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C. (x) about 900-1000° C.; (xi) about 1000-1100° C.; and (xii) about >1100° C.

Optionally, the method comprises adding a matrix to said aerosol, smoke or vapour; optionally wherein said matrix is selected from the group consisting of: (i) a solvent for said aerosol, smoke or vapour or analyte therein; (ii) an organic solvent; (iii) a volatile compound; (iv) polar molecules; (v) water; (vi) one or more alcohols; (vii) methanol; (viii) ethanol; (ix) isopropanol; (x) acetone; (xi) acetonitrile; (xii) 1-butanol; (xiii) tetrahydrofuran; (xiv) ethyl acetate; (xv) ethylene glycol; (xvi) dimethyl sulfoxide; an aldehyde; (xviii) a ketone; (xiv) non-polar molecules; (xx) hexane; (xxi) chloroform; and (xxii) propanol.

Optionally, the method may be carried out using negative ion mode, so optionally, the method comprises analysing spectrometric data obtained using negative ion mode. Optionally, the method may be carried out using positive ion mode, so optionally, the method comprises analysing spectrometric data obtained using positive ion mode. Optionally, the method comprises analysing spectrometric data obtained using negative ion mode and analysing spectrometric data obtained using positive ion mode.

The mass and/or ion mobility spectrometer may obtain data in negative ion mode only, positive ion mode only, or in both positive and negative ion modes. Positive ion mode spectrometric data may be combined with negative ion mode spectrometric data.

Ion mobility spectrometric data may be obtained using different ion mobility drift gases. This data may then be combined.

The matrix and/or aerosol, smoke or vapour may be doped with one or more additives to, for example, enhance the solvation or dilution of analyte with the matrix, or for enhancing the ionisation of the analyte within the aerosol, smoke or vapour.

The doping compound may be an acidic or basic additive such as, for example, formic acid or diethylamine.

The matrix and/or doping compound may cause derivatisation of the analyte in the aerosol, smoke or vapour. For example, the matrix and/or doping compound may cause the derivatisation of cholesterol or steroids in the analyte. This may render the analyte more easily ionised.

Rapid Evaporative Ionisation Mass Spectrometry ("REIMS")

Although various different ambient ionisation ion sources may be used in the invention to analyse a variety of targets, a method of REIMS analysis on a cell population will now be described in order to assist in understanding the embodiments.

Figure 1B:
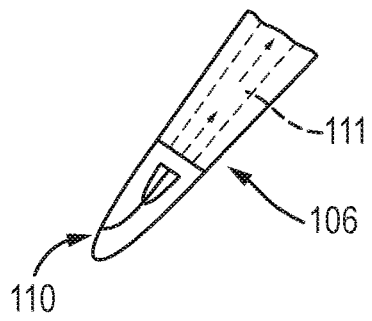
Figure 1C:
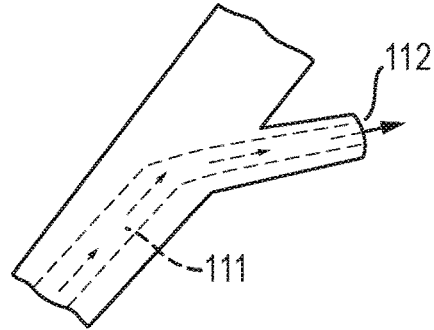

FIG. 1A shows apparatus that may be used to analyse a cell population. The apparatus comprises a pair of handheld electrodes 106,108 in the form of a forceps 102 (i.e. the first device); an RF power supply 103 for supplying an RF voltage to the electrodes 106,108; an inlet to a mass spectrometer 105; and tubing 104 connecting a port 112 at the rear end of the forceps 102 to the inlet of the spectrometer 105. The forceps 102 and RF power supply 103 may be configured such that the forceps 102 are bipolar forceps. As shown in FIG. 1B, an open entrance port 110 is provided in the tip of one of the electrodes 106 at the front of the forceps 102. This entrance port 110 opens up into a conduit 111 within the electrode 106. The conduit 111 extends through the electrode 106 to an exit port 112 in the rear of the forceps 102, as shown in FIG. 1C.

As shown in FIG. 1A, the sample/target to be analysed may be provided in the form of a cell pellet 101. The cell pellet may be provided in a container 107 such as an Eppendorf tube. The forceps 102 may be inserted into contact with the cell pellet 101 so as to obtain biomass from the cell pellet 101 on the tips of the electrodes 106,108. The two electrodes 106,108 may be subsequently brought into close proximity with each other, e.g., by pinching the biomass between the tips of the forceps 102. The RF power supply 103 may be triggered, e.g., using a foot switch, so as to energise the electrodes 106,108. This causes the cell line biomass to be rapidly heated (e.g. by Joule or diathermy heating), due to its non-zero impedance, and smoke, aerosol or vapour to be emitted from the biomass. The smoke, aerosol or vapour may contain charged molecular species of analytes in the biomass.

The smoke, aerosol or vapour may then be captured or otherwise aspirated through the entrance port 110 and into the conduit 111 in the forceps 102. The smoke, aerosol or vapour is then drawn through the conduit 111, out of the exit port 112, along the tubing 104 and into the inlet of the mass spectrometer 105. The inherent vacuum system of the mass spectrometer may be used to draw the smoke, aerosol or vapour from the entrance port 110 to the inlet of the spectrometer 105. Alternatively, a Venturi device may be used to draw the smoke, aerosol or vapour from the entrance port 110 to the inlet of the spectrometer 105.

FIG. 1D shows a schematic of an embodiment of an interface between the first device (e.g., forceps 102) and the mass spectrometer. The instrument may comprise an ion analyser 207 having an inlet 206 (which may correspond to inlet 5 in FIG. 1A), a vacuum region 208, a collision surface 209 and ion optics 212 (such as a Stepwave® ion guide) arranged within the vacuum region 208. The instrument also comprises a sample transfer tube 202 (corresponding to tubing 4 in FIG. 1) and a matrix introduction conduit 203. The sample transfer tube 202 has an inlet for receiving the smoke, aerosol or vapour sample 201 (which may correspond to that described in relation to FIG. 1) from a sample/target being investigated and an outlet that is connected to the inlet 206 of the ion analyser 207. The matrix introduction conduit 203 has an inlet for receiving a matrix compound and an outlet that intersects with the sample transfer tube 202 so as to allow the matrix 204 to be intermixed with the aerosol sample 201 in the sample transfer tube 202. A T-junction component may be provided at the junction between tubes 202, 203 and 206. The tubes 202, 203 and 206 may be removably inserted into the T-junction.

A method of operating the instrument shown in FIG. 1D will now be described. A sample/target, such as cell population material, may be subjected to the REIMS technique. For example, a first device (e.g., forceps 102) may be used to generate an aerosol, e.g., as described above in relation to FIGS. 1A-1C. The aerosol particles 201 are then introduced into the inlet of the sample transfer tube 202. A matrix compound 204 is introduced into the inlet of the matrix introduction conduit 203. The aerosol particles 201 and matrix compound 204 are drawn towards the inlet 206 of the ion analyser 207 by a pressure differential caused by the vacuum chamber 208 being at a lower pressure than the inlets to the tubes 202, 203. The aerosol particles 201 may encounter the molecules of matrix compound 204 in, and downstream of, the region that the sample transfer tube 202 intersects with the matrix introduction conduit 203. The aerosol particles 201 intermix with the matrix 204 so as to form aerosol particles containing matrix molecules 205, in which both the molecular constituents of the aerosol sample 201 and the matrix compound 204 are present. The matrix molecules 204 may be in excess compared to the molecular constituents of aerosol sample 201.

The particles 205 may exit the sample transfer tube 202 and pass into the inlet 206 of the ion analyser 207. The particles 205 then enter into the decreased pressure region 208 and gain substantial linear velocity due to the adiabatic expansion of gas entering the vacuum region 208 from the sample transfer tube 202 and due to the associated free jet formation. The accelerated particles 205 may impact on the collision surface 209, where the impact event fragments the particles 205, leading to the eventual formation of gas phase ions 210 of the molecular constituents of the aerosol sample 201 and the formation of matrix molecules 211. The collision surface 209 may be controlled and maintained at a temperature that is substantially higher than the ambient temperature.

The matrix 204 includes a solvent for the analyte 201, such that the analyte 201 dissolves by the matrix 204, thereby eliminating intermolecular bonding between the analyte molecules 201. As such, when the dissolved analyte 205 is then collided with the collision surface 209, the dissolved analyte 205 will fragment into droplets and any given droplet is likely to contain fewer analyte molecules than it would if the matrix were not present. This in turn leads to a more efficient generation of analyte ions 210 when the matrix in each droplet is evaporated. The matrix may include a solvent for said aerosol, smoke or vapour or analyte therein; an organic solvent; a volatile compound; polar molecules; water; one or more alcohols; methanol; ethanol; isopropanol; acetone; acetonitrile; 1-butanol; tetrahydrofuran; ethyl acetate; ethylene glycol; dimethyl sulfoxide; an aldehyde; a ketone; non-polar molecules; hexane; chloroform; or (xxii) propanol. Isopropanol is of particular interest.

The matrix molecules 211 may freely diffuse into the vacuum. In contrast, the gas phase ions 210 of the molecular constituents of the aerosol sample 201 may be transferred by the ion optics 212 to an analysis region (not shown) of the ion analyser 207. The ions 210 may be guided to the analysis region by applying voltages to the ion optics 212.

The ion optics 212 may be a StepWave® ion guide. The collision surface may be positioned along and adjacent to the central axis of the large opening of a StepWave® ion guide. As will be understood by those skilled in the art, a StepWave® ion guide comprises two conjoined ion tunnel ion guides. Each ion guide comprises a plurality of ring or other electrodes wherein ions pass through the central aperture provided by the ring or other electrodes. Ions enter a first of the ion guides, along with any neutrals that may be present, and travel through the first ion guide. Ions are then directed orthogonally into a second of the ion guides and are transmitted therethrough. Transient DC voltages or potentials are applied to the electrodes to drive the ions through them. The StepWave® ion guide is based on stacked ring ion guide technology and is designed to maximise ion transmission from the source to the mass analyser. The device allows for the active removal of neutral contaminants, since the neutrals are not directed orthogonally into the second ion guide, thereby providing an enhancement to overall signal to noise. The design enables the efficient capture of the diffuse ion cloud entering a first lower stage which is then may focused into an upper ion guide for transfer to the ion analyser. The ions are then analysed by the ion analyser, which may comprise a mass spectrometer or an ion mobility spectrometer, or a combination of the two. As a result of the analysis, chemical information about the sample 201 may be obtained.

A liquid trap or separator may be provided between the first device (e.g., forceps 2) and the analyser, which captures or discards undesired liquids that are aspirated by the probe whilst may allowing the smoke, aerosol or vapour itself to pass relatively uninhibited to the mass spectrometer. This prevents undesired liquid from reaching the analyser without affecting the measurement of the smoke, aerosol or vapour. The liquid trap or separator may be arranged to capture the liquid for later disposal.

As described above, although embodiments have been described in which REIMS is used to generate the smoke, aerosol or vapour for analysis, other ambient ionisation techniques may be used such as, for example, Desorption Electrospray Ionisation ("DESI").

Desorption Electrospray Ionisation ("DESI")

Desorption Electrospray Ionisation ("DESI") has also been found to be a particularly useful and convenient method for the real time rapid and direct analysis of biological material, e.g., a cell population. DESI techniques allow direct and fast analysis of surfaces without the need for prior sample preparation. The technique will now be described in more detail with reference to FIGS. 1E-1F.

As shown in FIGS. 1E-1F, the DESI technique is an ambient ionisation method that involves directing a spray of (primary) electrically charged droplets 301 onto a target 304. The electrospray mist is pneumatically directed at the target 304 by a sprayer 300 where subsequent splashed (secondary) droplets 305 carry desorbed ionised analytes (e.g. desorbed lipid ions). The sprayer 300 may be supplied with a solvent 306, a gas 307 (such as nitrogen) and a voltage from a high voltage source 308. After ionisation, the ions travel through air into an atmospheric pressure interface 309 of a mass spectrometer and/or mass analyser (not shown), e.g. via a transfer capillary 310. The ions may be analysed by the method described in relation to FIG. 1D, or by other methods. For example, the transfer capillary 310 of FIG. 1E may correspond to the sample transfer tube 202 in FIG. 1D. The transfer capillary 310 may be heated, e.g., to a temperature up to 500° C.

The DESI technique allows, for example, direct analysis of biological materials, such as a cell population, e.g., without requiring any advance sample preparation for the analysis.

General Methods of the Invention

Various embodiments of the present disclosure relate generally to the application of mass spectrometry and/or ion mobility spectrometry to the analysis of a target in vitro or ex vivo cell population and/or medium derived therefrom. Various embodiments of the invention also provide methods of drug discovery, testing, and/or production.

A number of optional features will be described in greater detail below. The invention provides method of analysis using mass spectrometry and/or ion mobility spectrometry comprising:
(a) using a first device to generate smoke, aerosol or vapour from a target in vitro or ex vivo cell population and/or medium derived therefrom; and
(b) mass analysing and/or ion mobility analysing said smoke, aerosol or vapour, ions derived therefrom, in order to obtain spectrometric data; and optionally
(c) analysing said spectrometric data in order to identify and/or characterise the target cell population or one or more cells and/or compounds present in said target cell population and/or medium derived therefrom.

Thus, optionally, the method may comprise a step of identifying and/or characterising the target cell population or one or more cells and/or compounds present in said target cell population and/or medium derived therefrom on the basis of said spectrometric data. It should be understood that any reference herein to "analysing" a target is intended to mean that the target is analysed on the basis of the spectrometric data. Thus, for example, by an expression, such as, "analysing spectrometric data in order to determine whether a cell population suffers from an infection" is meant that whether a cell population suffers from an infection is determined based upon the spectrometric data.

The method may optionally be a method of screening, e.g., for the purpose of drug development. Thus, optionally, the method may comprise a step of analysing the response of a cell population to a test agent or condition.

Optionally, the identity of a cell population or one or more cell types present therein may be analysed. Optionally, the infection of a cell population may be analysed. Optionally, the homogeneity and/or heterogeneity of a cell population may be analysed. Optionally, the genotype and/or phenotype of a cell population or one or more cell types present therein may be analysed. Optionally, the state of a cell population or one or more cell types present therein may be analysed. Optionally, a process involving a cell population or one or more cell types present therein may be analysed. Optionally, the effect of manipulating the genotype and/or phenotype of a cell population or one or more cell types present therein may be analysed. Optionally, the effect of manipulating the environmental conditions of a cell population may be analysed. Optionally, the method may be used to distinguish between 2 or more different cell types within a cell population. Optionally, the disease state of a cell population may be analysed. Optionally, the effect of a substance on a cell population may be analysed. Optionally, the utilisation, production and/or breakdown of a substance may be analysed. Optionally, a plurality of cell populations may be analysed to analyse their ability to utilise, produce and/or break down a substance. Thus, optionally, a plurality of cell populations may be screened to analyse their productivity or efficiency with respect to the production, breakdown and/or utilisation of a substance. Optionally, the viability of a cell population may be analysed.

In one aspect, the method may be a method of analysing a disease, a diseased cell, and/or a biomarker of a disease. Thus, the method may optionally comprise a step of analysing a disease, a diseased cell, and/or a biomarker of a disease.

The method may be a method of, or of obtaining information relevant to:
(i) diagnosing a disease;
(ii) monitoring the progression or development of a disease;
(iii) disease prognosis;
(iv) predicting the likelihood of a disease responding to treatment;
(v) monitoring the response of a disease to treatment; and/or
(vi) stratifying subjects;

Thus, the method may optionally comprise a step of
(i) diagnosing a disease;
(ii) monitoring the progression or development of a disease;
(iii) disease prognosis;
(iv) predicting the likelihood of a disease responding to treatment;
(v) monitoring the response of a disease to treatment; and/or
(vi) stratifying subjects.

The method may be a method of, or of obtaining information relevant to, predicting the viability of a cell population in terms of its long term viability, robustness and/or efficiency.

Details of suitable diseases are provided elsewhere herein.

In one aspect, the method may be a method of analysing a microbe, a microbial interaction, and/or a microbial biomarker. Thus, the method may optionally comprise a step of analysing a microbe, a microbial interaction, and/or a microbial biomarker.

In one aspect, the method may be a method of analysing the genotype and/or phenotype of a cell. Thus, the method may optionally comprise a step of analysing the genotype and/or phenotype of a cell.

In one aspect, the method may be a method of treatment. Thus, the method may optionally comprise a step of administering a therapeutically effective amount of a therapeutic agent to a subject in need thereof.

In one aspect, the method may be a method of analysing a compound. Thus, the method may optionally comprise a step of analysing a compound and/or a biomarker for a compound.

Optional features of any of these methods are discussed below. Thus, unless otherwise stated, any reference to "a method" or "the method" is intended to be a reference to any of the methods of the invention listed herein. It is explicitly intended that any of these features may be present in any combination in any of these methods.

The skilled person will appreciate that any of the methods provided herein may optionally be combined with one or more of the other methods provided herein and/or with one or more further methods.

For example, provided is a method which is a combination of two or more, e.g., three or more, four or more or five or more of the methods disclosed herein.

Target Cell Populations

The method may be carried out on a target cell population and/or medium derived therefrom. By "cell population" is meant an in vitro or ex vivo collection of cells. Thus, the cell population may be referred to as an "in vitro or ex vivo cell population". Thus, the term "cell population" does not extend to entire organisms, such as animals or humans.

The cell population may optionally, e.g., be primary cell culture, a secondary cell culture, a cell line, a xenograft-derived cell population and/or an organoid.

A "primary cell culture" is a culture of cells that were dissociated from the parental tissue using mechanical or enzymatic methods. A primary cell culture may, e.g., be an adherent cell culture or a cell suspension culture.

A "secondary cell culture" is a culture of cells which may e.g., be derived from a primary cell culture via multiple cell passages.

A "cell line" is a cell population which is typically uniform and which can be cultured in vitro for several passages. A cell line may, e.g., be derived from a secondary cell culture, from a tumour, and/or from an embryo. A cell line may optionally be "immortalised", in which case it can be cultured indefinitely. Immortalised cell lines typically have one or more mutations that override the cells' natural growth controls.

A "xenograft-derived cell population" is a cell population derived from a xenograft. A "xenograft" refers to cellular material, such as tissue, that originated from a first subject and was inserted into a second subject. Optionally, the xenograft may comprise or consist of tumour cells. For example, cells or tissue obtained from a human tumour may be xenografted into a host animal. Optionally, cells may be obtained from a xenograft to establish a xenograft-derived cell population.

Further details of cell lines and organoids are provided elsewhere herein. A cell population is a plurality of cells, which may optionally comprise extracellular compounds and/or extracellular medium. Thus, unless a "washed" cell population is used, the term "cell population" refers to cells and extracellular compounds within the cell population. Any reference herein to analysing a compound "in" a cell population should be understood to mean that the compound may be intracellular and/or extracellular.

As mentioned above, the method may be carried on medium derived from a cell population. By this is meant medium that was in contact with the cell population. Optionally, the medium derived from a cell population may be the medium in which the cell population was cultured, i.e. the extracellular medium, for a suitable period of time, e.g. at least 1, 2, 3, 4, 5, 6, 7, 8, 9, 10, 11, 12, 13, 14, 15, 16, 17, 18, 19, 20, 21, 22, 23, 24, 30, 45, 50, or 55 minutes, 1, 2, 3, 4, 5, 6, 7, 8, 9, 10, 11, 12, 13, 14, 15, 16, 17, 18, 19, 20, 21, 22, 23, or 24 hours and/or 1, 2, 3, 4, 5, 6, 7, 8, 9, 10, 11, 12, 13, 14, 15, 16, 17, 18, 19, 20, 21, 22, 23, or 24 days. During culture, cells may release one or more substances into the extracellular medium, so the medium may be referred to as "conditioned medium".

The extracellular medium may optionally comprise the cell population, or comprise one or more cells, or it may be cell-free. Cell-free extracellular medium may be prepared by removing the cells, e.g., through filtration and/or centrifugation as described elsewhere herein.

Thus, the target may optionally be medium derived from a cell population and the method may optionally comprise analysing the medium to analyse one or more compounds.

For example, the medium may be analysed to analyse the utilisation, production and/or breakdown of a substance.

Any references herein to carrying out a method on a cell population should be understood to encompass carrying out the method on the cell population and/or on medium derived from the cell population.

The cell population may optionally be a human or non-human animal cell population. Optionally, it may be mammalian, e.g., originate from a livestock, domestic or laboratory animal, e.g., be a rodent cell population. Optionally, it may be murine, guinea pig, hamster, rat, goat, pig, cat, dog, sheep, rabbit, cow, horse, alpaca, ferret, fowl, buffalo, and/or monkey.

The cell population may comprise or consist of one or more different cell types.

Unless otherwise specified herein, any reference herein to a "cell" should be understood to be a reference to a cell that is part of a cell population.

Optionally, the cell population may comprise or consist of adult, embryonic, and/or foetal cells, e.g., human embryonic cells or human adult cells.

Optionally, the cell population may comprise or consist of stem cells and/or differentiated cells. Optionally, stem cells may be totipotent stem cells, pluripotent stem cells, multipotent stem cells, and/or oligopotent stem cells.

Optionally, the cell population may comprise or consist of fibroblasts, epithelial cells, lymphocytes and/or macrophages.

Optionally, the cell population may comprise or consist of cells originating from, or having the characteristics of, cells of adrenal gland tissue, appendix tissue, bladder tissue, bone, bowel tissue, brain tissue, breast tissue, bronchi, ear tissue, oesophagus tissue, eye tissue, endometrioid tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and/or connective tissue, peritoneal tissue, blood vessel tissue and/or fat tissue; grade I, grade II, grade III or grade IV cancerous tissue; metastatic cancerous tissue; mixed grade cancerous tissue; a sub-grade cancerous tissue; healthy or normal tissue; or cancerous or abnormal tissue.

Optionally, the cell population may comprise or consist of adipocytes, endothelial cells, epidermal cells, epithelial cells, fibroblasts, glial cells, keratinocytes, mesenchymal cells, myoblasts, neuronal cells, squamous cells, stromal cells, and/or trophoblasts.

Optionally, the cell population may comprise or consist of cells having the identity of any one of the cell lines listed below.

Lung cancer—NCI-H23; NCI-H226; NCI-H322M; NCI-H460; NCI-H522; A549/ATCC; EK VX; HOP-18; HOP-62; HOP-92; LXFL 529; DMS 114; DMS 273; Renal cancer-UO-31; SN12C; A498; CAKI-1; RXF 393; RXF 631; ACHN; 786-0; TK-10;

Colon cancer—HT29; HCC-2998; HCT-116; SW-620; COLO 205; DLD-1; HCT-15; KM12; KM20L2;

Melanoma—LOX IMVI; MALME-3M; SK-MEL-2; SK-MEL-5; SK-MEL-28; M19-MEL; UACC-62; USACC-257; M14;

Central nervous system (CNS) cancer—SNB-19 (glioblastoma); SNB-75; SNB-78; U251; SF-268; SF-295; SF-539; XF 498;

Ovarian cancer—OVCAR-3; OVCAR-4; OVCAR-5; OVCAR-8; IGR-OV-1; SK-OV-3;

Leukemia—CCRF-CEM; K-562; MOLT-4; HL-60; RPMI-8226; SR.

Optionally, the cell population may comprise or consist of healthy and/or diseased cells. Diseased cells may optionally have a disease selected from any of the diseases listed elsewhere herein, optionally cancer.

Optionally, the cell population may comprise or consist of one or more of the following cell types: 3T3, Chinese hamster ovary (CHO), BHK, HEK293 (embryonic kidney cells), SKNBE2 (neuroblastoma), SW480 (colon carcinoma), Hela (cervical adenocarcinoma), PC3M, HOP62, T24, MES_SA (uterine sarcoma) and/or HepG2.

Optionally, the cell population may be mutant and/or transgenic.

Optionally, the cell population may be immortalised.

Optionally, the cell population may have, or be/have been genetically manipulated to have, one or more properties selected from auxotrophy, production of a desired compound, and/or secretion of a desired compound. Optionally, the cell population may be, or have been, genetically manipulated, e.g., be transgenic and/or have a knock-out genotype and/or phenotype.

Details of genetic manipulation and cell population properties are provided elsewhere herein.

Optionally, the method may comprise the analysis of one or more isogenic cell populations.

Any reference herein to the analysis of a "cell population" should be understood to mean that the entire cell population, or a sample thereof, may be analysed.

Optionally, a cell population may be optimised for analysis via a method provided herein, for example, for analysis wherein the ambient ionisation source is a REIMS ionisation source. In this regard, a cell population may optionally be optimised in that it expresses a specific receptor. The cell population may naturally express such a receptor, or it may have been genetically manipulated to express such a receptor. The optimised cell population may optionally be administered to a subject. This may facilitate subsequent analysis of the subject via a method provided herein.

The method may optionally be carried out on an entire cell population, or on a sample thereof, or on region thereof, particularly if the cell population is an organoid. It should be understood that any reference herein to a "cell population" may optionally be a "sample of a cell population". The method may optionally be carried out on a medium derived from a cell population, or on a sample thereof. Prior to performance of the method provided herein, the cell population or sample thereof, or medium or sample thereof, may optionally be dried, collected with a swab, and/or dispensed onto an absorbent carrier, e.g., a filter or paper. Optionally, the cell population or sample thereof may be provided as a pellet. A pellet may be prepared, e.g., by centrifuging a fluid containing the cell population, e.g., a liquid culture, at a suitable force and for a suitable time to sediment any cells, large structures and/or macromolecules to form a pellet. The remainder of the fluid, i.e. the supernatant, may then be discarded, e.g., by tipping it out, or via aspiration.

The pellet may be sampled straight from the bottom of the centrifuge tube, or it may be sampled from a support onto which it has been transferred. For example, prior to sampling, a pellet may optionally be transferred onto a glass or plastic support, such as a slide, or onto a swab, such as, a cotton swab.

The cell population, e.g., a pellet, may optionally be subjected to one or more washing steps, e.g., to remove the culture medium. Washing may be performed with a suitable buffer. Thus, the method may optionally be performed on a washed cell population.

The method may optionally involve the analysis of one or more different targets. Optionally, 2 or more targets from different cell populations, from different locations within an organoid, and/or from the same cell population at different time points, may be analysed. Optionally, the targets may be at 2 or more different locations, e.g., at 2 or more locations in an organoid.

Optionally, a target may be at one or more locations of an organoid known or suspected to be healthy; and one or more locations of an organoid known or suspected to be diseased.

Optionally, the method may involve the analysis of 2 or more locations of a target. Optionally, distinct locations of a target may be analysed, e.g., a series of points may be sampled, optionally with or without spatial encoding information for imaging purposes.

The method may optionally be carried out on a target that is native. By "native" is meant that the target has not been modified prior to performing the method provided herein. In particular, the target may be native in that the cell population is not subjected to a step of lysis or extraction, e.g., lipid extraction, prior to performance of the method provided herein. Thus, a target may be native in that all or substantially all of the cells in the cell population are intact. Thus, by native is meant that the target has not been chemically or physically modified and is thus chemically and physically native. Optionally, the target may be chemically native, i.e. it may be chemically unmodified, meaning that it has not been contacted with a chemical agent so as to change its chemistry. Contacting a target with a matrix is an example of a chemical modification.

Optionally, the target may be physically native, i.e. it may be physically unmodified, meaning that it has not been modified physically. Freezing and/or thawing are examples of physical modifications. The skilled person will appreciate that although physical actions, such as, freezing, may affect a specimen's chemistry, for the purpose of this invention such an action is not considered to be a chemical modification.

Thus, optionally the target may be chemically native, but not physically native, e.g., because it has been frozen.

Optionally, the target may be frozen, previously frozen and then thawed, and/or otherwise prepared. Optionally, the method may be carried out on a target that has not undergone a step of preparation specifically for the purpose of mass spectrometry analysis.

The target may not have been contacted with a solvent, or a solvent other than water, prior to generating the smoke, aerosol or vapour from the target.

Additionally, or alternatively, the target may not be contacted with a matrix prior to generating the smoke, aerosol or vapour from the target. For example, the target may not be contacted with a MALDI matrix or other matrix for assisting ionisation of material in the target.

Alternatively, the target may be contacted with a matrix, e.g., a MALDI matrix or other matrix for assisting ionisation of material in the target. The matrix may be added to said aerosol, smoke or vapour prior to the aerosol, smoke or vapour being ionised and/or impacting upon the collision surface.

The method may optionally be carried out on a target that has been prepared for a particular mass spectrometry analysis; and/or that has been prepared for any of the analytical methods mentioned elsewhere herein.

Target preparation (for any of the methods of the invention and/or any of the analytical methods disclosed herein) may optionally involve one or more of the following.

The cell population may optionally be deposited on a solid surface, such as, a glass or plastic slide.

The target may optionally be fixed chemically, e.g., to preserve cells from degradation, and to maintain the structure of the cell and of sub-cellular components such as cell organelles, e.g., nucleus, endoplasmic reticulum, and/or mitochondria. The fixative may, for example, be 10% neutral buffered formalin.

Freezing may optionally be performed, e.g., by contacting the cell population with a suitable cooling medium, such as, dry ice, liquid nitrogen, or an agent that has been cooled in dry ice or liquid nitrogen, e.g., isopentane (2-methyl butane). Frozen cell populations may optionally be stored at, e.g., between about −80 and −4 degrees Celsius, e.g., at −70 or −20 degrees Celcius.

The cell population may optionally be stained and/or labelled.

The term "sampling" is used herein to refer to the use of a device to generate smoke, vapour or aerosol from a target.

Any of the methods may optionally include automatic sampling, which may optionally be carried out using, e.g., a REIMS device. Any of the methods may optionally comprise using a disposable sampling tip.

Analysis of Identity or Authenticity

Human error and/or other circumstances can lead to misidentification, mislabelling, mix-ups, and the like, of cell populations. Thus, the identity of a particular cell population may be unknown, uncertain and/or unconfirmed. Optionally, the method may be used to identify a cell population, and/or to confirm the identity of a cell population.

By "identifying" a cell population is meant that at least some information about the type(s) of cells present in the cell population is obtained. This may optionally be the determination of the identity, and/or the confirmation of the identity of one or more cell types in the cell population. Confirming the identity of a cell population may also be referred to as confirming the authenticity of a cell population.

Thus, optionally the method may be performed on a cell population whose identity is unknown, to determine the identity of the cell population.

Optionally, the method may be performed on a cell population suspected of having a particular identity, to confirm or refute the identity of the cell population.

Optionally, the method may be performed on a cell population in need of authentication, to confirm the authenticity of the cell population.

Optionally, the cell population may be identified as comprising or consisting of adult, embryonic, and/or foetal cells.

Optionally, the cell population may be identified as comprising or consisting of stem cells and/or differentiated cells. Optionally, stem cells may be totipotent stem cells, pluripotent stem cells, multipotent stem cells, and/or oligopotent stem cells.

Optionally, the cell population may be identified as comprising or consisting of fibroblasts, epithelial cells, lymphocytes and/or macrophages.

Optionally, the cell population may be identified as comprising or consisting of cells originating from, or having the characteristics of, cells of adrenal gland tissue, appendix tissue, bladder tissue, bone, bowel tissue, brain tissue, breast tissue, bronchi, ear tissue, oesophagus tissue, eye tissue, endometrioid tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue; grade I, grade II, grade III or grade IV cancerous tissue; metastatic cancerous tissue; mixed grade cancerous tissue; a sub-grade cancerous tissue; healthy or normal tissue; or cancerous or abnormal tissue.

Optionally, the cell population may be identified as comprising or consisting of adipocytes, endothelial cells, epidermal cells, epithelial cells, fibroblasts, glial cells, keratinocytes, mesenchymal cells, myoblasts, neuronal cells, squamous cells, stromal cells, and/or trophoblasts.

Optionally, the cell population may be identified as comprising or consisting of any one of the cell lines listed elsewhere herein, e.g., having the identity of any one of the cell lines listed elsewhere herein.

Optionally, the cell population may be identified as comprising or consisting of healthy and/or diseased cells, wherein diseased cells may optionally have a disease selected from any of the diseases listed elsewhere herein.

Optionally, the cell population may be identified as comprising or consisting of mutant and/or transgenic cells.

Optionally, the cell population may be analysed (i) to confirm the identity or authenticity of said cell population; (ii) to detect a mutation in said cell population; and/or (iii) to detect an undesired variation in said cell population.

Analysis of Infection

A cell population may be at risk of infection with another cell type and/or a microbe. "Infection", with another cell type and/or microbe may also be referred to herein as "contamination". A particularly high risk is contamination with *Mycoplasma*.

Optionally, the method may be used to analyse whether infection is present in a cell population.

Optionally, the method may be used (i) to determine whether or not said cell population suffers from an infection; (ii) to determine whether or not said cell population is infection free; (iii) to determine whether or not said cell population has been cured of an infection; (iv) to determine the progression or stage of an infection of a cell population; or (v) to determine the progression or stage of a treatment for an infection of a cell population.

Optionally, if infection is determined, the infecting cell type and/or microbe may be identified.

Optionally, if infection is determined, the method may involve a step of treating/removing the infection, e.g., through contacting the cell population with an appropriate substance that is effective at selectively killing, or inhibiting the growth of, the infecting cell type and/or microbe. For example, if infection with *Mycoplasma* is determined, a suitable antibiotic may be used.

Analysis of Phenotype, Genotype and/or Homogeneity

A major area of on-going medical research is to gain greater understanding of the complex interactions between the 50,000 to 100,000 genes which make up the human genome in terms of interactions between different genes and interactions between genes and the environment. In particular, it is desired to gain a greater understanding of the relationship between a particular gene and a particular phenotype or observed characteristic.

There are several different types of genetic disease.

Firstly, there are single gene disorders which can be traced through families. A single gene disorder is the result of a single mutated gene. Over 4000 human diseases are caused by single gene defects and in many cases it has been possible to isolate the genes involved and to determine the types of mutation which underlie these conditions.

Secondly, there are polygenic or multigenic diseases which appear to have a genetic component but which do not follow any simple pattern of inheritance. These diseases reflect the effect of varying genetic susceptibility to a variety of different environmental agents.

Thirdly, there are genetic diseases which result from changes in the structure or number of our chromosomes.

Genetic mutations may alter the structure of a protein, e.g., by coding for a different amino acid, and/or by resulting in a shortened or elongated protein. Genetic mutations may alternatively or in addition result in a reduced output or absence of a gene product.

One of the best examples of genetic mutation comes from inherited disorders of haemoglobin (Hb). The structure of human haemoglobin changes during embryonic, fetal and adult life. All normal haemoglobins are tetramers of two pairs of dissimilar globin chains. Adult and fetal haemoglobins have α chains combined with β (HBA $α_2β_2$) or γ chains (HbF $α_2γ_2$). Over 400 structural haemoglobin variants has been identified but many of these cause no clinical disability.

However, other variants due to amino acid substitution alter the stability or function of the haemoglobin molecule which thereby results in a disease phenotype. For example, the substitution of glutamic acid for valine in the sixth position of the p chain causes the haemoglobin molecules to form linear stacks in the deoxy configuration which in turn cases the red cells to assume a sickled configuration. The resulting disease (sickle cell anaemia) results in chronic anaemia and tissue damage due to blockage of the microcirculation with sickled red cells. Other mutations affect oxygen transport or bind oxygen more avidly than normal causing oxygen starvation. Although the different phenotypes associated with these different genetic mutations are broadly the same, there may be considerable individual variation associated with an identical mutation. For example, sick cell anaemia can vary from being life-threatening to being symptomless and causing little disability.

Cystic fibrosis (CF) is another example of a monogenic disease which shows remarkable phenotypic variability.

The term "phenotype" is used to refer to the physical and/or biochemical characteristics of a cell whereas the term "genotype" is used to refer to the genetic constitution of a cell.

The term "phenotype" may be used to refer to a collection of a cell's physical and/or biochemical characteristics, which may optionally be the collection of all of the cell's physical and/or biochemical characteristics; and/or to refer to one or more of a cell's physical and/or biochemical characteristics. For example, a cell may be referred to as having the phenotype of a specific cell type, e.g., a breast cell, and/or as having the phenotype of expressing a specific protein, e.g., a receptor, e.g., HER2 (human epidermal growth factor receptor 2).

The term "genotype" may be used to refer to genetic information, which may include genes, regulatory elements and/or junk DNA. The term "genotype" may be used to refer to a collection of a cell's genetic information, which may optionally be the collection of all of the cell's genetic information; and/or to refer to one or more of a cell's genetic information. For example, a cell may be referred to as having the genotype of a specific cell type, e.g., a breast cell, and/or as having the genotype of encoding a specific protein, e.g., a receptor, e.g., HER2 (human epidermal growth factor).

The genotype of a cell may or may not affect its phenotype, as explained below.

The relationship between a genotype and a phenotype may be straightforward. For example, if a cell includes a functional gene encoding a particular protein, such as HER2, then it will typically be phenotypically HER2-positive, i.e. have the HER2 protein on its surface, whereas if a cell lacks a functional HER2 gene, then it will have a HER2-negative phenotype.

A mutant genotype may result in a mutant phenotype. For example, if a mutation destroys the function of a gene, then the loss of the function of that gene may result in a mutant phenotype. However, factors such as genetic redundancy may prevent a genotypic trait to result in a corresponding phenotypic trait. For example, human cells typically have 2 copies of each gene, one from each parent. Talking the example of a genetic disease, a cell may comprise 1 mutant (diseased) copy of a gene and one non-mutant (healthy) copy of the gene, which may or may not result in a mutant (diseased) phenotype, depending on whether the mutant gene is recessive or dominant. Recessive genes do not, or not significantly, affect a cell's phenotype, whereas dominant genes do affect a cell's phenotype.

It must also be borne in mind that many genotypic changes may have no phenotypic effect, e.g., because they are in junk DNA, i.e. DNA which seems to serve no sequence-dependent purpose, or because they are silent mutations, i.e. mutations which do not change the coding information of the DNA because of the redundancy of the genetic code.

The phenotype of a cell may be determined by its genotype in that a cell requires genetic information to carry out cellular processes and any particular protein may only be generated within a cell if the cell contains the relevant genetic information. However, the phenotype of a cell may also be affected by environmental factors and/or stresses, such as, temperature, nutrient and/or mineral availability, toxins and the like. Such factors may influence how the genetic information is used, e.g., which genes are expressed and/or at which level. Environmental factors and/or stresses may also influence other characteristics of a cell, e.g., heat may make membranes more fluid.

If a functional transgene is inserted into a cell at the correct genomic position, then this may result in a corresponding phenotype The insertion of a transgene may affect a cell's phenotype, but an altered phenotype may optionally only be observed under the appropriate environmental conditions. For example, the insertion of a transgene encoding a protein involved in a synthesis of a particular substance will only result in cells that produce that substance if the cells are provided with the required starting materials.

Optionally, the method may involve the analysis of the phenotype and/or genotype of a cell population.

The genotype and/or phenotype of cell population may be manipulated, e.g., to analyse a cellular process, to analyse a disease, such as cancer, to make a cell population more suitable for drug screening and/or production, and the like. Optionally, the method may involve the analysis of the effect of such a genotype and/or phenotype manipulation on the cell population, e.g., on the genotype and/or phenotype of the cell population.

The method may optionally be used to analyse a cell population after mutagenesis. Conventional methods for confirming whether or not a cell has been mutated can be difficult and/or time consuming. Optionally, the method may be used to analyse whether a cell has been mutated. A mutation may, e.g., be the introduction of a new gene, the silencing of a gene, an alteration in the expression of a gene, or give rise to an altered protein. Silencing may, e.g., be achieved via gene knock-out.

Optionally, the method may be used to analyse the effect of mutagenesis on a cell population, e.g., on the genotype and/or phenotype of a cell population.

Optionally, the method may analyse a cell population at 2 or more time points, e.g., before and after mutagenesis, and/or at 2 or more time points after mutagenesis.

Optionally, the cell population may be homogeneous or heterogeneous. By "homogeneous", "homogeneity" and derivatives of these terms is meant that the population is uniform, and by "heterogeneous", "heterogeneity" and derivatives of these terms is meant that the population is non-uniform.

By "degree of homogeneity" or "degree of heterogeneity" is meant the extent to which a cell population is homogeneous or heterogeneous, which may be expressed as a percentage. For example, a cell population may be considered to have a high degree of homogeneity if at least 60, 70, 75, 80, 85, 90, 91, 92, 93, 94, 95, 96, 97, 98, 99 or 100% of the cells are homogenous. A cell population may be considered to have a high degree of heterogeneity if at least 40, 45, 50, 55, 60, 70, 75, 80, 85, 90, 91, 92, 93, 94, 95, 96, 97, 98, 99 or 100% of the cells are heterogeneous.

The homogeneity and/or heterogeneity may be with respect to one or more genotypic and/or phenotypic features, e.g., at least 1, 2, 3, 4, 5, 6, 7, 8, 9 or 10 genotypic and/or phenotypic features, optionally with respect to the cells' entire genotype and/or phenotype.

Optionally, the method may involve the analysis of the degree of homogeneity and/or heterogeneity of the cell population.

During culture of a cell population, cells may grow and replicate. Replication may involve self-renewal, i.e. the production of a daughter cell having the same genotype and/or phenotype as the mother cell, and/or differentiation, i.e. the production of a daughter cell having a different genotype and/or phenotype compared to the mother cell.

Alternatively or in addition, cells may acquire one or more mutations and thus acquire a different genotype, which may manifest itself as a different phenotype.

In a heterogeneous cell population, one type may grow and/or replicate better or in a different way to another cell type, and/or one cell type may become dormant and/or die.

For these and/or other reasons, cell population may become more or less heterogeneous, so the method may optionally involve monitoring for any changes in the homogeneity and/or heterogeneity of the cell population.

Optionally, if the degree of homogeneity and/or heterogeneity of the cell population is higher or lower than desired, the method may involve a step of influencing the degree of homogeneity and/or heterogeneity. This may, e.g., involve the adjustment of culture conditions and/or the addition of a substance, to affect, e.g., the growth and/or differentiation rate of one or more of the cell types present in the cell population.

Manipulation of Genotype and/or Phenotype

Optionally, a cell population may be manipulated, e.g., the phenotype and/or genotype of some or all of the cells that make up the cell population may be manipulated.

The manipulation may optionally involve the exposure of a cell population or a portion thereof to a compound and/or radiation.

The manipulation may optionally be genetic manipulation.

Genetic manipulation may alter one or more genomic region(s) of a cell, which genomic region may be in the coding region of a gene, the non-coding region of a gene, a regulatory region, e.g., a promoter or enhancer, and/or in a region called "junk" DNA.

Genetic manipulation may optionally involve random mutagenesis. For example, cells may be exposed to a mutagen, which may, e.g., be selected from a chemical mutagen and/or radiation.

A compound, which may optionally be a chemical mutagen, may optionally be selected from, e.g., an alkylating agent, cross-linking agent, and/or polycyclic aromatic hydrocarbons (PAHs). Alkylating agents act by adding molecular components to DNA bases, which alters the protein product. Cross-linking agents create covalent bonds with DNA bases, while PAHs are metabolized by the human body into other potentially mutagenic molecules.

Radiation may optionally be selected from, e.g., light of a suitable wavelength, heat, and/or ionizing radiation. Ionizing radiation can penetrate cells and create ions in the cell contents. These ions can cause permanent alterations in DNA. Ionizing radiation may optionally be selected from, e.g., x rays, gamma rays, neutrons, electrons ("beta" particles), and/or alpha particles (helium nuclei). Ionizing radiation can alter the way two strands of DNA interact. It can rearrange entire sections of the chromosomes, altering relatively long stretches of DNA. Light may optionally be, e.g., UV light. This can cause covalent bonds to form between neighbouring thymine bases in the DNA, thereby altering the DNA at that location.

Alternatively or in addition to random mutagenesis, genetic manipulation may optionally involve targeted mutagenesis, which may optionally, e.g., be the knock-out, alteration, and/or insertion of genetic information. A cell that has been manipulated via targeted mutation may be referred to as a "transformed" cell, particularly if a new gene or gene variant, i.e. a "transgene" has been inserted. Similarly, a cell population comprising or consisting of cells that have been manipulated via targeted mutation may be referred to as a "transformed" cell population. Similarly, an organoid comprising or consisting of cells that have been manipulated via targeted mutation may be referred to as a "transformed" organoid.

Mutagenesis may optionally involve, e.g., one or more of the following techniques to introduce the desired genetic material, such as a transgene, into a cell: microinjection into the nucleus of a cell; a viral vector, e.g., an adenoviral or lentiviral vector; a liposome; calcium phosphate; a dendrimer; a cationic polymer, such as DEAE-dextran and/or polyethylenimine; sonication; electroporation; magnet-assisted transfection with magnetic particles; and/or particle bombardment.

Mutagenesis may optionally involve genome editing, e.g., using programmable nucleases, such as zinc-finger nucleases (ZFNs), transcription activator-like effector nucleases (TALENs), and/or clustered regularly interspaced short palindromic repeats (CRISPR)/CRISPR-associated protein 9 (Cas9).

Optionally, the method may involve a step of random and/or targeted mutagenesis, e.g., via any of the methods mentioned herein.

Properties of Cell Populations

The method may be carried out on a cell population having a desired property by selecting an existing cell population with the desired property. Alternatively or in addition, a cell population may be manipulated to impart a desired property unto the cell population. The method may optionally involve the analysis of one or more properties of a cell population.

Properties of a cell population that may be selected, manipulated, analysed or the like may optionally be selected from any of the properties listed below.

The cell population may optionally be auxotrophic with respect to one or more substances. Auxotrophy is the inability, or reduced ability, of a cell or organism to synthesize a particular substance required for its growth. An auxotroph is an organism that displays this characteristic; auxotrophic is the corresponding adjective. For example, an auxotroph may have a deficiency in a metabolic enzyme selected from adenine phosphoribosyl transferase (APRT) and/or dihydrofolate reductase (DHFR).

The cell population may optionally have the ability to produce a desired substance, e.g., a drug. Thus, the cell population may optionally have the ability to utilise a substance, e.g., to metabolise a substrate molecule to form a desired compound or precursor. Utilisation of a first substance may involve using a first substance as a substrate to produce a second substance; using a first substance as a general nutrient; and/or breaking down a first substance.

The cell population may optionally have a high specific productivity with respect to the production of a desired substance. The cell population may optionally have a high efficiency with respect to the utilisation and/or breakdown of a desired substance. It may optionally comprise high levels of, or have the ability to generate high levels of, one or more key metabolites linked to energy generation, regulation of cellular redox potential, and precursors for glycosylation. The method may optionally be used to determine whether a low productivity/efficiency cell population exhibits a different metabolic profile than its high productivity/efficiency counterpart. The method may optionally be used to analyse the specific productivity potential, and/or or efficiency with respect to the utilisation and/or breakdown of a desired substance, of a cell population.

The cell population may optionally have the ability to secrete a produced substance.

The cell population may optionally have the ability to replicate rapidly.

Lactate consumption may help control pH levels, which in turn may improve cell viability. The cell population may optionally have, or have the ability of, a high lactate consumption.

The method may optionally be used to analyse the metabolome, lipidome and/or proteome of a cell population.

The metabolome is a collection of some or all of the small-molecule metabolites present in a cell. The lipidome is a collection of some of all of the lipids present in a cell. The proteome is a collection of some of all of the proteins present in a cell. Although many proteins and some metabolites may not necessarily be analysed directly via the method provided herein, they may optionally be analysed indirectly, by analysing an indirect biomarker therefor.

The method may optionally involve the analysis of the state of a cell population or one or more cell types present therein. By "state" is meant the condition of a cell population or one or more cell types present therein, which may, e.g., be healthy and growing; healthy and not growing; stressed and growing; stressed and not growing; dying; or dead.

The method may optionally involve the analysis of the viability of a cell population. By "viability" is meant the minimum length of time that the cell population will continue to live. The viability may also be referred to as the "robustness", as robust cell populations are likely to live longer than non-robust cell populations.

The method may optionally involve the analysis of a cellular process. A cellular process may, e.g., be the production of a substance; the utilisation of a nutrient; a response to exposure to a substance; a response to exposure to an environmental condition and the like.

The method may optionally involve the identification of a spectrometric biomarker for a cell type, phenotype, genotype and/or property. As mentioned above, the identity and characteristics of many cell populations, e.g., cell lines, are known. In particular, data available for the NC60 cell lines includes drug sensitivity patterns for more than 100,000 compounds and natural products, global protein and gene expression data and common mutations associated with cancer. The method provided herein allows the identification of spectrometric biomarkers of these cell types or cell characteristics. Thus, the method may be used, e.g., to correlate a characteristic with spectrometric data, e.g., a spectrometric biomarker. The characteristic may, e.g., be a genotype and/or a phenotype, e.g., the sensitivity to a particular substance. For example, as discussed below, correlations between REIMS spectral features and gene expression profiles were identified by the inventor and are exemplified in case of fads2 and ugcg genes.

Drug Discovery and Screening of Agents, e.g., Cytotoxic Agents

It is known to use cell-based platforms to advance drug discovery, e.g., anti-cancer drug discovery, and it will be understood by those skilled in the art that cell-based compound screens and bioassays are essential for such drug discovery.

It is known to perform non-mass spectrometry high throughput cytotoxicity screening using a panel of cell populations covering various human cancer types. The information which is obtained from the process of performing such cytotoxicity screening may then be used for the selection of potential therapeutic agents and/or appropriate in vivo models for efficacy study.

Optionally, the method provided herein may be used for drug discovery and/or drug analysis. Thus, it may, e.g., be used as a screening method to screen potential therapeutic agents; or to screen known therapeutics to analyse their effects. For example, the method may be used to analyse the efficacy of a substance; the mechanism of action of a substance; and/or the safety of a substance. The efficacy may optionally be the therapeutic efficacy. The safety may optionally be the pharmacological safety.

Optionally the screening may be high-throughput screening. Optionally, the screening may be for, or of, a therapeutic agent effective against any of the diseases listed elsewhere herein, e.g., cancer or one or more specific types of cancer.

Thus, the method may optionally comprise exposing a cell population to a first substance and using the method to analyse the effect of said substance on the cell population. Details of suitable substances are discussed elsewhere herein.

Optionally, a second substance may be used, e.g., for comparison or control purposes. For example, the method may comprise exposing a first cell population to a first substance and a second cell population may be exposed to a second substance, analysing the first and the second cell population via mass spectrometry as discussed elsewhere herein and analysing any differences between the two cell populations. Optionally, the second substance may be a control substance, which may, e.g., be a negative control such as water or a buffer, or a positive control, such as an agent with a known effect, e.g., a known cytotoxic effect. Optionally, the first and the second cell population may be identical prior to performance of the method. For example, two samples may be taken from a single cell population to generate 2 cell populations. Optionally, the first and the second cell population may be isogenic. Optionally, the first and the second cell population may be phenotypically and/or genotypically different, e.g., they may be different cell types.

Analysing the effect of said substance on the cell population may comprise analysing a change in one or more properties of the cell population, details of which are discussed elsewhere herein.

Thus, optionally the method may comprise analysing said spectrometric data in order to determine whether or not said cell population has interacted with said substance in a manner which is of potential interest.

An "interaction in a manner which is of potential interest" is meant that the interaction results in a phenotypic and/or genotypic change. Optionally, the phenotypic and/or genotypic change may be a change in one or more properties of the cell population, details of which are provided elsewhere herein.

Optionally, the $EC_{50}$ of a test substance may be tested. $EC_{50}$ is the concentration of a drug that gives half-maximal response.

For example, the cytotoxicity of a test substance may be tested, e.g., the percentage of surviving cells as a function of the concentration of the test substance may be measured and cell populations which are sensitive and/or resistant to a test substance may be identified.

Optionally, the method may comprise analysing the susceptibility of a cell population to a substance, e.g., the susceptibility of a diseased cell population to a known or potential therapeutic agent. For example, the susceptibility of a cell population of a particular cancer type to an anti-cancer drug may be analysed.

Optionally, the method may also comprise a step of analysing the effect of an environmental condition of the cell population on the response of a cell population to said substance. Details of environmental conditions of the cell population are provided elsewhere herein. Thus, said method may optionally comprise the steps of (i) exposing the cell population to a substance; and (ii) changing an environmental condition of the cell population.

Optionally, the steps of (i) exposing the cell population to a substance; and (ii) changing an environmental condition of the cell population may be carried out simultaneously or sequentially in any order. Any of these steps, alone and/or in combination, may optionally be repeated, e.g., at least 2, 3, 4, 5, 6, 7, 8, 9 or 10 times.

Thus, a cell population may optionally, e.g., be exposed to a substance, and an environmental condition of the cell population may subsequently be changed; an environmental condition of the cell population may be changed, and a cell population may subsequently be exposed to a substance; and/or a cell population may be exposed to a substance, and an environmental condition of the cell population may simultaneously be changed.

It will be understood that optionally, one or more different substances and/or one or more different environmental conditions may be used in any of these methods. For example, a panel of different substances may optionally be used. The panel may, e.g., comprise or consist of members of a single class of drugs and/or members of two or more classes of drugs, e.g., known and unknown drugs.

For example, optionally, the substance may be a cytotoxic and/or cytostatic drug. Thus, e.g., one or more cell populations may be tested with one or more known cytotoxic/cytostatic drug, e.g., a non-chemotherapy approved cytotoxic/cytostatic drug. Optionally, one or more cell populations may, e.g., be tested using one or more potentially new therapeutic agents or cytotoxic/cytostatic drugs.

Optionally, one or more cell populations may be genetically modified and the modified cell population may be tested, e.g., with a known cytotoxic/cytostatic drug, and/or against a panel of potentially new therapeutic agents or cytotoxic/cytostatic drugs.

Optionally, one or more cell populations may be tested against a first substance and subsequently be tested against a second substance and optionally one or more further substances.

Analysis of a Change

The optional analysis of a change may be carried out in one or more different ways.

Optionally, a cell population may be analysed via the method provided herein at a first time and at a subsequent further time, e.g., second time, third, fourth, fifth, sixth, seventh, eighth, ninth, tenth, etc. time.

Thus, optionally, the method may comprise generating said aerosol, smoke or vapour from said target at a first time so as to obtain said first spectrometric data;

generating aerosol, smoke or vapour from said target, at a subsequent time;

mass analysing and/or ion mobility analysing the aerosol, smoke or vapour generated at the subsequent time, or ions derived therefrom, so as to obtain second spectrometric data; and comparing the first and subsequent spectrometric data to determine changes in the target. The subsequent time may be a second time, third, fourth, fifth, sixth, seventh, eighth, ninth, tenth, etc. time.

Optionally, between the first and a subsequent time, the cell population may be manipulated and/or exposed to a substance, which may optionally be selected from any of the agents listed herein, such as, a test agent.

Optionally, 2 or more, e.g., at least 2, 3, 4, 5, 6, 7, 8, 9, 10, 15, 20, 30, 40, 50, 60, 70, 80, 90, 100, 150, 200, 300, 400, 500, 600, 700, 800, 900, 1000, 2000, 3000, 4000, 5000, 6000, 7000, 8000, 9000, or 10000 identical and/or non-identical cell populations may be analysed simultaneously and/or sequentially. If a group of 3 or more cell populations are analysed, then the group may optionally comprise, e.g., 2 or more cell populations that are identical to one another, as well as 2 or more cell populations that are non-identical to one another.

Optionally, one or more further test agents and/or reference or control agents may be used. For example, a first cell population may be exposed to a first test agent and a second cell population may be exposed to a further test agent, a reference agent or a control agent.

Environmental Conditions

The method allows the analysis of a cell population under a defined environmental condition. This may optionally allow, e.g., cell populations to be analysed under conditions that mimic in vivo conditions, e.g., the conditions of a tumour or tumour microenvironment. Solid tumours typically develop hostile microenvironments characterized by irregular vascularization, poor oxygen ($O_2$) supply, and/or poor nutrient supply.

By "defined environmental condition" is meant that at least one environmental factor is controlled. For example, a controlled temperature or temperature range, or a controlled level of a particular nutrient, may be referred to as a defined environmental condition.

Optionally, the method may involve the analysis of the effect of one or more defined environmental conditions on a cell population. Optionally, the analysis may be of the effect of a change in one or more environmental conditions on a cell population.

The environmental condition may optionally be a condition that can influence cell population growth; differentiation; migration; cell state; and/or phenotype and/or genotype. Thus, the environmental condition may, e.g., be the nature and/or concentration of culture media components, particularly nutrient and/or mineral concentrations; the nature and extent of cell-cell contacts; temperature; pH; fluid balance; pressure; flow volume; and/or oxygen pressure. For example, the cell population may be exposed to hypoxia.

The environmental condition may optionally be altered by introducing the cell population into a host organism. Thus, optionally, the cell population may be introduced into a host organism, which may optionally be selected from a human or non-human animal. Optionally, it may be a livestock, domestic or laboratory animal, e.g., be a rodent. Optionally, it may be murine, guinea pig, hamster, rat, goat, pig, cat, dog, sheep, rabbit, cow, horse, alpaca, ferret, fowl, buffalo, and/or monkey. Thus, optionally the cell population may be exposed to, e.g., maintained and/or grown in, the in vivo environment of a host organism. The effect of such an exposure may optionally be analysed by the method provided herein. Prior to and/or after analysis of a target cell population, one or more of these conditions may optionally be appropriately modified. Such modification is within the competencies of one of ordinary skill in the art.

Thus, optionally the method may comprise one or more of the following: changing or varying the concentration of a nutrient which is supplied to a cell population; changing or varying the concentration of a mineral which is supplied to a cell population; changing or varying a pH level at which said cell population is maintained; changing or varying a temperature at which said cell population is maintained; changing or varying an oxygen, carbon dioxide or other gas level to which said cell population is exposed; changing or varying the concentration of a contamination control substance or an antibiotic to which said cell population is exposed; changing or varying the concentration of a catalyst, inducer or agent which prompts said cell population to generate a therapeutic or other product; and/or changing or varying a light level to which said cell population is exposed. Optionally, the effect of any of these changes may be analysed.

For example, the environmental condition may be a culture medium which has a low concentration of one or more lipids, and/or a low overall lipid concentration, as discussed below.

Analysis of Lipid Requirements

Compared with non-cancerous cells, cancer cells exhibit significant metabolic alterations with respect to several critical nutrients and substrates, e.g., the metabolism of glucose and glutamine. Cancer cells also exhibit increased demand for fatty acids, which they may synthesize endogenously from carbohydrates, such as citrate, or take up from exogenous sources. Lipoprotein lipase (LPL) and/or the fatty acid channel protein CD36 may be involved in the uptake of fatty acids, whereas fatty acid synthase (FASN) may be involved in fatty acid synthesis. The elevated rates of lipid synthesis occur through increased expression of various lipogenic enzymes. Increased lipid production appears to be critical for cancer cell survival, and expression of key lipogenic enzymes may be strongly correlated with cancer progression. Fatty acids may be incorporated into membranes as phospholipids, stored in lipid droplets, and/or used for the production of signalling lipids.

The de novo synthesis of lipids, which may be called lipogenesis, involves the conversion of acetyl-CoA into fatty acids, which may then be assembled into lipids. Acetyl-CoA may be derived from a variety of sources, e.g., from carbohydrates, e.g., via the glycolytic pathway.

Increased lipogenesis is a characteristic of a wide variety of cancers, so lipogenesis pathways are a potential anticancer target. To analyse the therapeutic potential of lipid synthesis inhibitors, a better understanding of the relationship between de novo lipid synthesis and exogenous lipids and their respective role in cancer cell proliferation and therapeutic response to lipogenesis inhibitors is of critical importance.

Thus, cancer cells require fatty acids. They may synthesise fatty acids from carbohydrates, and/or take up fatty acids from their surroundings, i.e. exogenous fatty acids. Some types of cancer cells appear to depend on exogenous fatty acids for survival, whereas other cancer types are capable of surviving in the absence of exogenous fatty acids.

Optionally, the method may therefore be used to analyse whether a cell population has a requirement for exogenous lipids, e.g., fatty acids, and/or the extent to which a cell population requires exogenous lipids, e.g., fatty acids. Thus, the method may, e.g., allow a determination to be made as to whether a particular cell population has a requirement for exogenous fatty acids. The method may, e.g., allow a determination to be made that a particular cell population is capable of a high level of lipogenesis. Such a population may be referred to as having a "lipogenic" or "highly lipogenic" phenotype and/or genotype.

Thus, the method may optionally involve culturing a cell population in a culture medium which has a low concentration of one or more lipids, and/or a low overall lipid concentration. Optionally, the method may involve culturing a cell population in a host organism. Such an environmental condition may simulate in vivo conditions of tumour cells, particularly cells in the centre of a tumour. The effect of such an environmental condition may be analysed by the method provided herein, and/or the effect of a substance on a cell population cultured under this environmental condition may be analysed.

If a cell population is not provided with sufficient levels of lipids via its culture medium, then one or more of the following may occur: the growth of the cell population may slow and/or halt; a proportion and/or all of the cell population may die; and/or the cells may synthesize lipids.

Cancer cells with a lipogenic phenotype and/or genotype may differ in their susceptibility to a substance. As mentioned above, the method provided herein may be used to determine whether a cell population has a lipogenic phenotype and/or genotype, and or whether it is susceptible to a substance, such as an anti-cancer agent, e.g., an inhibitor of a lipogenic pathway.

According to various embodiments REIMS analysis may be extended to cancer phenotyping studies.

Isotope Studies

Optionally, the method may be used in or with isotope studies.

Isotopes are variants of a particular chemical element which differ in neutron number, whilst having the same number of protons in each atom. Isotope studies may, e.g., involve the use of stable isotopes, i.e. non-radioactive isotopes. For example, isotopes of hydrogen (H), carbon (C), nitrogen (N), oxygen (O), fluorine (F) and/or sulphur (S) may be used. The term "different types of isotopes" is used to mean isotopes of different elements, so an isotope of C is a different type of isotope from an isotope of N.

In nature, one isotope of each element is typically most abundant, and any other stable isotopes of the element that may exist are typically far less abundant. For example, 1H is far more abundant than $_2$H, $_{12}$C is far more abundant than $_{13}$C, $_{14}$N is far more abundant than $_{15}$N, $_{16}$O is far more abundant than $_{17}$O or $_{18}$O, and $_{32}$S is far more abundant than $_{34}$S. The less abundant isotopes are the heavier ones, so they may be referred to as a "heavy isotope". In isotope studies, cells may be exposed to one or more heavy isotopes and cellular processes may then be analysed by analysing the fate of the heavy isotope(s).

Different nonradioactive stable isotopes can be distinguished by mass spectrometry, so the method provided herein may optionally be used in or with isotope studies.

Thus, optionally, the cell population may be exposed to one or more heavy isotopes, e.g., to one or more substances comprising or consisting of one or more heavy isotopes. The substance may optionally be selected from any of the substances listed elsewhere herein, e.g., any nutrients, e.g., glucose, glutamine o the like. A substance comprising or consisting of one or more heavy isotopes may be referred to as a "heavy-isotope substance". A heavy-isotope substance may optionally comprise a single heavy-isotope, 2 or more heavy-isotopes, or consist of heavy-isotopes. A heavy-isotope substance may optionally comprise a single type of heavy isotope or 2 or more, e.g., at least 2, 3, 4, 5, or 6 different types of heavy isotopes.

A substance may optionally be isotopically defined, i.e. it may be possible to use a substance in which one or more specific atoms are replaced with one or more heavy isotopes, which may allow an analysis of the fate of specific parts of a substance. Optionally, an analysis with a substance having a first atom replaced with a heavy isotope may be compared to an analysis with the corresponding substance having a different atom replaced with a heavy isotope.

For example, a heavy-isotope substance, such as, a nutrient, e.g., carbon source, may be used and the method may optionally be used to analyse whether and/or how the nutrient is used by the cell population. Thus, optionally, lipid metabolism, e.g., anabolism and/or catabolism may be analysed. In particular, the method may optionally be used to analyse the depletion or enrichment of a heavy isotope type in one or more metabolites, such as, fatty acid type(s). Thus, e.g., the presence or absence, and/or relative abundance, of one or more metabolites, fatty acids, lipids and/or biomarkers may be analysed prior to and/or after exposure of a cell population to a heavy isotope. Optionally, the analysis may be carried out at 2 or more time points, e.g., to monitor a change over time in the presence or absence, and/or relative abundance, of one or more metabolites, fatty acids, lipids and/or biomarkers.

Optionally, a cell population may be exposed to at least 2 types of heavy isotopes and/or at least 2 types of heavy isotope substances simultaneously and/or sequentially. Optionally, a cell population may be exposed to a first type of heavy isotope at a first time point and to a second type of heavy isotope at a second time point. Optionally, a cell population may be exposed to a first type of heavy isotope substance at a first time point and to a second type of heavy isotope substance at a second time point. For example, a cell population may be exposed to a heavy-isotope glucose at a first time point and to a heavy-isotope glutamine at a second time point.

Analysis of Radio-Tracers

Positron Emission Tomography (PET) is a radiotracer imaging technique, in which tracer compounds labelled with positron-emitting radionuclides are injected into the subject of the study. These radio-tracer compounds can then be used to track biochemical and physiological processes in vivo. One of the prime reasons for the importance of PET in medical research and practice is the existence of positron-emitting isotopes of elements such as carbon, nitrogen, oxygen and fluorine which may be processed to create a range of radio-tracer compounds which are similar to naturally occurring substances in the body.

Optionally, the radio-tracer may be a compound labelled with $^{11}C$, $^{13}N$, $^{15}O$, and/or $^{18}F$. Optionally, it may be selected from the compounds listed in the table below.

| Isotope | Tracer compound | Physiological process or function | Typical application |
|---|---|---|---|
| $^{11}C$ | methionine | protein synthesis | oncology |
| $^{11}C$ | flumazenil | benzodiazepine receptor antagonist | epilepsy |
| $^{11}C$ | raclopride | D2 receptor agonist | movement disorders |
| $^{13}N$ | ammonia | blood perfusion | myocardial perfusion |
| $^{15}O$ | carbon dioxide | blood perfusion | brain activation studies |
| $^{15}O$ | water | blood perfusion | brain activation studies |
| $^{18}F$ | Fluoro-deoxy-glucose | glucose metabolism | oncology, neurology, cardiology |
| $^{18}F$ | Fluoride ion | bone metabolism | oncology |
| $^{18}F$ | Fluoro-mizonidazole | hypoxia | oncology - response to radiotherapy |

Thus, e.g., if the biologically active molecule chosen is fluorodeoxyglucose (FDG), an analogue of glucose, the concentrations of tracer will indicate tissue metabolic activity as it corresponds to the regional glucose uptake. Use of this tracer to explore the possibility of cancer metastasis (i.e., spreading to other sites) is the most common type of PET scan in standard medical care (90% of current scans).

Optionally, a cell population may be exposed to a radio-tracer and the method may be used to analyse the location and/or concentration of a radio-tracer. Thus, the method may optionally be used to analyse the metabolism of a compound labelled with a positron-emitting radionuclide.

Isogenic Cell Populations

Optionally, the method may involve the use of 2 or more cell populations that are isogenic except for one or more genetic regions of interest. The term "isogenic" is used in the art to indicate that 2 cell populations are genetically identical or share essentially the same genetic information, except for one or more genetic regions of interest. Typically, 2 isogenic cell populations will differ in a single gene, which may optionally be linked to a reporter gene in which the isogenic cell populations may also differ.

Optionally, isogenic cell populations may differ with respect to an endogenous gene, e.g., one cell population may have a wild-type endogenous gene and another cell population may have a mutant version of said gene. Optionally, the mutant version may have an altered functionality or be a knock-out.

Optionally, isogenic cell populations may differ with respect to an exogenous gene, e.g., one cell population may comprise a first version of an exogenous gene and another cell population may have a second version of said exogenous gene; or one cell population may comprise a first exogenous gene and another cell population may have a second exogenous gene.

The method may thus optionally be used to analyse differences between 2 or more isogenic cell populations. The use of isogenic cell populations may be useful, e.g., to analyse the effect of a modification or change, e.g., to analyse the effect of a substance on a cell population; to analyse the effect of an environmental change on a cell population; and/or to analyse the production of a substance by a cell population.

Isogenic cell populations may be obtained, e.g., by transfecting a first cell population with a first vector that encodes a first transgene and a first marker and transfecting a second cell population with a second vector that encodes a second transgene and a second marker, the second being different from the first.

Optionally, the marker may, e.g., be a fluorescent marker, details of which are provided elsewhere herein.

Culture and analysis via the method provided herein of both cell population allows, e.g., screening for compounds with selective activity, e.g., toxicity, towards a gene of interest. Such drug screening is broadly applicable for mining therapeutic agents targeted to specific genetic alterations responsible for disease development.

Substances Such as Test Agents and/or Cytotoxic Anticancer Drugs

As mentioned elsewhere herein, the method may optionally be used to analyse the effect of a substance on a cell population; and/or to analyse the production of a substance.

Thus, the method may optionally involve the direct or indirect analysis of one or more substances. Unless otherwise stated, the terms "substance", "compound", "molecule" and "biomolecule" are used interchangeably herein.

As mentioned elsewhere herein, the method may also optionally involve a step of administering a treatment to a subject for which the target cell population is a model. Such a treatment step may, e.g., involve the administration of a therapeutic agent, which may optionally comprise or consist of any of the substances mentioned herein.

The compound may optionally be intracellular and/or extracellular. It may optionally be endogenous, i.e. produced by the cell population, and/or exogenous, i.e. added to the cell population.

The compound may optionally comprise or consist of any of the compounds or classes of compounds mentioned herein, e.g., any of the biomarker compounds mentioned herein.

Optionally, it may comprise or consist of, for example, a lipid, such as, a glycolipid or phospholipid; carbohydrate; DNA; RNA; protein, e.g., an antibody, enzyme or hormone; polypeptide, such as, a ribosomal peptide or a non-ribosomal peptide; oligopeptide; lipoprotein; lipopeptide; amino acid; and/or chemical molecule, optionally an organic chemical molecule.

The compound may optionally be linear, cyclic or branched.

The compound may optionally be a metabolite, such as, a primary or a secondary metabolite; an antibiotic; a quorum sensing molecule; a fatty acid synthase product; a pheromone; a protein; a peptide; and/or a biopolymer. It may optionally be an antibody or hormone.

The compound may optionally be characterised by one or more of the following functional groups: alcohol, ester, alkane, alkene, alkyne, ether, ketone, aldehyde, anhydride, amine, amide, nitrile, aromatic, carboxylic acid, alkyl halide, and/or carbonyl. Optionally, it may additionally be identified as being primary, secondary or tertiary, e.g., a primary alcohol, a secondary amine, or the like.

The substance may optionally be a test agent or a drug.

The substance may optionally be a known drug, e.g., an anti-cancer drug, e.g., a cytostatic and/or cytotoxic agent, which may optionally be selected from any of the substances listed below.

The substance may optionally be, e.g., an aromatase inhibitor; an anti-angiogenic agent; a Tubulin-binding agent; an inhibitor of lipogenic pathways; and/or a cytostatic agent; optionally selected from an alkylating agent, a cross-linking agent, an intercalating agent, a nucleotide analogue, an inhibitor of spindle formation, and/or an inhibitor of topoisomerase I and/or II.

It may, for example, be an antibody specific for a receptor expressed by cancer cells, which may optionally be conjugated to a chemotherapy drug or to a radioactive particle.

The antibody may optionally, for example, be selected from a HER-2/neu specific monoclonal antibody, such as, Trastuzumab (Herceptin); Adecatumumab, alemtuzumab, Blinatumomab, Bevacizumab, Catumaxomab, Cixutumumab, Gemtuzumab, Rituximab, Trastuzumab, and/or Ibritumomab.

The substance may optionally be, e.g., an anthracycline, an Epipodophyllotoxin, a Dactinomycin, a Camptothecin, a Taxane, a Vinca alkaloid, Soraphen A, and/or Simvastatin Cytotoxic anticancer drugs (sometimes known as antineoplastics) describe a group of medicines that contain chemicals which are toxic to cells. The cytotoxic drugs prevent cell replication and growth and hence are useful in the treatment of cancer. Most of the commonly used cytotoxic anticancer drugs were discovered through random high-throughput screening of synthetic compounds and natural products in cell-based cytotoxicity assays. Most of the compounds are DNA-damaging agents with a low therapeutic index.

An initial National Cancer Institute (NCI) high-throughput screen used the highly chemosensitive P388 leukemia cell line. However, this screen failed to identify drugs that were active against common adult solid tumours. As a result, the NCI implemented a new in vitro screen consisting of 60 human tumour cell lines representing nine common forms of cancer.

The following table shows commonly used natural product anticancer drugs and their corresponding mechanism of action:

| Drug class | Mechanism of action |
| --- | --- |
| Anthracyclines | Topoisomerase II inhibitors |
| Epipodophyllotoxins | Topoisomerase II inhibitors |
| Dactinomycin | Topoisomerase II inhibitors |
| Campthothecins | Topoisomerase I inhibitors |
| Taxanes | Tubulin-binding agents |
| Vinca alkaloids | Tubulin-binding agents |

The substance may optionally be selected from, e.g., anastrozole; azathioprine; bcg; bicalutamide; chloramphenicol; ciclosporin; cidofovir; coal tar containing products; colchicine; danazol; diethylstilbestrol; dinoprostone; dithranol containing products; dutasteride; estradiol; exemestane; finasteride; flutamide; ganciclovir; gonadotrophin, chorionic; goserelin; interferon containing products (including peginterferon); leflunomide; letrozole; leuprorelin acetate; medroxyprogesterone; megestrol; menotropins; mifepristone; mycophenolate mofetil; nafarelin; oestrogen containing products; oxytocin (including syntocinon and syntometrine); podophyllyn; progesterone containing products; raloxifene; ribavarin; sirolimus; streptozocin; tacrolimus; tamoxifen; testosterone; thalidomide; toremifene; trifluridine; triptorelin; valganciclovir; and/or zidovudine. These substances may optionally be referred to as non-chemotherapy approved cytotoxic/cytostatic drugs.

Alternatively or in addition, the substance may optionally be selected from, e.g., aldesleukin; alemtuzumab; amsacrine; arsenic trioxide; asparaginase; bleomycin; bortezomib; busulphan; capecitabine; carboplatin; carmustine; cetuximab; chlorambucil; cisplatin; cladribine; cyclophosphamide; cytarabine; dacarbazine; dactinomycin; daunorubicin; dasatinib; docetaxel; doxorubicin; epirubicin; estramustine; etoposide; fludarabine; fluorouracil; gemcitabine; gemtuzumab; hydroxycarbamide; idarubicin; ifosfamide; imatinib mesylate; irinotecan; lomustine; melphalan; mercaptopurine; methotrexate; mitomycin; mitotane; mitoxantrone; oxaliplatin; paclitaxel; pentamidine; pentostatin; procarbazine; raltitrexed; rituximab; temozolomide; thiotepa; topotecan; trastuzumab; vidaradine; vinblastine; and/or vincristine. These substances may optionally be referred to as non-chemotheraphy approved cytotoxic/cytostatic drugs.

The substance may optionally be selected, e.g., from Mescaline, PCP (Phencyclidine), Psilocybin, LSD, Heroin, Morphine, Codeine, dextroamphetamine, bupropion, cathinone, lisdexamfetamine, Allobarbital, Alphenal (5-allyl-5-phenylbarbituric acid), Amobarbital, Aprobarbital, Brallobarbital, Butobarbital, Butalbital, Cyclobarbital, Methylphenobarbital, Mephobarbital, Methohexital, Pentobarbital, Phenobarbital, Secobarbital, Talbutal, Thiamylal, and/or Thiopental. Ranitidine, phenylalanine PKU, dimethylamylamine, cocaine, diazepam, androstadienedione, stigmastadienone, androsteronehemisuccinate, 5α-androstan-3β,17β-diol-16-one, androsterone glucuronide, epitestosterone, 6-dehydrocholestenone, phenylalanine, leucine, valine, tyrosine, methionine, sitamaquine, terfenadine, prazosin, methadone, amitripyline, nortriptyline, pethidine, DOPA, ephedrine, ibuprofen, propranolol, atenolol, acetaminophen, bezethonium, citalopram, dextrorphan, paclitaxel, proguanil, simvastatin, sunitinib, telmisartan, verapamil, amitriptyline, pazopanib, tamoxifen, imatinib, cyclophosphamide, irinotecan, docetaxel, topotecan, acyl-carnitines (C2-C18), nicotine, cotinine, trans-3-hydroxycotinine, anabasine, amphetamine, amphetamine-like stimulants, methamphetamine, MDA, MDMA, MDEA, morphine, $\Delta^9$-THC, tacrolimus, benzethonium, meprobamate, O-desmethyl-cis-tramadol, carisoprodol, tramadol, nor-diazepam, EDDP, norhydrocodone, hydromorphone, codeine, temazepam, noroxycodone, alprazolam, oxycodone, buprenorphine, norbuprenorphine, fentanyl, propoxyphene, 6-monoacetylmorphine, caffeine, carbadox, carbamazepine, digoxigenin, diltiazem, diphenhydramine, propanolol, sulfadiazine, sulfamethazine, sulfathiazole, thiabendazole, ketamine, norketamine, BZE, AMP, MAMP, and/or 6-MAM.

Optionally, one or more cell populations may be tested with a known non-chemotherapy approved cytotoxic/cytostatic drug. Optionally, one or more cell populations may be tested using a panel of potentially new therapeutic agents or cytotoxic/cytostatic drugs.

Optionally, one or more cell populations may be genetically modified and the modified cell populations may be tested with a known cytotoxic/cytostatic drug or against a panel of potentially new therapeutic agents or cytotoxic/cytostatic drugs.

Optionally, one or more cell populations may be tested with a known cancer chemotherapy approved cytotoxic/cytostatic drug. Optionally, one or more cell populations may be tested using a panel of potentially new therapeutic agents or cytotoxic/cytostatic drugs.

Optionally, one or more cell populations may be genetically modified and the modified cell population may be tested with a known cancer chemotherapy approved cytotoxic/cytostatic drug or against a panel of potentially new therapeutic agents or cytotoxic/cytostatic drugs.

The substance may, e.g., be an antimicrobial. The term "antimicrobial" includes any agents that act against any type of microbe. Thus, the antimicrobial may optionally be selected from antibacterial, an antiviral, an antifungal, and an antiprotozoal. More particularly, it may optionally be selected from aminoglycosides, beta-lactam antibiotics, chloramphenicol, fluoroquinolones, glycopeptides, lincosamides, macrolides, polymixins, rifampins, streptogramins, sulphonamides, tetracyclines, and/or diaminopyrimidines.

The Aminoglycoside may optionally be selected from gentamicin, tobramycin, amikacin, streptomycin, kanamycin. The beta-lactam antibiotic may optionally be selected from a penicillin such as methicillin, penicillin, amoxicillin, ampicillin, carbenicillin, oxacillin or nafcillin; a cephalosporin, such as, cephalothin, cefamandole, cefotaxime, ceftazidime, cefoperazone, or ceftriaxone; a carbapenem, such as, imipenem, meropenem, ertapenem, ordoripenem; or a monobactam, such as, aztreonam. The fluoroquinolone may optionally be selected from Enrofloxacin, ciprofloxacin, Danofloxacin, Difloxacin, Ibafloxacin, Marbofloxacin, Pradofloxacin and Orbifloxacin. The glycopeptide may optionally be selected from vancomycin, teicoplanin and avoparcin. The lincosamide may optionally be selected from Lincomycin, Clindamycin and Pirlimycin. The macrolide may optionally be selected from Erythromycin, Tylosin, Spiramycin, Tilmicosin and Tulathromycin. The polymixin may optionally be selected from Polymixin B and colistin (Polymixin E). The rifampin may optionally be selected from Rifampin, Rifabutin and Rifapentine. The Streptogramin may optionally be selected from Virginiamycin. The sulfonamide may optionally be selected from Sulfadiazine, sulfamethoxazole and sulfadoxine. The tetracycline may optionally be selected from Chlortetracycline, oxytetracycline, demethylchlortetracycline, rolitetracycline, limecycline, clomocycline, methacycline, doxycycline and minocycline. The Diaminopyrimidine may optionally be selected from Trimethoprim, Aditoprim, Baquiloprim and/or Ormetoprim.

The substance may, e.g., be an anti-viral drug.

The substance may, e.g., be an anti-inflammatory drug, optionally selected from, e.g., steroids, diclofenac, ibuprofen, naproxen, celecoxib, mefenamic acid, etoricoxib, indomethacin, and/or aspirin.

Target Based Drug Discovery Identification of valid molecular targets has led to target-based drug discovery at the protein level as illustrated by the development of Imatinib (INN). Imatinib is a tyrosine-kinase inhibitor which is used in the treatment of multiple cancers including Philadelphia chromosome-positive (Ph$^+$) chronic myelogenous leukemia (CML).

Gleevec is the beta crystalline form of imatinib mesilate, the mesylate salt of imatinib.

In order to survive, cells need signalling through proteins (signal cascade) to keep them alive. Some of the proteins in this cascade use a phosphate group as an "on" switch. This phosphate group is added by a tyrosine kinase enzyme. In healthy cells, these tyrosine kinase enzymes are turned on and off as needed. In Ph-positive CML cells, one tyrosine kinase enzyme, BCR-Abl, is stuck on the "on" position, and keeps adding phosphate groups. Imatinib blocks this BCR-Abl enzyme and stops it from adding phosphate groups. As a result, these cells stop growing and the cells die by a process of cell death (apoptosis). Because the BCR-Abl tyrosine kinase enzyme exists only in cancer cells and not in healthy cells, imatinib works as a form of targeted therapy—only cancer cells are killed through the drug's action. In this regard, imatinib was one of the first cancer therapies to show the potential for such targeted action and is often cited as a paradigm for research in cancer therapeutics.

Imatinib was discovered by screening compound libraries for inhibitors of the protein kinase activity in vitro. Many of the proteins involved in cell cycle regulation, signal transduction and the regulation of apoptosis are enzyme or receptors. As a result, they are potentially amenable to inhibition by small molecules.

Nutrients

Cell populations require nutrients for survival and/or growth. One or more suitable nutrients may therefore be used to culture a cell population. Optionally, a mixture of different nutrients may be used, e.g., a mixture comprising one or more of the nutrients listed below. As discussed elsewhere herein, the type and/or level of any nutrients may be altered, e.g., when analysing the effect of environmental conditions.

Any nutrient may optionally be a heavy-isotope nutrient.

Suitable nutrients are well known, but a nutrient may optionally comprise or consist of, e.g., a carbohydrate, optionally selected from monosaccharides, disaccharides, oligosaccharides, and/or polysaccharides. It may optionally be selected from sucrose, glucose, fructose, maltose, starch, lactose, galactose, lactulose, and/or trehalose.

A nutrient may optionally comprise or consist of, e.g., an amino acid, a peptide, a polypeptide, or protein, optionally selected from an essential amino acid, a non-essential amino acid, and/or a peptide, polypeptide or protein comprising one or more essential and/or non-essential amino acids. Essential amino acids may be selected from phenylalanine, valine, threonine, tryptophan, methionine, leucine, isoleucine, lysine, and/or histidine. Optionally, a nutrient may be glutamine.

A nutrient may optionally comprise or consist of a vitamin, e.g., vitamin A, B, C, D, or E.

A nutrient may optionally comprise or consist of a lipid, e.g., a fatty acid, lecithin, and/or a sterol.

Culture Media

The cell population may be maintained in a cell culture medium. The cell culture medium may optionally comprise a complex component, such as blood or a derivative thereof, e.g., serum, or be a serum-free defined medium. Unless it is desired to test an environmental factor relating to the cell culture medium, the cell culture medium may optionally be sterile, isotonic, have a physiological pH, and/or comprise all of the minerals and nutrients required by the cell population.

One or more of the following culture medium components may optionally be optimised or altered: (i) Nutrients, which may be optimised to include all essential nutrients at sufficient levels, or which may be altered, e.g., to insufficient levels of one or more nutrients; minerals which may be optimised to include all essential minerals at sufficient levels, or which may be altered, e.g., to insufficient levels of one or more minerals;

(ii) pH, which may optimised to be physiological, e.g., between 6.5 and 7.5, e.g., about 6.8, 7, 7.2 or 7.4, or which may be altered, e.g., to be above or below physiological, e.g., below 6.5 or about 7.5;

(iii) temperature, which may be optimised to be at a physiological temperature of about 37° C., or may be altered to be above physiological, e.g., at least 37.5, 38, 38.5, 39, 39.5, 40, 40.5, 41, 41.5, 42, 42.5, 43, 44, or 45, and/or up to 70, 60, 55, 50, 45, 40° C., or below physiological, e.g., about 36, 35, 34, 33, 32, 31 or 30° C.;

(iv) levels of gases, e.g., oxygen and/or $CO_2$, to which the cell population is exposed to, which may be optimised to be at a physiological levels, or may be altered to be above physiological or below physiological, e.g., hypoxic conditions, such as <2% oxygen. For example, oxygen levels may be set at about 20% or at about 2-8%, and/or $CO_2$ levels may be set at about 5%.

Optionally, the cell population may be cultured on or with feeder cells, e.g., on a layer of feeder cells, or the cell population may be cultured in the absence of any feeder cells.

Optionally, the cell population may be cultured in the presence of one or more hormones, cytokines, chemokines and the like.

Oxidative Stress

The method may optionally be used to analyse oxidative stress. For example, the cell population may be exposed to a substance and/or environmental condition that causes or induces oxidative stress. Optionally, a biomarker of oxidative stress may be analysed. The biomarker may, e.g., be selected from any of the substances mentioned below.

Oxidative stress, which can be defined as an imbalance between the production and removal of reactive oxygen species (ROS) has been implicated in many types of nerve cell death in the central nervous system (CNS) and also in the eye.

The presence of high concentrations of ROS can overwhelm the cell's natural defence mechanisms and activate pathways that lead to programmed cell death. Although the precise mechanisms that give rise to the increases in ROS may vary from condition to condition, the cell death pathways appear to have several features in common. Among these features is that death proceeds by a series of steps and that the inhibition of any one of these steps can often rescue the nerve cells from death. Certain agents can ameliorate the cell death process in circumstances that involve oxidative stress.

One model of the induction of oxidative stress in nerve cells utilises the amino acid glutamate. Glutamate is the major excitatory neurotransmitter in the CNS and in the eye, but it has also been implicated in nerve cell death after acute neurologic insults and in several different ocular diseases, including glaucoma, diabetic retinopathy, and various forms of retinal ischemia.

Although glutamate is present in synaptic nerve terminals in millimolar concentrations, the extracellular concentrations are normally high only during the brief periods of synaptic transmission. However, certain forms of injury can result in extended periods of elevated extracellular glutamate levels. High levels of extracellular glutamate have been shown to be toxic to nerve cells in culture through two distinct processes: excitotoxicity which occurs through the activation of ionotropic glutamate receptors, and a programmed cell death pathway called oxidative glutamate toxicity, or oxytosis which is mediated by a series of disturbances to the intracellular redox system.

Increases in the endogenous levels of ROS are key elements in the cell death cascade in both of these processes.

In glutamate excitotoxicity, the activation of ionotropic glutamate receptors leads to an excessive influx of $Ca^{+2}$, which activates a cell death cascade involving the accumulation of mitochondrially generated ROS.

In oxidative glutamate toxicity, glutamate inhibits the uptake of cystine, which is essential for glutathione (GSH) biosynthesis, resulting in the depletion of GSH from the cells. GSH is the most abundant intracellular thiol and the major intracellular antioxidant. The glutamate-induced loss of GSH from cells leads to a biphasic increase in mitochondrially derived ROS that can eventually reach levels many times higher than those in untreated cells. These high levels of ROS lead to $Ca^{+2}$ influx, which is mediated by a cobalt-sensitive, cGMP-gated $Ca^{+2}$ channel and subsequently to cell death.

The central role of ROS in the cell death cascade in oxidative glutamate toxicity is demonstrated by the protection provided by exogenous antioxidants such as vitamin E and propyl gallate. The importance of mitochondrial ROS production is further demonstrated by the observation that the mitochondrial uncoupler cyanide p-trifluoromethoxyphenylhydrazone (FCCP), as well as other mitochondrial inhibitors, blocks cell death in this model, by inhibiting ROS production.

Substance Production and/or Utilisation by Cell Populations

Cell populations may be used for the production of substances, such as, biopharmaceuticals, e.g., antibodies, hormones and/or cytokines. Cell populations may utilise a first substance as a substrate to produce a second substance. Cell populations may be used to break down substances, optionally into useful and/or less harmful substances. They may, e.g., be used to break down industrial waste products, pollutants, herbicides, pesticides, explosives, and the like. The method may therefore optionally be used to analyse the ability of a cell population to utilise and/or produce a substance; and/or to analyse the utilisation and/or production of a substance by a cell population.

Optionally, the method may involve the purification of a substance, so it may include a step of purifying a substance. A step of purifying the substance may, e.g., comprise one or more of lysis of cells; centrifugation, e.g., to achieve isopycnic banding and/or non-equilibrium settling; filtration; membrane separation, which may, e.g., be microfiltration, ultrafiltration, and/or dialysis; extraction, which may, e.g., be fluid extraction, and/or liquid/liquid extraction; precipitation, which may, e.g., be fractional precipitation; chromatography, which may, e.g., be ion-exchange chromatography, gel filtration chromatography, affinity chromatography, hydrophobic interaction chromatography, high performance liquid chromatography ("HPLC"), and/or adsorption chromatography. Optionally, it may involve precipitation of a free acid form of said substance, and, optionally, conversion of a free acid form of said substance to a salt of said compound.

Identification of Utilisation/Production Cell Populations

Optionally, the method may be used as a screening method, e.g., to identify a suitable utilisation/production cell population, and/or to distinguish between cell populations with different utilisation/production properties.

Cells may optionally be manipulated, e.g., genetically manipulated, to generate a cell population having one or more desired properties. Optionally, the method may involve an analysis to identity/select a cell population which has successfully been manipulated, e.g., to identify a cell population having the desired genotype and/or phenotype.

Conventional methods for deriving a suitable utilisation/production cell population, e.g., a high-producing cell line from parental line, may be quite time-consuming and laborious and may, e.g., take more than six months in industrial settings. The first step may be genetic manipulation, which is exemplified in the discussion below by the insertion of a transgene. Once the transgene enters the nucleus, the integration site of the gene may be random, and expression of the transgene may, in part, be dictated by the surrounding chromosomal structure. High expression of the transgene may be very desirable. Optionally, the method provided herein may be used to speed up the process of identifying/selecting a suitable production cell population.

A large number, e.g., a pool of at least or about 50,000, 40,000, 30,000, 20,000, 10,000, 5,000, 1,000 or 500 cell populations may be screened to select a small number, e.g., about or no more than 1, 2, 3, 4, 5, 6, 7, 8, 9, 10, 20, 30, 40, 50, 80, 100 or 200 candidate cell populations.

Optionally, one or more strategies may be used to improve the generation and/or selection of cells that have a transgene integrated at a transcriptionally active site. For example, the transgene construct may optionally include: a mutant DHFR gene with reduced enzymatic activity or a DHFR gene driven by a weak promoter; chromatin opening elements like scaffold or matrix attachment regions (S/MARs) and/or ubiquitous chromatin opening elements (UCOS) to promote accessibility of DNA for transcription at the integration site; and/or one or more antibiotic resistance gene(s).

If the DHFR system is used, then, following mutagenesis, cells stably expressing the transgene construct and hence the DHFR enzyme may optionally be selected using cultivation in the absence of glycine, hypoxanthine and thymidine. Optionally, the cells may be exposed to MTX to increase the selective pressure, which may result in genomic rearrangements and amplification of the transgene construct.

If an antibiotic resistance gene is used, then, following mutagenesis, cells stably expressing the transgene construct and hence the antibiotic resistance factor, may optionally be selected using the relevant antibiotic.

A selection strategy, e.g., one of the ones mentioned herein, may yield a heterogeneous population of cells having different transgene construct integration sites, copy numbers and the like.

Optionally, a series of limiting dilutions, e.g., in multi-well plates, may be carried out to isolate uniform cell populations, which may optionally be screened to select candidate cell lines.

Optionally, candidate cell populations may be evaluated in more detail and/or on a larger scale to select one or more final candidates.

Optionally, the method provided herein may be used to analyse cells at any stage of such a process of deriving a suitable utilisation/production cell population. Optionally, expression of the transgene and/or one or more factors that influence the growth, efficiency and/or productivity of a cell may be analysed. This allows the rapid selection of a small number of candidates. For example, the pool of cells may be reduced by a factor of about or at least 10, 20, 30, 40, 50, 60, 70, 80, 90, 100, 200, 500 or 1000.

Thus, optionally, the method may involve analysing a plurality of cell cultures, each cell culture comprising one or more cell populations. This may optionally involve generating a plurality of spectrometric data and determining from said plurality of spectrometric data a first subset of cell cultures which are of potential interest for utilising a substance and/or producing a biosynthesized substance.

The method may optionally further involve the use of liquid chromatography based analysis, e.g., liquid chromatography mass spectrometry ("LCMS") analysis; liquid chromatography ion mobility spectrometry ("LCIMS") analysis; liquid chromatography tandem mass spectrometry ("LCMS/MS") analysis; liquid chromatography followed by $MS^E$ spectrometry ("$LCMS^E$") analysis; liquid chromotography followed by ion mobility separation and then mass spectrometry ("LC-IMS-MS") analysis; and/or liquid chromotography followed by ion mobility separation and then $MS^E$ spectrometry ("$LC\text{-}IMS\text{-}MS^E$") analysis. Such a liquid chromatography based analysis may optionally be used to analyse said first subset of cell cultures, e.g., to generate a second subset of cell cultures. Optionally, the method may comprise classifying or dividing cell populations into subsets based on spectrometric data, liquid chromatography based analysis data, or a combination of spectrometric data and liquid chromatography based analysis data.

However, the ambient ionisation mass spectrometry methods mentioned herein are must faster than liquid chromatography based analysis, so, optionally, the method optionally does not involve the use of a liquid chromatography based analysis, e.g., any of the ones listed above.

Thus, optionally, the method may be used in the process of drug manufacture and production.

Conventionally, a very large number (e.g., approximately 50,000) of potential batches of a cell culture may be produced. Liquid chromatography mass spectrometry (LCMS) may then be performed on each of the cell cultures in order to determine a small subset of cell cultures which are of greatest interest in terms of taking on into full production.

However, it will be appreciated that subjecting approximately 50,000 separate batches of cell populations to LCMS analysis is a complex and time consuming process.

One particular advantage of the method provided herein is that the method provided herein enables experimental results to be produced on essentially an instantaneous basis. Furthermore, the method provided herein lends itself to automation and a large number of cell cultures can be analysed either in sequence and/or in parallel in a comparatively short period of time. Certainly, it is possible to analyse approximately 50,000 separate batches of cell cultures on a timescale which is several orders of magnitude faster than conventional LCMS approaches.

Accordingly, one particular application of REIMS and related ionisation techniques is the ability to analyse a large number of cell cultures in a short period of time.

This analysis enables the large number of cell cultures, e.g., 50,000, to be reduced to a very small candidate list of, for example, just ten cell cultures which can then be taken on to full production/utilisation.

Alternatively, other embodiments are contemplated wherein REIMS analysis may be performed on the approximately 50,000 batches enabling a first subset of cell cultures to be established. The first subset of cell cultures may comprise, for example, approximately 1000 batches. LCMS can then be performed on this reduced number of 1000 samples in order to determine a second subset of cell cultures (e.g., 10) which are the most promising to be taken on to full production. Although this alternative approach still involves using LCMS, the two-stage process still results in considerable time savings since only e.g., 1000 batches need to be analysed by LCMS (c.f. approximately 50,000 as per the conventional approach).

Substance Utilisation/Production and Quality Control

A general process of utilising and/or producing substance, such as a (bio)therapeutic product, via cell culture may include one or more of the following steps:
1. Set up cell culture apparatus with suitable cell culture conditions;
2. Inoculate with cell population, e.g., starter culture grown on smaller scale;
3. Allow cells to grow
4. If utilisation/production of substance is not automatic (e.g., if dependent on a particular temperature or nutrient), adjust conditions to induce utilisation/production;
5. Monitor culture conditions and adjust as required;
6. Monitor substance utilisation/production;
7. Harvest substance or breakdown product
   from culture medium, if substance or breakdown product is secreted
   from cells, if substance or breakdown product accumulates within cells
8. Purify substance or breakdown product, e.g., by removing any contaminants.

During a process of utilising and/or producing a substance via cell culture, analysis may be carried out, e.g., via the method described herein described herein, e.g., for monitoring the culture conditions and/or substance utilisation/production. This may optionally involve obtaining a sample from the cell population for analysis. The skilled person will be aware of suitable sample acquisition methods, such as pipetting, using a swab or the like. The sample may optionally be processed, e.g., a liquid sample may be filtered or processed to generate a pellet as mentioned elsewhere herein. Optionally, a swab may be used, which may optionally be analysed without further processing using the method with a REIMS ion source.

Optionally, any adjustments to the culture conditions may be made, e.g., if the analysis reveals the necessity for an adjustment. The culture pH may be measured, e.g., with a pH meter, and optionally adjusted, e.g., by adding an acid or a base as required. Nutrient use may be monitored by analysing, e.g., respiration. The Respiratory Quotient, i.e. the ratio of the Carbon Dioxide Evolution Rate to the Oxygen Uptake Rate, may be analysed. Metabolic products, e.g., the substance of interest, a breakdown product and/or contaminants, may be analysed.

Thus, optionally, the method may involve analysing, e.g., monitoring, a process of utilising and/or producing a substance via culture of a cell population. Optionally, the invention provides a method of utilising and/or producing a substance via culture of a cell population, wherein said method includes a step of analysing the utilisation and/or production process via a method of analysis of the invention. Optionally, said method further comprises a step of adjusting the culture conditions on the basis of the analysis.

Thus, the method may optionally comprise analysing the utilisation and/or production of a substance by a cell population. There is provided a method of producing a substance, comprising (a) using a first device to generate smoke, aerosol or vapour from a target in vitro or ex vivo cell population and/or medium derived therefrom; (b) mass and/or ion mobility analysing said smoke, aerosol or vapour, or ions derived therefrom, in order to obtain spectrometric data; and (c) analysing said spectrometric data in order to analyse the production of a substance by said target cell population. Also provided is a method of identifying a cell population capable of utilising and/or producing a substance, comprising (a) using a first device to generate an smoke, aerosol or vapour from a target in vitro or ex vivo cell population and/or medium derived therefrom; (b) mass and/or ion mobility analysing said smoke, aerosol or vapour, or ions derived therefrom, in order to obtain spectrometric data; and (c) analysing said spectrometric data in order to identify a cell population capable of utilising and/or producing a substance.

Any of these methods may optionally comprise analysing said spectrometric data in order to (i) determine whether said cell population utilises and/or produces said substance; (ii) determine the rate at which said cell population utilises and/or produces said substance; (iii) determine whether said cell population produces any by-products; and/or (v) determine the mechanism by which said cell population utilises and/or produces said substance. Optionally, two or more cell populations may be analysed in order to determine which cell population utilises and/or produces said substance at a higher rate and/or at a higher purity. Optionally, a plurality of cell populations may be analysed and divided into 2 or more subsets based on said analysis. For example, cell populations may be divided based on said analysis into subsets based on (i) their ability or inability to utilise and/or produce said substance; (ii) the rate of utilisation and/or production of said substance; (iii) the production of any by-products; and/or (iv) the mechanism of utilisation and/or production. Optionally, based on the analysis cell populations may be divided into (i) a first subset capable of utilising and/or producing said substance and a second subset incapable of utilising and/or producing said substance; (ii) a first subset and a second subset, wherein said first subset utilises and/or produces the substance at a higher rate compared to the second subset; (iii) a first subset and a second subset, wherein said first subset produces no by-products, or fewer by-products compared to the second subset; and/or (iv) a first subset and a second subset, wherein said first subset utilises and/or produces the substance via a different mechanism compared to the second subset.

Optionally, the method may further comprise a step of subjection the cell population or cell population subset to liquid chromatography mass spectrometry ("LCMS") analysis prior to and/or after the method of analysis. Optionally, based on said LCMS analysis, cell population may be divided into subsets, or a said cell population subset as mentioned above may be divided into further subsets.

Optionally, the cell population or cell population subset may be cultured under conditions suitable to utilise and/or produce said substance.

Optionally, the method does not comprise a step of subjection a cell population, or cell population subset, to liquid chromatography mass spectrometry ("LCMS") analysis.

Optionally, the method may be used to monitor the utilisation and/or production of a substance, particularly to monitor the production of by-products. This may involve analysing a sample from a cell population at various time points, as discussed elsewhere herein.

Click Chemistry

"Click Chemistry" is a term that was introduced by K. B. Sharpless in 2001 to describe reactions that are high yielding, wide in scope, create only by-products that can be removed without chromatography, are stereospecific, simple to perform, and can be conducted in easily removable or benign solvents.

A typical click chemistry (click reaction) is the copper-catalyzed 1,3-dipolar cycloadditions between azides and acetylenes.

A click reaction may, e.g., happen between a fluorescent probe comprising an alkyne and a biomolecule comprising an azide.

Thus, click chemistry may be used for attaching a probe or substrate of interest to a specific biomolecule, a process called bioconjugation. The possibility of attaching fluorophores and other reporter molecules has made click chemistry a very powerful tool for identifying, locating and characterizing both old and new biomolecules.

One of the earliest and most important methods in bioconjugation was to express a reporter on the same open reading frame as a biomolecule of interest. Notably, green fluorescent protein ("GFP") is expressed in this way at the N- or C-terminus of many proteins. However, this approach comes with several difficulties. For instance, GFP is a very large unit and can often affect the folding of the protein of interest. Moreover, by being expressed at either terminus, the GFP adduct can also affect the targeting and expression of the desired protein. Finally, using this method, GFP can only be attached to proteins, and not post-translationally, leaving other important biomolecular classes (nucleic acids, lipids, carbohydrates, etc.) out of reach.

To overcome these challenges, chemists have opted to proceed by identifying pairs of biorthogonal reaction partners, thus allowing the use of small exogenous molecules as biomolecular probes. A fluorophore can be attached to one of these probes to give a fluorescence signal upon binding of the reporter molecule to the target—just as GFP fluoresces when it is expressed with the target.

Optionally, the method provided herein may involve monitoring a click chemistry reaction, e.g., to detect the end-products and/or any by-products of a click chemistry reaction. Optionally, the method may be used in combination with click chemistry, e.g., before or after a click chemistry reaction. Optionally, the method may be used instead of click chemistry. For example, the method may allow the analysis of biomarkers that would conventionally be analysed by using click chemistry, thus obviating the need for a click chemistry reaction.

Further Definitions

The method may be carried out on "target", which may be a cell population or a sample thereof and/or medium derived from a cell population. The term "target entity" is used herein to refer to the entity which it is desired to analyse within the target. Thus, any reference to a "target" should be understood to mean a target comprising one or more different target entities. Thus, the target entity may, e.g., be a particular cell type, microbe and/or compound. Optionally, the target comprises only one type of target entities.

Any reference herein to "analysis", "analysing" and derivatives of these terms should be understood to be an analysis based on the spectrometric data generated via the method provided herein.

The terms "analysis", "analysing" and derivatives of these terms are used herein to encompass any of the following: detection of a target entity or biomarker therefor; identification of a target or target entity or biomarker therefor; characterisation of a target or target entity or biomarker therefor; determination of a status, e.g., a disease status, or biomarker therefor, and the like.

The analysis may be qualitative and/or quantitative. Thus, optionally, any type of analysis may involve determining the concentration, percentage, relative abundance or the like of the target entity. For example, the percentage of cells of one type within a cell population, and/or the concentration of a compound may be analysed. Optionally, an increase or decrease in a target entity or biomarker therefor may be analysed.

The terms "detection", "detecting" and derivatives of these terms are used interchangeably herein to mean that the presence or absence of a target entity or biomarker therefor is determined.

The terms "identify", "identification" and derivatives of these terms are used interchangeably herein to mean that information about the identity of a target, target entity or biomarker therefor is obtained. This may optionally be the determination of the identity, and/or the confirmation of the identity. This may optionally include information about the precise identity of the target, target entity or biomarker therefor. However, it may alternatively include information that allows the target entity to be identified as falling into a particular classification, as discussed elsewhere herein.

By "identifying" a microbe is meant that at least some information about the identity is obtained, which may, for example, be at any taxonomic level.

By "identifying" a cell is meant that at least some information about the cell type is obtained. By "identifying" a diseased cell is meant that it is determined or confirmed that a cell is diseased.

By "identifying" a compound is meant that at least some information about the structure and/or function of the compound is obtained, e.g., the information may optionally allow a compound to be identified as comprising or consisting of a compound selected from any of the types disclosed herein, and/or as being characterised by one or more of the functional groups disclosed herein.

The term "monitoring" and derivations of this term as used herein refer to the determination whether any changes take place/have taken place. Typically, it is determined whether any changes have taken place over time, i.e. since a previous time point. The change may, for example, be the response to a substance, the production of a substance, and/or the development and/or progression of a disease, such as, any of the diseases mentioned herein. Optionally, the method may involve analysing a target and, on the basis of one or more of the following monitoring a disease: detecting a target entity; identifying a target entity; detecting an increase in a target entity; detecting a decrease in a target entity.

The term "prognosis" and derivations of this term as used herein refer to risk prediction of the severity of disease or of the probable course and clinical outcome associated with a disease. Thus, the term "method of prognosis" as used herein refers to methods by which the skilled person can estimate and/or determine a probability that a given outcome will occur. The outcome to which the prognosis relates may be morbidity and/or mortality. In particular, the prognosis may relate to "progression-free survival" (PFS), which is the length of time that a subject lives with the disease without the disease progressing. Thus, PFS may, for example, be the time from the start of therapy to the date of disease progression, or the time from the end of therapy to the date of disease progression.

Optionally, the method may involve analysing a target and, on the basis of one or more of the following making a prognosis: detecting a target entity; identifying a target entity; detecting an increase in a target entity; detecting a decrease in a target entity.

By "progressing" or "progression" and derivations of these terms is meant that the disease gets worse, i.e. that the severity increases. For example, in the case of cancer, it may mean that the cancer becomes malignant or more malignant.

The prognosis may relate to overall survival. By "overall survival" (OS) is meant the length of time that a subject lives with the disease before death occurs. Overall survival may, for example, be defined as the time from diagnosis of the disease; the time of treatment start; or the time of treatment completion, until death. Overall survival is typically expressed as an "overall survival rate", which is the percentage of people in a study or treatment group who are still alive for a certain period of time after they were diagnosed with, or started treatment for, or completed treatment for, a disease. The overall survival rate may, for example, be stated as a five-year survival rate, which is the percentage of people in a study or treatment group who are alive five years after their diagnosis or the start or completion of treatment.

Statistical information regarding the average (e.g., median, mean or mode) OS and PFS of subjects having a particular type of disease is available to those skilled in the art. A determination whether a subject has, or is likely to have, an increased or decreased OS or PFS compared to such an average may therefore be made.

A response to treatment may, e.g., be a decrease in the cell growth rate, a cessation of growth, and/or cell death. Alternatively or in addition, a response to treatment may involve the appearance or disappearance of one or more biomarkers, and/or an increase or decrease in the expression of one or more biomarkers.

The term "treatment" or "treating" as used herein refers to a course of action which is aimed at bringing about a medical benefit for a subject. The treatment may be prophylactic or therapeutic.

Optionally, the method may involve analysing a target and, on the basis of one or more of the following, determining that a subject should or should not receive a particular treatment: detecting a target entity; identifying a target entity; detecting an increase in a target entity; detecting a decrease in a target entity.

Optionally, the method may involve analysing a target and, on the basis of one or more of the following, determining that a subject has or has not, or is likely to or not likely to, respond/responded a particular treatment: detecting a target entity; identifying a target entity; detecting an increase in a target entity; detecting a decrease in a target entity.

Optionally, the method may involve analysing a target and, on the basis of one or more of the following, administering a particular treatment to a subject: detecting a target entity; identifying a target entity; detecting an increase in a target entity; detecting a decrease in a target entity.

Organoids

As mentioned above, the cell population may optionally be an organoid.

Mammalian tissues, particularly organs, are challenging to study as they are typically only poorly accessible to experimental manipulation and/or analysis. However, mammalian tissues may be generated ex vivo or in vitro via three-dimensional (3D) culture techniques. This allows the real-time study of such tissues, optionally including the independent manipulation of various factors, e.g., genetic, and/or microenvironmental factors.

Tissue generated ex vivo or in vitro via a 3D culture technique are referred to herein as "organotypic tissue" or "organoid", terms which are used interchangeably herein. Thus, these terms are used herein to encompass models of organs and/or models of tumours.

Organotypic tissue may be generated from organ "explants", i.e. cells, or pieces of tissue, that were isolated from primary mammalian organs, or tumour explants, i.e. cells or pieces of tissue isolated from a tumour. Explants may, e.g., be obtained from resected tissue and/or biopsies. Organotypic tissue may alternatively be generated by expanding ES cells, iPS cells or primary stem cells that have been purified from organs.

An organotypic tissue is a tissue which is formed in vitro and comprises a collection of cells that form three-dimensional structures and resemble their in vivo counterparts. Unlike classical two-dimensional cell cultures, organoid systems permit 3D cell growth, cell movement, cell differentiation and more physiologically representative cell-cell interactions. In contrast to traditional 2D cell cultures, organoids share similar physical, molecular and physiological properties with the in vivo tissue of the same type. Organoids therefore represent effective models for understanding organ development, tissue morphogenesis, and/or the genetic or molecular basis of diseases. They have use in drug-screening, drug testing, and/or tissue replacement therapies.

Thus, the method may optionally comprise analysing an organoid. One or more regions of an organoid may be analysed. Thus, the target may be an organoid or a part thereof. Unless otherwise stated, any reference herein to analysing an organoid should be understood to encompass optionally analysing part of an organoid.

As mentioned elsewhere herein, the methods of the present invention provide spectrometric data on the cell types from which the aerosols are generated. Thus, the present methods permit biomarker analysis, e.g., lipidomic fingerprinting, of cell types and/or, in the present context, organoid types.

It is within the competencies of one of ordinary skill in the art to provide an organoid for their particular purposes. Methods for the production of organoids are well-known in the art. Optionally, the method may comprise a step of producing an organoid.

By an "organoid" is meant an organised tissue formed in vitro or ex vivo, said tissue having a cellular organisation and gross morphology similar to that of the same tissue type in vivo, for at least a subset of the cells of the tissue. Such cellular organisation and gross morphology is termed "in vivo-like gross and cellular morphology" herein.

An "organoid", as used herein, may optionally include a scaffold which is a pre-formed solid support that imparts or provides short-term (hours to two weeks in culture) structure or support to the tissue or is required to form the tissue.

By "at least a subset of cells" is meant at least two cells, e.g., at least 10%, 15%, 20%, 25%, 30%, 35%, 40%, or 50% of the cells of the tissue. Optionally, substantially all of the cells within the organoid have a cellular organisation and gross morphology similar to that of the same tissue type in vivo. By "substantially all of the cells" is meant at least 90, 91, 92, 93, 94, 95, 96, 97, 98, or 99% of the cells.

By "in vivo-like gross and cellular morphology" is meant a three-dimensional shape and cellular organisation substantially similar to that of the tissue in vivo.

By "three-dimensional" is meant an organised tissue having x, y and z axes wherein x and y of the axes are at least 2 mm with z at least 0.05 mm thick, and wherein 1, 2 or all of the axes are as great as 20 cm. Optionally, a three-dimensional tissue may be transferred between in vivo and in vitro environments one or more times, e.g., exactly or at least 2, 3, 4, 5, 6, 7, 8, 9 or 10 times without undergoing any substantial structural and/or shape changes.

The organoid may be any type of organoid, e.g., an organoid of any of the cell and/or tissue types mentioned elsewhere herein. Optionally, the organoid may be selected from, e.g., cerebral organoids, thyroid organoids, intestinal organoids (e.g., small intestinal, colonic, rectum, duodenum or ileum organoids), testicular organoids, hepatic organoids, pancreatic organoids, gastric organoids, epithelial organoids, lung organoids, kidney organoids, muscle organoids, prostate organoids, breast organoids, blood vessel organoids, lymphatic vessel organoids and/or retinal organoids.

Optionally, the organoid may be prepared from terminally differentiated cells of the desired organ, e.g., an "intestinal organoid" may be derived from terminally differentiated intestinal cells. However, more typically, organoids may be produced from stem cells. Optionally, the organoid may be prepared from an explant or cells from a patient.

The term "similar to that of the same tissue type in vivo" means that the organoid has genetic and phenotypic characteristics that allow it to be recognised by the skilled person as being from or associated with a particular tissue type (such as the tissues listed above). It does not mean that the organoid necessarily has to be genetically and phenotypically identical to the corresponding in vivo tissue type.

An organoid that has the in vivo genotype and phenotype of the intestine is, for the purposes of this invention, comprised within the definition of an "intestinal organoid". The same applies mutatis mutandis for the other organoid types listed above.

Optionally, the organoid may be a mammalian organoid, i.e. it may be derived from cells or an explant taken from a mammal. The mammal may be any mammal of interest, e.g., selected from the mammals listed elsewhere herein. Optionally, the organoid may be a non-human organoid. Optionally, the organoid may be a human organoid.

Optionally, the organoid may be diseased, e.g., cancerous. Optionally, it may have been generated from a diseased explant or cells. Optionally, it may have been generated from a healthy explant or cells. Optionally, a disease state may be induced in the organoid, e.g., via genetic manipulation and/or via the use of a disease-causing agent.

Optionally, the genotype and/or phenotype of the explant and/or cells may be altered prior to the generation of an organoid. Optionally, the genotype and/or phenotype of the organoid may be altered during or after the generation of the organoid. Optionally, the genotype and/or phenotype of a mature organoid may be altered.

The manipulation of the genotype and/or phenotype may optionally be achieved via any of the genotype and/or phenotype manipulation methods mentioned elsewhere herein.

The term "mature organoid" as used herein means an organoid in which substantially all of the cells within the organoid are differentiated, optionally terminally differentiated. By "differentiated" is meant cells with numerous mature-like characteristics, either chemical or physical. By "terminally differentiated" is meant is not capable of further proliferation or differentiation into another cell or tissue type.

An organoid may comprise a single cell type. More typically, an organoid may comprise a mixture of different cell types.

Organoids are typically sufficiently small that they can be sustained without a blood supply. Therefore, optionally the organoid herein lacks vasculature. Recent developments in organoid production technology have resulted in organoids comprising vasculature. Thus, optionally the organoid herein comprises vasculature.

The organoid may, e.g., be a free-floating multicellular sphere, optionally in which highly polarized cells localize around a central lumen.

In the methods of the present invention, the organoid which is analysed may exist in vitro or ex vivo, or it may be in vivo in that it may have previously been transplanted into a subject. Optionally, the method may include a step of transplanting an organoid into a subject. The transplant may optionally be orthotopical, i.e. into the organ of origin, e.g., an organoid generated from a diseased explant or diseased cells may be transplanted orthotopically and the interaction between the organoid and the organ of origin may be analysed.

The organoid which is analysed may be a specimen of an organoid that has previously been implanted into a subject, said specimen having subsequently been removed from the subject. The subject may be any subject of interest, e.g., selected from any of the subjects listed elsewhere herein.

The provision of spectrometric data from a particular organoid (herein a "target organoid") may be useful in itself. Such data may be analysed, e.g., by using reference spectrometric data, as discussed elsewhere herein. Alternatively or in addition, information can be obtained from a comparison of the spectrometric data obtained from the target organoid with the spectrometric data obtained from one or more other organoids (herein "comparator organoids").

The skilled person is well aware of the structure of an organoid of a given organ and knows how to produce said organoid. Optionally, the method may include one or more steps of producing an organoid, which may, e.g., be selected from the following steps:

1. Obtain suitable cells, e.g., from a cell bank, a patient, or generate de novo:
2. Set up culture apparatus to required conditions;
3. Seed cells within culture apparatus and allow to grow;
4. Monitor culture conditions and adjust as required; and
5. Analyse organoid or a part thereof.

Any of the steps may optionally be performed as many times as necessary or desired, e.g., at least 1, 2, 3, 4, 5, 6, 7, 8, 9, or 10 times. Steps 3 can be performed as many times as necessary, wherein the same and/or different cell types may be added to the culture apparatus each time the step is performed. Step 3 may be performed before or after step 4, or simultaneously with step 4. If step 3 is performed multiple times, each performance may separately be performed before or after step 4, or simultaneously with step 4.

Step 5 may be carried out repeatedly at suitable intervals to monitor the organoid. If the analysis in step 5 reveals it to be necessary, step 3 and/or step 4 may optionally be repeated once or more as described above.

In step 1, the cells are optionally stem cells, i.e. cells that are not terminally differentiated. The cells may be totipotent stem cells, pluripotent stem cells, multipotent stem cells or oligopotent stem cells. Alternatively, they may be unipotent cells. The term "stem cell" as used herein encompasses totipotent, pluripotent, multipotent and oligopotent stem cells. Optionally, the stem cells are embryonic stem cells, fetal stem cells, adult stem cells, amniotic stem cells or induced pluripotent stem cells (iPSCs).

Totipotent stem cells are those can differentiate into embryonic and extraembryonic cell types. Pluripotent stem cells, such as embryonic stem cells and iPSCs are those that can differentiate into any cell derived from any of the three germ layers. A multipotent cell is a cell which has the potential to give rise to cells from multiple, but a limited number of lineages. An example of a multipotent cell is a hematopoietic cell, a blood stem cell that can differentiate into several types of blood cells, but cannot develop into brain cells or other types of cells. Mesenchymal stem cells, or MSCs, are multipotent stem cells that can differentiate into a variety of cell types including osteoblasts (bone cells), chondrocytes (cartilage cells) and adipocytes (fat cells). Oligopotent stem cells can differentiate into only a few cell types; examples include lymphoid and myeloid stem cells. Unipotent cells can produce only one cell type, their own, but have the property of self-renewal, which distinguishes them from other non-stem cells such as progenitor cells. An induced pluripotent stem cell (abbreviated as iPSC or iPS cell) is a type of pluripotent stem cell artificially derived from a non-pluripotent cell, typically an adult somatic cell, by inducing a "forced" expression of certain genes.

Alternatively, the cells may be non-stem cells, e.g., progenitor cells or terminally differentiated cells with no differentiation potential.

Optionally, in step 1, tissue or cell explants may be used, which may optionally be diseased, e.g., cancerous.

In some embodiments, the cells obtained in step 1 are a population of cells with different differentiation potentials.

The skilled person will be aware of the particular cell type to obtain for their particular desired purposes.

Various methods and apparatuses for culturing organoids are known in the art (see for instance Shamir and Ewald, Nature Reviews Molecular Cell Biology 15, 647-664 (2014))

Step 2 optionally comprises mixing disaggregated or partially disaggregated cells with a solution of extracellular matrix components to create a suspension. By "extracellular matrix components" is meant compounds, whether natural or synthetic compounds, which function as substrates for cell attachment and growth.

The composition of the solution of extracellular matrix components may vary according to the tissue to be produced. Representative extracellular matrix components include, but are not limited to, collagen, laminin, fibronectin, vitronectin, elastin, glycosaminoglycans, and/or proteoglycans, and/or combinations of some or all of these components. An optional solution is Matrigel, which is a gelatinous protein mixture secreted by Engelbreth-Holm-Swarm (EHS) mouse sarcoma cells produced and marketed by Corning Life Sciences. Matrigel resembles the complex extracellular environment found in many tissues and is used by cell biologists as a substrate for culturing cells.

The culture medium may be undefined or defined and optionally be serum-free. Suitable culture conditions, media and nutrients are discussed elsewhere herein.

Step 3 optionally comprises placing the tissue explant or cells, e.g., the above-mentioned suspension, in a vessel having a three dimensional geometry which approximates the in vivo gross morphology of the tissue. The cells and any extracellular matrix components are optionally then allowed to coalesce or gel within the vessel. Optionally, the vessel is placed within a culture chamber and surrounded with media under conditions in which the cells are allowed to form an organized tissue.

The vessel may optionally comprise tissue attachment surfaces. By "tissue attachment surfaces" is meant surfaces having a texture, charge or coating to which cells may adhere in vitro. Examples of attachment surfaces include, without limitation, stainless steel wire, VELCRO, suturing material, native tendon, covalently modified plastics and silicon rubber tubing having a textured surface.

In general, the vessel containing the organoid may be placed in a standard culture chamber (e.g., wells, dishes, or the like), and the chamber may then be filled with culture medium until the vessel is submerged. The precise composition of the culture medium will however vary according to the tissue to be produced, the necessity of controlling the proliferation or differentiation of some or all of the cells in the tissue, the length of the culture period and the requirement for particular constituents to mediate the production of a particular bioactive compound. The culture vessel may be constructed from a variety of materials in a variety of shapes as described.

Step 4 above may require the replenishment, addition or removal of one or more culture media components.

Culture media may comprise any combination of components that permits maintenance of the organoid tissue. An exemplary medium for long term viability of an organoid consists of DMEM with high glucose, 10% horse serum, 5% fetal calf serum, and 100 units/ml penicillin.

Optionally, at any stage of the organoid production process, there is a step of engrafting mature organoids into a host animal, which may e.g., be selected from any of the animals mentioned elsewhere herein, to allow them to further develop.

Step 5 above is a step of analysing an organoid. The results of the analysis may indicate that step 3 and/or step 4 should be repeated one or more times, optionally with modification.

The methods of the present invention may comprise obtaining spectrometric data from one or more locations of a target organoid and analysing said spectrometric data.

If the target is an organoid, then the method may optionally be used to determine one or more properties of said organoid. Analysis using the method provided herein in step 5 above provides particular advantages in the organoid production process; namely the rapid obtaining of the results of an analysis of one or more of the organoids' properties.

Optionally, the property of the organoid that is analysed is a property of the organoid as a whole. Alternatively, the property of the organoid that is analysed is a property of a region within said organoid. Thus, the methods of the invention can be performed on a chosen or randomly selected region of an organoid.

Optionally, the property analysed is the cell type of which the organoid or region thereof is comprised. When producing organoids, it is important to ensure that the desired cell type(s) is/are located within the desired regions of the organoid. This is particularly the case in the production of organoids from stem cells and the production of organoids that comprise multiple cell types. The production of organoids from stem cells requires controlled differentiation of stem cells into specific desired cell type(s), potentially in only certain regions of the organoid. Differentiation of stem cells into an off-target cell type would lead to the production of an organoid that less accurately represented the corresponding in vivo organ tissue. Different cell types will be distinguishable by characteristic spectrometric data. Thus, the method may be used to identify one or more cell types present in an organoid or a region thereof; details of cell identification are provided elsewhere herein. If the analysis reveals that an undesired cell type is present, then the production process can be re-started, or the undesired cells excised from the organoid or contacted with one or more agents that induce apoptosis.

As mentioned above, organoids may optionally be produced from stem cells. In such embodiments, optionally the property that is analysed is the differentiation potential of the cells in the organoid or a region thereof. The differentiation potential of cells in the organoid should reduce over time during the organoid production process, so their differentiation status should change. Therefore, of particular interest to the skilled person producing a particular organoid is the timing of cell differentiation. The differentiation potential or status is a phenotypic and/or genotypic property of a cell, which may be analysed by the method provided herein as discussed elsewhere herein. The skilled person may need to add to or remove from the culture media factors that influence cell differentiation at specific time points.

This aspect of the organoid production process can be analysed using the method provided herein. Cells with differing differentiation potentials, e.g., pluripotent, multipotent, oligopotent, progenitor and/or fully differentiated cells, will be distinguishable by characteristic spectrometric data. If the analysis reveals that cells within the organoid have an undesirable differentiation potential, then ameliorative steps can be taken. Such steps are optionally the excision of the undesirable cells and/or application of one or more agents to induce or deplete differentiation potential as required.

Thus, the methods of the present invention permit, e.g., rapid analysis of the growing tissue during organoid production processes to ensure that it comprises the desired cell types, does not comprise undesired cell types and/or comprises the desired cell types at the desired positions within the organoid structure. The analysis method provided herein permits the skilled person to modify the culture conditions of the organoid during and/or after the development process, thereby increasing the likelihood that organoids of the desired type will be produced and/or maintained.

Optionally, the property analysed is the phenotypic and/or genotypic condition of the cells of the organoid or the cells of a region of the organoid. Optionally, by phenotypic and/or genotypic condition is meant the viability of the cells therein, the disease state of the cells therein, and/or the level of oxidative damage/stress within the cells therein, particularly the level of lipid oxidation. Cells having different phenotypic and/or genotypic conditions will be distinguishable by characteristic spectrometric data. Thus, the phenotype and/or genotype of the organoid may be analysed by the method provided herein, as discussed elsewhere herein.

Optionally, the method may involve the analysis of the effect of environmental conditions on an organoid, details of which are discussed elsewhere herein. After analysis of any property of a target organoid as described herein, one or more of these conditions may optionally be appropriately modified. Such modification is within the competencies of one of ordinary skill in the art.

Optionally, if an undesirable disease state is detected, for instance infection of the cells of the organoid by an infectious agent, then steps can be taken to remove the infection through treatment with appropriate agents, and/or through excision of the infected cells.

Once produced, organoids can be maintained in culture. However, different organoid types degrade, i.e. lose functionality and/or optimal condition over time. This is particularly problematic in certain organoid types, e.g., neurons in cerebral organoids decline and are replaced by glia by 15 months after production.

The present methods permit analysis of organoids as described above not only during the organoid production process, but also once the organoid has been produced. In other words, the methods permit analysis of a mature organoid or a region thereof. The cell type, migration, differentiation potential, and/or condition of cells of a mature organoid or a region thereof may also be analysed. Spectrometric data obtained from the target organoid or region thereof may be compared to spectrometric data from the same organoid or region thereof at an earlier time point to determine changes in properties of the organoid over time. Thus, the method may optionally be used to monitor any changes in the properties of an organoid.

In certain instances it may be desirable to prepare an organoid that is a model of a particular disease. Organoids may be produced that exhibit disease specific phenotypes. Such organoids have great use in the study of diseases and the study of potential therapies, including, but not limited to, their use in methods of screening agents for therapeutic efficacy.

The preparation of organoids with disease specific phenotypes is within the competencies of one of ordinary skill in the art. Optionally, the disease state is induced through genetic modification of the cells from which the organoid is produced, or through application of one or more disease-inducing agents to the organoid. Optionally the disease state is cancer, an infection, and/or a disease selected from any of the diseases disclosed elsewhere herein.

The method may optionally comprise the step of analysing the disease state of the organoid or a region thereof. Analysing the disease state may comprise analysing the incidence of, severity of, or progression of a disease state. Cells of differing disease states will result in characteristic spectrometric data.

Optionally, the analysis of the disease state may occur once or more during the production of an organoid with a disease state phenotype. In this way, generation of the disease state phenotype can be monitored and encouraged or discouraged as desired.

Optionally, the analysis of the disease state is performed on mature organoids.

Optionally, the methods may comprise analysis of the disease states of organoids with different genotypes and/or phenotypes to reveal the role of specific genotypes and/or phenotypes in the incidence, severity and/or progression of diseases.

The method may optionally comprise analysing the disease state of an organoid produced following administration of a candidate compound, wherein said candidate compound prevents, treats, induces, and/or enhances the disease state in question. In this way, the methods of the invention permit the use of organoids in compound screens.

Thus, the present invention also provides a compound screening method comprising the steps of:
i) contacting an organoid with a candidate compound;
ii) obtaining spectrometric data from said organoid or a region thereof as described elsewhere herein; and
iii) analysing said data to determine one or more properties of said candidate compound.

The organoid may be an organoid as described anywhere else herein. Optionally, the organoid or region thereof displays a disease state genotype and/or phenotype. Typically, the property to be analysed is the effect of the compound on the disease state of the organoid.

Candidate compounds that may be screened optionally include but are not limited to toxins, cytokines, neurotransmitters, growth factors, morphogens, inhibitors, stimulators, bacteria, viruses, DNA, anti-sense nucleic acids, drugs, peptides, natural compounds, and/or any of the other compounds listed elsewhere herein.

Optionally the methods comprise analysing the disease state of the organoid following genetic modification thereof, for instance via genome editing techniques.

Optionally, the organoid is present in a kit that comprises a plurality (i.e., at least 6, optionally 24, 48, 96, and even up to several thousand) of organized tissues individually contained in a container.

The generation and/or analysis of organoids will now be described by reference to specific embodiments, but it should be understood that the principles described below apply mutatis mutandis to the generation and/or analysis of any type or organoids.

Optionally, the organoid may be sectioned and/or sequentially disassociated, e.g., mechanically and/or enzymatically, for example with trypsin, to obtain different layers of an organoid, and/or to derive cells from different layers of an organoid. Different layers, or cells derived from different layers, of the organoid may then be analysed. During organoid growth and/or maintenance, different layers of an organoid may have been exposed to different environmental conditions, and/or been exposed to different concentrations of a substance, as substances may not penetrate each layer at the same rate. Thus, the method may optionally be used to analyse one or more different layers of an organoid, or cells derived therefrom.

Human Colon Carcinoma Organoids

Human colon carcinoma LIM1863 cells may be grown as free-floating multicellular spheres (organoids) in which highly polarized cells localize around a central lumen. These organoids resemble colonic crypts in that they contain morphologically differentiated columnar and goblet cells.

LIM1863 cells may be cultured in RPMI 1640 medium containing 5% FCS, α-thioglycerol (10 μm), insulin (25 units/l), and hydrocortisone (1 mg/L), with 10% $CO_2$ at 37° C.

The LIM1863 cells ($6\times10^8$ cells) may be washed four times with 30 ml of RPMI 1640 medium and cultured for 24 h in 150 ml serum-free RPMI medium supplemented with 0.6% insulin-transferrin-selenium solution.

Culture medium (CM) may be collected and centrifuged at 4° C. (480×g for 5 min followed by 2,000×g for 10 min) to remove intact cells and cell debris. CM may be centrifuged at 10,000×g for 30 min to isolate sMVs.

According to an embodiment CM may be filtered using a VacuCap® 60 filter unit fitted with a 0.1 μm Supor® Membrane and then concentrated to 500 μl using an Amicon® Ultra-15 Ultracel centrifugal filter device with a 5K nominal molecular weight limit.

Pancreatic Cancer Organoids

Pancreatic cancer is one of the most lethal malignancies due to its late diagnosis and limited response to treatment. Tractable methods to identify and interrogate pathways involved in pancreatic tumorigenesis are desired. Pancreatic organoids can be rapidly generated from resected tumours and biopsies, survive cryopreservation, and exhibit ductal- and disease-stage-specific characteristics. Orthotopically transplanted neoplastic organoids recapitulate the full spectrum of tumour development by forming early-grade neoplasms that progress to locally invasive and metastatic carcinomas. Due to their ability to be genetically manipulated, organoids are a platform to probe genetic cooperation. Comprehensive transcriptional and proteomic analyses of murine pancreatic organoids have revealed genes and pathways altered during disease progression. The confirmation of many of these protein changes in human tissues demonstrates that organoids are a useful model system to discover important characteristics of pancreatic cancer.

Human Mammary Explant Culture

The mammary explant culture system and mammary epithelial cell culture system provide useful in vitro models to examine the responsive ness of noncancerous mammary tissue to agents that affect cell proliferation, cytodifferentiation and neoplastic transformation at the molecular, biochemical and cellular levels. The tissue culture technology and biomarker assays established for the murine models have been optimized for human mammary tissue.

Explant cultures may be prepared from human mammary terminal duct lobular unit (TDLU) obtained from surgical samples. The TDLU are the endocrine responsive and proliferatively active intact organoids that represent target tissue for carcinogenesis.

According to an embodiment these organoids may be maintained in a chemically defined, serum-free Waymouth's MB 752/1 medium supplemented with 5 pg/ml insulin, 1 ng/ml E2, 2 mM L-glutamine and antibiotics.

The medium may be routinely changed every 48 hr and the cultures may be maintained in a humidified atmosphere of 95% air: 5% CO2 at 37° C.

According to an embodiment the human mammary epithelial 184-E5 cell line may be maintained in chemically defined, serum-free KBM-MEM medium supplemented with 10 pg/ml insulin, 10 ng/ml epidermal growth factor, 10 pg/ml transferrin, 0.5 pg/ml hydrocortisone, and 5 pg/ml gentamycin (24,25).

The medium may be routinely changed every 48 hr and the cells may be subcultured by a 1:4 split when approximately 70% confluent.

Xenografts

Cells and/or tissue may optionally be xenografted into a host organism for a suitable period of time, e.g., at least 1, 2 3, 4, 5, 6, 7, 8, 9, 10, 11, 12, 13, 14, 15, 16, 17, 18, 19, 20, 21, 2, 23, or 24 hours and/or 1, 2 3, 4, 5, 6, 7, 8, 9, 10, 11, 12, 13, 14, 15, 16, 17, 18, 19, 20, 21, 2, 23, or 24 days. For example, cells or tissue obtained from a human tumour may be xenografted into a host animal. Optionally, the method may involve making a xenograft and/or removing a xenograft or sample thereof from a host organism. Optionally, the method may be performed on a provide xenograft.

Optionally, the xenograft may comprise or consist of tumour cells. Optionally, cells may be obtained from a xenograft to establish a xenograft-derived cell population. A xenograft-derived cell population, may optionally be analysed, e.g., to analyse the impact of the host environment on the cell population. Optionally, a cell population may be analysed prior to an after xenografting, and/or a xenograft-derived population may be compared to a cell population that is not xenograft-derived.

Imaging

According to the various embodiments herein, ion imaging may be used to generate an image or map of one or more properties of the target, e.g., if the target is an organoid. This may be achieved by using the first device to generate aerosol, smoke or vapour from multiple different regions of the target; ionising analytes in the smoke, aerosol or vapour originating from the different regions to produce analyte ions (or ions derived therefrom, e.g., fragment ions); and then analysing the analyte ions (or ions derived therefrom) to obtain spectrometric data for each of the regions of the target. The spectrometric data is correlated to the region of the target to which it relates (i.e. from where the smoke, aerosol or vapour that generated the spectrometric data originated from) so as to generate image or map data. An image or map of the target can then be generated based on the image or map data. For example, one or more properties of each region of the target may be determined from the spectrometric data and this may be included in the image or map data and hence mapped as a function of location within the target. The image or map data may then be displayed to a user.

The first device may be stepped between multiple spaced apart regions of the target so as to generate the aerosol, smoke or vapour from discrete regions of the target. Alternatively, a plurality of devices may be used to generate the aerosol, smoke or vapour from discrete regions of the target, optionally simultaneously. These plurality of devices may not move across the target, although may move into and out of engagement with the target. Alternatively, the first device may be moved across or through the target continuously so as to generate aerosol, smoke or vapour from the different regions of the target. Any movements of the first device, or the plurality of devices, may be automated and controlled by a machine.

The spectrometric data for each region may be analysed and converted into data representative of the type, condition or constituent(s) of the material at that region in the target.

The representative data may then be displayed as an image or map showing the type, condition or constituents of the material as a function of location in the target.

For example, the representative data may indicate the type, level, presence and/or absence of: diseased; cancerous; and/or necrotic material at each of the regions in the target. For example, the spectrometric data may be used to identify and/or display the locations of margins of diseased, cancerous, and/or necrotic tissue in the target. These tissue types, such as tumour tissue, may closely resemble normal tissue and may have indistinct boundaries, making it difficult to determine where the tumour ends and the normal tissue begins. The method provided herein enables the locations of such tissue margins to be identified.

Additionally, or alternatively, the spectrometric data may be used to identify and/or display the location and/or margins of one or more cell or tissue type of interest. For example, the cell or tissue type of interest may comprise diseased and/or cancerous and/or necrotic tissue or cells in the target; and/or the cell or tissue type of interest may comprise healthy tissue or cells.

The representative data may indicate the different type of cells or constituents in the target.

Additionally, or alternatively, the representative data may indicate the presence and/or distribution of one or more types of microbes within the target.

Additionally, or alternatively, the representative data may indicate the presence and/or distribution of one or more types of compounds within the target.

Additionally, or alternatively, the representative data may indicate the type or level of biomarker in the target, and the distribution of the type or level of biomarkers within a target may be identified and/or displayed.

The ion imaging and map data may be generated and/or displayed in real-time.

Ion imaging mass spectrometry technology, such as DESI-MS and/or REIMS technology, may optionally be used to obtain the spectrometric data for the different regions of the target. A REIMS technology device may optionally be used in cutting and/or pointing mode.

Some ion imaging mass spectrometry technology, such as DESI-MS, does not destroy the entirety of an organoid, so such a technology may optionally be used to analyse an organoid, wherein at least some cells of the organoid survive the method of analysis.

This ion imaging analysis may optionally be combined with a further analysis of the specimen. Details of further analysis methods and tools are provided elsewhere herein. Optionally, the results of mass spectrometry imaging may be correlated with the results of a further analysis.

More details as to how to perform ion imaging are discussed below with reference to a particular example of DESI imaging. It will be understood that the specific parameters discussed were those used in an assay by the inventor, and that any of these parameters may be varied.

Specimens, such as infected tissue sections or cell cultures, smeared onto the surface of a standard glass microscope slide, were subjected to DESI-MS imaging analysis using an Exactive mass spectrometer (Thermo Fisher Scientific Inc., Bremen, Germany) Exactive instrument parameters are listed in the Table below.

Thermo Exactive instrumental parameters used for DESI-MS imaging.

| Parameter | Setting. |
| --- | --- |
| Polarity | negative |
| Resolution | 100,000 |
| Mass range | 200-1050 |
| Spray voltage | −4.5 kV |
| Capillary temperature | 250° C. |
| Capillary voltage | −50 V |
| Tube lens voltage | −150 V |
| Skimmer Voltage | −24 V |
| Max. injection time | 1000 ms |

-continued

| Parameter | Setting. |
| --- | --- |
| Microscans | 1 |
| AGC target | 5e6 |

Methanol/water (95:5 v/v) was used as the electrospray solvent at a flow-rate of 1.5 µL/min. Nitrogen N4.8 was used as nebulising gas at a pressure of 7 bars. All solvents used were of LC-MS grade (Chromasolv, Sigma Aldrich, St Louis, Mo., USA). The height distance between the DESI sprayer and the sample surface was set to 2 mm with the distance between the sprayer and sniffer set to 14 mm. The distance between the sample surface and the inlet capillary of the mass spectrometer was <<1 mm. The angle between the sprayer tip and the sample surface was set at 80°. The collection angle between inlet capillary and sample was set to 10°.

The general principle underlying imaging processes using DESI MS is that rather than point-by-point sampling, horizontal line scans are performed over the specimen surface by moving the automated sampling platform at a speed that covers the area determined as a pixel (spatial resolution) in the time the mass spectrometer requires to complete one scan (acquire one mass spectrum). This results in each one file per row of the resulting image (number of rows determined by sample height divided by spatial resolution).

For image analysis, individual horizontal line scans were converted into .imzML files using the imzML Converter Version 1.1.4.5 (www.maldi-msi.org). Single ion images and RGB images were generated using MSiReader Version 0.05 (146) with linear interpolation (order 1) and 0.005 Da bin size.

Biomarkers

The method may optionally involve the analysis of one or more biomarkers. A biomarker may be an objective, quantifiable characteristic of, e.g., a cell type, disease status, microbe, compound, and/or biological process.

The term "biomarker" is sometimes used explicitly herein, but it should also be understood that any of the analyses mentioned herein may optionally be the analysis of a biomarker. Thus, e.g., any reference to analysing a "cell type" should be understood optionally to be "analysing a biomarker for a cell type"; any reference to analysing a "phenotype and/or genotype" should be understood optionally to be "analysing a phenotype and/or genotype biomarker"; and so on.

The biomarker may optionally be a spectrometric biomarker. The term "spectrometric biomarker" is used herein to refer to spectrometric data that is characteristic of a cell type, disease status, microbe, compound, and/or biological process, but for simplicity, a spectrometric biomarker may simply be referred to as a "biomarker".

By "characteristic of a cell type" is meant that the biomarker may optionally be used to analyse, e.g., detect, identify and/or characterise said cell type. Optionally, the biomarker may be used to distinguish between cells originating from different tissues; between genotypically and/or phenotypically different cell types; between an animal cell and a microbial cell; between a normal and an abnormal cell; between a wild-type and a mutant cell; and/or between a diseased and a healthy cell.

By "characteristic of a disease status" is meant that the biomarker may optionally be used to analyse the disease status of a target. Optionally, the biomarker may be used to distinguish between healthy and diseased cells; and/or to analyse the severity, grade, and/or stage of a disease.

By "characteristic of a microbe" is meant that the biomarker may optionally be used to analyse, e.g., detect, identify and/or characterise said microbe. As discussed elsewhere herein, identification may be on any level, for example, on a taxonomic level. A biomarker that allows identification of a microbe as belonging to a particular taxonomic level may be referred to as a "taxonomic marker" or "taxonomic biomarker". Thus, a taxonomic marker may be specific for a Kingdom, Phylum, Class, Order, Family, Genus, Species and/or Strain.

By "characteristic of a compound" is meant that the biomarker may optionally be used to analyse, e.g., detect, identify and/or characterise said compound.

By "characteristic of a biological process" is meant that the biomarker may optionally be used to analyse a biological process. Optionally, the biomarker may be used to analyse the start, progression, speed, efficiency, specificity and/or end of a biological process.

Different cell types, disease states, compounds, microbes, biological progresses and the like may be characterised by the presence or absence, and/or relative abundance, of one or more compounds, which may serve as biomarkers. Any reference herein to a biomarker being a particular compound, or class of compounds, should be understood optionally to be the spectrometric data of that compound, or class of compounds.

For example, a reference to a "C24:1 sulfatide (C48H91NO11 S)" biomarker should be understood to be a reference to the spectrometric data corresponding to C24:1 sulfatide (C48H91 NO11 S) which may, e.g., be a signal corresponding to m/z of about 888.6; whereas a reference to a "glycosylated ceramide" biomarker should be understood to be a reference to the spectrometric data corresponding to glycosylated ceramide, which may, e.g., be a signal corresponding to m/z of 842, 844 or 846.

As explained above, a biomarker may be indicative of a cell type, disease status, microbe, compound, and/or biological process. A biomarker which is indicative of cancer may therefore be referred to as a "cancer biomarker"; a biomarker which is indicative of *Pseudomonas aeruginosa* may be referred to as a "*Pseudomonas aeruginosa* biomarker" and so on.

Optionally, a spectrometric biomarker may be identified as being the spectrometric data of a particular compound, or class of compounds. Thus, a signal corresponding to a particular mass, m/z, charge state and/or ion mobility (e.g., due to cross-sectional shape or area) may optionally be identified as being indicative of the presence of a particular compound, or class of compounds.

Optionally, a spectrometric signal may serve as a biomarker even if a determination has not been made as to which particular compound, or class of compounds gave rise to that signal. Optionally, a pattern of spectrometric signals may serve as a biomarker even if a determination has not been made as to which particular compounds, or class of compounds, gave rise to one or more signals in that pattern, or any of the signals in a pattern.

The work disclosed herein has led to the identification of a range of biomarkers, as well as allowing the identification of further biomarkers. Optionally, the biomarker may be selected from any of the biomarkers disclosed herein, including in any of the Examples and/or Tables. Optionally, the biomarker may be a biomarker of the substituted or unsubstituted form of any of the biomarkers mentioned herein; and or of an ether, ester, phosphorylated and/or glycosylated form, or other derivative, of any of the biomarkers mentioned herein.

Optionally, the biomarker may be a biomarker of a lipid; a protein; a carbohydrate; a DNA molecule; an RNA molecule; a polypeptide, such as, a ribosomal peptide or a non-ribosomal peptide; an oligopeptide; a lipoprotein; a lipopeptide; an amino acid; and/or a chemical compound, optionally an organic chemical molecule or an inorganic chemical molecule.

A biomarker may optionally be the clear-cut presence or absence of a particular compound, which may optionally manifest itself as the presence or absence of a spectrometric signal corresponding to a specific mass, charge state, m/z and/or ion mobility.

A biomarker may optionally be the relative abundance of a particular biomolecule or compound, which may optionally manifest itself as the relative intensity of a spectrometric signal corresponding to a specific mass, charge state, m/z and/or ion mobility A biomarker may optionally be the relative abundance of more or more compounds, which may optionally manifest itself as the relative intensity of two or more spectrometric signals corresponding to two or more mass, charge state, m/z and/or ion mobility.

Thus, a biomarker may optionally be an increased or decreased level of one or more compounds, e.g., a metabolite, a lipopeptide and/or lipid species, which may optionally manifest itself as an increase and/or decrease in the intensity of two or more spectrometric signals corresponding to two or more mass, charge state, m/z and/or ion mobility The presence, absence and relative abundance of a variety of compounds may be referred to as a molecular "fingerprint" or "profile". The totality of the lipids of a cell may be referred to as a lipidomic fingerprint/profile, whereas the totality of metabolites produced by a cell may be referred to as a metabolomic fingerprint/profile.

Thus, the biomarker may be a molecular fingerprint, e.g., a lipid fingerprint and/or a metabolomic fingerprint, more particularly e.g., a (i) a lipidomic profile; (ii) a fatty acid profile; (iii) a phospholipid profile; (iv) a phosphatidic acid (PA) profile; (v) a phosphatidylethanolamine (PE) profile; (vi) a phosphatidylglycerol (PG) profile; (vii) a phosphatidylserines (PS) profile; or (viii) a phosphatidylinositol (PI) profile.

By way of example, phosphatidylglycerol may be found in almost all bacterial types, but it may be present in different bacteria in different relative amounts. Phosphatidylglycerol may be present at a level of only 1-2% in most animal tissues. It may therefore be a biomarker for bacteria in an animal specimen, and/or be a biomarker for specific types of bacteria.

The biomarker may optionally be a direct biomarker or an indirect biomarker. By "direct" biomarker is meant that the spectrometric data is produced directly from the biomarker. For example, if a particular compound has a specific spectrometric signal or signal pattern, then obtaining this signal or signal pattern from a sample provides direct information about the presence of that compound. This may be the case, for example, for a metabolite produced in significant amounts by a cell or microbe. Optionally, in such an example, the spectrometric data from the compound may alternatively or in addition serve as an indirect biomarker for the cell or microbe that produced this compound.

By "indirect" biomarker is meant that the spectrometric data is produced from one or more biomarkers that is/are indicative of a particular compound, biological process, and/or type of microbe or cell. Thus, an indirect biomarker is spectrometric data generated from one or more molecules that provides information about a different molecule. For example, a molecular fingerprint, such as, a lipid fingerprint, may be indicative of the expression of a particular protein, e.g., a receptor; or of a particular cell type or microbial type.

A lipid biomarker may optionally be selected from, e.g., fatty acids, glycerolipids, sterol lipids, sphingolipids, prenol lipids, saccharolipids and/or phospholipids. A brief overview of various lipids is provided below, but it must be appreciated that any particular lipid may fall into more than one of the groups mentioned herein.

A fatty acid is an aliphatic monocarboxylic acid. The fatty acid may optionally have a carbon chain comprising precisely or at least 4, 6, 8, 10, 12, 14, 16, 18, 20, 22, 24, 26, 28, 30, 32, 36, 38 or 40 carbons. It may optionally be monounsaturated, polyunsaturated, or saturated. It may optionally be an eicosanoid. It may, for example, be oleic acid, palmitic acid, arachidonic acid, a prostaglandin, a prostacyclin, a thromboxane, a leukotriene, or an epoxyeicosatrienoic acid.

The glycerolipid may optionally be selected from e.g., monoacylglycerol, diacylglycerol, and/or triacylglycerol.

The sterol may optionally be selected from free sterols, acylated sterols (sterol esters), alkylated sterols (stearyl alkyl ethers), sulfated sterols (sterol sulfate), sterols linked to a glycoside moiety (stearyl glycosides) and/or acylated sterols linked to a glycoside moiety (acylated sterol glycosides).

The sterol may optionally have an aliphatic side chain of precisely or at least 8, 9, 10, 11, 12, 13, 14, 15, 16, 17, 18, 19, 10, 21, 22, 23, 24, 25, 26, 27, 28, 29, 20, 35 or 40 carbon atoms. The number of carbon atoms in the aliphatic side chain may be expressed by the letter C followed by the number, e.g., C27 for cholesterol. It may, for example, be selected from cholesterol, cholesterol sulphate, ergosterol, lanosterol, dinosterol (4a,23,24-trimethyl-5a-cholest-22E-en-3b-ol), oxysterol and/or a derivative of any thereof.

A phospholipid may comprise two fatty acids, a glycerol unit, a phosphate group and a polar molecule. The Phospholipid may optionally comprise an ester, ether and/or other O-derivative of glycerol. The phospholipid may optionally be selected from, e.g., Phosphatidylglycerol, diphosphatidylglycerol (cardiolipin), Acylphosphatidylglycerol (1,2-diacyl-sn-glycero-3-phospho-(3'-acyl)-1'-sn-glycerol), and/or plasmalogen.

The phosphatidylglycerol lipid may optionally be selected from phosphatidic acids (PAs), phosphatidylethanolamines (PEs), phosphatidylglycerols (PGs), phosphatidylcholines (PCs), phosphatidylinositols (PIs) and/or phosphatidylserines (PSs).

A sphingolipid is a lipid containing a sphingoid. It may optionally be selected from, e.g., a ceramide, i.e. an N-acylated sphingoid; sphingomyelin, i.e. a ceramide-1-phosphocholine; phosphoethanolamine dihidroceramide, and/or a glycosphingolipid, i.e. a lipid containing a sphingoid and one or more sugars. For example, it may optionally be a glycosylated ceramide.

The biomarker may optionally be a metabolite, such as, a primary or a secondary metabolite; an antibiotic; a quorum sensing molecule; a fatty acid synthase product; a pheromone; and/or a biopolymer.

A biomarker compound may optionally be characterised by one or more of the following functional groups: alcohol, ester, alkane, alkene, alkyne, ether, ketone, aldehyde, anhydride, amine, amide, nitrile, aromatic, carboxylic acid, alkyl halide, and/or carbonyl. Optionally, it may additionally be identified as being primary, secondary or tertiary, e.g., a primary alcohol, a secondary amine, or the like.

For example, it may optionally be a terpene; prenylquinone; sterol; terpenoid; alkaloid; glycoside; surfactin; lichenysin, 2-Heptyl-3-hydroxy-4(1H)-quinolone or 2-heptyl-3,4-dihydroxyquinoline ("PQS" or Pseudomonas quinolone signal); 4-hydroxy-2-heptylquinoline ("HHQ"); phenol, such as, a natural phenol; phenazine; biphenyl; dibenzofurans; beta-lactam; polyketide; rhamnolipid; mycolic acids; and/or polyhydroxyalkanoates;

The biomarker may optionally be selected from, e.g., Glycerophosphocholines, Sphingomyelins, Glycerophospholipids, Galactoceramides, Glycerophosphoinositols, Glycerophosphoserines, Glycerophosphoglycerols, Cholesterol sulphate, sulfatides, seminolipids, citric acid, Glycerophosphoethanolamines, Glycerophosphoethanolamines, 2-hydroxyglutarate, glutamine, glutamate, succinate, fumarate, palmitoylglycine, ubiquinones, gadoteridol and/or any of the other biomarkers mentioned herein, including any of the Tables.

The inventors have identified inter alia the following biomarkers:

Mycolic acids for bacteria belonging to the Corynebacterineae suborder such as *Mycobacterium* spp., *Corynebacterium* spp. and *Rhodococcus* spp. In particular, the following mycolic acids have been detected from the corresponding genera: *Mycobacterium* spp.: C77-C81 (even and odd numbered, 0-2 unsaturations); *Corynebacterium* spp.: C28-C36 (even numbered, 0-2 unsaturations); *Nocardia* spp.: C48-C56 (even numbered, 0-3 unsaturations); *Rhodococcus* spp.: C28-C38 (even and odd numbered, 0-4 unsaturations).

A variety of sphingolipid species were found to be specific for members of the Bacteroidetes phylum. These sphingolipids include oxidized ceramides species, phosphoethanolamine dihydroceramides and C15:0-substituted phosphoglycerol dihydroceramides and dihydroceramide. Among those sphingolipid species, a series of galactosylated sphingolipids was found to be specific for *Bacteroides fragilis* (*Bacteroides fragilis* alpha-Galactosylceramides).

Among bacteria, plasmalogens are highly specific for anaerobic bacteria such as *Clostridium* spp. and *Fusobacterium* spp. This is due to the fact that aerobic bacteria lost the biochemical pathway required for plasmalogen synthesis. Humans are able to synthesize plasmalogens (although via a different biochemical pathway from anaerobes), although these were generally found to have longer chain lengths than bacterial plasmalogens.

Other biomarkers that are indicative of a certain group of bacteria include, for instance, lipopeptides that are produced specifically by certain *Bacillus* species, such as, surfactin for *B. subtilis* and lichenysin for *B. licheniformis*. Production of these two molecules also enables straightforward differentiation of these otherwise very closely related bacteria. A further example includes PQS-derived quorum-sensing molecules and mono- and di-rhamnolipid species found for *Pseudomonas aeruginosa*.

Quorum sensing is a form of cell-to-cell communication which relies on the principle that when a single microbe releases quorum sensing molecules into the environment, the concentration of such molecules is too low to be detected. However, when sufficient bacteria are present, quorum sensing molecule concentrations reach a threshold level that allows the microbes to sense a critical cell mass and, in response, to activate or repress particular genes. Quorum sensing molecules may therefore also be referred to as autoinducers. Pathogens may use quorum sensing molecules as virulence factors.

Some examples of quorum sensing molecules are listed above. Additional examples include N-acyl homoserine lactones (N-acyle HSLs), such as, 3-oxo-$C_8$-HSL, 3-oxo-$C_{10}$-HSL, or 3-oxo-$C_{12}$-HSL; diketopiperazines; 3-hydroxypalmitic acid methyl ester; and peptide-based quorum sensing molecules, such as, that of *Staphylococcus aureus*, which is an oligopeptide that has been termed the autoinducing peptide (AIP), encoded by the gene agrD. The active AIP is 7-9 amino acids, with a 5-membered thiolactone ring.

By way of example, sphingomyelin lipids may optionally be a biomarker, e.g., for cancer; ergosterol may optionally be a biomarker, e.g., for fungi; dinosterol may optionally be a biomarker, e.g., for dinoflagellates; cholesterol sulphate may optionally be a biomarker, e.g., for cancer; 2-hydroxyglutarate may optionally be a biomarker, e.g., for cancer; and/or one or more sulfatides may optionally be a biomarker, e.g., for cancer, for example, astrocytoma. Optionally, the sulfatide may be selected from $C_{48}H_{91}NO_{11}S$, $C_{48}H_{92}NO_{12}S$, and/or $C_{50}H_{94}NO_{11}S$.

Iso-C15:0-substituted phosphoglycerol dihydroceramides may be specific for the Porphyromonadaceae family. m/z=566.4790 may be a biomarker for members of the Flavobacteria class.

Diseases

As mentioned elsewhere herein, the cell population may be diseased, e.g., it may originate from diseased tissue, and/or have been manipulated to be diseased.

The analysis may optionally relate to a disease or condition, such as, any of the diseases or conditions listed in this section and/or elsewhere herein. The terms "disease" and "condition" are used interchangeably herein.

The disease may optionally be a skin condition, which may optionally be selected, for example, from Acne, Alopecia, Boils, Bowen's Disease, Bullous pemphigoid (BP), Carbuncle, Cellulitis, Chilblains, Cysts, Darier's disease, Dermatitis, Dermatomyositis, Eczema, Erythema, Exanthema, Folliculitis, Frostbite, Herpes, Ichthyosis, Impetigo, Intertrigo, Keratosis, Lichen planus, Linear IgA disease, Melanoma, Moles, Onychomycosis, Papilloma, Petechiae, Prurigo, Psoriasis, Rosacea, Scabies, Scleroderma, Sebaceous Cyst, Shingles/Chickenpox, Telangiectasia, Urticaria (Hives), Warts and/or Xeroderma.

The disease may optionally be a liver condition, which may optionally be selected from, for example, hepatitis, fatty liver disease, alcoholic hepatitis, liver sclerosis and/or cirrhosis.

The disease may optionally be a lung condition, which may optionally be selected from, for example, Asthma, Atelectasis, Bronchitis, Chronic obstructive pulmonary disease (COPD), Emphysema, Lung cancer, Pneumonia, Pulmonary edema, Pneumothorax, and/or Pulmonary embolus.

The thyroid gland is an endocrine gland which normally produces thyroxine (T4) and triiodothyronine (T3). The disease may optionally be a thyroid condition, which may optionally be, e.g., hypothyroidism or hyperthyroidism.

The disease may optionally be a cancer or tumour, which may optionally be selected from, for example, carcinomas, sarcomas, leukaemias, lymphomas and gliomas.

More particularly, it may optionally be selected from, for example, Acute Lymphoblastic Leukemia (ALL), Acute Myeloid Leukemia (AML), Adrenocortical Carcinoma, adenoma, Anal Cancer, Appendix Cancer, Astrocytomas, Basal Cell Carcinoma, Bile Duct Cancer, Birch-Hirschfield, Blastoma, Bladder Cancer, Bone Cancer, Ewing Sarcoma, Osteosarcoma, Malignant Fibrous Histiocytoma, Brain Stem Glioma, Brain cancer, glioblastoma multiforme ("GBM"), Astrocytomas, Spinal Cord cancer, Craniopharyngioma, Breast Cancer, Bronchial Tumour, Burkitt Lymphoma, Carcinoid Tumour, Cervical Cancer, Cholangiocarcinoma, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Childhood, Ductal Carcinoma In Situ (DCIS), Endometrial Cancer, Ependymoma, Esophageal Cancer, Esthesioneuroblastoma, Fibroadenoma, Intraocular Melanoma, Retinoblastoma, Fallopian Tube Cancer, Gallbladder Cancer, Gastric (Stomach) Cancer, Germinoma, Hairy Cell Leukemia, Head and Neck Cancer, Heart Cancer, Hepatocarcinoma, Hodgkin Lymphoma, Hypopharyngeal Cancer, Kahler, Kaposi Sarcoma, Kidney cancer, Laryngeal Cancer, Leiomyoma, Lip and Oral Cavity Cancer, Liver Cancer, Lung Cancer (such as, Non-Small Cell or Small Cell), Lymphoma, Lymphoblastoma, Male Breast Cancer, Malignant Fibrous Histiocytoma of Bone, Melanoma, Melanocarcinoma, Medulloblastoma, Merkel Cell Carcinoma, Mesothelioma, Mouth Cancer, Myeloma, Multiple Myeloma, Mycosis Fungoides, Myeloproliferative disorder, Nasal Cavity and Paranasal Sinus Cancer, Nasopharyngeal Cancer, Neuroblastoma, Nephroblastoma, Non-Hodgkin Lymphoma, Oral Cancer, Oropharyngeal Cancer, Osteosarcoma, Ovarian Cancer, Pancreatic Cancer, Papillomatosis, Paraganglioma, Parathyroid Cancer, Penile Cancer, Peritoneal cancer, Pharyngeal Cancer, Pheochromocytoma, Pineoblastoma, Pituitary Tumour, Prostate Cancer, Rectal Cancer, Retinoblastoma, Rhabdomyosarcoma, Salivary Gland Cancer, Sézary Syndrome, Skin Cancer, Seminoma, Teratoma, Testicular Cancer, Throat Cancer, Thyroid Cancer, thoracic cancer, Urethral Cancer, Vaginal Cancer, Vulvar Cancer, Waldenstrom macroglobulinemia, and/or Wilm's tumour. In the above list, any reference to a "cancer" or a "tumour" should be understood to include a reference to a "cancer and/or a tumour" of that type.

Optionally, a brain cancer may be glioblastoma multiforme, glioblastoma, giant cell glioblastoma, recurrent gliobastoma, anaplastic astrocytoma, oligodendroglioma and/or diffuse astrocytoma.

If the cancer is breast cancer, it may optionally be selected from, for example, ductal carcinoma in situ (DCIS), lobular carcinoma in situ (LCIS), Invasive breast cancer (NST), Invasive lobular breast cancer, Inflammatory breast cancer, breast cancer associated with Paget's disease and angiosarcoma of the breast.

The cancer may optionally be caused by, associated with, and/or characterised by a mutation or other genetic variation, which may optionally result in the altered expression of a molecule, e.g., a molecule comprising or consisting of a lipid, such as, a glycolipid or phospholipid; a carbohydrate; DNA; RNA; a protein; a polypeptide, such as, a ribosomal peptide or a non-ribosomal peptide; an oligopeptide; a lipoprotein; a lipopeptide; an amino acid; and/or a chemical compound, optionally an organic chemical compound. More particularly, a mutation may optionally result in the altered expression of a protein and/or metabolite.

A cancer may optionally express one or more metabolites that may serve as a biomarker for that cancer. For example, optionally a metabolite such as succinate, fumarate, 2-HG, and/or any of the other metabolites mentioned herein may accumulate in a cancer.

Subtypes of cancer may optionally be identified, e.g., based on such altered expression. For example, a cancer may optionally be identified as being of a particular subtype based on the expression, or lack thereof, of a receptor, e.g., selected from estrogen receptors (ER), progesterone receptors (PR) and human epidermal growth factor receptor 2

(HER2). A cancer may therefore, for example, be referred to as ER negative if it lacks expression of ER; or be referred to as triple-negative breast cancer (TNBC), if it is ER−, PR− and Her2−.

The mutation may optionally, e.g., be in a gene encoding isocitrate dehydrogenase 1 (IDH1) and/or 2 (IDH2) yielding mutant enzymes capable of converting alpha-ketoglutarate to 2-hydroxyglutarate (2-HG). Such a mutation may optionally be present, e.g., in a glioma, intrahepatic cholangiocarcinoma, acute myelogenous leukaemia (AML) and/or chondrosarcomas. 2-HG may thus be referred to as an oncometabolite. 2-HG may be present in very small amounts in normal tissues, whereas it may be present in high concentrations, e.g., several micromoles per gram of tumour, in mutant tumours.

Thus, a cancer subtype may have a specific biomarker. The method provided herein may optionally involve the analysis of a cancer subtype.

The method may optionally involve the analysis of the phenotype and/or genotype of a cancer, which may optionally involve an analysis of any of the mutations discussed above.

The disease may optionally be necrosis, which may optionally be caused by, or associated with, for example, injury, infection, cancer, infarction, toxins, inflammation, lack of proper care to a wound site, frostbite, diabetes, and/or arteriosclerosis. Optionally, the necrosis may be necrosis of cancerous or non-cancerous tissue. The necrosis may optionally, for example, be coagulative, liquefactive, caseous, fat necrosis, fibrinoid necrosis and/or gangrenous necrosis.

The disease may optionally be selected from an autoimmune disorder, an inflammatory disease, tropical sprue, a food intolerance, an infection, a cancer, and/or any of the of the disorders mentioned herein.

More particularly, the disease may optionally be selected from, for example, asthma, Coeliac disease, gastritis, peptic duodenitis, Gluten-sensitive enteropathy; allergy and/or intolerance to an allergen, e.g., to milk, soy, tree nut(s), egg, wheat, meat, fish, shellfish, peanut, seed, such as sesame, sunflower, and/or poppy seeds, garlic, mustard, coriander, and/or onion; Hashimoto's thyroiditis; Irritable bowel syndrome; Graves's disease; reactive arthritis; psoriasis; multiple sclerosis; Systemic lupus erythematosus (SLE or lupus); ankylosing spondylitis; progressive systemic sclerosis (PSS); glomerulonephritis; autoimmune enteropathy; IgA deficiency; common variable immunodeficiency; Crohn's disease; colitis, such as, lymphocytic colitis, collagenous colitis and/or ulcerative colitis; diffuse lymphocytic gastroenteritis; ulcer; intestinal T-cell lymphoma; infection, e.g., pharyngitis, bronchitis, and/or infection with a microbe selected, for example, from Giardia, *Cryptosporidium, Helicobacter* and/or any of the other microbes mentioned herein.

The method may optionally allow an analysis of metabolic differences between various conditions.

Analysis and/or Treatment of Disease

The method provided herein may optionally be used to study disease. For example, the cell population may serve as an in vitro or ex vivo model of a disease. Optionally, the cell population may have been derived from a subject and/or be xenograft-derived.

Thus, optionally, a cell population having a particular disease may be used to monitor the progress of that disease at the cellular level. Optionally, the cell population may be manipulated, mutated, and/or exposed to a substance and/or environmental condition as discussed elsewhere herein and the effect thereof may be analysed to determine the effect of such a manipulation, mutation, substance and/or environmental condition on a disease.

The method may optionally be used to monitor the progress of disease. The method may optionally be used to assess the effectiveness of a therapeutic or test substance.

Optionally, serial (periodic) analysis of a target for a change may be used to assess whether or not a therapeutic or test substance has been effective; the extent to which a therapeutic or test substance has been effective; whether or not a disease is re-occurring or progressing in the cell population; and/or to assess the likely clinical outcome (prognosis) of the disease for a subject.

Any reference in this context to a "subject" is intended to be a subject having the disease for which the cell population is a model.

Optionally, any of the methods provided herein may also include a step of determining whether a subject should receive a treatment with a therapeutic substance, e.g., the substance tested on the cell population.

Suitable treatments or substances are discussed elsewhere herein. Particularly, if the method involves a determination that a disease is likely to respond to treatment, and/or that a diseased cell population has responded to treatment, then the method may include a step of determining that a subject should receive an appropriate treatment.

Optionally, any of the methods provided herein may also include a step of determining, for a subject who is receiving, or has received, treatment, whether the treatment should be altered or ceased, based on the treatment response determined for the model cell population. For example, the method may optionally include a step of determining that the treatment dose and/or frequency should be increased or decreased. In particular, if the method involves a determination that one or more biomarkers for a disease are increased in the model cell population, have increased over time, or have not decreased (or not decreased sufficiently) in response to a treatment, then the method may optionally include a step of determining that the treatment dose and/or frequency should be increased; and if the method involves a determination that one or more biomarkers for a disease are not increased in the model cell population, have decreased over time, or have decreased in response to a treatment, then the method may optionally include a step of determining that the treatment dose and/or frequency should be decreased or that the treatment may be ceased; or vice versa.

The method may include a step of determining that a particular treatment should be replaced by another treatment, for example that one drug should be replaced with another drug. In particular, if the method involves a determination that one or more biomarkers for a disease are increased in the model cell population, have increased over time, or have not decreased (or not decreased sufficiently) in response to a treatment, then the method may include a step of determining that the treatment should be replaced by another treatment; and if the method involves a determination that one or more biomarkers for a disease are not increased in the model cell population, have decreased over time, or have decreased in response to a treatment, then the method may include a step of determining that the treatment should not be replaced by another treatment; or, vice versa.

Optionally, any of the methods provided herein may also include a step of administering a treatment to said subject. The method may then, for example, be referred to as a method of diagnosis and treatment; monitoring and treatment; prognosis and treatment; prediction and treatment; or stratification and treatment.

Optionally, any of the methods provided herein may be used in conjunction with any other known methods, particularly a known diagnostic, prognostic, predictive, and/or monitoring method for a disease.

Cell Population Infection

As mentioned elsewhere, a potential infection of a cell population may be analysed. The infection may be, e.g., by another cell type and/or by a microbe.

A "microbe", also known as a micro-organism, is an organism which is too small to be visible to the naked eye, i.e. is microscopic. A microbe may be selected from bacteria, fungi, archaea, algae, protozoa and viruses. Although the terms bacteria, fungi, archaea, algae, protozoa and viruses technically denote the plural form, it is common practice to use them also to denote the singular form. Consequently, the terms "bacteria" and "bacterium" are used interchangeably herein; the terms "fungi" and "fungus" are used interchangeably herein; the terms "archaea" and "archaeum" are used interchangeably herein; the terms "protozoa" and "protozoum" are used interchangeably herein; and the terms "viruses" and "virus" are used interchangeably herein.

In the case of a microbe, analysis may optionally be on any taxonomic level, for example, at the Kingdom, Phylum or Division, Class, Order, Family, Genus, Species and/or Strain level.

"Taxonomy" is the classification of organisms, and each level of classification may be referred to as a "taxon" (plural: taxa). Organisms may be classified into the following taxa in increasing order of specificity: Kingdom, Phylum or Division, Class, Order, Family, Genus, Species and Strain. Further subdivisions of each taxon may exist. It must be appreciated that within the vast scientific community there are some discrepancies within some taxonomic classifications. There may also be a lack of consensus with regard to the nomenclature of certain microbes, resulting in a particular microbe having more than one name or in two different microbes having the same name.

As a shorthand, the term "type" of microbe is used to refer to a microbe that differs from another microbe at any taxonomic level.

In some embodiments, the microbe may be selected from bacteria, fungi, archaea, algae and protozoa. In some embodiments, it may be selected from bacteria and fungi. In some embodiments, it may be selected from bacteria.

The microbe may be single-cellular or multi-cellular. If the microbe is a fungus, it may optionally be filamentous or single-cellular, e.g., a yeast.

A fungus may optionally be yeast. It may optionally be selected from the genus *Aspergillus, Arthroascus, Brettanomyces Candida, Cryptococcus, Debaryomyces, Geotrichum, Pichia, Rhodotorula, Saccharomyces, Trichosporon*, and *Zygotorulaspora*.

It may optionally be selected from the species *Arthroascus schoenii, Brettanomyces bruxellensis, Candida albicans, C. ascalaphidarum, C. amphixiae, C. antarctica, C. argentea, C. atlantica, C. atmosphaerica, C. blattae, C. bromeliacearum, C. carpophila, C. carvajalis, C. cerambycidarum, C. chauliodes, C. corydali, C. dosseyi, C. dubliniensis, C. ergatensis, C. fructus, C. glabrata, C. fermentati, C. guilliermondii, C. haemulonii, C. insectamens, C. insectorum, C. intermedia, C. jeffresii, C. kefyr, C. keroseneae, C. krusei, C. lusitaniae, C. lyxosophila, C. maltosa, C. marina, C. membranifaciens, C. milleri, C. mogii, C. oleophila, C. oregonensis, C. parapsilosis, C. quercitrusa, C. rugosa, C. sake, C. shehatea, C. temnochilae, C. tenuis, C. theae, C. tolerans, C. tropicalis, C. tsuchiyae, C. sinolaborantium, C. sojae, C. subhashii, C. viswanathii, C. utilis, C. ubatubensis, C. zemplinina, Cryptococcus neoformans, Cryptococcus uniguttulatus, Debaryomyces carsonii, Geotrichum capitatum, Trichosporon asahii, Trichosporon mucoides, Trichosporon inkin, Saccharomyces cerevisiae, Pichia acaciae, Pichia anomala, Pichia capsulata, Pichia farinosa, Pichia guilliermondii, Pichia spartinae, Pichia ohmeri, Rhodotorula glutinous, Rhodotorula mucilaginosa, Saccharomyces boulardii, Saccharomyces cerevisiae*, and/or *Zygotorulaspora florentinus*.

The bacteria may optionally be of a genus selected from, e.g., *Abiotrophia, Achromobacter, Acidovorax, Acinetobacter, Actinobacillus, Actinomadura, Actinomyces, Aerococcus, Aeromonas, Anaerococcus, Anaplasma, Bacillus, Bacteroides, Bartonella, Bifidobacterium, Bordetella, Borrelia, Brevundimonas, Brucella, Burkholderia Campylobacter, Capnocytophaga, Chlamydia, Citrobacter, Chlamydophila, Chryseobacterium, Clostridium, Comamonas, Corynebacterium, Coxiella, Cupriavidus, Delftia, Dermabacter, Ehrlichia, Eikenella, Enterobacter, Enterococcus, Escherichia, Erysipelothrix, Facklamia, Finegoldia, Francisella, Fusobacterium, Gemella, Gordonia, Haemophilus, Helicobacter, Klebsiella, Lactobacillus, Legionella, Leptospira, Listeria, Micrococcus, Moraxella, Morganella, Mycobacterium, Mycoplasma, Neisseria, Nocardia, Orientia, Pandoraea, Pasteurella, Peptoniphilus, Peptostreptococcus, Plesiomonas, Porphyromonas, Pseudomonas, Prevotella, Proteus, Propionibacterium, Rhodococcus, Ralstonia, Raoultella, Rickettsia, Rothia, Salmonella, Serratia, Shigella, Staphylococcus, Stenotrophomonas, Streptococcus, Tannerella, Treponema, Ureaplasma, Vibrio* or *Yersinia*.

The virus may optionally be a DNA virus, and RNA virus or a retrovirus. It may optionally be a single stranded (ss) or a double stranded (ds) virus. More particularly, it may optionally be a ssDNA, dsDNA, dsRNA, ssRNA (positive strand), ssRNA (negative strand), ssRNA (reverse transcribed) or dsDNA (reverse transcribed) virus.

It may optionally be selected from one or more of the Herpesviridae; the Adenoviridae; Papillomaviridae; Polyomaviridae; Poxviridae; Anelloviridae; Mycodnaviridae; Parvoviridae; Reoviridae; Coronaviridae; Astroviridae; Caliciviridae; Flaviviridae; Picornaviridae; Togaviridae; Rhabdoviridae; Filoviridae; Paramyxoviridae; Arenaviridae; Bunyaviridae; Orthomyxoviridae; Retroviridae; Epadnaviridae; Hepevirus; and/or Deltavirus.

Confocal Microscopy

The principle of confocal imaging aims to overcome some limitations of traditional wide-field fluorescence microscopes. In a conventional (i.e., wide-field) fluorescence microscope, the entire specimen is flooded evenly in light from a light source. All parts of the specimen in the optical path are excited at the same time and the resulting fluorescence is detected by the microscope's photodetector or camera including a large unfocused background part.

In contrast, a confocal microscope uses point illumination and a pinhole in an optically conjugate plane in front of the detector to eliminate out-of-focus signal (the name "confocal" stems from this configuration). As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity. As a result, relatively long exposures may be required.

As only one point in the sample is illuminated at a time, 2D or 3D imaging requires scanning over a regular raster (i.e., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples.

Optionally, cell imaging may be performed using a confocal microscope.

Flow Cytometry

Optionally, the method may additionally include a step of flow cytometry, e.g., prior to and/or after the mass and/or ion mobility spectrometric analysis. For example, the method may optionally be carried out on a cell population that was previously analysed via flow cytometry, e.g., it may optionally be carried out on a sub-population of cells sorted via fluorescence-assisted cell sorting ("FACS").

Optionally, the method may comprise separating labelled cells from unlabelled cells prior into a first and a second subset, optionally a labelled and an unlabelled subset. This separation may optionally be before and/or after the generation of spectrometric data. Thus, optionally, the target may be a subset of a cell population, wherein the subset has been generated using flow cytometry, e.g., FACS.

Optionally, said steps of separating labelled cells from unlabelled cells may be carried out prior to performing the method provided herein. Optionally, (i) at least one of said subsets may be analysed directly via the method of any preceding claim; (ii) at least one subset may be introduced directly into a mass spectrometer and/or ion mobility spectrometer; and/or (iii) a FACS device may be coupled, optionally directly, to a device, optionally as defined elsewhere herein, e.g., a mass spectrometer and/or ion mobility spectrometer.

In biotechnology, flow cytometry is a laser-based biophysical technology employed, e.g., in cell counting, cell sorting, biomarker detection and protein engineering. Flow cytometry may optionally be used, e.g., for analysing the expression of cell surface and/or intracellular molecules, characterizing and/or identifying different cell types in a heterogeneous cell population, assessing the purity of isolated subpopulations, and/or analysing cell size and volume. It allows simultaneous multi-parameter analysis of single cells.

It may particularly be used to measure fluorescence intensity produced by ligands that bind to specific cell-associated molecules, e.g., (i) fluorescent-labelled antibodies detecting proteins; or (ii) propidium iodide binding to DNA.

The staining procedure may involve making a single-cell suspension from cell culture or tissue samples. The cells may then incubated, e.g., in tubes and/or microtiter plates, with unlabelled or fluorochrome-labelled antibodies. Cells may be suspended in a stream of fluid and passed by an electronic detection apparatus.

Flow cytometers are able to analyse several thousands or particles per second. A flow cytometer comprises a flow cell in which a liquid stream carries and aligns cells so that they pass single file through a light beam for sensing. The impedance or conductivity of the cells and various optical properties of the cells may be measured.

Flow cytometry is routinely used in the diagnosis of health disorders, especially blood cancers, but has many other applications in basic research, clinical practice and clinical trials. A common variation is to physically sort particles based on their properties, so as to purify populations of interest, e.g., by fluorescence-assisted cell sorting ("FACS").

Fluorescence-activated cell sorting (FACS) is a method of sorting a heterogeneous mixture of biological cells into two or more containers, one cell at a time, based upon the specific light scattering and fluorescent characteristics of each cell. Thus, FACS allows the physical sorting of a heterogeneous mixture of cells into 2 or more different sub-populations.

As mentioned above, cells may be labelled with fluorescent labels that are specific for a particular cellular marker. If a cell population is heterogeneous for that marker only the marker-positive subpopulation of the cells will become labelled.

A FACS apparatus may then be used to sort the cells. The cell suspension is entrained in the centre of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell per droplet. Just before the stream breaks into droplets, the flow passes through a fluorescence measuring station where the fluorescent character of interest of each cell is measured. An electrical charging ring is placed just at the point where the stream breaks into droplets. A charge is placed on the ring based on the immediately prior fluorescence intensity measurement, and the opposite charge is trapped on the droplet as it breaks from the stream. The charged droplets then fall through an electrostatic deflection system that diverts droplets into containers based upon their charge. In some systems, the charge is applied directly to the stream, and the droplet breaking off retains charge of the same sign as the stream. The stream is then returned to neutral after the droplet breaks off.

Fluorescent Labelling

Optionally, a molecule on or within one or more of the cells may be labelled. The label may, e.g., be a fluorescent label.

The following table details a list of fluorochromes for immunofluorescence microscopy:

| Fluorochromes | excitation (nm) | emission (nm) |
|---|---|---|
| AMCA | 347 | 445 |
| Alexa Fluor 350 | 345 | 440 |
| Alexa Fluor 488 | 488 | 520 |
| Cy2 | 492 | 510 |
| FITC | 496 | 518 |
| Bodipy-FL | 503 | 511 |
| TRITC | 544 | 572 |
| Cy3 | 550 | 570 |
| LRSC | 572 | 590 |
| Rhodamine Red-X | 570 | 590 |
| Texas Red | 596 | 620 |
| Cy5 | 650 | 670 |
| Alexa Fluor 647 | 650 | 668 | wherein AMCA is aminomethylcoumarin acetic acid, Cy2 is cyanine, FITC is fluorescein isothiocyanate, TRITC is tetramethylrhodamine isothiocyanate, Cy3 is indocarbocyanine, LRSC is lissamine rhodamine sulfonyl chloride and Cy5 is indodicarbocyanine.

Green fluorescent protein ("GFP") is a protein composed of 238 amino acid residues (26.9 kDa) that exhibits bright green fluorescence when exposed to light in the blue to ultraviolet range. Although many other marine organisms have similar green fluorescent proteins, GFP traditionally refers to the protein first isolated from the jellyfish *Aequorea victoria*. The GFP from *A. victoria* has a major excitation peak at a wavelength of 395 nm and a minor one at 475 nm. Its emission peak is at 509 nm, which is in the lower green portion of the visible spectrum. The fluorescence quantum yield (QY) of GFP is 0.79. The GFP from the sea pansy (*Renilla reniformis*) has a single major excitation peak at 498 nm.

In cell and molecular biology, the GFP gene is frequently used as a reporter of expression. In modified forms it has been used to make biosensors, and many animals have been created that express GFP as a proof-of-concept that a gene can be expressed throughout a given organism. The GFP gene can be introduced into organisms and maintained in their genome through breeding, injection with a viral vector, or cell transformation. To date, the GFP gene has been introduced and expressed in many bacteria, yeast and other fungi, fish (such as zebrafish), plant, fly and mammalian cells, including human.

Analysis of Spectrometric Data

Any of the methods of the invention may optionally involve the analysis of spectrometric data; more particularly, the analysis of spectrometric data from a target, e.g., a first target location.

The analysis of a target may be based solely on the analysis of spectrometric data, or it may optionally involve one or more further analytical tools, details of which are discussed elsewhere herein.

In some embodiments, the spectrometric data may optionally provide direct information about the target or target entity.

For example, if a particular cell type has a specific spectrometric signal pattern, then obtaining this signal pattern from a target provides direct information about the presence, identity and/or characteristics of that cell type.

For example, if a particular microbe has a specific spectrometric signal pattern, then obtaining this signal pattern from a target provides direct information about the presence, identity and/or characteristics of that microbe.

For example, if a particular compound has a specific spectrometric signal pattern, then obtaining this signal pattern from a target provides direct information about the presence, identity and/or characteristics of that compound. This may be the case, for example, for a compound which is secreted by a cell and/or by a microbe, or for an agent, such as, a drug or a metabolite thereof.

However, in other embodiments, spectrometric data may optionally provide indirect information about the target or target entity. This may be the case, for example, for a compound which is produced, but not secreted, by a cell and/or by a microbe. The presence of this compound may optionally be detected indirectly by detecting a spectrometric signal pattern which is characteristic of a cell and/or microbe containing said compound.

Spectrometric data obtained from a target, e.g., a first target location, may optionally be compared to one or more other spectrometric data, which may conveniently be referred to herein as "reference", "control" or "comparator" spectrometric data. As explained elsewhere herein, analysing spectrometric data may optionally comprise analysing one or more sample spectra so as to classify an aerosol, smoke or vapour sample. This may comprise developing a classification model or library using one or more reference sample spectra, or may comprise using an existing library.

Optionally, an analysis may be made to determine whether spectrometric data obtained from a target matches or corresponds sufficiently to the "reference", "control" or "comparator" spectrometric data to make a positive determination.

The term "reference" spectrometric data is used herein to mean spectrometric data from a known cell type, microbe or compound. Reference spectrometric data may optionally be publicly available, or the skilled person may generate a library of reference spectrometric data. The method may optionally involve comparing the spectrometric data to one or more reference spectrometric data. If the spectrometric data obtained from a target matches or corresponds sufficiently to a reference spectrometric data, then optionally a positive determination may be made. Optionally, a positive determination may be made if the spectrometric data corresponds more closely to one library entry than any other library entry. If the spectrometric data obtained from a target does not match or correspond sufficiently to a reference spectrometric data, then optionally a negative determination may be made.

The term "comparator" spectrometric data is used herein to mean spectrometric data obtained from a second target. The first and second targets may be different cell populations, or 2 separate samples obtained from the same cell population. The method may optionally involve comparing the spectrometric data to one or more comparator spectrometric data. If the spectrometric data obtained from a target matches or corresponds sufficiently to a comparator spectrometric data, then optionally a positive determination may be made. If the spectrometric data obtained from a target does not match or correspond sufficiently to a comparator spectrometric data, then optionally a negative determination may be made.

The term "control" spectrometric data is used herein to mean spectrometric data obtained from the first target at an earlier point in time. Control spectrometric data may, for example, be used when monitoring, e.g., the growth and/or substance production by a cell culture. Any of the methods may optionally involve comparing the spectrometric data to one or more control spectrometric data. If the spectrometric data obtained from a target matches or corresponds sufficiently to a control spectrometric data, then optionally a positive determination may be made. If the spectrometric data obtained from a target does not match or correspond sufficiently to a control spectrometric data, then optionally a negative determination may be made.

By a "positive determination" is meant that the presence, identity and/or characteristics of a particular cell type, microbe and/or compound is determined. For example, a positive determination may involve determining that a target entity of a particular classification is present; that a target entity has a certain characteristic; and/or that a particular compound is present.

For example, in the case of a microbial target entity, a positive determination may, e.g., involve determining that a microbe of a particular taxonomic rank is present; that a particular microbe has a certain characteristic, such as, resistance to a particular drug; and/or that a particular compound is being produced by a microbe.

For example, in the case of a cell target entity, a positive determination may, e.g., involve determining that a cell has a particular identity; and/or that a cell has a certain characteristic, such as, that it expresses a particular biomarker.

For example, in the case of a compound target entity, a positive determination may, e.g., involve determining that a particular type of compound is present; and/or that a compound has a certain characteristic, such as, a particular glycosylation pattern.

Thus, for example, if the spectrometric data of a first sample matches or corresponds sufficiently to a reference spectrometric data, then the presence in the first sample of a target entity corresponding to the entity from which the reference spectrometric data was obtained may optionally be confirmed. If the spectrometric data of a first sample matches or corresponds sufficiently to a reference spectrometric data, then the target entity present in the first sample may optionally be identified as corresponding to the identity of the entity from which the reference spectrometric data was obtained. If the spectrometric data of a first sample matches or corresponds sufficiently to a reference spectrometric data, then the target entity present in the first sample may optionally be characterised as having a characteristic corresponding to the characteristic of the entity from which the reference spectrometric data was obtained. If the spectrometric data of a first sample matches or corresponds sufficiently to a reference spectrometric data, then a determination may optionally be made that the target entity present in the first sample produces the compound produced by the entity from which the reference spectrometric data was obtained.

As explained elsewhere herein, by determining or confirming the "identity" of a microbe or cell is meant that at least some information about the identity is obtained, which may, for example, be at any taxonomic level. Thus, for example, if the reference spectrometric data is from *Mycoplasma*, then in one embodiment a match or sufficient correspondence may optionally be used to identify the first microbe as belonging to the genus *Mycoplasma*, whereas in another embodiment a match or sufficient correspondence may optionally be used to identify the first microbe as belonging to the species *Mycoplasma genitalium*.

As another example, if the spectrometric data of a first sample matches or corresponds sufficiently to a comparator spectrometric data, then the presence in the first sample of a target entity corresponding to the entity from which the comparator spectrometric data was obtained may optionally be confirmed. If the spectrometric data of a first sample matches or corresponds sufficiently to a comparator spectrometric data, then the target entity present in the first sample may optionally be identified as corresponding to the identity of the entity from which the comparator spectrometric data was obtained. If the spectrometric data of a first sample matches or corresponds sufficiently to a comparator spectrometric data, then the target entity present in the first sample may optionally be characterised as having a characteristic corresponding to the characteristic of the entity from which the comparator spectrometric data was obtained. If the spectrometric data of a first sample matches or corresponds sufficiently to a comparator spectrometric data, then a determination may optionally be made that the target entity present in the first sample produces the compound produced by the entity from which the comparator spectrometric data was obtained.

In other words, a match or sufficient correspondence to a reference or comparator spectrometric data respectively may be used to confirm that the first target entity and the reference or comparator entity respectively have the same identity, whereas the lack of a match or sufficient correspondence to a reference or comparator spectrometric data respectively may be used to confirm that the first target entity and the reference or comparator entity respectively do not have the same identity.

By a "negative determination" is meant that the absence of a particular target entity is determined; and/or that it is determined that a target entity does not have a particular identity and/or characteristic.

For example, a negative determination may involve determining that a particular target entity is not present; that a particular target entity does not have a certain characteristic; and/or that a particular compound is not present.

For example, in the case of a microbial target entity, a negative determination may, e.g., involve determining that a microbe of a particular taxonomic rank is not present; that a particular microbe does not have a certain characteristic such as resistance to a particular drug; and/or that a particular compound is not being produced.

For example, in the case of a cell target entity, a negative determination may, e.g., involve determining that a particular cell type, e.g., a HeLa cell, is not present; and/or that a cell does not have a certain characteristic, such as, that it does not express a particular cancer marker.

For example, in the case of a compound target entity, a negative determination may, e.g., involve determining that a particular type of compound is not present; and/or that a compound does not have a certain characteristic, such as, a particular glycosylation pattern.

Thus, for example, if the spectrometric data of a first sample does not match or correspond sufficiently to a reference spectrometric data, then the absence or insufficient presence in the first sample of a target entity corresponding to the entity from which the reference spectrometric data was obtained may optionally be confirmed. If the spectrometric data of a first sample does not match or correspond sufficiently to a reference spectrometric data, then the target entity present in the first sample may optionally be identified as not corresponding to the identity of the entity from which the reference spectrometric data was obtained. If the spectrometric data of a first sample does not match or correspond sufficiently to a reference spectrometric data, then the target entity present in the first sample may optionally be characterised as not having a characteristic corresponding to the characteristic of the entity from which the reference spectrometric data was obtained. If the spectrometric data of a first sample does not match or correspond sufficiently to a reference spectrometric data, then a determination may optionally be made that the target entity present in the first sample does not produce, or insufficiently produces, the compound produced by the entity from which the reference spectrometric data was obtained.

As another example, if the spectrometric data of a first sample matches or corresponds sufficiently to a control spectrometric data, then a determination may be made that no, or no significant, change has taken place, whereas if the spectrometric data of a first sample does not match or correspond sufficiently to a control spectrometric data, then a determination may be made that a change, optionally a significant change, has taken place. Examples of a change may, for example, be the presence of a contaminating or infiltrating cell, microbe and/or compound; or a change in the cell or microbe's behaviour or its environment, such as, a change in the cell or microbe's growth rate, respiration rate; rate of production of a compound, such a secreted compound; environmental temperature, pH, nutrient availability and so on.

As mentioned elsewhere herein, the method may optionally involve the analysis of biomarkers.

If a biomarker for a target entity or disease status is known (e.g., from the prior art or from the work disclosed herein), then the method may optionally involve analysing the target for the presence of the spectrometric signal of that biomarker. The spectrometric signal of any biomarker may optionally be looked up in the literature, a database, or, if necessary, it may easily be determined experimentally.

For example, as determined herein, phosphatidylethanolamines such as PE(38:3) are a biomarker for fads2 gene expression, with a spectrometric signal of m/z about 768.5578. When analysing a cell population target to try to distinguish between cells expressing the fads2 gene and cells not expressing this gene, the method may optionally involve analysing the target for the presence of a spectrometric signal of m/z about 768.5578.

As mentioned elsewhere herein, the analyte giving rise to a particular spectrometric signal, e.g., a particular m/z, may optionally be further characterised, e.g., using MS/MS. Thus, ionic species in the mass spectra may optionally be identified based on exact mass measurements, e.g., with a mass deviation <3 ppm, and/or MS/MS fragmentation patterns. Isobaric lipids with different headgroups may optionally be differentiated by ion mobility.

Thus, optionally, the method may involve analysing the target for the presence of a spectrometric signal of one or more biomarkers, optionally selected from any of the biomarkers mentioned herein.

A biomarker for diseased cells may optionally be determined, e.g., by subtracting the spectrometric signals obtained from normal cells from the spectrometric signals obtained from diseased cells, to arrive at spectrometric signals that are specific for the diseased cells.

The spectrometric data may comprise one or more sample spectra. Obtaining the spectrometric data may comprise obtaining the one or more sample spectra. Analysing the spectrometric data may comprise analysing the one or more spectra. Obtaining the one or more sample spectra may comprise a binning process to derive a set of time-intensity pairs and/or a set of sample intensity values for the one or more sample spectra. The binning process may comprise accumulating or histogramming ion detections and/or intensity values in a set of plural bins. Each bin in the binning process may correspond to particular range of times or time-based values, such as masses, mass to charge ratios, and/or ion mobilities. The bins in the binning process may each have a width equivalent to a width in Da or Th (Da/e) in a range selected from a group consisting of: (i) < or >0.01; (ii) 0.01-0.05; (iii) 0.05-0.25; (iv) 0.25-0.5; (v) 0.5-1.0; (vi) 1.0-2.5; (vii) 2.5-5.0; and (viii) < or >5.0. It has been identified that bins having widths equivalent to widths in the range 0.01-1 Da or Th (Da/e) can provide particularly useful sample spectra for classifying some aerosol, smoke or vapour samples, such as samples obtained from tissues. The bins may or may not all have the same width. The widths of the bin in the binning process may vary according to a bin width function. The bin width function may vary with a time or time-based value, such as mass, mass to charge ratio and/or ion mobility. The bin width function may be non-linear (e.g., logarithmic-based or power-based, such as square or square-root based). The bin width function may take into account the fact that the time of flight of an ion may not be directly proportional to its mass, mass to charge ratio, and/or ion mobility. For example, the time of flight of an ion may be directly proportional to the square-root of its mass and/or mass to charge ratio.

Spectrometric Library

The terms "spectrometric library" and "spectrometric database" are used interchangeably herein.

The skilled person may use any publicly available spectrometric data as reference spectrometric data. Examples of useful databases are: LipidMaps, LipidBlast and LipidXplorer, details of which are provided in the following publications: "LipidBlast—in-silico tandem mass spectrometry database for lipid identification" by Kind et al., Nat Methods. 2013 August; 10(8): 755-758; "LipidXplorer: A Software for Consensual Cross-Platform Lipidomics" by Herzog et al. PLoS ONE 7(1): e29851; and "Lipid classification, structures and tools" by Fahy et al. Biochimica et Biophysica Acta (BBA)—Molecular and Cell Biology of Lipids, Volume 1811, Issue 11, November 2011, Pages 637-647, Lipidomics and Imaging Mass Spectrometry, see also http://www.lipidmaps.org/.

Alternatively or in addition, the skilled person may construct a spectrometric library by obtaining spectrometric data from one or more samples, which may optionally, in the case of microbes, include type culture strains and/or clinical and/or environmental microbial isolates; in the case of cells or tissues, the sample(s) may optionally include a cell line, cell culture, tissue sample and the like; in the case of compound, the sample(s) may optionally be purchased or synthesised.

Type culture strains and cell lines may optionally be obtained from culture collections, such as, the American Type Culture Collection (ATCC) (10801 University Boulevard, Manassas, Va. 20110 USA).

The present inventors generated a spectrometric library using over 1500 microbial strains, including clinical isolates and type culture strains from the ATCC, encompassing about 95 genera and about 260 species of bacteria and fungi. To expedite the generation of the spectrometric library, the inventors set up high throughput culturing, automated colony imaging, colony picking and REIMS analysis.

The present inventors have also generated spectrometric libraries using tissues and/or cell lines, details of which are provided elsewhere herein, including in the Examples.

The generation of a spectrometric library from microbes, cell lines and/or tissues may optionally be combined with a further analysis, e.g., taxonomic classification and/or histology, e.g., based on any of the further analytical tools discussed elsewhere herein. For example, the tool may be DNA analysis. This may involve DNA sequencing, optionally preceded by DNA isolation and/or amplification using, e.g., PCR. For bacteria, sequencing of all or part of the 16S rRNA gene is particularly suitable, whereas for fungi, sequencing of all or part of the internal transcribed spacer (ITS) region is particularly suitable.

Analysing Sample Spectra

The step of analysing the spectrometric data may comprise analysing one or more sample spectra so as to classify an aerosol, smoke or vapour sample.

Analysing the one or more sample spectra so as to classify the aerosol, smoke or vapour sample may comprise unsupervised analysis of the one or more sample spectra (e.g., for dimensionality reduction) and/or supervised analysis of the one or more sample spectra (e.g., for classification).

Analysing the one or more sample spectra may comprise unsupervised analysis (e.g., for dimensionality reduction) followed by supervised analysis (e.g., for classification).

Analysing the one or more sample spectra may be performed as discussed elsewhere herein.

A list of analysis techniques which are intended to fall within the scope of the present invention are given in the following table:

| Analysis Techniques |
| --- |
| Univariate Analysis |
| Multivariate Analysis |
| Principal Component Analysis (PCA) |
| Linear Discriminant Analysis (LDA) |
| Maximum Margin Criteria (MMC) |
| Library Based Analysis |
| Soft Independent Modelling Of Class Analogy (SIMCA) |
| Factor Analysis (FA) |
| Recursive Partitioning (Decision Trees) |
| Random Forests |
| Independent Component Analysis (ICA) |
| Partial Least Squares Discriminant Analysis (PLS-DA) |
| Orthogonal (Partial Least Squares) Projections To Latent Structures (OPLS) |
| OPLS Discriminant Analysis (OPLS-DA) |
| Support Vector Machines (SVM) |
| (Artificial) Neural Networks |
| Multilayer Perceptron |
| Radial Basis Function (RBF) Networks |
| Bayesian Analysis |
| Cluster Analysis |
| Kernelized Methods |
| Subspace Discriminant Analysis |
| K-Nearest Neighbours (KNN) |
| Quadratic Discriminant Analysis (QDA) |
| Probabilistic Principal Component Analysis (PPCA) |
| Non negative matrix factorisation |
| K-means factorisation |
| Fuzzy c-means factorisation |
| Discriminant Analysis (DA) |

Combinations of the foregoing analysis approaches can also be used, such as PCA-LDA, PCA-MMC, PLS-LDA, etc.

Analysing the sample spectra can comprise unsupervised analysis for dimensionality reduction followed by supervised analysis for classification.

By way of example, a number of different analysis techniques will now be described in more detail.

Multivariate Analysis—Developing a Model for Classification

By way of example, a method of building a classification model using multivariate analysis of plural reference sample spectra will now be described.

Figure 15:
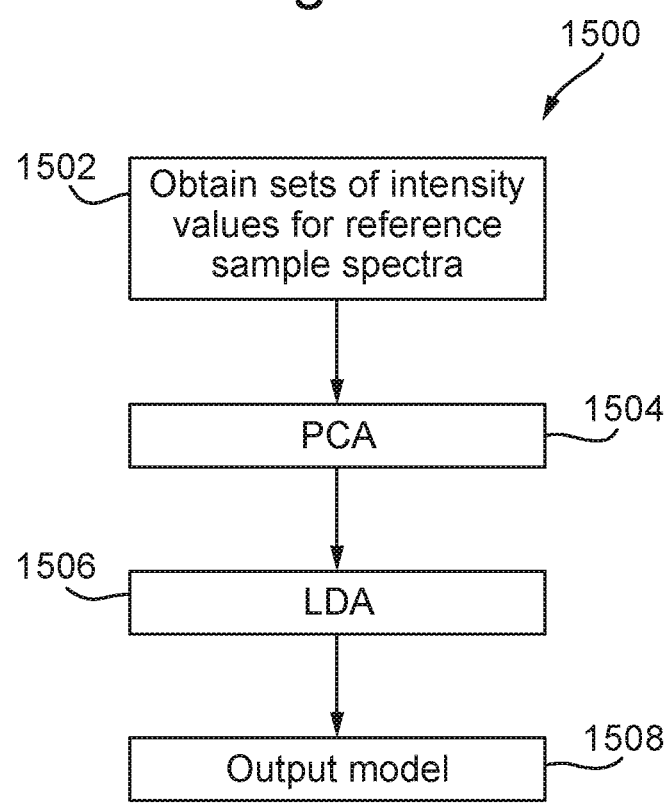
FIG. 15 shows a method of analysis that comprises building a classification model according to various embodiments.

FIG. 15 shows a method 1500 of building a classification model using multivariate analysis. In this example, the method comprises a step 1502 of obtaining plural sets of intensity values for reference sample spectra. The method then comprises a step 1504 of unsupervised principal component analysis (PCA) followed by a step 1506 of supervised linear discriminant analysis (LDA). This approach may be referred to herein as PCA-LDA. Other multivariate analysis approaches may be used, such as PCA-MMC. The PCA-LDA model is then output, for example to storage, in step 1508.

The multivariate analysis such as this can provide a classification model that allows an aerosol, smoke or vapour sample to be classified using one or more sample spectra obtained from the aerosol, smoke or vapour sample. The multivariate analysis will now be described in more detail with reference to a simple example.

Figure 16:
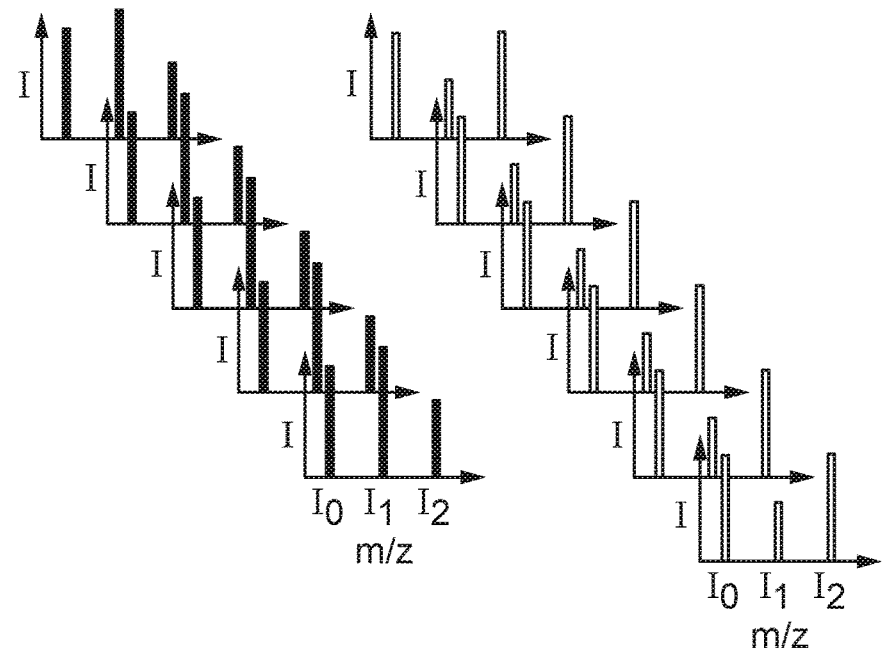
FIG. 16 shows a set of reference sample spectra obtained from two classes of known reference samples.

FIG. 16 shows a set of reference sample spectra obtained from two classes of known reference samples. The classes may be any one or more of the classes of target described herein. However, for simplicity, in this example the two classes will be referred as a left-hand class and a right-hand class.

Each of the reference sample spectra has been pre-processed in order to derive a set of three reference peak-intensity values for respective mass to charge ratios in that reference sample spectrum. Although only three reference peak-intensity values are shown, it will be appreciated that many more reference peak-intensity values (e.g., ~100 reference peak-intensity values) may be derived for a corresponding number of mass to charge ratios in each of the reference sample spectra. In other embodiments, the reference peak-intensity values may correspond to: masses; mass to charge ratios; ion mobilities (drift times); and/or operational parameters.

Figure 17:
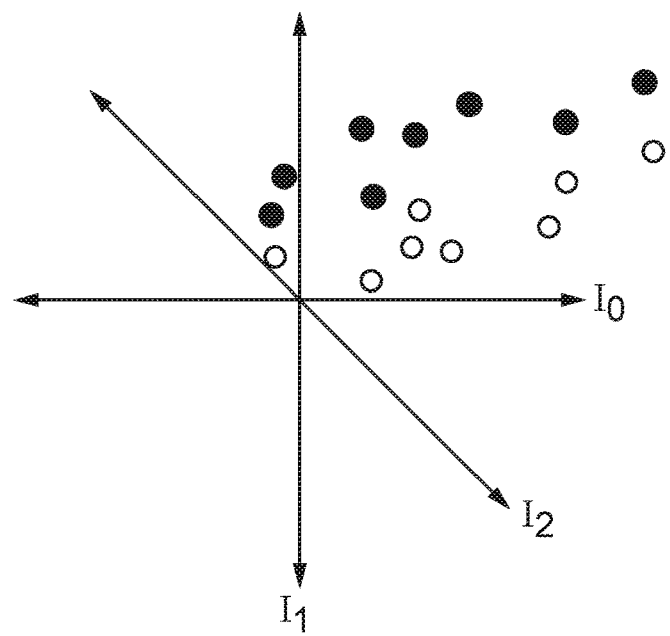
FIG. 17 shows a multivariate space having three dimensions defined by intensity axes, wherein the multivariate space comprises plural reference points, each reference point corresponding to a set of three peak intensity values derived from a reference sample spectrum.

FIG. 17 shows a multivariate space having three dimensions defined by intensity axes. Each of the dimensions or intensity axes corresponds to the peak-intensity at a particular mass to charge ratio. Again, it will be appreciated that there may be many more dimensions or intensity axes (e.g., ~100 dimensions or intensity axes) in the multivariate space. The multivariate space comprises plural reference points, with each reference point corresponding to a reference sample spectrum, i.e., the peak-intensity values of each reference sample spectrum provide the co-ordinates for the reference points in the multivariate space.

The set of reference sample spectra may be represented by a reference matrix D having rows associated with respective reference sample spectra, columns associated with respective mass to charge ratios, and the elements of the matrix being the peak-intensity values for the respective mass to charge ratios of the respective reference sample spectra.

In many cases, the large number of dimensions in the multivariate space and matrix D can make it difficult to group the reference sample spectra into classes. PCA may accordingly be carried out on the matrix D in order to calculate a PCA model that defines a PCA space having a reduced number of one or more dimensions defined by principal component axes. The principal components may be selected to be those that comprise or "explain" the largest variance in the matrix D and that cumulatively explain a threshold amount of the variance in the matrix D.

Figure 18:
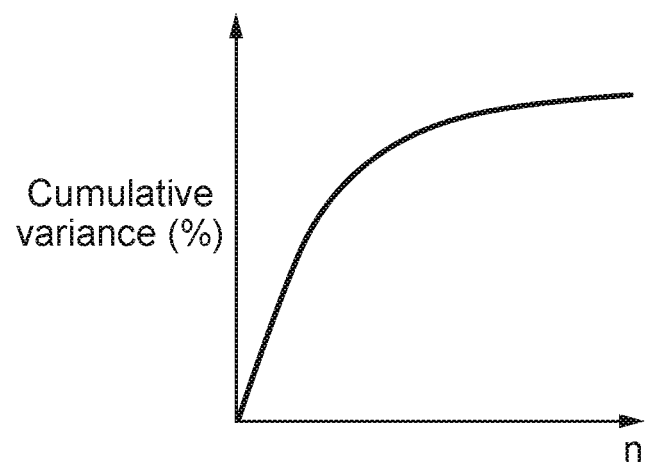
FIG. 18 shows a general relationship between cumulative variance and number of components of a PCA model.

FIG. 18 shows how the cumulative variance may increase as a function of the number n of principal components in the PCA model. The threshold amount of the variance may be selected as desired.

The PCA model may be calculated from the matrix D using a non-linear iterative partial least squares (NIPALS) algorithm or singular value decomposition, the details of which are known to the skilled person and so will not be described herein in detail. Other methods of calculating the PCA model may be used.

The resultant PCA model may be defined by a PCA scores matrix S and a PCA loadings matrix L. The PCA may also produce an error matrix E, which contains the variance not explained by the PCA model. The relationship between D, S, L and E may be:

$$D = SL^T + E \qquad (1)$$

Figure 19:
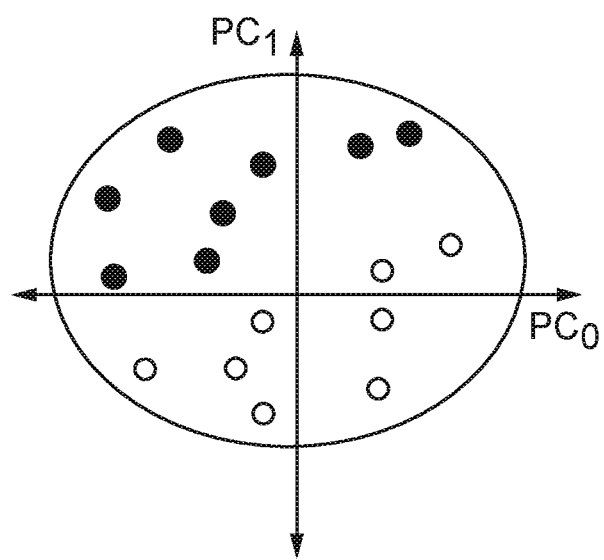
FIG. 19 shows a PCA space having two dimensions defined by principal component axes, wherein the PCA space comprises plural transformed reference points or scores, each transformed reference point or score corresponding to a reference point of FIG. 17.

FIG. 19 shows the resultant PCA space for the reference sample spectra of FIGS. 16 and 17. In this example, the PCA model has two principal components $PC_0$ and $PC_1$ and the PCA space therefore has two dimensions defined by two principal component axes. However, a lesser or greater number of principal components may be included in the PCA model as desired. It is generally desired that the number of principal components is at least one less than the number of dimensions in the multivariate space.

The PCA space comprises plural transformed reference points or PCA scores, with each transformed reference point or PCA score corresponding to a reference sample spectrum of FIG. 16 and therefore to a reference point of FIG. 17.

As is shown in FIG. 19, the reduced dimensionality of the PCA space makes it easier to group the reference sample spectra into the two classes. Any outliers may also be identified and removed from the classification model at this stage.

Further supervised multivariate analysis, such as multi-class LDA or maximum margin criteria (MMC), in the PCA space may then be performed so as to define classes and, optionally, further reduce the dimensionality.

As will be appreciated by the skilled person, multi-class LDA seeks to maximise the ratio of the variance between classes to the variance within classes (i.e., so as to give the largest possible distance between the most compact classes possible). The details of LDA are known to the skilled person and so will not be described herein in detail.

The resultant PCA-LDA model may be defined by a transformation matrix U, which may be derived from the PCA scores matrix S and class assignments for each of the transformed spectra contained therein by solving a generalised eigenvalue problem.

The transformation of the scores S from the original PCA space into the new LDA space may then be given by:

$$Z=SU \quad (2)$$

where the matrix Z contains the scores transformed into the LDA space.

Figure 20:
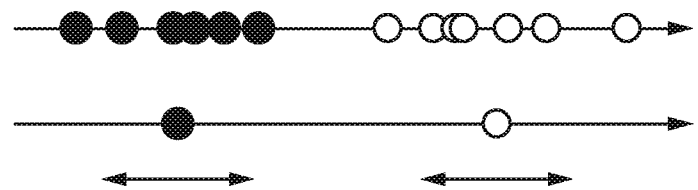
FIG. 20 shows a PCA-LDA space having a single dimension or axis, wherein the LDA is performed based on the PCA space of FIG. 19, the PCA-LDA space comprising plural further transformed reference points or class scores, each further transformed reference point or class score corresponding to a transformed reference point or score of FIG. 19.

FIG. 20 shows a PCA-LDA space having a single dimension or axis, wherein the LDA is performed in the PCA space of FIG. 19. As is shown in FIG. 20, the LDA space comprises plural further transformed reference points or PCA-LDA scores, with each further transformed reference point corresponding to a transformed reference point or PCA score of FIG. 19.

In this example, the further reduced dimensionality of the PCA-LDA space makes it even easier to group the reference sample spectra into the two classes. Each class in the PCA-LDA model may be defined by its transformed class average and covariance matrix or one or more hyperplanes (including points, lines, planes or higher order hyperplanes) or hypersurfaces or Voronoi cells in the PCA-LDA space.

The PCA loadings matrix L, the LDA matrix U and transformed class averages and covariance matrices or hyperplanes or hypersurfaces or Voronoi cells may be output to a database for later use in classifying an aerosol, smoke or vapour sample.

The transformed covariance matrix in the LDA space $V'_g$ for class g may be given by $$V'_g = U^T V_g U \quad (3)$$

where $V_g$ are the class covariance matrices in the PCA space.

The transformed class average position $z_g$ for class g may be given by $$s_g U = z_g \quad (4)$$

where $s_g$ is the class average position in the PCA space.

Multivariate Analysis—Using a Model for Classification

By way of example, a method of using a classification model to classify an aerosol, smoke or vapour sample will now be described.

Figure 21:
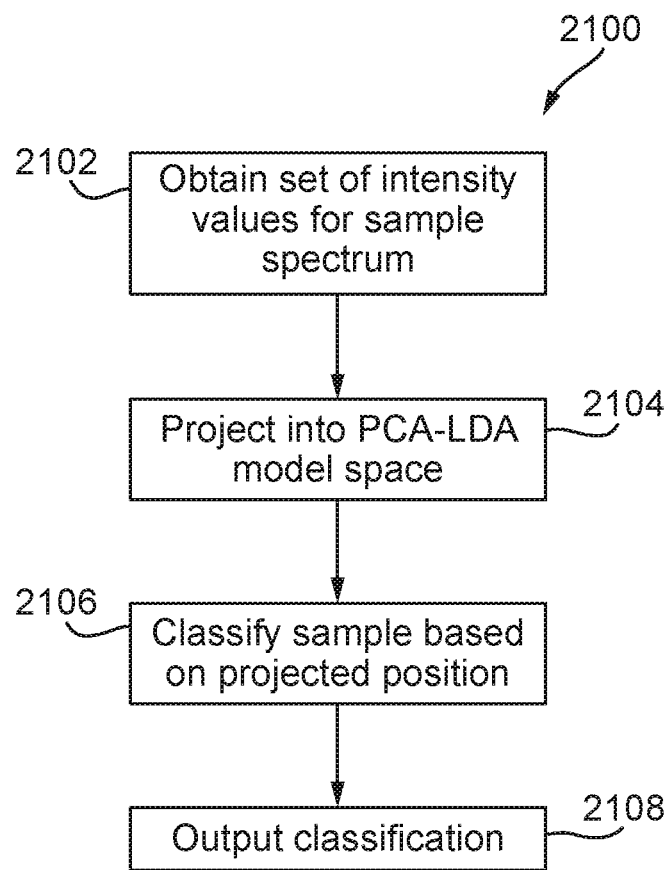
FIG. 21 shows a method of analysis that comprises using a classification model according to various embodiments.

FIG. 21 shows a method 2100 of using a classification model. In this example, the method comprises a step 2102 of obtaining a set of intensity values for a sample spectrum. The method then comprises a step 2104 of projecting the set of intensity values for the sample spectrum into PCA-LDA model space. Other classification model spaces may be used, such as PCA-MMC. The sample spectrum is then classified at step 2106 based on the project position and the classification is then output in step 2108.

Classification of an aerosol, smoke or vapour sample will now be described in more detail with reference to the simple PCA-LDA model described above.

Figure 22:
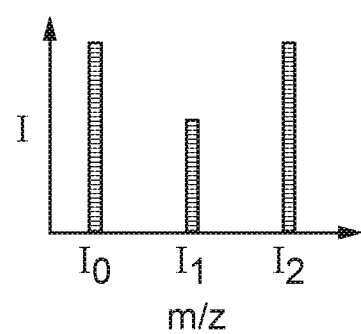
FIG. 22 shows a sample spectrum obtained from an unknown sample.

FIG. 22 shows a sample spectrum obtained from an unknown aerosol, smoke or vapour sample. The sample spectrum has been pre-processed in order to derive a set of three sample peak-intensity values for respective mass to charge ratios. As mentioned above, although only three sample peak-intensity values are shown, it will be appreciated that many more sample peak-intensity values (e.g., ~100 sample peak-intensity values) may be derived at many more corresponding mass to charge ratios for the sample spectrum. Also, as mentioned above, in other embodiments, the sample peak-intensity values may correspond to: masses; mass to charge ratios; ion mobilities (drift times); and/or operational parameters.

The sample spectrum may be represented by a sample vector $d_x$, with the elements of the vector being the peak-intensity values for the respective mass to charge ratios. A transformed PCA vector $s_x$ for the sample spectrum can be obtained as follows:

$$d_x L = s_x \quad (5)$$

Then, a transformed PCA-LDA vector $z_x$ for the sample spectrum can be obtained as follows:

$$s_x U = z_x \quad (6)$$

FIG. 23 again shows the PCA-LDA space of FIG. 20. However, the PCA-LDA space of FIG. 23 further comprises the projected sample point, corresponding to the transformed PCA-LDA vector z, derived from the peak intensity values of the sample spectrum of FIG. 22.

In this example, the projected sample point is to one side of a hyperplane between the classes that relates to the right-hand class, and so the aerosol, smoke or vapour sample may be classified as belonging to the right-hand class.

Alternatively, the Mahalanobis distance from the class centres in the LDA space may be used, where the Mahalanobis distance of the point $z_x$ from the centre of class g may be given by the square root of:

$$(z_x - z_g)^T (V'_g)(z_x - z_g) \quad (8)$$

and the data vector $d_x$ may be assigned to the class for which this distance is smallest.

In addition, treating each class as a multivariate Gaussian, a probability of membership of the data vector to each class may be calculated.

Library Based Analysis—Developing a Library for Classification

By way of example, a method of building a classification library using plural input reference sample spectra will now be described.

Figure 24:
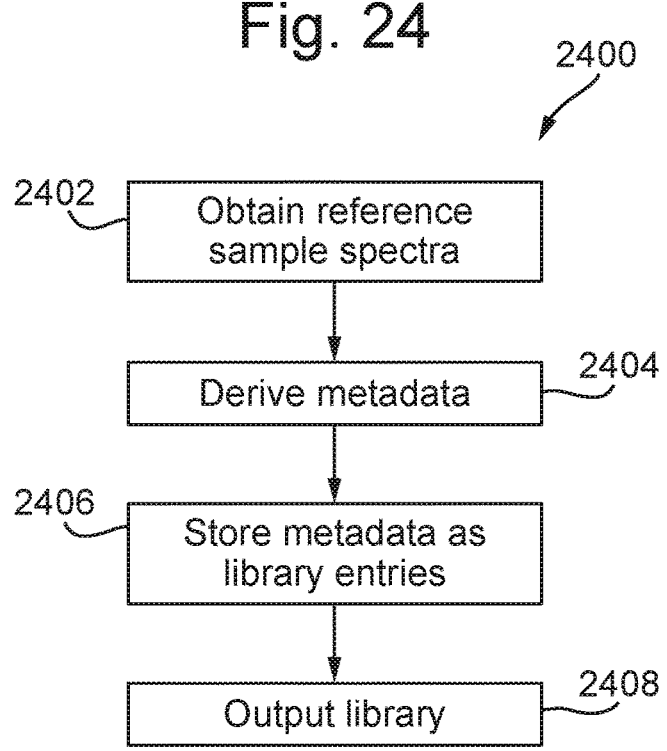
FIG. 24 shows a method of analysis that comprises building a classification library according to various embodiments.

FIG. 24 shows a method 2400 of building a classification library. In this example, the method comprises a step 2402 of obtaining plural input reference sample spectra and a step 2404 of deriving metadata from the plural input reference sample spectra for each class of sample. The method then comprises a step 2406 of storing the metadata for each class of sample as a separate library entry. The classification library is then output, for example to electronic storage, in step 2408.

A classification library such as this allows an aerosol, smoke or vapour sample to be classified using one or more sample spectra obtained from the aerosol, smoke or vapour sample. The library based analysis will now be described in more detail with reference to an example.

In this example, each entry in the classification library is created from plural pre-processed reference sample spectra that are representative of a class. In this example, the reference sample spectra for a class are pre-processed according to the following procedure: First, a re-binning process is performed. In this embodiment, the data are resampled onto a logarithmic grid with abscissae:

$$x_i = \left\lfloor N_{chan} \log \frac{m}{M_{min}} \bigg/ \log \frac{M_{max}}{M_{min}} \right\rfloor$$

where $N_{chan}$ is a selected value and [x] denotes the nearest integer below x. In one example, $N_{chan}$ is $2^{12}$ or 4096.

Then, a background subtraction process is performed. In this embodiment, a cubic spline with k knots is then constructed such that p % of the data between each pair of knots lies below the curve. This curve is then subtracted from the data. In one example, k is 32. In one example, p is 5. A constant value corresponding to the q % quantile of the intensity subtracted data is then subtracted from each intensity. Positive and negative values are retained. In one example, q is 45.

Then, a normalisation process is performed. In this embodiment, the data are normalised to have mean $\bar{y}_i$. In one example, $\bar{y}_i = 1$.

An entry in the library then consists of metadata in the form of a median spectrum value $\mu_i$ and a deviation value $D_i$ for each of the $N_{chan}$ points in the spectrum.

The likelihood for the i'th channel is given by:

$$Pr(y_i | \mu_i, D_i) = \frac{1}{D_i} \frac{C^{C-1/2} \Gamma(C)}{\sqrt{\pi} \, \Gamma(C-1/2)} \frac{1}{\left(C + \frac{(y_i - \mu_i)^2}{D_i^2}\right)^c}$$

where $\frac{1}{2} \leq C < \infty$ and where $\Gamma(C)$ is the gamma function.

The above equation is a generalised Cauchy distribution which reduces to a standard Cauchy distribution for C=1 and becomes a Gaussian (normal) distribution as $C \to \infty$. The parameter $D_i$ controls the width of the distribution (in the Gaussian limit $D_i = \sigma_i$ is simply the standard deviation) while the global value C controls the size of the tails.

In one example, C is 3/2, which lies between Cauchy and Gaussian, so that the likelihood becomes:

$$Pr(y_i | \mu_i, D_i) = \frac{3}{4} \frac{1}{D_i} \frac{1}{(3/2 + (y_i - \mu_i)^2 / D_i^2)^{3/2}}$$

For each library entry, the parameters $\mu_i$ are set to the median of the list of values in the i'th channel of the input reference sample spectra while the deviation $D_i$ is taken to be the interquartile range of these values divided by $\sqrt{2}$. This choice can ensure that the likelihood for the i'th channel has the same interquartile range as the input data, with the use of quantiles providing some protection against outlying data.

Library-Based Analysis—Using a Library for Classification

By way of example, a method of using a classification library to classify an aerosol, smoke or vapour sample will now be described.

Figure 25:
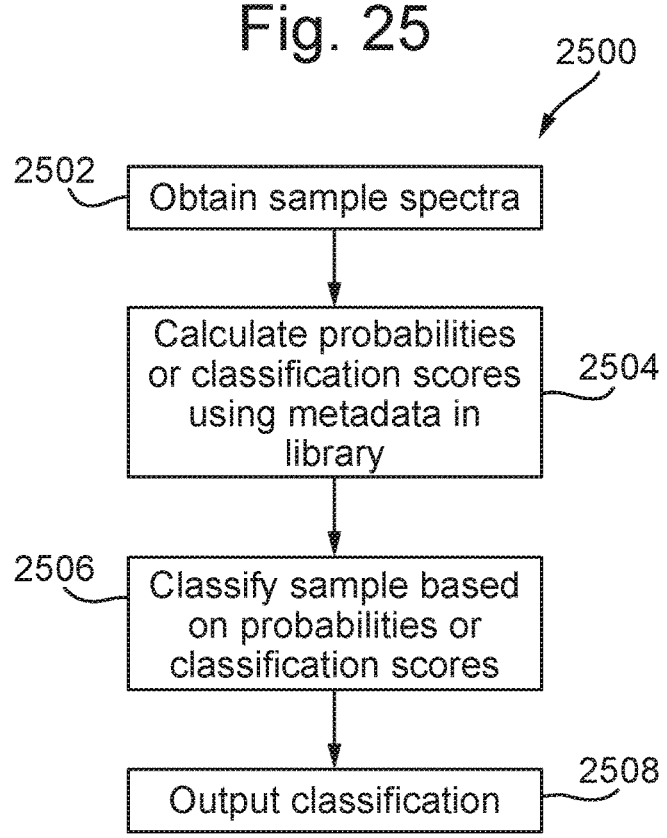
FIG. 25 shows a method of analysis that comprises using a classification library according to various embodiments.

FIG. 25 shows a method 2500 of using a classification library. In this example, the method comprises a step 2502 of obtaining a set of plural sample spectra. The method then comprises a step 2504 of calculating a probability or classification score for the set of plural sample spectra for each class of sample using metadata for the class entry in the classification library. The sample spectra are then classified at step 2506 and the classification is then output in step 2508.

Classification of an aerosol, smoke or vapour sample will now be described in more detail with reference to the classification library described above.

In this example, an unknown sample spectrum y is the median spectrum of a set of plural sample spectra. Taking the median spectrum y can protect against outlying data on a channel by channel basis.

The likelihood $L_s$ for the input data given the library entry s is then given by:

$$L_s = Pr(y | \mu, D) = \prod_{i=1}^{N_{chan}} Pr(y_i | \mu_i, D_i)$$

where $\mu_i$ and $D_i$ are, respectively, the library median values and deviation values for channel i. The likelihoods $L_s$ may be calculated as log likelihoods for numerical safety.

The likelihoods $L_s$ are then normalised over all candidate classes 's' to give probabilities, assuming a uniform prior probability over the classes. The resulting probability for the class s is given by:

$$Pr(s | y) = \frac{L_s^{(1/F)}}{\sum_s L_s^{(1/F)}}$$

The exponent (1/F) can soften the probabilities which may otherwise be too definitive. In one example, F=100. These probabilities may be expressed as percentages, e.g., in a user interface.

Alternatively, RMS classification scores $R_s$ may be calculated using the same median sample values and derivation values from the library:

$$R_s(y, \mu, D) = \sqrt{\frac{1}{N_{chan}} \sum_{i=1}^{N_{chan}} \frac{(y_i - \mu_i)^2}{D_i^2}}$$

Again, the scores $R_s$ are normalised over all candidate classes 's'.

The aerosol, smoke or vapour sample may then be classified as belonging to the class having the highest probability and/or highest RMS classification score.

Further Analytical Tools

Any of the methods of the invention may optionally include a step of using one or more additional analytical tools. Such a tool may, for example, be selected from microscopic examination; nucleic acid analysis, for example, using restriction enzymes, hybridisation, polymerase chain reaction (PCR) amplification and/or sequencing; and/or testing for antigens. Such tools are well known in the art, but brief details are provided below.

The specimen may be examined visually, without any additional aids, such as, a microscope.

Microscopic examination may, for example, optionally be light microscopy and/or electron microscopy.

Nucleic acid analysis may optionally involve isolation and purification of DNA and/or RNA.

Nucleic acid analysis via PCR amplification may, for example, optionally involve amplification of all or part of a suitable gene. For example, in the case of a microbe, the gene may be the bacterial 16S rRNA gene, and universal and/or species-specific primers may be used. Other examples of suitable microbial genes which may optionally be analysed alternatively or in addition include, for example, microbial species-specific genes or virulence genes, for example, Shiga toxin (stx), intimin (eae), flagellar H-antigen genes fliC-fliA, hsp65, rpoB and/or recA. For fungi, PCR amplification of all or part of the internal transcribed spacer (ITS) is particularly suitable. When analysing human or animal cells, PCR may, e.g., be used to amplify a disease-specific and/or a tissue-specific gene.

Optionally, the PCR may be Real-time PCR or quantitative PCR. Optionally, Reverse-transcriptase polymerase chain reaction (RT-PCR) may be used to analyse RNA expression.

Nucleic acid analysis with restriction enzymes may, for example, optionally involve restriction-fragment length polymorphism (RFLP) analysis. RFLP, is a technique that exploits variations in the length of homologous DNA sequences. RFLP analysis may involve a restriction digest, i.e. incubating a DNA with a suitable restriction enzyme such as BamHI, HindIII or EcoRI. Each restriction enzyme can recognise and cut a specific short nucleic acid sequence. The resulting DNA fragments may then be separated by length, for example, through agarose gel electrophoresis. The DNA fragments in the gel may optionally be stained, for example, with ethidium bromide, and the pattern of the fragments of different length may be determined.

Optionally, the DNA fragment may be transferred to a membrane via the Southern blot procedure. The membrane may then be exposed to a labelled DNA probe to allow hybridisation to occur. The label may, for example, be or comprise a radioactive isotope or digoxigenin (DIG). Any unhybridised probe may then be washed off. The label may then be detected and the pattern of the fragments which have hybridised to the labelled probe may be determined.

Sequencing may, for example, optionally involve the dideoxy or chain termination method. In this method, the DNA may be used as a template to generate a set of fragments that differ in length from each other by a single base. The fragments may then be separated by size, and the bases at the end may be identified, recreating the original sequence of the DNA.

Hybridisation analysis may, for example, optionally include DNA-DNA hybridization of one or more selected DNA fragments, genes or whole genomic DNA from a first cell or microbe to a labelled DNA probe to determine the genetic similarity between the first cell or microbe and the known or comparator cell or microbe. Hybridisation analysis may, for example, involve transfer of the DNA to a membrane via the Southern blot procedure, labelling and detection as described above.

Nucleic acid analysis may optionally involve e.g., denaturing gradient gel electrophoresis (DGGE) and/or temperature gradient gel electrophoresis (TGGE).

Fatty acid profiling of cells or microbes may, for example, optionally be carried out using gas-chromatography coupled to a flame ionisation detector (GC-FID), or high performance liquid chromatography (HPLC).

With respect to microbial colony morphology, one or more of the following may, for example, optionally be examined: size; whole colony shape, which may, for example, be circular, irregular, or rhizoid; colony edge, which may, for example, be smooth, filamentous, or undulating; elevation, which may, for example, be flat, raised, convex or crateriform; surface, which may, for example, be wrinkled, rough, waxy, or glistening; opacity, which may, for example, be transparent, translucent, or opaque; pigmentation; colour, which may, for example, be red, yellow, or white; and/or water solubility.

With respect to the morphology of individual microbes, this may, for example, optionally be determined to be a *coccus* (spherical), *bacillus* (rod-shaped), spiral (twisted), or pleomorphic. Cocci may optionally be a single coccus, diplococcic, streptococci, tetrads, sarcinae or staphylococci. Bacilli may optionally be a single *bacillus*, diplobacilli, streptobacilli or coccobacilli. Spirals may optionally be vibrio, spirilla or Spirochetes.

With respect to the morphology of mammalial cells, this may, for example, optionally be determined to be fibroblastic, epithelial-like, lymphoblast-like, and/or neuronal, with or without an axon.

Culture-based screening for nutrient requirements may optionally involve inoculating cells or microbes onto on into one or more different growth media, such as different selective media, and observing in/on which media cell or microbial growth occurs, and to what extent the growth differs between different media.

Culture-based screening for antimicrobial sensitivity may optionally involve inoculating microbes onto one or more different growth media, which may be done, for example, by streaking or plating the microbes onto a petri dish containing a suitable nutrient agar. An antimicrobial agent may then be added, which may be done, for example, by placing a filter paper disk impregnated with the antimicrobial onto the growth medium. Several disks each containing a different antimicrobial agent may be added onto a single petri dish. A determination may then be made as to whether a zone of growth inhibition occurs around any of the disk(s), and, if so, how large this zone is.

Immunohistochemical analysis may involve contacting the cells with one or more labelled agents, such as antibodies. Thus, the presence of specific antigens, particularly on the cell surface of a cell or microbe, may optionally be tested for by using specific antibodies. Testing for antigens may also be referred to as serotyping. The antibodies may be polyclonal or monoclonal. If the antibodies are specific for a particular cell type, then the number of cells of that type may be assessed. The test may optionally involve simply detecting the presence or absence of agglutination, i.e. the formation of complexes of cells/microbes and antibodies. Alternatively or in addition, the antibodies may be labelled and the assay may involve, for example, an enzyme-linked immunosorbent assay ("ELISA") and/or fluorescence activated cell sorting ("FACS").

The antibody may optionally be selected from e.g., a CD3 or CD8 antibody.

Flow cytometry may optionally be used to analyse the properties of cells or microbes in a sample or specimen, e.g., the number of cells/microbes, percentage of live cells/microbes, cell/microbe size, cell/microbe shape, and/or the presence of particular antigens on the cell/microbe surface.

Western blot hybridization may optionally be used to analyse proteins and/or peptides.

Optionally, in situ hybridization of labelled probes to tissues, microbes and/or cells may be performed, optionally using an array format. The method may be Fluorescence in situ hybridization (FISH), which may, e.g., be used to analyse chromosomal abnormalities and/or to map genes.

Analysis of Medium Derived from a Cell Population

Optionally, medium derived from a cell population may be analysed. Thus, there is provided a method of analysis using mass spectrometry and/or ion mobility spectrometry comprising:

(a) using a first device to generate smoke, aerosol or vapour from a target culture medium derived from an in vitro or ex vivo cell population;

(b) mass analysing and/or ion mobility analysing said smoke, aerosol or vapour, or ions derived therefrom, in order to obtain spectrometric data; and (c) analysing said spectrometric data in order to identify and/or characterise one or more compounds present in said target culture medium.

Such a method may, e.g., provide information about the compounds present in the culture medium, which may optionally in turn provide information about the cell population from which the culture medium was derived. Any of the information provided herein with respect to a cell population and the analysis thereof applies mutatis mutandis to the method of analysing a culture medium derived from a cell population.

Shotgun Lipidomic Characterization of the NCI-60 Cell Line Panel Using Rapid Evaporative Ionization Mass Spectrometry A methodological background was established for fundamental studies aimed at the exploration of the molecular background of REIMS-based tissue identification. Furthermore, comprehensive shotgun lipidomics data on the NCI-60 cell line collection was also obtained.

According to an embodiment Rapid Evaporative Ionization Mass Spectrometry (REIMS) may be applied to the shotgun lipidomic fingerprinting of cancer cell lines. Experimental data relating to various embodiments and details of the experimental scheme are presented below.

According to an embodiment spectral reproducibility was assessed for a set of three different cell lines.

The NCI-60 cell line panel was then subjected to REIMS analysis and the resulting dataset was investigated for its distinction of different tissue types of origin and the correlation with publicly available gene and protein expression profiles. Significant correlations between REIMS spectral features and gene expression profiles were identified and are exemplified in case of fads2 and ugcg genes.

REIMS is an attractive means to study cell lines as it involves minimal sample preparation and analysis times in the range of several seconds.

Culturing of Cell Lines

Cells were cultured in RPMI 1640 medium, with the exception of HEK and HeLa cells in the *Mycoplasma* study which were cultured in Gibco DMEM medium (Invitrogen, Carlsbad, Calif., USA). In all cases, media were supplemented with 10% (v/v) fetal bovine serum and with 2 mM glutamine, 100 units/mL penicillin, and 100 mg/mL streptomycin (Invitrogen-Gibco, Carlsbad, Calif., USA). Cells were incubated in 75 cm$^2$ tissue culture flasks at 37° C. under conditions of humidified 37° C., 5% carbon dioxide atmosphere. Cell lines were regularly screened for *mycoplasma* contamination using the MycoAlert™ *Mycoplasma* Detection Kit (Lonza Group Ltd, Basel Switzerland). At 80%-90% confluence in 75 cm$^2$ tissue culture flasks, cells were rinsed with Phosphate Buffered Saline (PBS, pH: 7.2) solution, and were detached using 0.1% trypsin/EDTA for 10 minutes. The trypsin was subsequently neutralized with excess culture medium (RPMI). The cell suspension was centrifuged at 250×g for five minutes. After centrifugation the cells were re-suspended and washed two times in 10 mL PBS. A third wash was performed in an Eppendorf tube with only 1 mL PBS. The cell pellets were frozen and stored at −80° C. until further analysis.

*Mycoplasma* Infection and Treatment

*Mycoplasma*-infected HEK and HeLa cell lines were treated with 25 μg/mL Plasmocin™ *Mycoplasma* Elimination Reagent (InvivoGen, San Diego, Calif., USA) for 14 days.

REIMS Analysis

For REIMS analysis, two handheld electrodes in the form of a forceps were used as the sampling probe (irrigated bipolar forceps, obtained from Erbe Elektromedizin, Tübingen, Germany). A Valleylab Force EZc power-controlled electrosurgical unit (Covidien, Dublin, Ireland) was used at 60 W power setting in bipolar mode as radiofrequency alternating current power supply (470 kHz, sinusoidal). An approximately 1.5 m long ⅛ inch outer diameter, ¹⁄₁₆ inch inner diameter PTFE tubing (Fluidflon PTFE tubing; LIQ-UID-scan GmbH Co. KG, Überlingen, Germany) was employed to connect the embedded fluid transfer line of the bipolar forceps with the inlet capillary of a mass spectrometer. The inherent vacuum system of the mass spectrometer was used for aspiration of the analyte-containing aerosol created during analysis. This setup is shown in FIGS. 1A-1C.

As shown in FIGS. 1A-1C a sample may be provided in the form of a cell pellet 101 in an Eppendorf tube. A sampling probe 102 may be used to sample the cell pellet 101. The sampling probe 102 may be energized by a RF power supply 103. Application of a RF voltage to the sampling probe 102 results in the generation of an aerosol which is transmitted via transfer tubing 104 to the inlet 105 of a mass spectrometer.

The particular instrumental settings which were used are given in the table below:

| Parameter | Setting |
| --- | --- |
| Injection time | 1000 ms |
| Microscans | 1 |
| Ion mode | negative |
| Mass range | 150-2000 |
| Tube Lens Voltage | −160 V |
| Capillary Voltage | −50 V |
| Skimmer Voltage | −24 V |
| Capillary Temperature | 250° C |
| Automatic Gain Control | On |
| AGC Target | High dynamic range |
| Resolution | 50,000 at m/z 200 |

Mass spectrometric analysis of the cell line biomass was performed directly on a thawed cell pellet without further sample pre-processing steps. 0.1-1.5 mg of cell biomass was taken up between the tips of the forceps and the two electrodes were subsequently brought into close proximity (i.e. by pinching the biomass between the tips of the forceps). The RF power supply was triggered using a foot switch. The cell line biomass is rapidly heated up due to its non-zero impedance and an aerosol containing charged molecular species of the analytes is produced and transferred directly into the mass spectrometer. Multiple technical replicates were recorded for each cell line.

Data Analysis

Raw mass spectrometric files were converted into mzML format using the MSConvert tool (part of the ProteoWizard 3.0.4043 suite) and subsequently imported as imzML format into MATLAB (Mathworks, Natick, Mass.; http://www.mathworks.co.uk/) for data pre-processing. All REIMS spectra were linearly interpolated to a common sampling interval of 0.01 Da. Recursive segment wise peak alignment was then used to remove small mass shifts in peak positions across spectral profiles. The aligned data were subjected to total ion count (TIC) data normalization and log-based transformation. Pattern recognition analysis and visualization were performed either in Matlab or in RStudio (Boston, Mass., USA, see also www.r-project.com). The mass range of m/z 150-1000 was used for data analysis. For self-identity experiments, the data set was filtered to keep a reduced set of m/z values: a m/z value was kept, if the difference between the available samples were significantly different at alpha=0.01 threshold level based on the Kruskal-Wallis test.

Ionic species in the mass spectra were identified based on exact mass measurements (mass deviation <3 ppm) and MS/MS fragmentation patterns.

Spectral Content

Spectral content comprises fatty acids and all glycerophospholipid species undergoing ionization in negative ion mode, including phosphatidic acids (PAs), phosphatidylethanolamines (PEs), phosphatidylglycerols (PGs), phosphatidylserines (PSs), phosphatidylinositols (PIs) in agreement with earlier REIMS studies performed on bulk tissue samples. All observed ions displayed a single negative charge, the vast majority by forming the quasi-molecular [M-H]- ion. In addition, [M-NH3—H]- was observed in case of PEs. Various ceramide, glycosylated ceramide, diglyceride and triglyceride species were detected as [M+Cl]- ions.

Reproducibility Dataset

For each cross-validation run, a principal component analysis (PCA) transformation of the training data set with pre-determined number of principal components (PCs) was calculated in R and a prediction score was calculated for each test sample using the 3 nearest neighbor (3-NN) method. The training data in the 'reproducibility set' was selected as follows: for each measurement day, a cell line with defined passage (p) and flask number (A/B) was kept as part of the training data (e.g., HeLa p4 A) if samples were available from at least two different biological replicates (i.e. A1-3). Such sets from each of the three cell lines were combined randomly to produce balanced training data where each cell line is represented by similar number of samples. All of the remaining samples constituted the test set.

Figure 2:
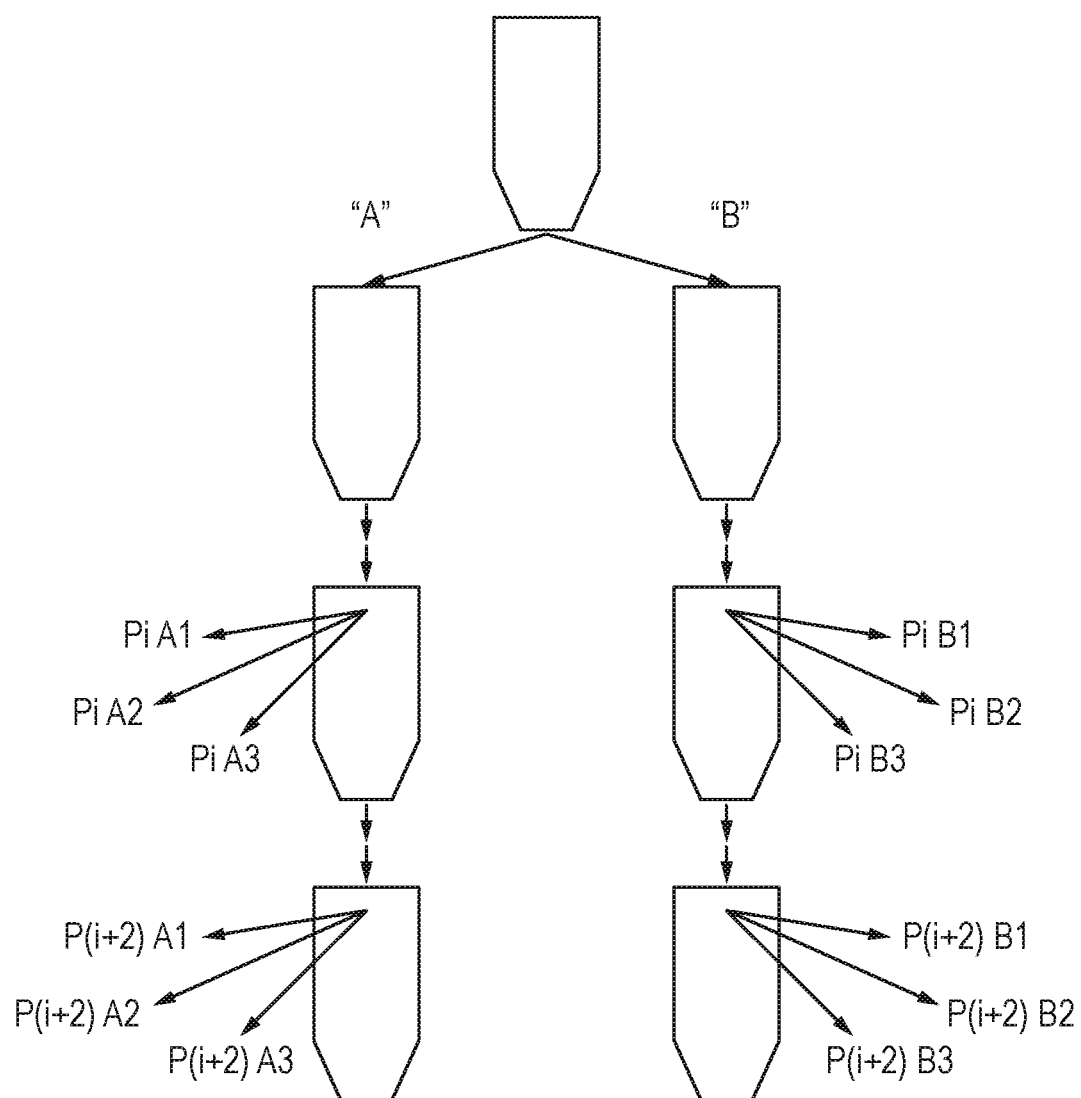
FIG. 2 shows the experimental scheme used for assessment of REIMS spectral reproducibility.

FIG. 2 shows the experimental scheme used for assessment of REIMS spectral reproducibility. In particular, flasks A and B are shown.

All of the remaining samples constituted the test set. The resulting cross-validation results can be seen in the table below.

The table below shows cross-validation results for SNB-19, HeLa and MES-SA cell lines based on PCA model comprising the first 4 principal components and using 3 nearest neighbour as classifier:

| kept in test set | predicted | | | correct |
|---|---|---|---|---|
| | HeLa | MES-SA | SNB-19 | |
| HeLa p6 A day2 (9 samples) | 63 | — | — | 100% |
| MES-SA p8 A day1 (9 samples) | 2 | 57 | — | 97% |
| SNB-19 p4 A day1 (9 samples) | — | — | 54 | 100% |
| HeLa p4 B day2 (9 samples) | 62 | 1 | — | 98% |
| MES-SA p10 B day1 (9 samples) | 17 | 42 | — | 71% |
| SNB-19 p4 B day2 (7 samples) | — | — | 56 | 100% |
| HeLa p4 A day1 (9 samples) | 49 | 14 | — | 78% |
| MES-SA p10 A day3 (12 samples) | — | 56 | — | 100% |
| SNB-19 p6 A day2 (7 samples) | — | 1 | 55 | 98% |

Cross-validations were performed based on a PCA model created of a training set as described elsewhere herein. Following this procedure, three different training sets were generated and subjected to PCA analysis. These training sets comprised between 25-28 sampling points, which represent <15% of the overall sample points (n=203). The composition of the training sets and corresponding cross-validation results are shown in the Table above. Consistently, the cross-validation results show >98% correct classification for SNB-19 samples, with only a single misclassification observed in case of the third training set, which was tentatively associated with the unequal sample size for MES-SA (n=12) and SNB-19 (n=7). Unequal sample size is known to lead to a bias in PCA calculations towards the larger sample subset, which explains the misclassification of SNB-19 cells as MES-SA.

Spectral Reproducibility in NCI-60 Cell Line Panel

The table below shows the different cell lines present in the NCI-60 cell line panel and respective number of replicates which were used.

| Tissue of origin | Cell line | No of biological replicates | No of technical replicates |
|---|---|---|---|
| Breast | BT549 | 1 | 4 |
| | HS-578-T | 1 | 6 |
| | MCF-7 | 1 | 12 |
| | MDA-MB-231 | 2 | 10 (6 + 4) |
| | MDA-MB-468 | 1 | |
| | TD-47-D | 1 | 11 |
| CNS | SF268 | 2 | 18 (8 + 10) |
| | SF295 | 2 | 18 (8 + 10) |
| | SF539 | 1 | 8 |
| | SNB-19 | 1 (3) | 10 (10 + ? + ?) |
| | SNB-75 | not measured | |
| | U251 | 1 | 9 |
| Colon | COLO-205 | 1 | 10 |
| | HCC2998 | 1 | 7 |
| | HCT-15 | 1 | 7 |
| | HCT-116 | 1 | 11 |
| | HT-29 | 2 | 9 (5 + 4) |
| | KM-12 | 1 | 7 |
| | SW-620 | 1 | 12 |
| Leukaemia | CCRF-CEM | 1 | 10 |
| | HL-60 | 1 | 7 |
| | K562 | 1 (2) | 9 |
| | MOLT-4 | 1 | 6 |
| | RPMI-8226 | 1 | 5 |
| | SR | 1 | 8 |
| Melanoma | LOX-IMVI | 1 | 9 |
| | M14 | 2 | 15 (7 + 8) |
| | Malme-3M | 1 | 6 |
| | MDA-MB-435 | 2 | 14 (4 + 10) |
| | SK-MEL-2 | 1 | 10 |
| | SK-MEL-5 | 1 | 8 |
| | SK-MEL-28 | 1 | 9 |

-continued

| Tissue of origin | Cell line | No of biological replicates | No of technical replicates |
|---|---|---|---|
| | UACC62 | 1 | 6 |
| | UACC257 | 1 | 9 |
| Non small cell lung cancer | A549 | 1 | 10 |
| | EKVX | 1 | 9 |
| | HOP-62 | 1 | 6 |
| | HOP-92 | 1 | 13 |
| | NCI-H23 | 1 | 11 |
| | NCI-H226 | 1 | 9 |
| | NCI-H322M | 1 | 7 |
| | NCI-H460 | 1 | 9 |
| | NCI-H522 | 1 | 9 |
| Ovarian | IGROV-1 | 2 | 8 (5 + 3) |
| | NCI-ADR-RES | 1 | 9 |
| | OVCAR-3 | 1 | 6 |
| | OVCAR-4 | 1 | 7 |
| | OVCAR-5 | 1 | 10 |
| | OVCAR-8 | 1 | 8 |
| | SK-OV-3 | 1 | 9 |
| Prostate | DU-145 | 1 | 9 |
| | PC-3 | 1 | 11 |
| Renal | 786-0 | 1 | 9 |
| | A498 | 1 | 11 |
| | ACHN | 1 | 10 |
| | CAKI-1 | 1 | 6 |
| | RXF393 | 1 | 6 |
| | SN-12-C | 1 | 8 |
| | TK-10 | 1 | 9 |
| | UO31 | 1 | 7 |

Biological replicates were analysed in of six out of the 58 cell lines used in this study. To assess the specificity of the REIMS spectral patterns toward individual cell lines, cross-validations were performed by omitting one replicate from the PCA model building process, and then projecting it into the resulting data space and classifying each data point based on its three nearest neighbour.

Figure 3:
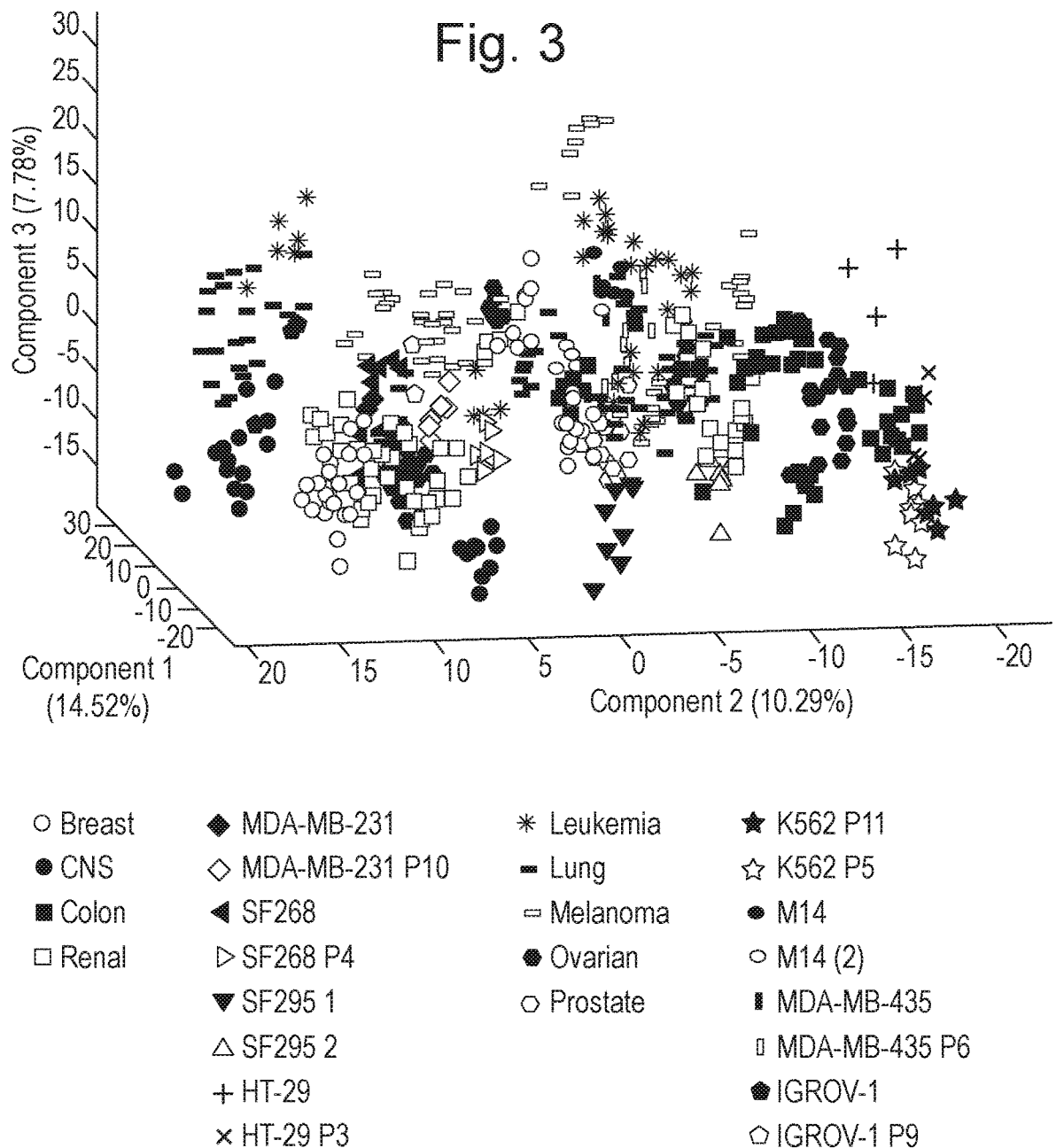
FIG. 3 shows a PCA plot of NCI-60 cell line panel, m/z 150-1000, with replicates highlighted.

FIG. 3 shows a PCA plot of NCI-60 cell line panel, m/z 150-1000, with replicates highlighted.

The table below shows the results of cross-validation results of the PCA model shown in FIG. 3. Cross-validations were performed as described above leaving a whole biological replicate out at a time. Good identification results (100%) were obtained for leukemia K562, melanoma MDA-MB-231 and MDA-MB-435 cell lines. One replicate of CNS SF295 was classified correctly. However, a second one is only correctly assigned in case of 50% of the data points. The misclassified samples were all wrongly assigned as SNB-19, another CNS cell line. The same is true for IGROV-1, of which the misclassified replicate falls into OVCAR-8, another ovarian cancer cell line. In the case of small sample number, correct classification becomes more difficult, but still the cell identity of a large proportion of HT-29 samples were correctly predicted.

Overall, the good prediction results further supports that REIMS spectral profiles can be used characterise and classify human cell line samples.

Cross-Validation Results for Replicates in NCI-60 Dataset

In the case of some cell lines, two biological replicates have been measured. For these cell lines both replicate was retained one by one and supplemented with samples from all other cell lines as the training set. The other biological replicate constituted the test set.

The table below shows cross-validation results for replicated NCI-60 cell lines based on PCA model of the entire NCI-60 dataset comprising the first 10 principal components. Three nearest neighbour as classifier:

| kept in test set | predicted | correct |
|---|---|---|
| K562 P5 (9 samples) | LE:K562 (9) | 100% |
| K562 P11 (9 samples) | LE:K562 (9) | 100% |
| MDA-MB-231 (6 samples) | BR:MDAMB231 (4) | 100% |
| MDA-MB-231 P10 (4 samples) | BR:MDAMB231 (6) | 100% |
| SF295 1 (10 samples) | CNS:SF295 (4), CNS:SNB19 (4) | 50% |
| SF295 2 (8 samples) | CNS:SF295 (10) | 100% |
| M14 (7 samples) | ME:M14 (5), ME:MDAMB435 (1), ME:SKMEL28 (2) | 63% |
| M14 (2) (8 samples) | ME:M14 (1), ME:MDAMB435 (6) | 14% |
| MDA-MB-435 (10 samples) | ME:MDAMB435 (4) | 100% |
| MDA-MB-435 P6 (4 samples) | ME:MDAMB435 (10) | 100% |
| HT-29 (5 samples) | CO:HT29 (3), OV:OVCAR5 (1) | 75% |
| HT-29 P3 (4 samples) | CO:HT29 (4) CO:COLO205 (1) | 80% |
| IGROV-1 (5 samples) | OV:IGROV1 (3) | 100% |
| IGROV-1 P9 (3 samples) | OV:OVCAR8 (4) RE:UO31 (1) | 0% |

Correlation with Gene Expression Data

Gene expression for the NCI-60 cell line panel was obtained from the CellMiner online data query tool. For each available gene and filtered m/z value the gene expression and the binned signal intensity across the cell lines was correlated using Pearson's correlation coefficient with 1000 iterations. The bootstrapped correlation value was defined as the lower 95% confidence interval level of the 1000 iterations, resulting in a total of 26065 (genes)×17878 (filtered m/z)=465990070 values.

Bootstrapped Correlation Analysis

For each available gene and binned m/z value with sufficient variance a bootstrapped correlation coefficient was calculated, resulting in a total of 26065×5452=142106380 correlation values. In the case of each gene—m/z value pair, the gene expression and the binned signal intensity across the 58 cell lines was correlated using Pearson's correlation coefficient with 1000 iterations. The bootstrapped correlation value was defined as the lower 95% confidence interval level of the 1000 iterations.

Comparison of Cell Line and Bulk Cancer Tissue Spectra

Figure 4:
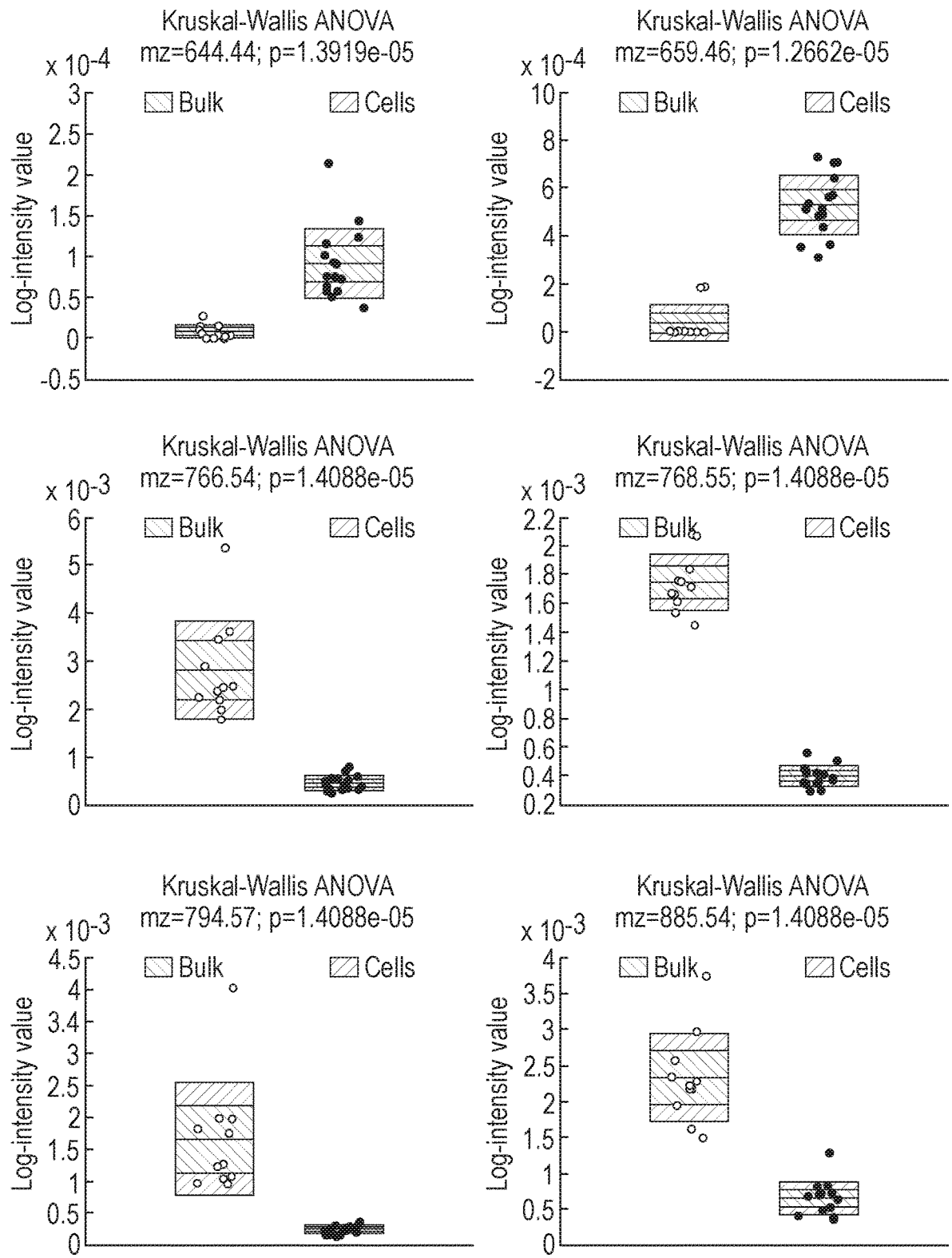
FIG. 4 shows the results of a comparison of cell line and bulk cancer tissue spectra. Shown are m/z values that were found to be significantly increased in either bulk cancerous tissue or cancer cell lines. M/z values were analysed using one-way ANOVA. The m/z that are significantly increased in either bulk cancerous tissue or cancer cell lines are m/z 644.44 (p=1.3919e−05), m/z 659.46 (p+1.2662e−05), m/z 766.54 (p=1.4088e−05), m/z 768.55 (p=1.4088e−05), m/z 794.57 (p=1.4088e−05), m/z 885.54 (p=1.4088e−05), m/z 750.54 (p=1.4088e−05), m/z 790.53 (p=2.1978e−05), and m/z 750.54 (p=1.4088e−05)

FIG. 4 shows the results of a comparison of cell line and bulk cancer tissue spectra, indicating mass to charge ratio values that were found to be significantly increased in either bulk cancerous tissue or cancer cell lines.

Correlation of REIMS Spectral Data with Protein Expression Data

Protein expression data was obtained from online source of the Technische Universität München, Germany (Gholami et al., supra). The fads2 gene encodes the fatty-acid desaturase 2 protein. However, for this protein data was only available in case of 29 members of the NCI-60 cell line panel.

To assess the agreement of data for gene and protein expression, both were plotted as a function of phospholipid species PE(38:3) and the ratio of PE(38:3)/PE(38:2).

Figure 5A:
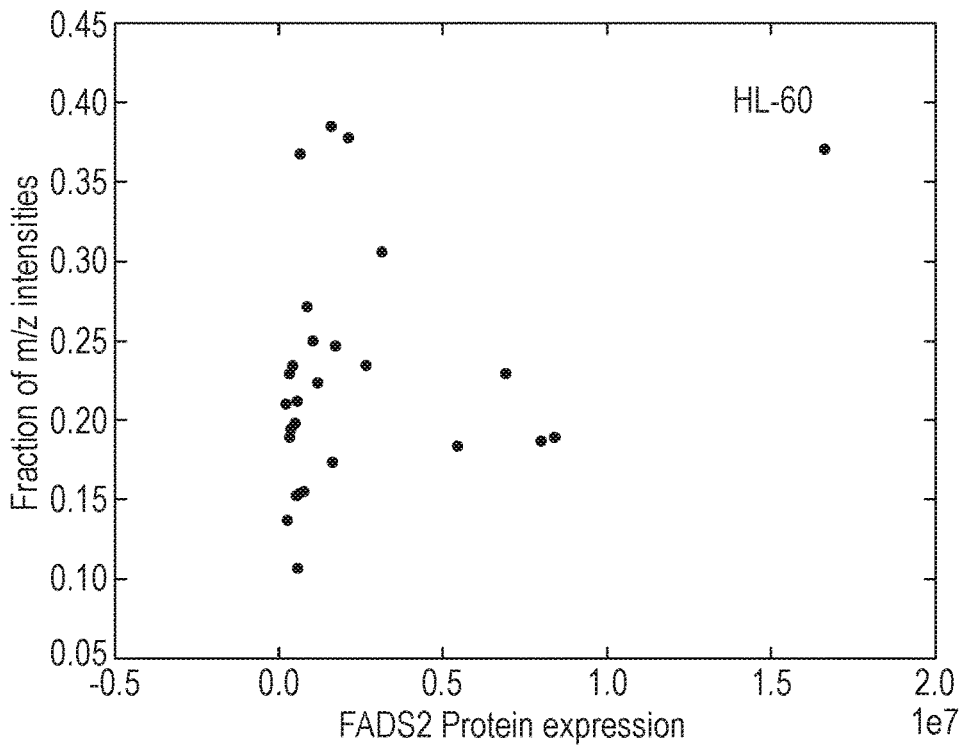
FIG. 5A shows PE(38:3)/PE(38:2) peak intensity ratio
Figure 5B:
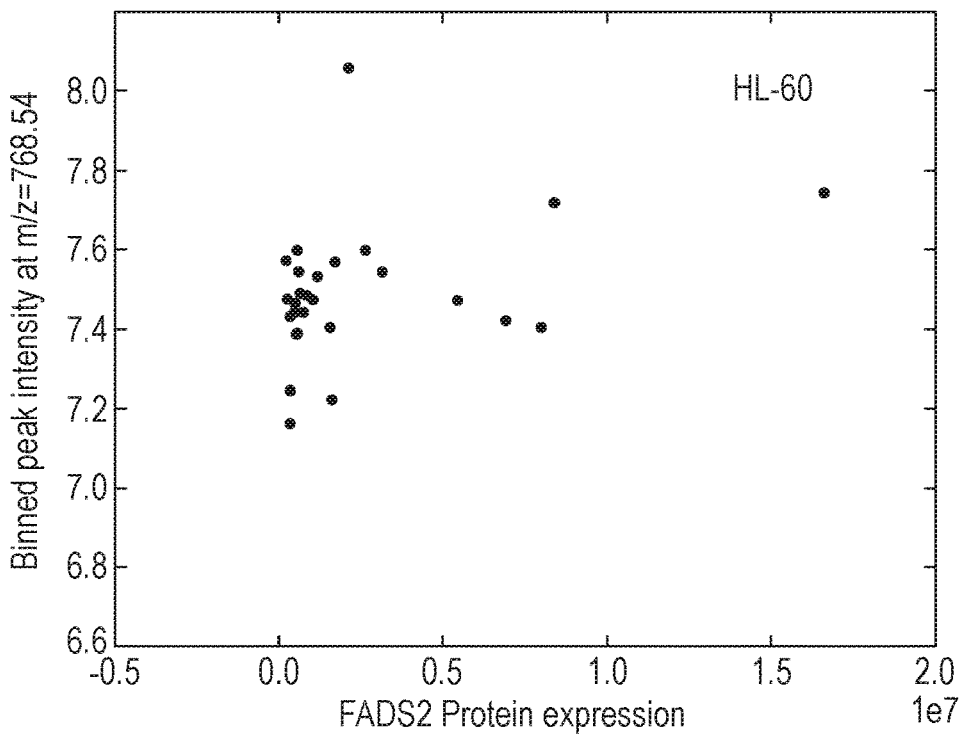
FIG. 5B shows PE(38:3) peak intensity as a function of FADS2 protein expression (for FADS2 protein expression see Gholami, Amin M., et al., *Global Proteome Analysis of the NCI-60 Cell Line Panel*. Cell Reports, 2013. 4(3): p. 609-620)

FIG. 5A shows phospholipid species PE(38:3)/PE(38:2) peak intensity ratio and FIG. 5B shows PE(38:3) peak intensity as a function of fads2 protein expression.

Correlation of Glycosylated Lipids with Ugcg Gene

Fragmentation spectra were recorded for peak set at m/z=842-846 recorded using a Waters Xevo G2-XS Q-ToF® instrument with a collision energy set at 35 eV. Fragmentation spectra showed similar behaviour and thus similar structural backbone. The main fragments observed are due to loss of HCl ($\Delta m=36$ Da) and loss of a hexose moiety HCl ($\Delta m=198$ Da). The loss of the hexose moiety as major fragmentation pathway agrees well with spectra of reference standards as found at Lipid Maps for the corresponding [M-H]$^-$ ion. No differentiation can be made between glycosylated and galactosylated ceramides.

Safety Considerations

To avoid any negative health impact originating from aerosolized cancer cells, the analysis site was enclosed into a Class safety level glove box compartment equipped with UV light source and HEPA filters.

Robustness of REIMS Spectral Profiles

In order to show that REIMS spectral patterns are reproducible and sufficiently specific to differentiate between different human cancer cell lines, three different cell lines (HeLa-cervical adenocarcinoma, MES-SA—uterine sarcoma and SNB-19-glioblastoma) were analyzed in an experiment designed to test spectral reproducibility.

The experimental scheme accounts for variance introduced by different culture batches or the passage number and for analytical variance introduced by the multiple measurements. Reference is made to FIG. 2.

Replicates were randomly analyzed over three analysis days in order to assess the analytical variance and robustness of a REIMS-based lipid profiling method. In addition, the influence of freeze-thaw cycles on spectral variance was investigated and was found to be insignificant.

Figure 6A:
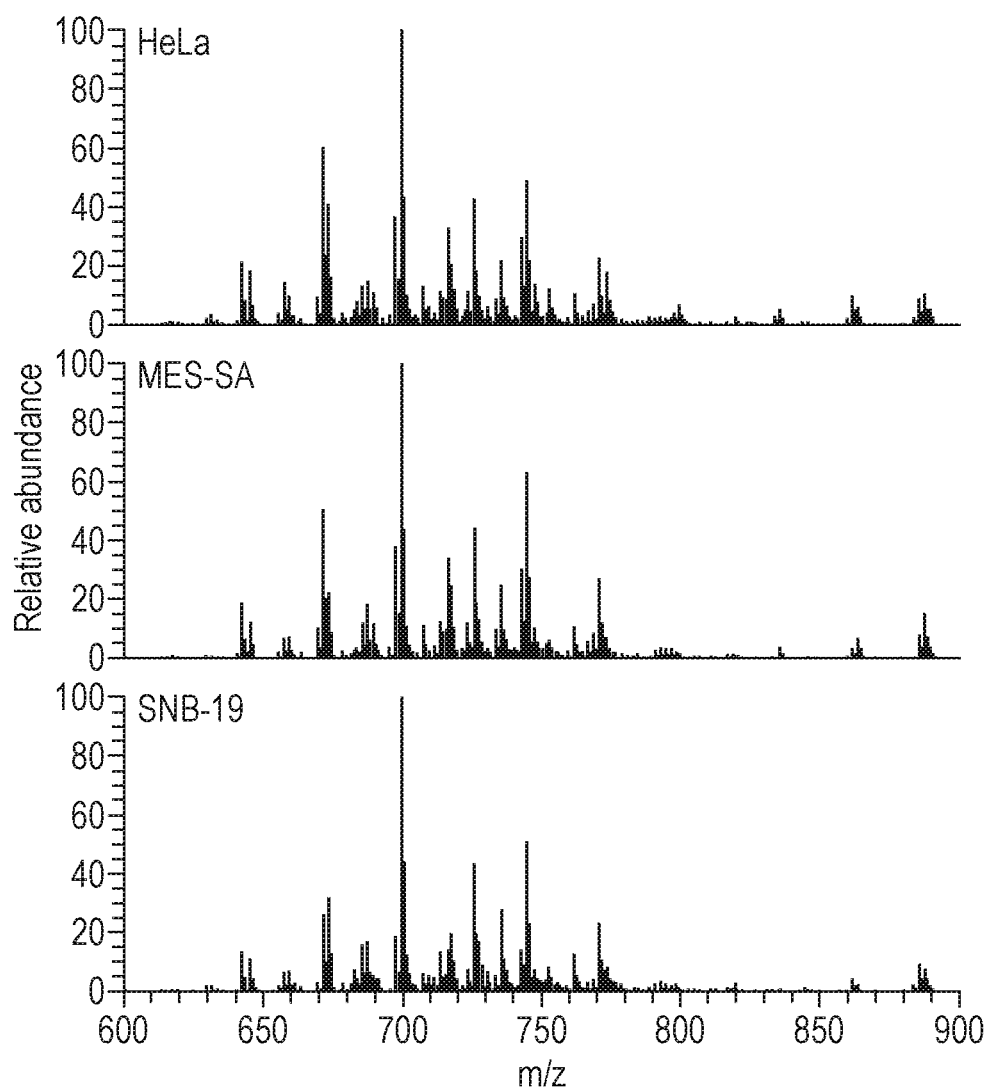
FIG. 6A shows representative mass spectral profiles between m/z 600-900 as obtained for HeLa, MES-SA and SNB cell line pellets respectively.

Raw REIMS mass spectrometric profiles of the three cell lines show significant similarities as is apparent from FIG. 6A. The main spectral content comprises predominantly glycerophospholipid-type membrane lipid components such as phosphatidylethanolamines (PEs), phosphatidylinositols (PIs), phosphatidylglycerols (PGs), phosphatidic acids (PAs) and phosphatidylserines (PSs) as well as other complex lipids including ceramides and glycosylated ceramide species. All observed ions displayed a single negative charge, the vast majority by forming the quasi-molecular [M-H]$^-$ ion. In addition, [M-NH$_3$—H]$^-$ was observed in case of PEs. Sphingolipid species were detected as [M+Cl]$^-$ ions.

For clinically oriented applications, REIMS spectral profiles were largely analyzed using supervised multivariate statistical analyses such as linear discriminant analysis (LDA) to explore the differentiation of various tissue types or healthy and diseased tissues.

In the experimental results presented below the analysis was restricted to exploratory unsupervised analysis methods to confirm that REIMS profiles would reproducibly cluster into different groups corresponding to cell line identities.

Figure 6B:
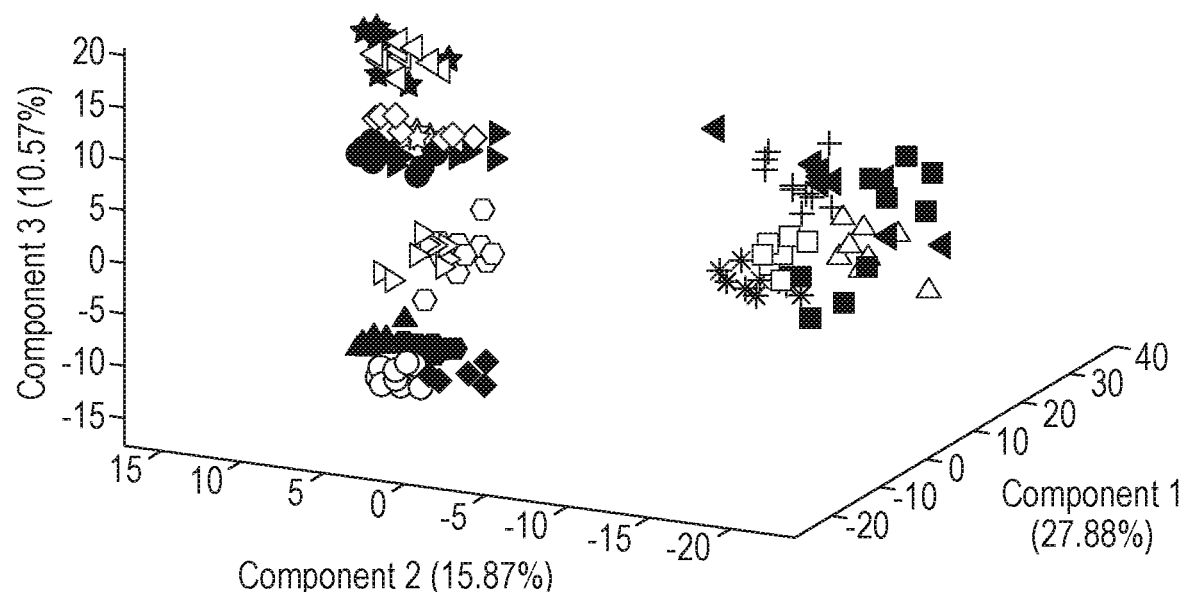
FIG. 6B shows 3-dimensional PCA plot of averaged REIMS data collected from several independent cultures of HeLa, MES-SA and SNB-19 cells over the spectral mass range of m/z 600-900, wherein circles, squares and triangles represent different measurement times (day 1, day 2 or day 3) and shades reflect passage numbers (p4 for 4 passages and p6 for 6 passages)

PCA of the REIMS profiles defined three clusters, as shown in FIG. 6B, corresponding to the three cell lines. SNB-19 cells are clearly differentiated from HeLa and MES-SA cells along the first principal component. The second and the third principal component allow the full separation of HeLa and MES-SA cell lines from each other. A slight separation along the second principal component due to passage numbers was observed for HeLa and SNB-19, however, analytical and biological variances were found to be small compared to the inherent spectral differences of the cell lines. These results suggest that although there is an expected biological and analytical variance, the REIMS spectral profiles obtained from cell line pellets show sufficient reproducibility and specificity to characterize and distinguish human cancer cell lines.

REIMS Profile of the NCI-60 Cell Line Panel

Following confirmation that REIMS spectral patterns are able to distinguish between three cancer cell lines, the entire NCI-60 panel consisting of 60 human different cancer cell lines was profiled. Based on amount of available biomass after culture, 4 to 15 individual measurement points were made for each cell line. Several biological replicates were also included (the detailed sample set is given in a table above).

Figure 7:
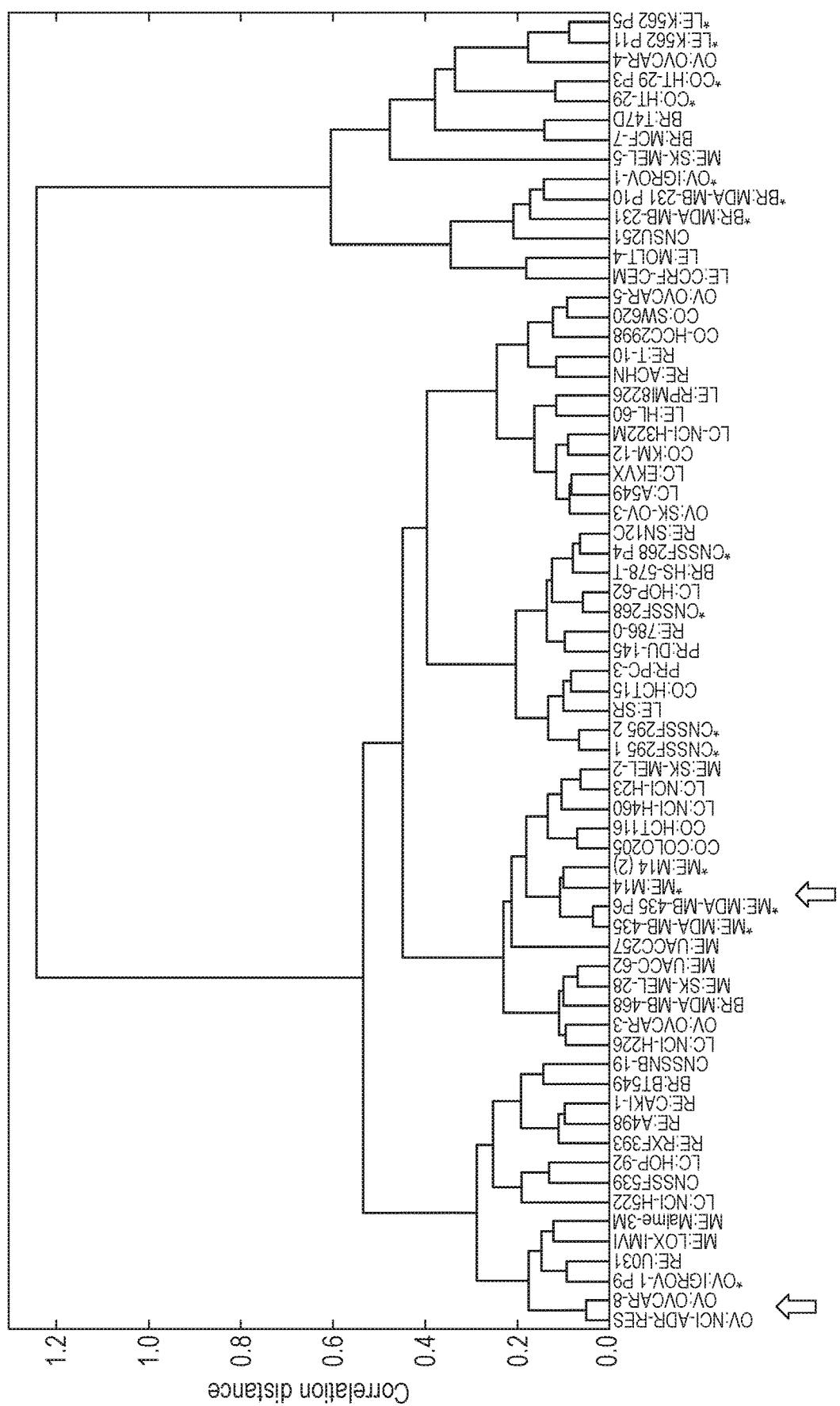
FIG. 7 shows a hierarchical cluster analysis and shows how lipidomic profiles revealed by REIMS distinguish cell lines of the NCI-60 panel consisting of ovarian (OV), renal (RE), melanoma (ME), central nervous system (CNS), breast (BR), lung (LC), colon (CO), leukemia (LE) and prostate (PR) origin, wherein the cluster dendrogram of the NCI-60 panel includes independently cultured replicates (highlighted by asterisks) or biologically related cell lines (arrows) and wherein distance was calculated using Pearson correlation and agglomeration via the Ward metric.

Hierarchical cluster analysis as shown in FIG. 7 and principal component analysis (as shown in FIG. 3) of the filtered sample averages indicated that the 60 cells are characterized by unique REIMS profiles.

Biological replicates showed the expected level of similarity as indicated by the cluster analysis (FIG. 7) or the cross-validation results given in table above.

Profiling studies revealed that the MDA-MB-435 cells more closely resembled melanoma cell lines than the other breast tumor lines (Ross, Nat Genet 2000).

Consistent with gene expression, SNP and karyotype analyses, the REIMS profiles also confirmed that MDA-MB-435 and M14 are of the same origin (FIG. 7, arrows).

Karyotyping has also found that the NCI-ADR-RES is in fact a drug resistant derivative of OVCAR-8.

As shown in FIG. 7, these cell lines (indicated by arrows) also show close similarity based on their REIMS profiles. Taken together, these results confirm that REIMS profiles are strongly associated with the biological identity of cancer cell lines.

Gene and protein expression patterns of the NCI-60 panel were found to correlate with tissue types whereas metabolomic signatures did not differentiate between tissue origins.

Clustering of the cell lines based on their REIMS lipid profile showed extensive heterogeneity within most tissue types, except for melanoma samples (FIG. 7).

REIMS profiles of the NCI60 panel were subsequently compared to bulk cancer samples of ovarian and colon adenocarcinomas analyzed using the same experimental setup. A PCA plot of the resulting dataset is shown in FIG. 8 and reveals clear differences between cell lines and bulk tissue specimens along the first principal component suggesting strong differences among their membrane lipid composition. A tentative separation according to tissue type of origin can be observed for both cell lines and tissue specimens, although more pronounced in the latter. Only a small number of tissue specimens (n=4) were available in case of ovarian tumors, but based on previous studies a significant increase in separation power can be expected for larger sample sets. Nevertheless, the direction of separation is similar in both cases, indicating similar lipidomic differences.

Representative spectral profiles of both ovarian and colon cancer tissue and cell line samples are shown in FIGS. 9A-9D.

Figure 9A:
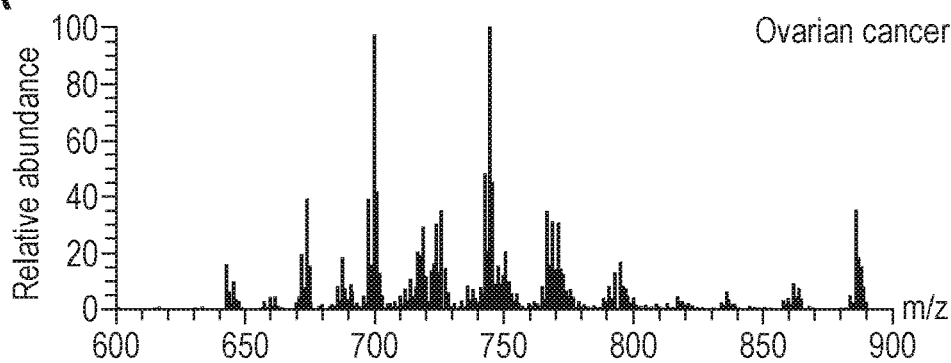
FIGS. 9A-9D show a comparison of spectral profiles for bulk tissue samples and cell lines of the corresponding tissue type of origin.
Figure 9B:
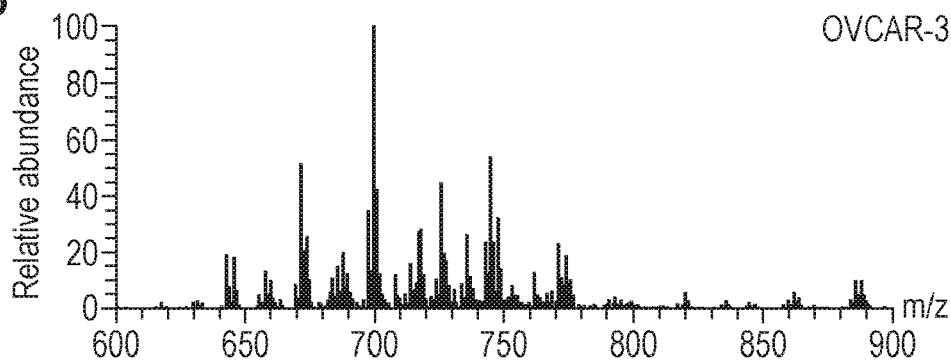
Figure 9C:
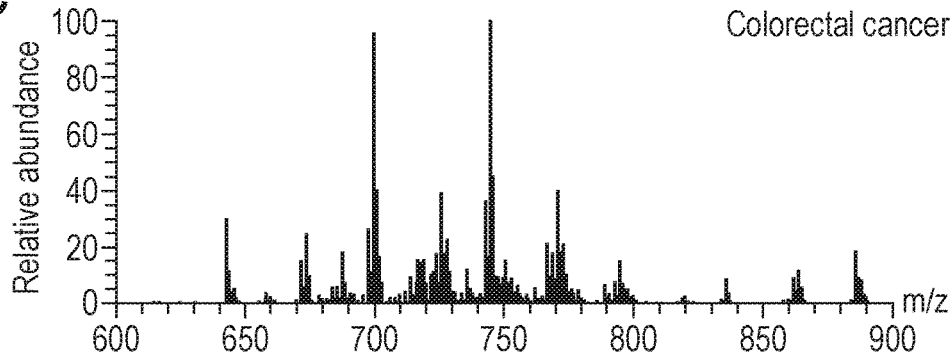
Figure 9D:
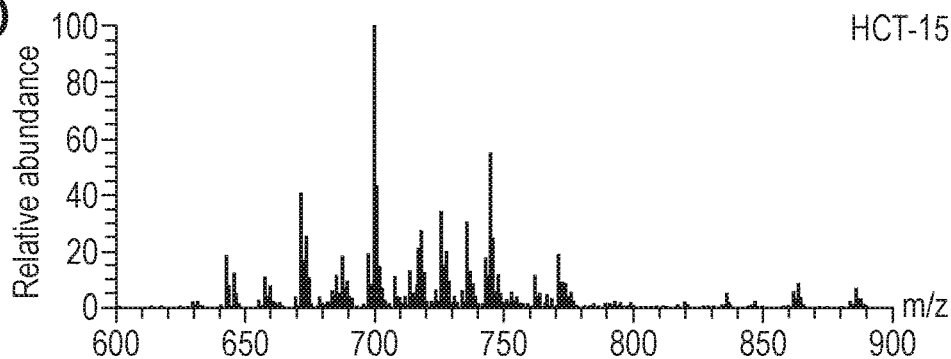

FIG. 9A shows the mass spectral profile for bulk ovarian cancer tissue, FIG. 9B shows a corresponding mass spectral profile for ovarian cancer cell line OVCAR-3, FIG. 9C shows a mass spectral profile for bulk colorectal cancer tissue and FIG. 9D shows a mass spectral profile for colon cancer cell line HCT-15.

Bulk tissue samples (c.f. in vitro cultured cell lines) display larger amounts of long-chain phosphatidylinositols such as PI (38:4) at m/z 885.55. Similar trends were observed in case of certain phosphatidylethanolamines. For example, the peaks detected in the mass range of m/z 790-794 corresponding to PE(40:6)-PE(40:4) species or those occurring at m/z 766.54 and 768.55 corresponding to PE(38:4) and PE(38:3), respectively. On the other hand, m/z 645.45, corresponding to PA (32:1), was found in significantly higher proportions in cell lines.

The characteristic differences in lipid composition may be due to the uniform lipid content of the culturing medium, which does not recapitulate the complex lipid source of real tumors that rely on dietary and liver-synthesized lipids as well as de-novo lipid synthesis (see FIG. 8 for a statistical analysis of distinct spectral features associated with cell lines and bulk tumors).

Correlation with Gene Expression Data

Cells established from different tissues were found to be more similar to each other than to the matching clinical samples. The limitations of cell lines as surrogates for clinical tumors are well known, but an advantage of the NCI-60 panel is the wealth of pharmacological data based on exposure of the cells to large numbers of drugs and other chemical compounds. The NCI-60 has been characterized more extensively than any other set of cell lines. The relationship of global patterns has yielded valuable biological insight and revealed the target and mechanism of action of anticancer compounds.

The availability of the REIMS and gene expression profiles enables identification of the relation of lipidome and transcriptome features in the NCI-60 cell lines.

In order to identify lipid-gene associations, the REIMS dataset was correlated to gene expression data obtained via the CellMiner online query tool. Using an exhaustive strategy, the patterns of each binned m/z intensity were correlated with each gene's expression profile across the cell lines as described above.

Figure 10A:
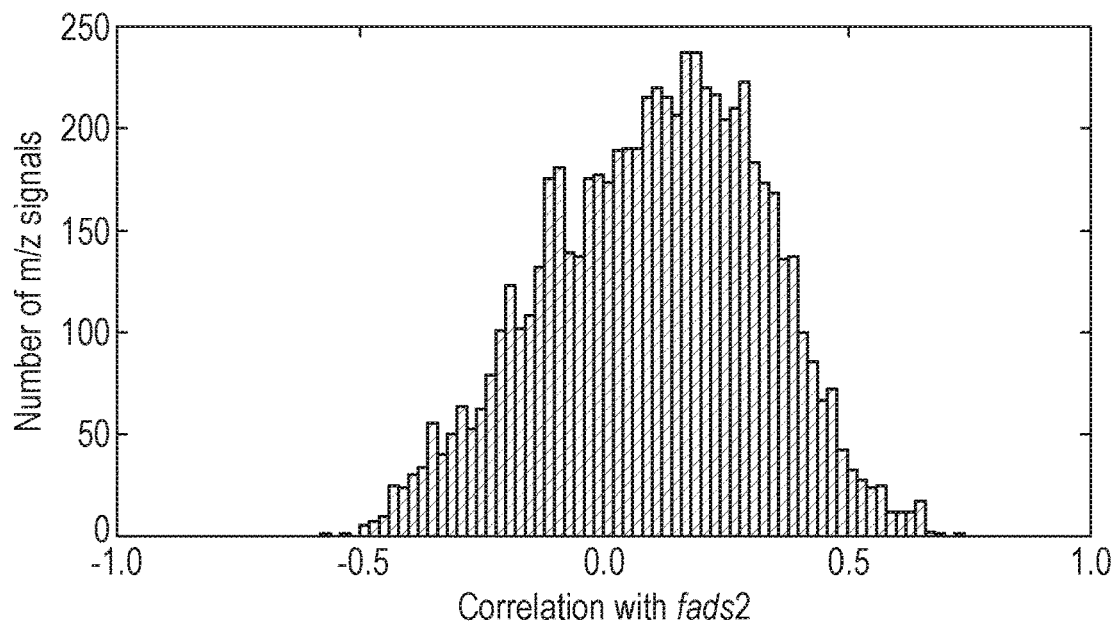
FIG. 10A shows a histogram of the correlation values between the fads2 gene expression profile and binned m/z peak intensities.
Figure 10B:
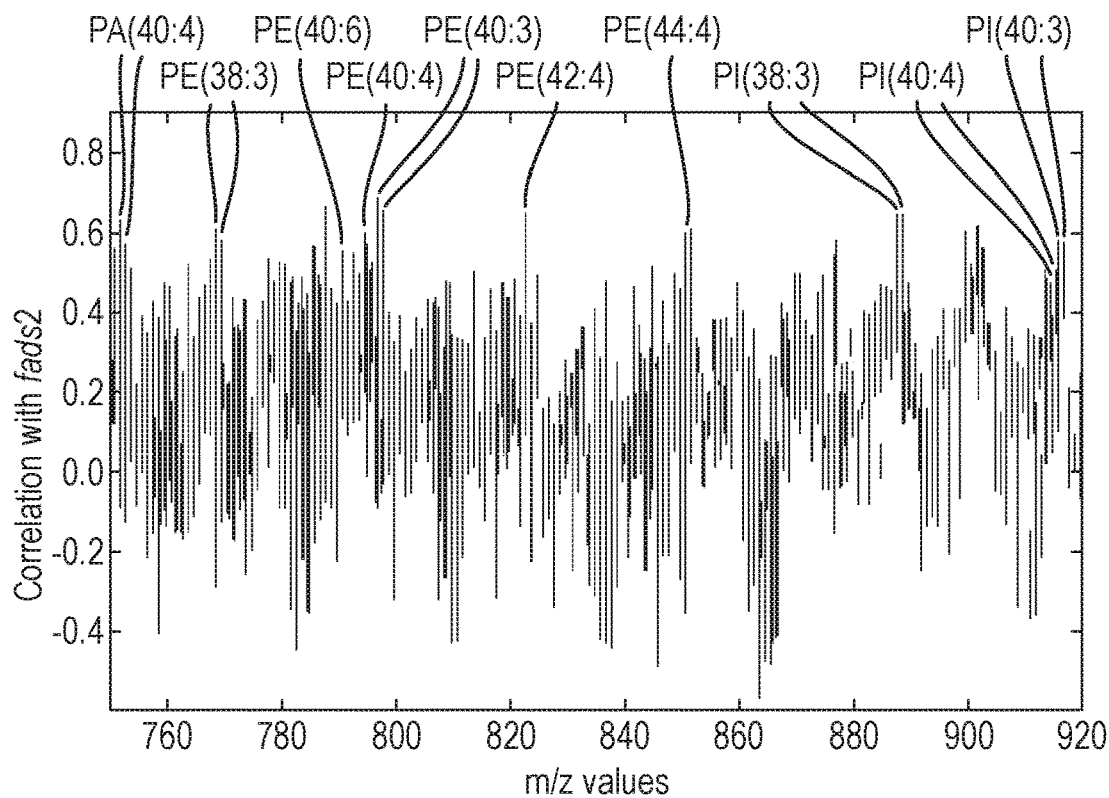
FIG. 10B shows correlation values with fads2 gene expression as a function of m/z values, and the putative lipids corresponding to the highly correlated m/z signals.

Strong positive correlation was observed between the expression intensities of several genes playing an important role in lipid metabolism and the lipid profiles of the 60 cells. Positively associated lipid-gene pairs may reflect a causally relevant relation if the gene product is a rate-limiting factor in the production of the given lipid species. For example, the expression pattern of the fads2 gene was found to be significantly correlated with the abundance of several lipids, as reflected by the intensity of m/z peaks within the REIMS data set (FIG. 10). The mammalian $\Delta$6-desaturase encoded by the fads2 gene catalyzes the biosynthesis of polyunsaturated fatty acids from precursor essential fatty acids such as linoleic acid C18:2n-6 and linolenic acid C18:3n-3. Other reported substrates include C16:0, C20:2n-6, C20:3n-3, C24:4n-6 and C24:5n-3.

Peaks showing significant correlation to fads2 gene expression could be putatively assigned to various unsaturated glycerophospholipids. One of the correlated binned peaks (corresponding to m/z=768.54) was attributed to a peak centering at m/z=768.5578, which in turn was assigned to PE(38:3) based on exact mass measurements, and PE(18:0/20:3) based on MS/MS data.

Figure 11A:
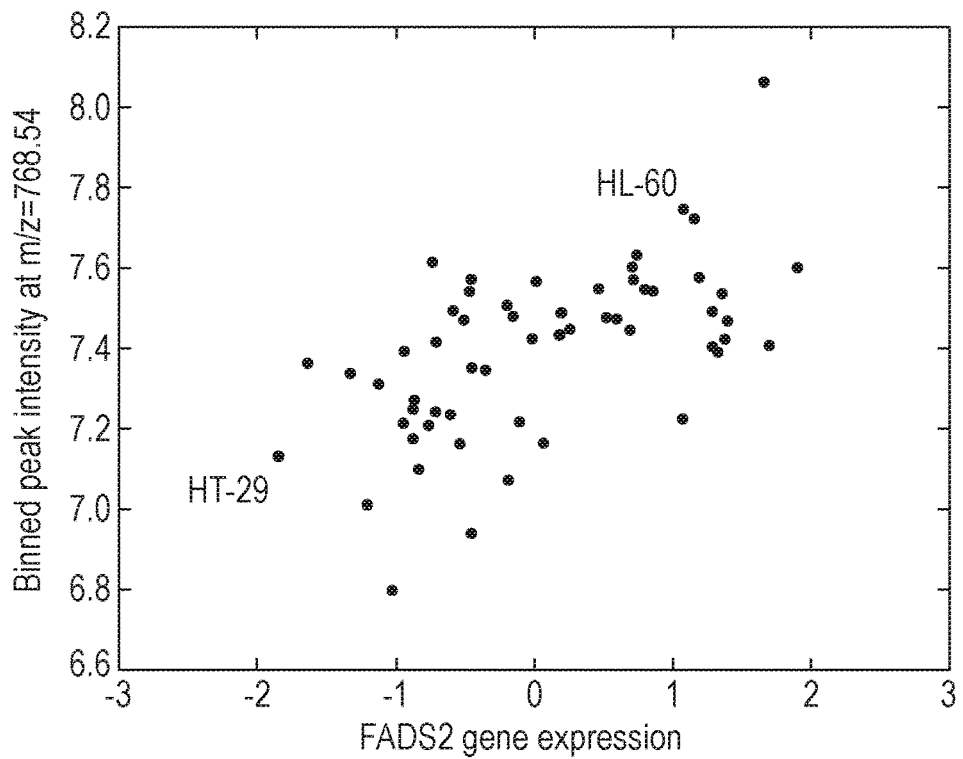
FIG. 11A shows binned peak intensity of m/z 786.54 correlated with scaled fads2 gene expression.
Figure 11B:
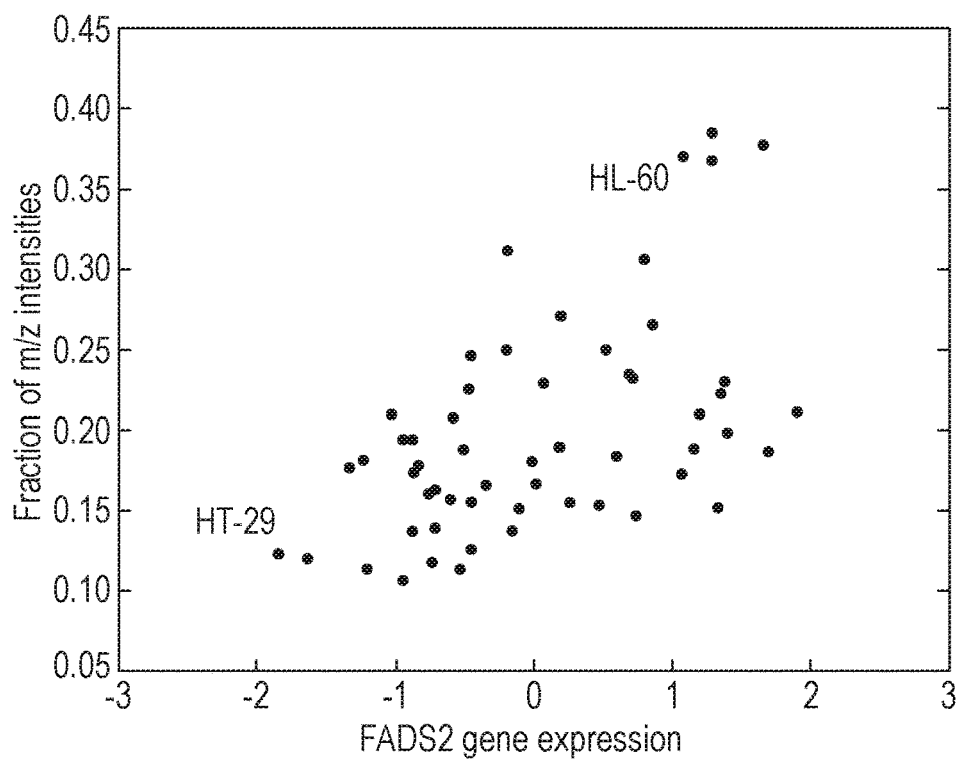
FIG. 11B shows ratio of intensity values of peaks at m/z 768.55 and 770.57 correlated with scaled fads2 gene expression.
Figure 11C:
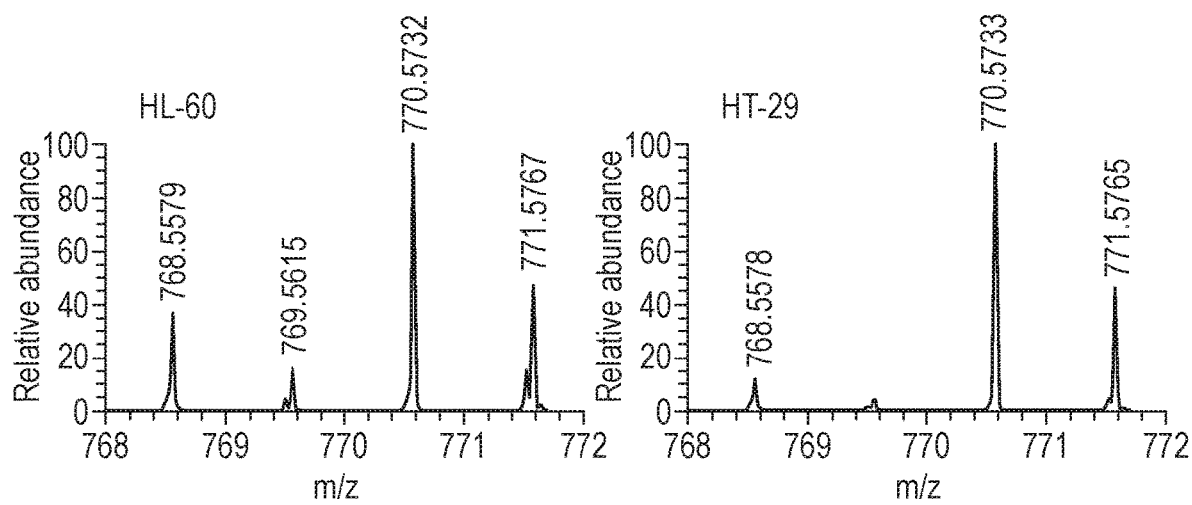
FIG. 11C shows relative abundance of peaks m/z 768.55 and 770.57 in the raw REIMS data obtained in HL-60 (leukemia, left) and HT-29 (colon, right) cells.

Assuming that both enzyme substrate and product would be incorporated into the same phospholipid species, the putative substrate can be indirectly attributed to PE(38:2) at m/z=770.5733. Indeed, it was found that the relative abundance of PE(38:2) and PE(38:3) shows significant correlation to fads2 gene expression levels across the NCI-60 cells (FIG. 11B).

Correlation of PE(38:3)/PE(38:2) intensity ratio or PE(38:3) abundance was verified using protein expression data as shown and described above in relation to FIG. 5. Thus, consistently with the enzymatic activity of the mammalian $\Delta$6-desaturase, cells expressing higher fads2 levels are expected to have lower PE(38:2) and higher PE(38:3) levels. Raw REIMS profiles of HL-60 and HT-29 cells (showing high and low fads2 expression levels, respectively) verify this hypothesis: in HT-29 cells, PE(38:3) accounts for approximately 15% of relative abundance compared to PE(38:2), for HL-60 the relative abundance increases to approximately 40% of the PE(38:2).

Figure 12A:
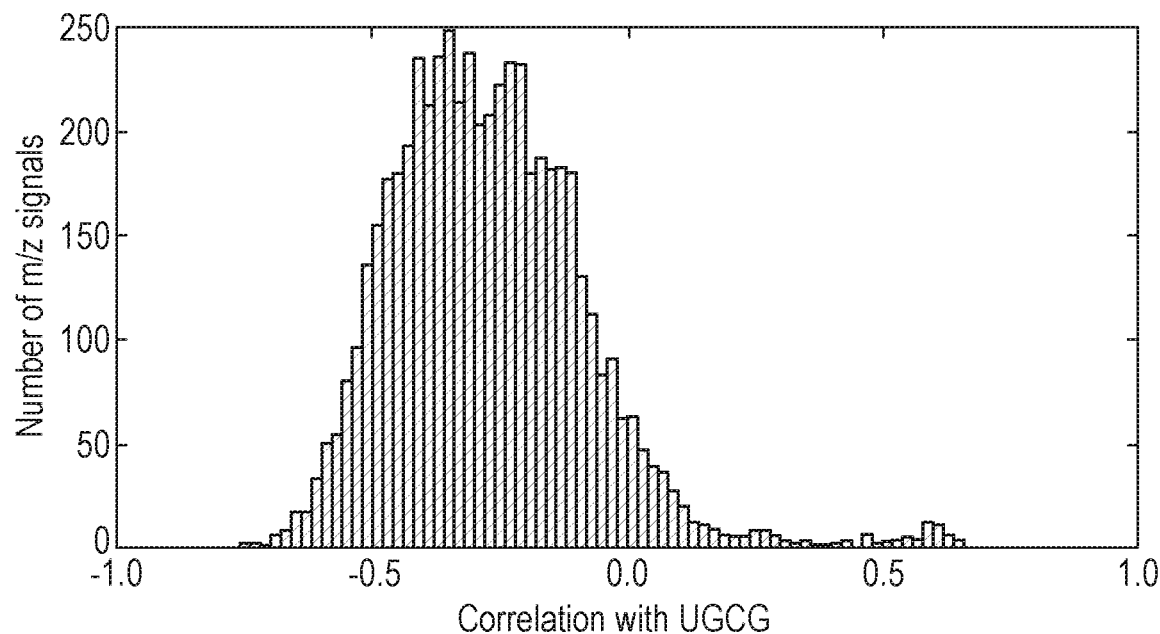
FIG. 12A shows a histogram of the correlation values between ugcg gene expression levels and m/z peak intensities.
Figure 12B:
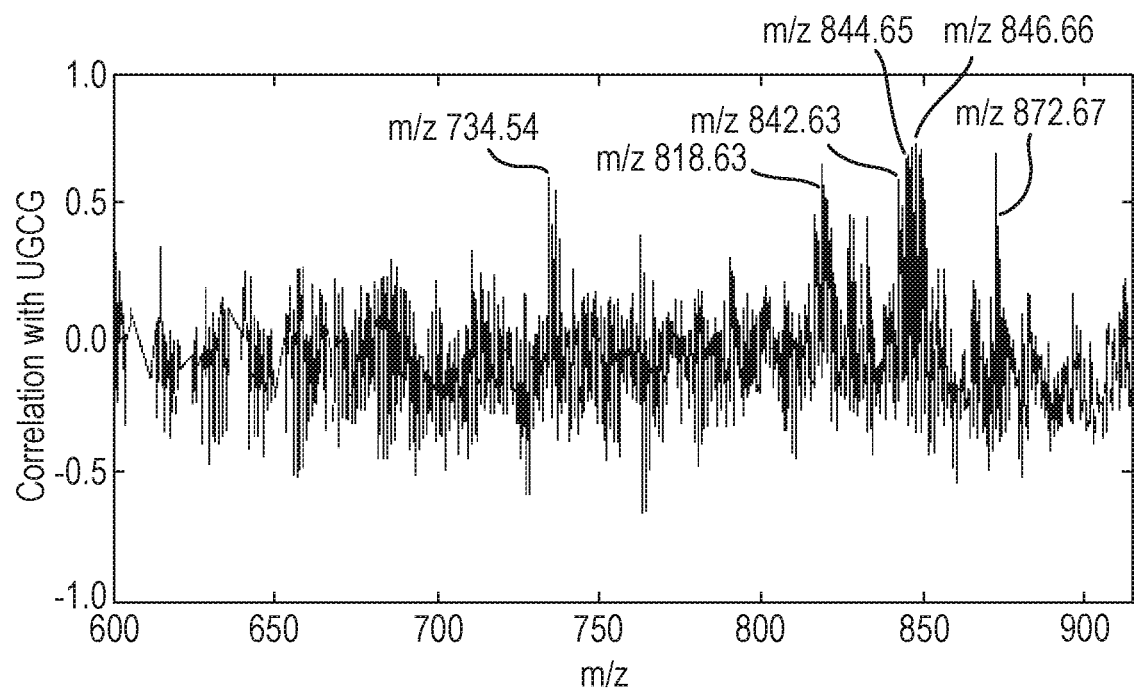
FIG. 12B shows correlation values with ugcg gene expression as a function of m/z values.

Strong correlations have also been found in case of ugcg gene expression (FIG. 12). This gene encodes the UDP-glucose ceramide glucosyltransferase (UGCG) enzyme, which catalyzes the first glycosylation step in glycosphingolipid biosynthesis, having ceramides and UDP-glucose as substrates. Glycosylated lipids are enriched in lipid rafts/lipid micro-domains and play fundamental roles in a variety of cellular processes. Positive correlations were observed for several signals between m/z=700-900 and their respective isotopes as shown in FIG. 12B and the table below.

Figure 13:
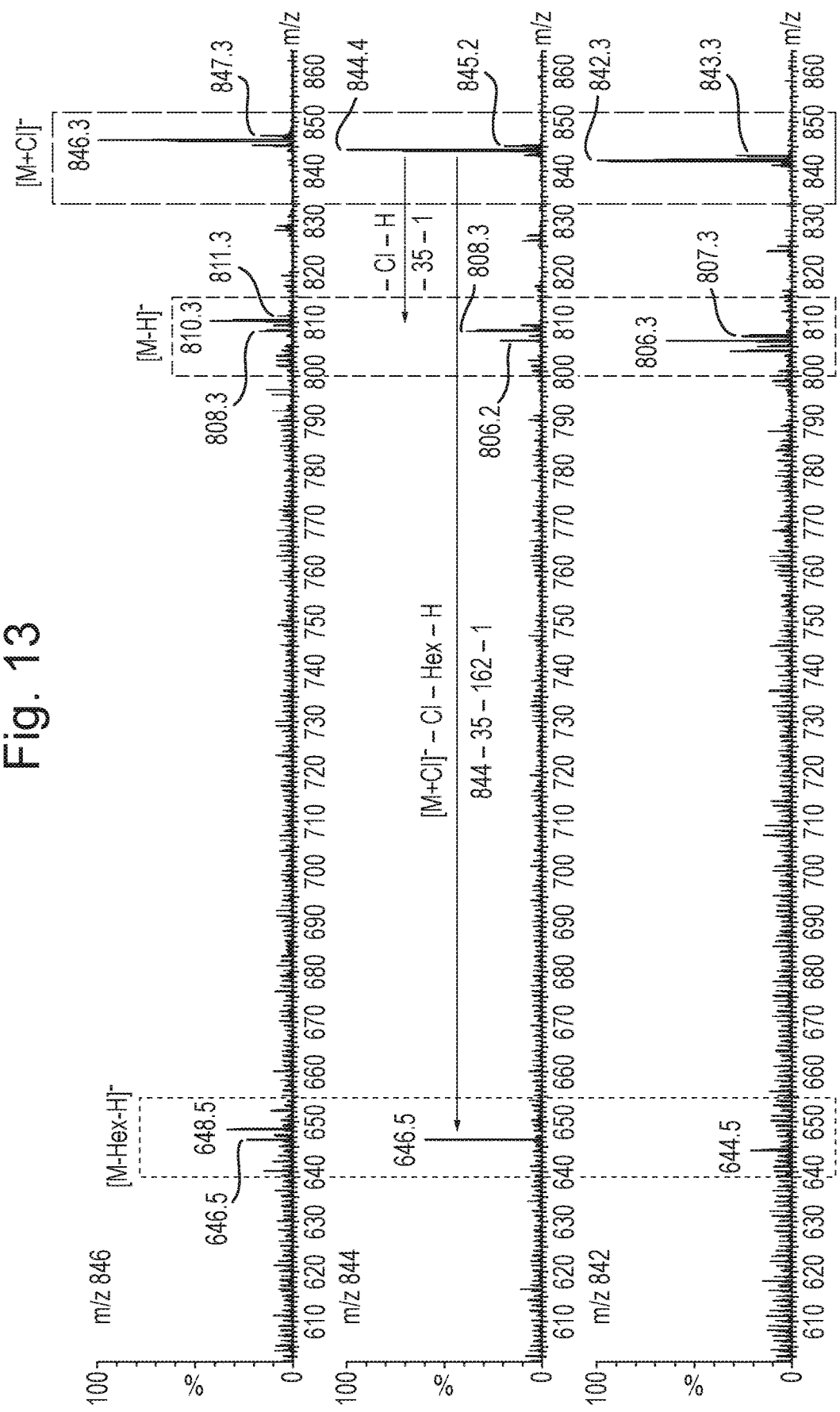
FIG. 13 shows MS/MS spectra for parent ions of m/z=842, 844, and 846 identified as glycosylated ceramides.
Figure 14A:
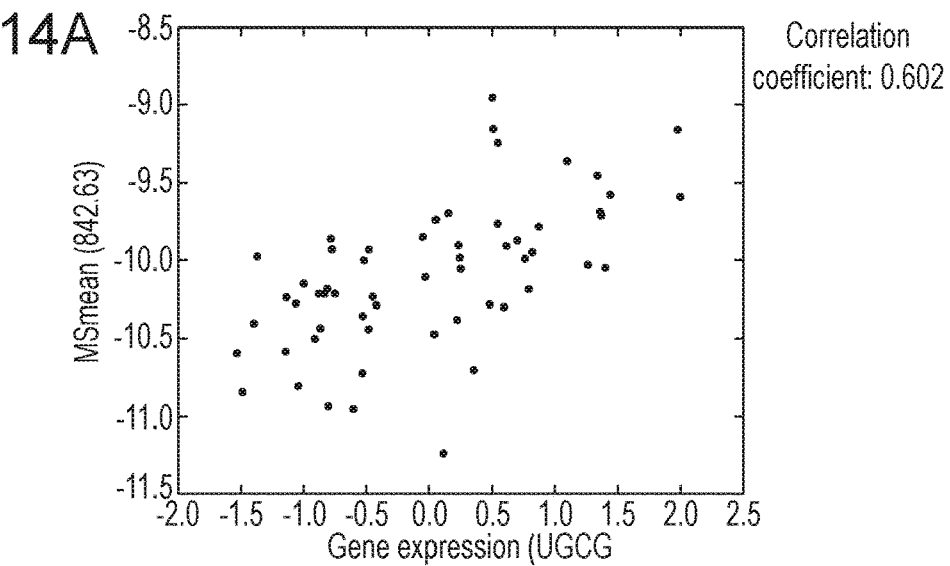
FIG. 14A shows mass spectrometric signal intensity (TIC normalised and log-transformed) as a function of ugcg gene expression for m/z=842.63.
Figure 14B:
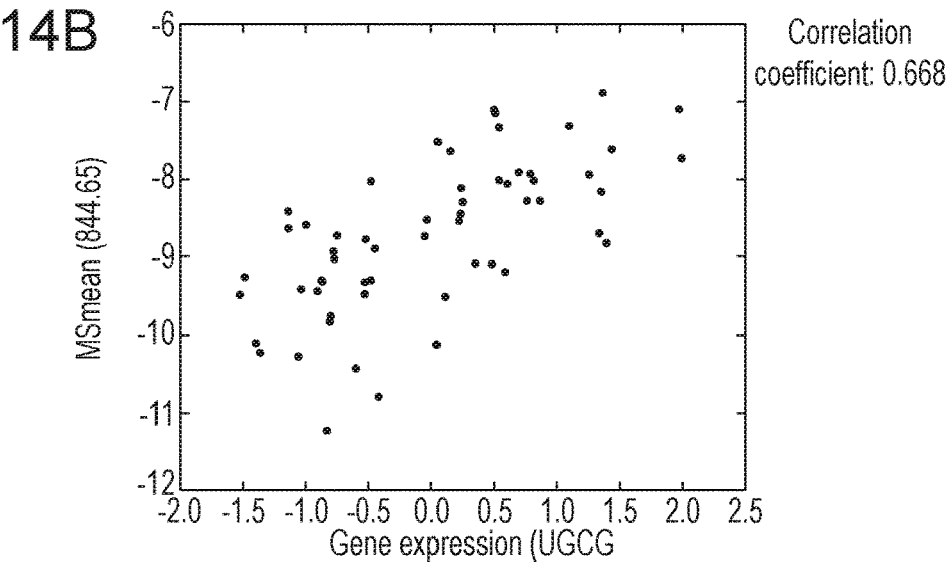
FIG. 14B shows for m/z=844.65.
Figure 14C:
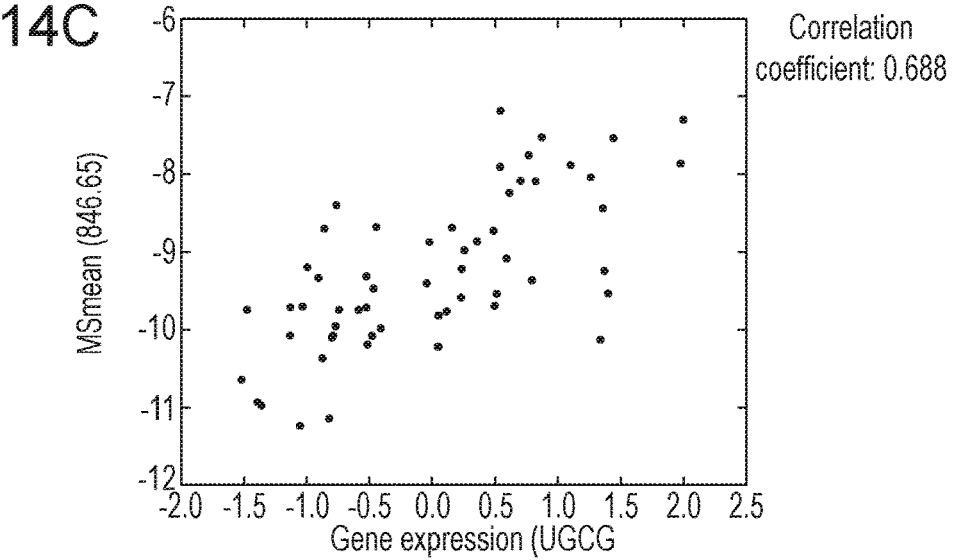
FIG. 14C shows for m/z=846.65.
Figure 14D:
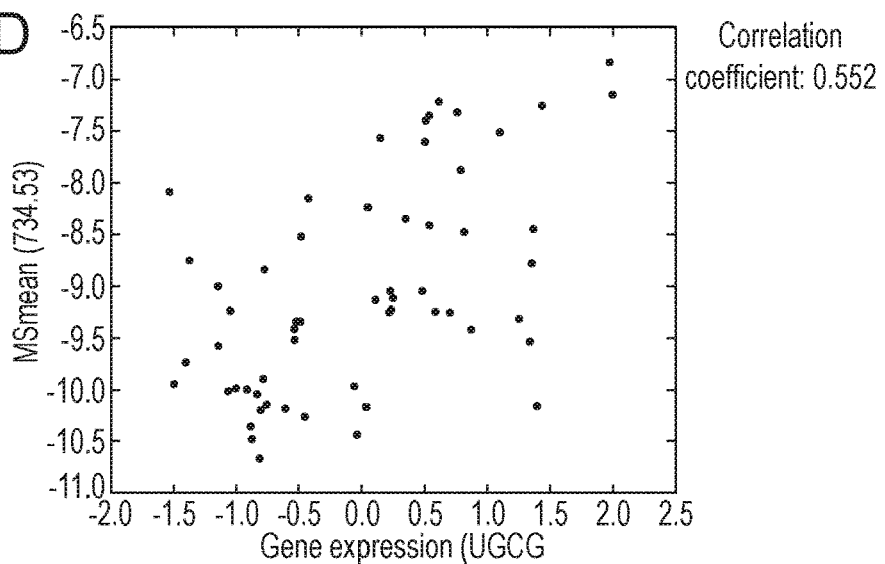
FIG. 14D shows for m/z=735.53.
Figure 14E:
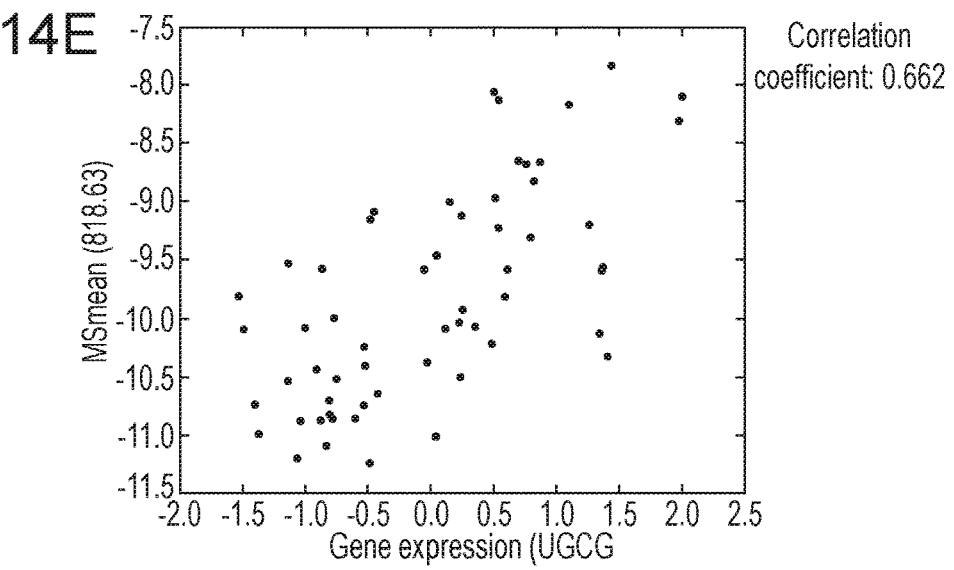
FIG. 14E shows for m/z=818.63.
Figure 14F:
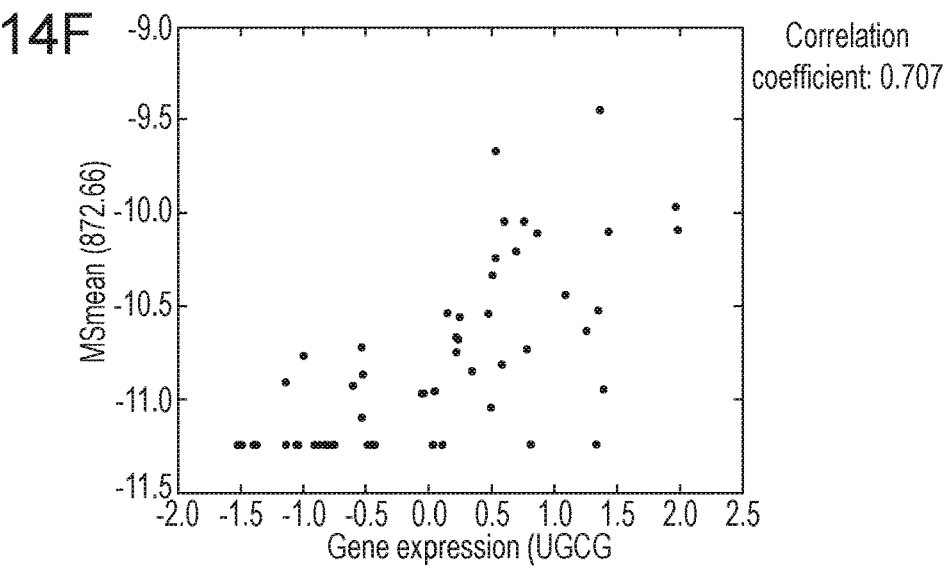
FIG. 14F shows for m/z=872.66.

Based on exact mass measurements and MS/MS experiments, these species were tentatively identified as homologous mono-hexosylated ceramides in form of [M+Cl]$^-$ ions. Isotopic patterns recorded for these species and MS/MS data support the presence of a chloride in the adduct ion. All ions show analogous fragmentation behavior, displaying a loss of the chloride ion ($\Delta$m=35 Da) and additional loss of the hexose moiety ($\Delta$m=198 Da, loss of HCl and $C_6H_{10}O_5$). Using tandem mass spectrometry only it is not possible to differentiate between glucosylated and galactosylated ceramide species as they exhibit identical fragment ions. Exemplary tandem mass spectra and mass spectrometric signal intensities as a function of gene expression numbers can be found in FIG. 13 and FIG. 14, respectively. No negative correlation was observed for the ugcg gene expression with the precursor ceramide species nor the ratio of glucosylceramides to precursor ceramides. This is associated with the fact that ceramides are ubiquitous precursors in sphingolipid biosynthesis and there are numerous biosynthetic pathways where ceramides act as substrates, intermediates or products.

The following table shows spectrometric signals that show strong positive correlation with the ugcg gene expression for the NCI-60 dataset:

| Exp. mass | Exact mass | $\Delta$ppm | Tentative ID | Formula | Adduct | Correlation coefficient |
| --- | --- | --- | --- | --- | --- | --- |
| 734.5355 | 734.5343 | 0.2 | GlyCer(d18:1/16:0) | $C_{40}H_{77}NO_8$ | [M + Cl]$^-$ | 0.552 |
| 818.6295 | 818.6282 | 0.2 | GlyCer(d18:1/22:0) | $C_{46}H_{89}NO_8$ | [M + Cl]$^-$ | 0.662 |
| 842.6312 | 842.6332 | -0.2 | GlyCer(d18:1/24:2) | $C_{48}H_{89}NO_8$ | [M + Cl]$^-$ | 0.602 |
| 844.6451 | 844.6439 | 0.1 | GlyCer(d18:1/24:1) | $C_{48}H_{91}NO_8$ | [M + Cl]$^-$ | 0.668 |
| 846.6627 | 846.6595 | 0.4 | GlyCer(d18:1/24:0) | $C_{48}H_{93}NO_8$ | [M + Cl]$^-$ | 0.688 |
| 872.6733 | 872.6752 | -0.2 | GlyCer(d18:1/26:1) | $C_{50}H_{95}NO_8$ | [M + Cl]$^-$ | 0.707 |

Other lipid species detected at m/z=860.6411, 862.6552 and 864.6775 showed positive correlations with the expression profiles of a number of genes encoding proteins involved in sphingolipid synthesis, e.g., fa2h, a gene encoding a protein that catalyzes the synthesis of 2-hydroxysphingolipids. Further genes include the degs2 gene, which encodes the Delta(4)-desaturase, sphingolipid 2 protein, and the nr1h3 gene, which encodes the Liver X receptor alpha protein. Liver X receptors are part of the control system for transcriptional programs involved in lipid homeostasis and inflammation and might thus indirectly influence the increase of certain sphingolipid species.

Analysis of *Mycoplasma*-Infected Cell Lines

Cell cultures frequently get infected by *Mycoplasma*, a genus of bacteria that lack a cell wall around their cell membrane. *Mycoplasma* infection can alter many physiological processes and thus lead to misleading experimental results if a study is performed using infected cells. Plasmocin® (InvivoGen, San Diego, Calif., USA) is a commercially available antibiotic treatment that is frequently used to eradicate *mycoplasma* infection in cell cultures.

REIMS profiles of *Mycoplasma*-free, *Mycoplasma*-infected and Plasmocin® cured HeLa and HEK cell lines were recorded.

The data was pre-processed as described for the NCI-60 dataset. For each HeLa and HEK cell lines, ANOVA tests were performed to determine significant differences between *Mycoplasma* positive and negative samples.

Adjusted p-values were obtained using the adaptive Benjamini-Hochberg (BH) procedure to correct for multiple testing.

Figure 26:
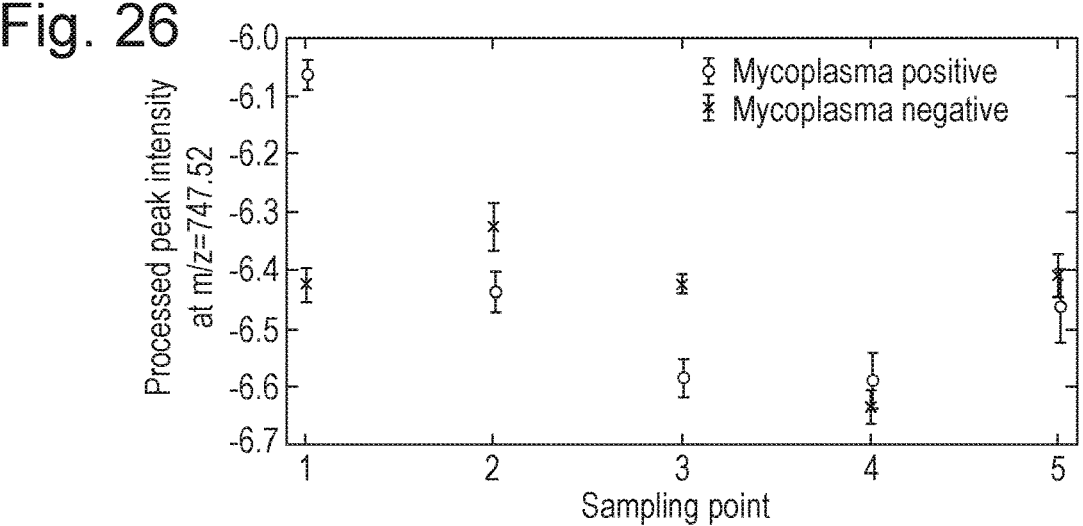
FIG. 26 shows peak intensities for m/z=747.52 in *Mycoplasma* infected and *Mycoplasma*-free cell lines during the duration of the Plasmocin® treatment wherein day 1 corresponds with the original (*Mycoplasma* positive or negative) sample, day 2 corresponds with the addition of Plasmocin®, day 3 corresponds with Plasmocin® still being present, day 4 corresponds with the removal of Plasmocin® and wherein day 5 corresponds with all samples being *Mycoplasma*-free.

FIG. 26 shows the time-dependent raw intensities in course of Plasmocin® treatment of the *mycoplasma* infection in case of m/z=747.5183.

Sampling point #1 corresponds with day 1 and the original *mycoplasma* positive or negative sample and sampling point #2 corresponds with day 2 and the addition of Plasmocin® antibiotic. Sampling point #3 corresponds with day 3. Sampling point #4 corresponds with the removal of Plasmocin® antibiotic. Sampling point #5 corresponds with all samples being Plasmocin® free.

Figure 23:
FIG. 23 shows the PCA-LDA space of FIG. 20, wherein the PCA-LDA space further comprises a PCA-LDA projected sample point derived from the peak intensity values of the sample spectrum of FIG. 22.
Figure 27A:
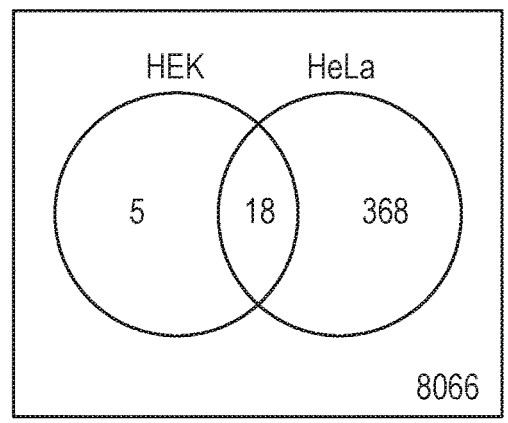
FIG. 27A shows a number of significantly higher m/z signals in *Mycoplasma*-infected versus *Mycoplasma*-free samples in HEK and HeLa cell lines. For FIG. 27B *Mycoplasma*-infected (+) and *Mycoplasma*-free (−) HEK (rectangle) and HeLa (triangle) cells were either treated (t) or untreated (u). Samples are shown as a function of PC1 and PC2 of PCA transformed samples in the space of the 18 overlapping m/z signals.
Figure 28A:
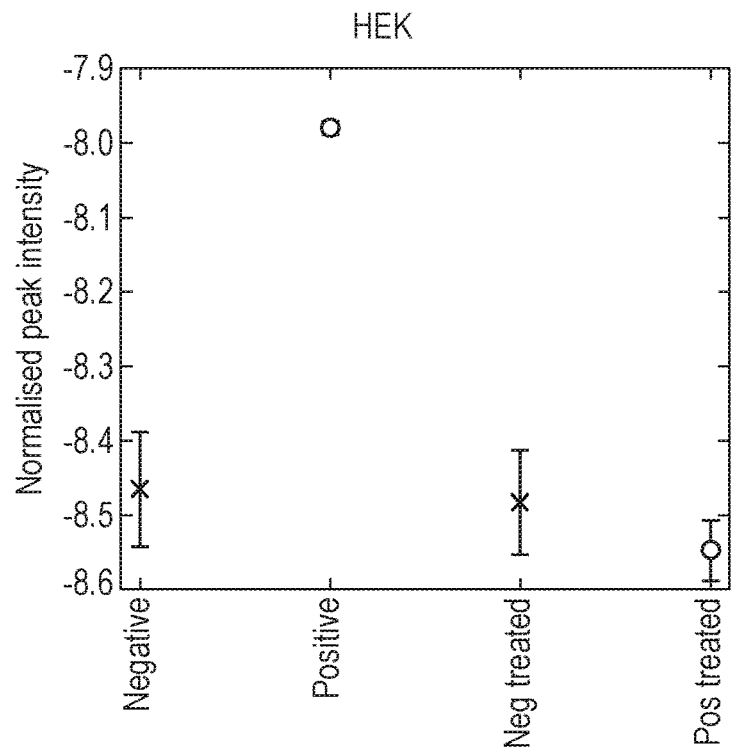
FIGS. 28A and 28B show intensities of TIC normalised and log-transformed signals at m/z=819.52 (corresponding to PG(40:7)) in *Mycoplasma*-free, *Mycoplasma*-infected and Plasmocin™ treated samples in HeLa (FIG. 28A) and HEK cell lines (FIG. 28B).
Figure 28B:
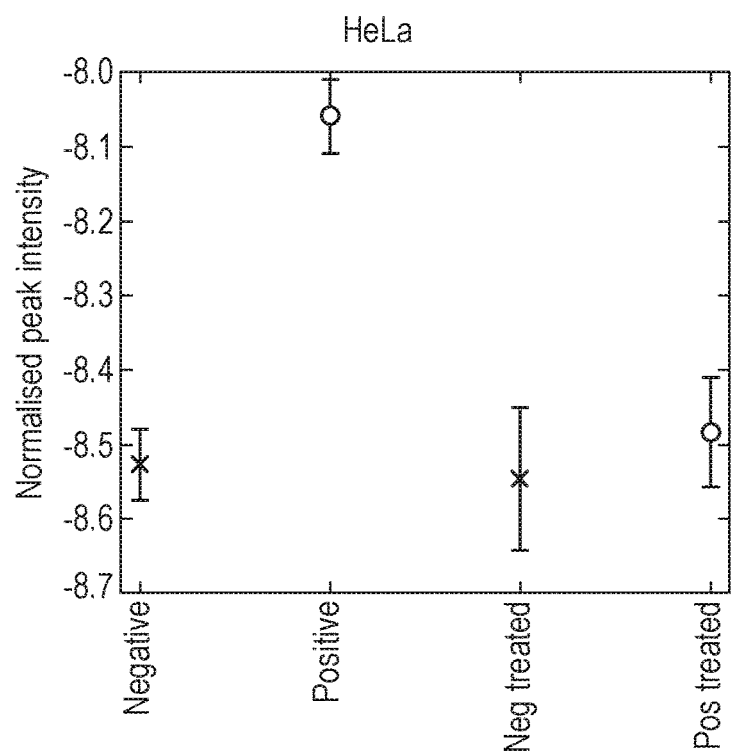

As shown in FIG. 27A, 23 and 386 binned m/z signals were significantly higher in *Mycoplasma*-infected HEK and HeLa cells, respectively. The higher number of significantly increased peaks may be explained with a higher number of sampling points (contributing to higher power in significance testing) or may reflect the increased reactivity of HeLa cells to *Mycoplasma* infection. Interestingly, we found no signals showing reduced intensity in *Mycoplasma*-infected cell lines (p=0.15). Table 15 lists the annotation of the 18 m/z signals that were found to be significantly increased across all *Mycoplasma*-infected cells (p=1.37E−20). As an example, changes in the intensity of m/z 819.52 (identified as PG(40:7) based on exact mass measurements) are shown in *Mycoplasma*-free, *Mycoplasma*-infected and Plasmocin™-treated HEK and HeLa cells (FIGS. 28A and B). This m/z value, along with the signal corresponding to its isotope, was found to be increased in *Mycoplasma*-infected HeLA and HEK cells, whereas the intensity returned to pre-infection levels upon successful Plasmocin™ treatment. Similar results were obtained for the other m/z signals shown in Table 15.

Figure 27B:
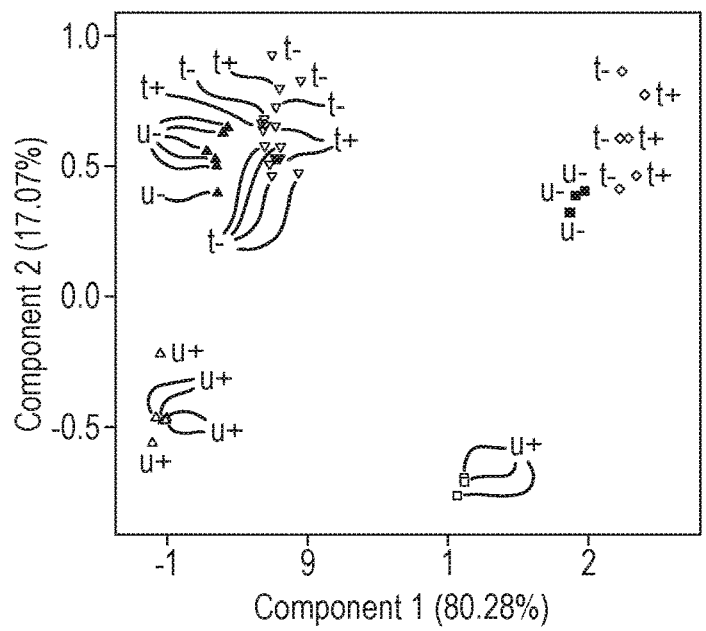

In the 18 dimensional space of these m/z signals, *Mycoplasma*-infected and *Mycoplasma*-free HEK and HeLa samples were analyzed by PCA (FIG. 27B). The first principal component (PC1) reveals differences between the two different cell lines while the second PC separates *Mycoplasma*-free and *Mycoplasma*-infected samples.

Trends in the spectral intensities of these species were found to be significantly different in case of the healthy and infected cell lines, suggesting that the lipid metabolism has been perturbed by *mycoplasma* infection. The above approach demonstrates the applicability of the REIMS method to study changes during *Mycoplasma* infection and as possible use for *Mycoplasma* screening.

CONCLUSION

The above described experiments demonstrate the applicability of a REIMS-based shotgun lipidomic characterization approach for human cancerous cell lines. Individual cancer cell lines were found to exhibit reproducible and cell line-specific spectral profiles while spectra could be acquired in less than five seconds. This does not only allow rapid identification of cell lines based on their spectral fingerprint, but also detailed characterization of membrane lipid composition in order to study the changes in the cell membrane composition in different cancer phenotypes.

By continued analysis of the correlation between REIMS spectral data and gene and protein expression data, the sensitivity of the REIMS spectral method for tumor phenotypic characterization can be assessed in detail. In addition, this technique enables investigations to be performed of gene knock-out models for changes in lipid metabolism or the effects of feeding experiments with stable isotope-labelled nutrient sources.

TABLE 1

Table of biomarkers: phospholipids and their spectrometric signals
Identified phospholipids detected in the mass range m/z = 600-900 for all analysed microbial species.
Only phospholipids with relative abundances >5% and only the most abundant acyl chain combination
were included. Solid growth media on which bacteria were grown is given in parentheses. ID based solely
on exact mass when lipid composition given as sum carbon number rather than individual acyl chains.

| Nominal mass m/z | C. koseri (CBA) | E. coli (CBA) | K. pneumoniae (LB) | P. mirabilis (MCC) | P. aeruginosa (LB) | S. marascens (MCC) | S. aureus (CBA) | S. agalactiae (CBA) | S. pyogenes (CBA) |
|---|---|---|---|---|---|---|---|---|---|
| 645 | | | | | | | | | PA(32:1)* |
| 659 | | | PA(16:0/17:1) | PA(16:0/17:1) | | PA(16:0/17:1) | | | |
| 661 | | | | | | | PA(33:0)* | | |
| 665 | | | | | | | | | PG(12:0/16:0) |
| 671 | | | | | | | | | PA(34:2)* |
| 673 | | | | PA(16:0/18:1) | PA(16:0/18:1) | | | | PA(16:0/18:1)* |
| 675 | | | | | | | PG(15:0/15:0-H$_2$O) | | PG(30:0-H$_2$O)* |
| 688 | PE(16:1/16:0) | | | PE(16:1/16:0) | | | | | |
| 691 | | | | | | | | | PG(14:0/16:1) |
| 693 | PG(16:0/14:0) | PG(16:0/14:0) | | | | | PG(15:0/15:0) | PG(15:0/15:0) | PG(14:0/16:0) |

TABLE 1-continued

Table of biomarkers: phospholipids and their spectrometric signals
Identified phospholipids detected in the mass range m/z = 600-900 for all analysed microbial species.
Only phospholipids with relative abundances >5% and only the most abundant acyl chain combination
were included. Solid growth media on which bacteria were grown is given in parentheses. ID based solely
on exact mass when lipid composition given as sum carbon number rather than individual acyl chains.

| Nominal mass m/z | C. koseri (CBA) | E. coli (CBA) | K. pneumoniae (LB) | P. mirabilis (MCC) | P. aeruginosa (LB) | S. marascens (MCC) | S. aureus (CBA) | S. agalactiae (CBA) | S. pyogenes (CBA) |
|---|---|---|---|---|---|---|---|---|---|
| 697 | | | | | | | | | PA(36:3)* |
| 699 | | | | | | | | | PA(18:1/18:1)* |
| 701 | | | | | | | | PG(32:1)-H$_2$O* | PG(32:1)-H$_2$O* |
| 702 | PE(16:0/17:1) | PE(16:0/17:1) | PE(16:0/17:1) | PE(16:0/17:1) | | PE(16:0/17:1) | | | |
| 707 | | | | | | | PG(15:0/16:0) | | |
| 716 | PE(18:1/16:0) | | | PE(18:1/16:0) | PE(18:1/16:0) | PE(17:0/17:1) | | | |
| 717 | | | | | | | | PG(32:2)* | PG(16:1/16:1) |
| 719 | PG(16:1/16:0) | PG(16:1/16:0) | PG(16:0/16:1) | PG(16:0/16:1) | PG(16:0/16:1) | PG(16:0/16:1) | | PG(16:0/16:1) | PG(16:0/16:1) |
| 721 | | | | | | | PG(15:0/17:0) | PG(15:0/17:0) | PG(16:0/16:0) |
| 725 | | | | | | | | | PA(16:1/18:2) |
| 727 | | | | | | | | | PG(16:1/18:1)-H$_2$O |
| 729 | | | | | | | | PG(16:0/18:1)-H$_2$O* | PG(16:0/18:1)-H$_2$O |
| 730 | | | | PE(16:0/19:1) | | | | | |
| 733 | PG(16:0/17:1) | PG(16:0/17:1) | PG(16:0/17:1) | PG(16:0/17:1) | PG(16:0/17:1) | PG(16:0/17:1) | | | |
| 735 | | | | | | | PG(15:0/18:0) | | |
| 743 | | | | | | | | PG(16:0/18:3) | PG(16:1/18:2) |
| 745 | PG(16:1/18:1) | PG(16:1/18:1) | PG(16:1/18:1) | | PG(16:1/18:1) | PG(16:1/18:1) | | PG(16:0/18:2)* | PG(16:1/18:1) |
| 747 | PG(16:0/18:1) | PG(16:0/18:1) | PG(16:0/18:1) | PG(16:0/18:1) | PG(16:0/18:1) | PG(16:0/18:1) | | PG(16:0/18:1) | PG(16:0/18:1) |
| 749 | | | | | | | PG(15:0/19:0) | PG(15:0/19:0) | PG(16:0/18:1)* |
| 752 | | | | | | | | | |
| 759 | | PG(17:1/18:1) | PG(17:1/18:1) | | PG(17:1/18:1) | PG(17:1/18:1) | | | |
| 761 | | PG(16:0/19:1) | PG(16:0/19:1) | PG(16:0/19:1) | PG(16:0/19:1) | PG(16:0/19:1) | | | |
| 763 | | | | | | | PG(15:0/20:0) | | |
| 770 | | | | | | | | | PE(38:2)* |
| 771 | | | | | | | | PG(36:3)* | PG(18:1/18:1)* |
| 773 | PG(18:1/18:1) | PG(18:1/18:1) | PG(17:1/19:1) | | PG(17:1/19:1) | PG(18:1/18:1) | | PG(36:2)* | PG(18:1/18:1) |
| 775 | | | | | | | | PG(36:1)* | PG(18:0/18:1) |
| 787 | | | PG(18:1/19:1) | | | | | | |
| 801 | | | PG(19:1/19:1) | | | | | | |

*Signal intensity not sufficient to obtain meaningful MS/MS data;
Abbreviations: PG = phosphatidylglycerol, PE = phosphatidylethanolamine, CBA = Columbia blood agar, LB = lysogenic broth agar, MCC = McConkey agar.

TABLE 2

Table of biomarkers: cardiolipins and their spectrometric signals
Cardiolipin species that were identified for *Staphylococcus epidermidis* ATCC 12228.

| Compound | Sum formula | Exact mass [M − H]− | Exp. mass | Mass Deviation |
|---|---|---|---|---|
| CL(62:0) | $C_{71}H_{138}O_{17}P_2$ | 1323.9335 | 1323.9268 | 5.0 ppm |
| CL(63:0) | $C_{72}H_{140}O_{17}P_2$ | 1337.9492 | 1337.9426 | 4.9 ppm |
| CL(64:0) | $C_{73}H_{142}O_{17}P_2$ | 1351.9649 | 1351.9601 | 3.6 ppm |
| CL(65:0) | $C_{74}H_{144}O_{17}P_2$ | 1365.9806 | 1365.9758 | 3.5 ppm |
| CL(66:0) | $C_{75}H_{146}O_{17}P_2$ | 1379.9962 | 1379.9913 | 3.5 ppm |
| CL(67:0) | $C_{76}H_{148}O_{17}P_2$ | 1394.0119 | 1394.0070 | 3.5 ppm |
| CL(68:0) | $C_{77}H_{150}O_{17}P_2$ | 1408.0275 | 1408.0238 | 2.6 ppm |
| CL(69:0) | $C_{78}H_{152}O_{17}P_2$ | 1422.0432 | 1422.0400 | 2.3 ppm |
| CL(70:0) | $C_{79}H_{154}O_{17}P_2$ | 1436.0588 | 1436.0561 | 1.9 ppm |
| CL(71:0) | $C_{80}H_{156}O_{17}P_2$ | 1450.0745 | 1450.0748 | 0.2 ppm |
| CL(72:0) | $C_{81}H_{158}O_{17}P_2$ | 1464.0900 | 1464.0970 | 4.8 ppm |

TABLE 3

Table of biomarkers: mycolic acids and their spectrometric signals
Identified mycolic acids as detected in different *Corynebacterium* species.

| Compound | Sum formula | Exact mass [M − H]− | Exp. mass | Mass Deviation | MS/MS fragments |
|---|---|---|---|---|---|
| alpha-Mycolic acid C28:0 | $C_{28}H_{55}O_3$ | 439.415669 | 439.4159 | 0.5 ppm | — |
| alpha-Mycolic acid C30:0 | $C_{30}H_{59}O_3$ | 467.446969 | 467.4473 | 0.7 ppm | 227 (C14:0), 255 (C16:0) |
| alpha-Mycolic acid C32:1 | $C_{32}H_{61}O_3$ | 493.462619 | 493.4634 | 1.6 ppm | — |
| alpha-Mycolic acid C32:0 | $C_{32}H_{63}O_3$ | 495.478269 | 495.4786 | 0.7 ppm | 255 (C16:0) |
| alpha-Mycolic acid C34:2 | $C_{34}H_{63}O_3$ | 519.478269 | 519.4788 | 1.0 ppm | — |
| alpha-Mycolic acid C34:1 | $C_{34}H_{65}O_3$ | 521.493919 | 521.4942 | 0.5 ppm | 255 (C16:0), 281 (C18:1) |
| alpha-Mycolic acid C36:2 | $C_{36}H_{67}O_3$ | 547.509569 | 547.5102 | 1.2 ppm | 281 (C18:1) |

TABLE 4

Table of biomarkers: mycolic acids and their spectrometric signals
Identified mycolic acids as detected in *Rhodococcus* species.

| Compound | Sum formula | Exact mass [M − H]− | Exp. mass | Mass Deviation |
|---|---|---|---|---|
| alpha-Mycolic acid C28:0 | $C_{28}H_{56}O_3$ | 439.4157 | 439.4159 | 0.5 ppm |
| alpha-Mycolic acid C30:1 | $C_{30}H_{58}O_3$ | 465.4313 | 465.4315 | 0.4 ppm |
| alpha-Mycolic acid C30:0 | $C_{30}H_{60}O_3$ | 467.4470 | 467.4472 | 0.4 ppm |
| alpha-Mycolic acid C31:1 | $C_{31}H_{60}O_3$ | 479.4470 | 479.4473 | 0.6 ppm |
| alpha-Mycolic acid C31:0 | $C_{31}H_{62}O_3$ | 481.4626 | 481.4630 | 0.8 ppm |
| alpha-Mycolic acid C32:2 | $C_{32}H_{60}O_3$ | 491.4470 | 491.4475 | 1.0 ppm |
| alpha-Mycolic acid C32:1 | $C_{32}H_{62}O_3$ | 493.4626 | 493.4634 | 1.6 ppm |
| alpha-Mycolic acid C32:0 | $C_{32}H_{64}O_3$ | 495.4783 | 495.4786 | 0.6 ppm |
| alpha-Mycolic acid C33:2 | $C_{33}H_{62}O_3$ | 505.4626 | 505.4630 | 0.8 ppm |
| alpha-Mycolic acid C33:1 | $C_{33}H_{64}O_3$ | 507.4783 | 507.4785 | 0.4 ppm |
| alpha-Mycolic acid C33:0 | $C_{33}H_{66}O_3$ | 509.4939 | 509.4943 | 0.8 ppm |
| alpha-Mycolic acid C34:3 | $C_{34}H_{62}O_3$ | 517.4626 | 517.4632 | 1.2 ppm |
| alpha-Mycolic acid C34:2 | $C_{34}H_{64}O_3$ | 519.4783 | 519.4788 | 1.0 ppm |
| alpha-Mycolic acid C34:1 | $C_{34}H_{66}O_3$ | 521.4939 | 521.4944 | 1.0 ppm |
| alpha-Mycolic acid C34:0 | $C_{34}H_{68}O_3$ | 523.5096 | 523.5100 | 0.8 ppm |
| alpha-Mycolic acid C35:3 | $C_{35}H_{64}O_3$ | 531.4783 | 531.4784 | 0.2 ppm |
| alpha-Mycolic acid C35:2 | $C_{35}H_{66}O_3$ | 533.4939 | 533.4946 | 1.3 ppm |
| alpha-Mycolic acid C35:1 | $C_{35}H_{68}O_3$ | 535.5096 | 535.5100 | 0.7 ppm |
| alpha-Mycolic acid C35:0 | $C_{35}H_{70}O_3$ | 537.5252 | 537.5259 | 1.3 ppm |
| alpha-Mycolic acid C36:3 | $C_{36}H_{66}O_3$ | 545.4939 | 545.4944 | 0.9 ppm |
| alpha-Mycolic acid C36:2 | $C_{36}H_{68}O_3$ | 547.5096 | 547.5102 | 1.1 ppm |
| alpha-Mycolic acid C36:1 | $C_{36}H_{70}O_3$ | 549.5252 | 549.5260 | 1.5 ppm |
| alpha-Mycolic acid C36:0 | $C_{36}H_{72}O_3$ | 551.5409 | 551.5424 | 2.7 ppm |
| alpha-Mycolic acid C37:3 | $C_{37}H_{68}O_3$ | 559.5096 | 559.5102 | 1.1 ppm |
| alpha-Mycolic acid C37:2 | $C_{37}H_{70}O_3$ | 561.5252 | 561.5257 | 0.9 ppm |
| alpha-Mycolic acid C37:1 | $C_{37}H_{72}O_3$ | 563.5409 | 563.5418 | 1.6 ppm |
| alpha-Mycolic acid C37:0 | $C_{37}H_{74}O_3$ | 565.5565 | 565.5573 | 1.4 ppm |
| alpha-Mycolic acid C38:4 | $C_{38}H_{74}O_3$ | 571.5096 | 571.5098 | 0.3 ppm |
| alpha-Mycolic acid C38:3 | $C_{38}H_{74}O_3$ | 573.5252 | 573.5261 | 1.6 ppm |
| alpha-Mycolic acid C38:2 | $C_{38}H_{74}O_3$ | 575.5409 | 575.5415 | 1.0 ppm |
| alpha-Mycolic acid C38:1 | $C_{38}H_{74}O_3$ | 577.5565 | 577.5579 | 2.4 ppm |
| alpha-Mycolic acid C39:2 | $C_{38}H_{76}O_3$ | 589.5565 | 589.5578 | 2.2 ppm |

TABLE 5

Table of biomarkers: mycolic acids and their spectrometric signals
Identified mycolic acids as detected in *Nocardia* species.

| Compound | Sum formula | Exact mass [M − H]− | Exp. mass | Mass Deviation |
|---|---|---|---|---|
| alpha-Mycolic acid C48:3 | $C_{48}H_{90}O_3$ | 713.6817 | 713.6797 | 2.8 ppm |
| alpha-Mycolic acid C48:2 | $C_{48}H_{92}O_3$ | 715.6974 | 715.6959 | 2.1 ppm |
| alpha-Mycolic acid C50:3 | $C_{50}H_{94}O_3$ | 741.7130 | 741.7114 | 2.2 ppm |
| alpha-Mycolic acid C50:2 | $C_{50}H_{96}O_3$ | 743.7287 | 743.7285 | 0.3 ppm |
| alpha-Mycolic acid C52:3 | $C_{52}H_{94}O_3$ | 769.7443 | 769.7430 | 1.7 ppm |
| alpha-Mycolic acid C52:2 | $C_{52}H_{96}O_3$ | 771.7600 | 771.7588 | 1.6 ppm |
| alpha-Mycolic acid C53:3 | $C_{53}H_{96}O_3$ | 783.7600 | 783.7596 | 0.5 ppm |
| alpha-Mycolic acid C53:2 | $C_{53}H_{94}O_3$ | 785.7756 | 785.7754 | 0.3 ppm |
| alpha-Mycolic acid C54:4 | $C_{54}H_{96}O_3$ | 795.7600 | 795.7594 | 0.8 ppm |
| alpha-Mycolic acid C54:3 | $C_{54}H_{98}O_3$ | 797.7756 | 797.7739 | 2.1 ppm |
| alpha-Mycolic acid C54:2 | $C_{54}H_{100}O_3$ | 799.7913 | 799.7902 | 1.4 ppm |
| alpha-Mycolic acid C55:4 | $C_{55}H_{102}O_3$ | 809.7756 | 809.7748 | 1.0 ppm |
| alpha-Mycolic acid C55:3 | $C_{54}H_{104}O_3$ | 811.7913 | 811.7907 | 0.7 ppm |
| alpha-Mycolic acid C55:2 | $C_{54}H_{106}O_3$ | 813.8069 | 813.8061 | 1.0 ppm |
| alpha-Mycolic acid C56:5 | $C_{56}H_{102}O_3$ | 821.7756 | 821.7748 | 1.0 ppm |
| alpha-Mycolic acid C56:4 | $C_{56}H_{104}O_3$ | 823.7913 | 823.7907 | 0.7 ppm |
| alpha-Mycolic acid C56:3 | $C_{56}H_{106}O_3$ | 825.8069 | 825.8053 | 1.9 ppm |
| alpha-Mycolic acid C56:2 | $C_{56}H_{108}O_3$ | 827.8226 | 827.8213 | 1.6 ppm |
| alpha-Mycolic acid C57:4 | $C_{57}H_{106}O_3$ | 837.8069 | 837.8050 | 2.3 ppm |
| alpha-Mycolic acid C57:3 | $C_{57}H_{108}O_3$ | 839.8226 | 839.8215 | 1.3 ppm |
| alpha-Mycolic acid C58:5 | $C_{58}H_{106}O_3$ | 849.8069 | 849.8068 | 0.1 ppm |

TABLE 5-continued

Table of biomarkers: mycolic acids and their spectrometric signals
Identified mycolic acids as detected in *Nocardia* species.

| Compound | Sum formula | Exact mass [M − H]− | Exp. mass | Mass Deviation |
|---|---|---|---|---|
| alpha-Mycolic acid C58:4 | $C_{58}H_{108}O_3$ | 851.8226 | 851.8218 | 0.9 ppm |
| alpha-Mycolic acid C58:3 | $C_{58}H_{110}O_3$ | 853.8382 | 853.8375 | 0.8 ppm |
| alpha-Mycolic acid C59:3 | $C_{59}H_{112}O_3$ | 867.8539 | 867.8537 | 0.2 ppm |
| alpha-Mycolic acid C60:4 | $C_{60}H_{112}O_3$ | 879.8539 | 879.8537 | 0.2 ppm |
| alpha-Mycolic acid C60:3 | $C_{60}H_{114}O_3$ | 881.8695 | 881.8683 | 1.4 ppm |

TABLE 6

Table of biomarkers: mycolic acids and their spectrometric signals
Identified mycolic acids as detected in different *Mycobacterium* species.

| Compound | Sum formula | Exact mass [M − H]− | Exp. mass | Mass Deviation |
|---|---|---|---|---|
| alpha-Mycolic acid C77:2 | $C_{77}H_{150}O_3$ | 1122.1512 | 1122.1525 | 1.2 ppm |
| alpha-Mycolic acid C78:2 | $C_{78}H_{152}O_3$ | 1136.1669 | 1136.1684 | 1.3 ppm |
| alpha-Mycolic acid C79:2 | $C_{79}H_{154}O_3$ | 1150.1825 | 1150.1833 | 0.7 ppm |
| Epoxy/keto-Mycolic acid C79:1 or Methoxy-Mycolic acid C79:2 | $C_{79}H_{154}O_4$ | 1166.1774 | 1166.1769 | 0.4 ppm |
| Epoxy/keto-Mycolic acid C80:1 or Methoxy-Mycolic acid C80:2 | $C_{80}H_{156}O_4$ | 1180.1931 | 1180.1897 | 2.9 ppm |
| Epoxy/keto-Mycolic acid C81:1 or Methoxy-Mycolic acid C81:2 | $C_{81}H_{158}O_3$ | 1194.2087 | 1194.2102 | 1.3 ppm |

TABLE 7

Table of biomarkers: sphingolipids and their spectrometric signals.
Identified sphingolipid species in members of the Bacteroidetes phylum.

| Formula | Experimental mass | Exact mass | Mass Deviation | Observed in |
|---|---|---|---|---|
| Ceramide Phosphorylethanolamine/Phosphoethanolamine Dihydroceramides (PE—DHC) | | | | |
| $C_{36}H_{74}N_2O_7P^-$ | 677.5253 | 677.5239 | 2.0 | *B. fragilis, B. ovatus, B. thetaiotaomicron, B.* |
| $C_{37}H_{76}N_2O_7P^-$ | 691.5411 | 691.5396 | 2.2 | *uniformis, B. vulgatus, P. bivia, P. distonasis* |
| $C_{38}H_{78}N_2O_7P^-$ | 705.5569 | 705.5552 | 2.4 | |
| Ceramides | | | | |
| $C_{34}H_{69}NO_4Cl^-$ | 590.4934$^a$ | 590.4921 | 2.2 | *B. fragilis, B. ovatus, B. thetaiotaomicron, B.* |
| $C_{35}H_{71}NO_4Cl^-$ | 604.5090 | 604.5077 | 2.1 | *uniformis, B. vulgatus, P. bivia, P. distonasis* |
| $C_{36}H_{73}NO_4Cl^-$ | 618.5246 | 618.5234 | 1.9 | |
| *Bacteroides fragilis* α-Galactosylceramides | | | | |
| $C_{40}H_{79}NO_9Cl^-$ | 752.5465 | 752.5449 | 2.1 | *B. fragilis* |
| $C_{41}H_{81}NO_9Cl^-$ | 766.5623 | 766.5605 | 2.3 | |
| $C_{42}H_{83}NO_9Cl^-$ | 780.5781 | 780.5762 | 2.4 | |
| C15:0 substituted Phosphoglycerol Dihydroceramides (subPG—DHC) | | | | |
| $C_{50}H_{100}O_{10}NP$ | 904.7007 | 904.7028 | 2.3 | *B. fragilis, B. ovatus, B. thetaiotaomicron, B.* |
| $C_{51}H_{102}O_{10}NP$ | 918.7163 | 918.7185 | 2.4 | *uniformis, B. vulgatus, P. distonasis* |
| $C_{52}H_{104}O_{10}NP$ | 932.7324$^b$ | 932.7337 | 1.4 | |
| $C_{53}H_{106}O_{10}NP$ | 946.7481$^b$ | 946.7484 | 0.3 | |
| $C_{54}H_{108}O_{10}NP$ | 960.7637$^b$ | 960.7624 | 1.3 | |
| Unsubstituted Phosphoglycerol Dihydroceramides (unPG—DHC) | | | | |
| $C_{37}H_{76}O_9NP$ | 708.5184 | 708.5199 | 2.1 | *P. distonasis* |
| $C_{39}H_{80}O_9NP$ | 736.5497 | 736.5484 | 1.8 | |

TABLE 8

Table of biomarkers: quorum-sensing molecules and their spectrometric signals
Identified quorum-sensing molecules in *Psuedomonas aeruginosa*.

| Compound | Sum formula | Exact mass | Exp. mass | Mass Deviation |
|---|---|---|---|---|
| 2-Heptylquinoline-4(1H)-one | $C_{16}H_{21}NO$ | [M − H]− = 242.1550 | 242.1552 | −0.8 ppm |
| 2-Heptyl-3-hydroxy-4(1H)-quinolone (PQS) | $C_{16}H_{21}NO_2$ | [M − H]− = 258.1499 | 258.1502 | −1.2 ppm |
| Hydroxynonenylquinoline | $C_{18}H_{23}NO$ | [M − H]− = 268.1707 | 268.1711 | −1.5 ppm |
| Hydroxynonylquinoline | $C_{18}H_{25}NO$ | [M − H]− = 270.1863 | 270.1868 | −1.9 ppm |
| Hydroxyundecenylquinoline | $C_{20}H_{26}NO$ | [M − H]− = 296.2020 | 296.2023 | −1.0 ppm |

TABLE 9

Table of biomarkers: Rhamnolipids and their spectrometric signals.
Rhamnolipid species commonly produced by *P. aeruginosa* strains.

| Compound | Sum formula | Exact mass [M − H]− | Exp. mass | Mass Deviation |
|---|---|---|---|---|
| Rha-C$_{20}$ | $C_{26}H_{48}O_9$ | 503.3225 | 503.3224 | 0.2 ppm |
| Rha-C$_{22:1}$ | $C_{28}H_{50}O_9$ | 529.3382 | 529.3384 | −0.4 ppm |
| Rha-C$_{22}$ | $C_{28}H_{52}O_9$ | 531.3539 | 531.3538 | 0.2 ppm |
| Rha-Rha-C$_{20}$ | $C_{32}H_{58}O_{13}$ | 649.3805 | 649.3804 | 0.2 ppm |
| Rha-Rha-C$_{22}$ | $C_{34}H_{62}O_{13}$ | 677.4118 | 677.4116 | −0.3 ppm |
| Rha-Rha-C$_{22:1}$ | $C_{34}H_{60}O_{13}$ | 675.3961 | 675.3965 | −0.6 ppm |

TABLE 10

Table of biomarkers: Surfactins and their spectrometric signals.
Surfactin species detected in positive and negative ion mode for *Bacillus subtilis*.

| | Negative ion mode | | | Positive ion mode | | |
|---|---|---|---|---|---|---|
| Compound | Exp. mass | Exact mass $[M - H]^-$ | $\Delta$ppm | Exp. mass | Exact mass $[M + Na]^+$ | $\Delta$ppm |
| Surfactin(C13) | 1006.6453 | 1006.6440 | 1.3 | 1030.6389 | 1030.6416 | 2.6 |
| Surfactin(C14) | 1020.6604 | 1020.6597 | 0.7 | 1044.6545 | 1044.6573 | 2.7 |
| Surfactin(C15) | 1034.6754 | 1034.6753 | 0.1 | 1058.6702 | 1058.6729 | 2.6 |

TABLE 11

Table of biomarkers: Lichenysins and their spectrometric signals
Lichenysin compounds detected in *Bacillus licheniformis*.

| Compound | Exp. mass | Exact mass $[M - H]^-$ | $\Delta$ppm |
|---|---|---|---|
| Lichenysin (C13) | 1005.6594 | 1005.6600 | 0.6 |
| Lichenysin (C14) | 1019.6748 | 1019.6756 | 0.8 |
| Lichenysin (C15) | 1033.6906 | 1033.6913 | 0.7 |
| Lichenysin (C16) | 1047.7055 | 1047.7070 | 1.4 |

TABLE 12

Table of biomarkers
Mass spectrometric signals that show strong positive correlation
with the ugcg gene expression for a cell line (NCI60) dataset.

| Exp. mass | Exact mass | $\Delta$ppm | Tentative ID | Formula | Adduct | Correlation coefficient |
|---|---|---|---|---|---|---|
| 734.5355 | 734.5343 | 0.2 | GlyCer(d18:1/16:0) | $C_{40}H_{77}NO_8$ | $[M + Cl]^-$ | 0.552 |
| 818.6295 | 818.6282 | 0.2 | GlyCer(d18:1/22:0) | $C_{46}H_{89}NO_8$ | $[M + Cl]^-$ | 0.662 |
| 842.6312 | 842.6332 | −0.2 | GlyCer(d18:1/24:2) | $C_{48}H_{89}NO_8$ | $[M + Cl]^-$ | 0.602 |
| 844.6451 | 844.6439 | 0.1 | GlyCer(d18:1/24:1) | $C_{48}H_{91}NO_8$ | $[M + Cl]^-$ | 0.668 |
| 846.6627 | 846.6595 | 0.4 | GlyCer(d18:1/24:0) | $C_{48}H_{93}NO_8$ | $[M + Cl]^-$ | 0.688 |
| 872.6733 | 872.6752 | −0.2 | GlyCer(d18:1/26:1) | $C_{50}H_{95}NO_8$ | $[M + Cl]^-$ | 0.707 |

TABLE 13

Table of biomarkers for Mycoplasma
List of m/z peak that are significantly higher in Mycoplasma
infected samples compared to Mycoplasma free samples in
both HEK and HeLa cell lines. Column 2 displays the corresponding
binned peak, column 2 highlights putative isotope peaks, while
column 4 shows the tentative annotation of the binned peak.
Phosphatidylglycerol and sphingomyelin species,
that are main Mycoplasma constituents are written in bold.

| significantly different binned m/z | corresponding m/z signal | Annotation |
|---|---|---|
| 687.54 | 687.5468 | |
| 722.51 | 722.5156 | PE(P-36:4) |
| 733.53 | 733.5231 | PE(P-38:4) |
| 747.52 | 747.5193 | PG(34:1) |
| 748.53 | 748.5243 | Isotope of irk = 747.52 |
| 753.51 | 753.5090 | PG(P-36:4) |
| 764.52 | 764.5264 | PE(38:5) |
| 764.53 | 764.5262 | PE(38:5) |
| 766.53 | 766.5412 | PE(38:4) |
| 773.54 | 773.5359 | PG(36:2) |
| 774.54 | 774.5391 | PG(36:2), Isotope of m/z = 773.54 |
| 774.55 | 774.5391 | PG(36:2), Isotope of m/z = 773.54 |
| 775.56 | 775.5520 | PG(36:1) |
| 776.56 | 776.5564 | PG(36:1), Isotope of m/z = 775.56 |
| 776.57 | 776.5564 | PG(36:1), Isotope of m/z = 775.56 |
| 819.52 | 819.5189 | PG(40:7) |
| 820.53 | 820.5268 | PG(40:7), Isotope of m/z = 819.52 |
| 820.54 | 820.5268 | PG(40:7), Isotope of m/z = 819.52 |

TABLE 14

Table of biomarkers: microbial taxon-specific biomarkers
Taxon-specific markers obtained for various microbes. No markers were calculated where the size of sample set was insufficient.

| | Phylum | Class | Order | Family | Genus | Species | No. |
|---|---|---|---|---|---|---|---|
| Gram - negative | Bacteroidetes<br>381.2765<br>393.2764<br>590.4923<br>591.4963<br>592.4883<br>604.5083<br>605.5113<br>606.5033<br>616.4724<br>623.5024<br>624.5054<br>637.5044<br>639.4954<br>640.4993<br>653.5113<br>654.5143<br>677.5238<br>691.5395<br>705.5562 | Bacteroidetes<br>616.5094<br>617.5124<br>618.5233<br>619.5273<br>620.5184<br>627.4883<br>628.4913<br>635.5004<br>636.5044<br>637.5044<br>644.5033<br>648.5003<br>697.5743<br>698.5763<br>711.5902<br>712.5933 | Bacteroidales | Bacteroidaceae<br>576.4764<br>820.7522 | *Bacteroides* | *Bacteroides acidifaciens*<br>*Bacteroides caccae*<br>*Bacteroides eggerthii*<br>*Bacteroides fragilis*<br>*Bacteroides helcogenes*<br>*Bacteroides ovatus*<br>*Bacteroides pyogenes*<br>*Bacteroides thetaiotaomicron*<br>*Bacteroides uniformis*<br>*Bacteroides vulgatus* | 2<br>2<br>2<br>5<br>1<br>3<br>1<br>3<br>3<br>3 |
| | | | | Porphyromonadaceae<br>814.7063<br>815.7112<br>828.7232<br>829.7262<br>840.6842<br>841.6942<br>843.7432<br>854.7022<br>858.6972<br>872.7072<br>908.7401<br>909.7431<br>910.7471<br>918.7191<br>921.7912<br>932.7332<br>933.7362<br>934.7422<br>944.7342<br>945.7372<br>946.7472<br>947.7502<br>948.7562<br>949.7592<br>958.7461<br>959.7501<br>960.7611<br>961.7661<br>962.7691 | *Parabacteroides* | *Parabacteroides distasonis*<br>*Parabacteroides johnsonii* | 5<br>2 |
| | | | | Prevotellaceae<br>661.5283<br>675.5453<br>676.5503<br>870.8002<br>908.7401<br>922.7552<br>923.7612<br>953.5113 | *Prevotella* | *Prevotella bivia* | 7 |
| | | | | Rikenellaceae | *Alistipes* | *Alistipes onderdonkii* | 1 |
| | | Flavobacteria<br>324.2545<br>333.2084<br>390.2324<br>392.2484<br>393.2504<br>552.4643<br>553.4674<br>553.4674<br>554.4714<br>556.4034<br>565.4654<br>566.4794<br>567.4834<br>568.4864<br>600.4664<br>601.4723<br>618.4773<br>619.4813<br>620.4883<br>651.4953<br>651.4953<br>891.7411 | Flavobacteriales | Flavobacteriaceae | *Chryseobacterium*<br><br><br>*Elizabethkingia*<br><br>*Myroides* | *Chryseobacterium indologenes*<br>*Chryseobacterium* sp<br>*Elizabethkingia meningoseptica*<br>*Myroides odoratimimus* | 3<br>1<br>4<br>2 |

TABLE 14-continued

Table of biomarkers: microbial taxon-specific biomarkers
Taxon-specific markers obtained for various microbes. No markers were calculated where the size of sample set was insufficient.

| Phylum | Class | Order | Family | Genus | Species | No. |
|---|---|---|---|---|---|---|
| Fusobacteria 227.2015 644.4652 645.4633 646.4833 647.4812 648.4832 673.4443 696.4953 714.5492 856.6782 865.6632 884.7083 | Fusobacteria | Fusobacteriales | Fusobacteriaceae | *Fusobacterium* | *Fusobacterium gonidiaformans* | 3 |
| | | | | | *Fusobacterium necrophorum* | 7 |
| | | | | | *Fusobacterium peridontiam* | 4 |
| | | | | | *Fusobacterium* sp | 1 |
| Proteobacteria 768.5182 782.5342 783.5293 | Alpha-Proteobacteria | Caulobacterales 769.5502 770.5562 771.5582 795.5572 797.5723 818.5673 957.6261 | Caulobacteraceae | *Brevundimonas* | *Brevundimonas diminuta* | 2 |
| | | Rhizobiales 439.4155 440.4195 739.5313 784.5902 785.5932 799.5132 | Rhizobiaceae | *Rhizobium* | *Rhizobium radiobacter* | 5 |
| | | Rhodospirillales 662.5393 722.5753 729.5813 733.5752 733.6173 734.5753 747.6283 757.6173 | Acetobacteraceae | *Roseomonas* | *Roseomonas mucosa* | 6 |
| | | | | | *Roseomonas* sp | 1 |
| | Beta-Proteobacteria | Burkholderiales | Alcaligenaceae | *Achromobacter* | *Achromobacter* sp | 3 |
| | | | | | *Achromobacter xylosoxidans* | 3 |
| | | | | *Alcaligenes* | *Alcaligenes faecalis* | 3 |
| | | | Burkholderiaceae 589.4013 590.4083 591.4184 592.4214 | *Burkholderia* | *Burkholderia cepacia* complex | 7 |
| | | | Comamonadaceae 520.3044 | *Acidovorax* | *Acidovorax temperans* | 2 |
| | | | | *Comamonas* | *Comamonas kerstersii* | 2 |
| | | | | | *Comamonas* sp | 1 |
| | | | | *Delftia* | *Delftia acidovorans* | 4 |
| | | | | | *Delftia dentocariosa* | 1 |
| | | | | | *Delftia* sp | 2 |
| | | | Sutterellaceae | *Sutterella* | *Sutterella wadsworthensis* | 2 |
| | | Neisseriales 494.3855 502.3674 526.3673 527.3704 528.3653 544.3774 | Neisseriaceae | *Eikenella* | *Eikenella corrodens* | 1 |
| | | | | *Kingella* | *Kingella kingae* | 3 |
| | | | | | *Kingella* sp | 1 |
| | | | | *Neisseria* | *Neisseria cineria* | 1 |
| | | | | | *Neisseria elongata* | 2 |
| | | | | | *Neisseria flavescens* | 3 |
| | | | | | *Neisseria gonorrhoea* | 4 |
| | | | | | *Neisseria lactamica* | 3 |
| | | | | | *Neisseria meningitidis* | 4 |
| | | | | | *Neisseria mucosa* | 2 |
| | Epsilon-Proteobacteria 730.5422 731.5452 867.6582 993.8381 | Campylobacterales | Campylobacteraceae 867.6582 993.8381 | *Campylobacter* | *Campylobacter coli* | 1 |
| | | | | | *Campylobacter fetus* | 3 |
| | | | | | *Campylobacter jejuni* | 3 |
| | | | | | *Campylobacter* sp | 6 |
| | | | Helicobacteraceae 271.2284 272.2305 299.2595 300.2625 400.2644 | *Helicobacter* | *Helicobacter pylori* | 3 |

TABLE 14-continued

Table of biomarkers: microbial taxon-specific biomarkers
Taxon-specific markers obtained for various microbes. No markers were calculated where the size of sample set was insufficient.

| Phylum | Class | Order | Family | Genus | Species | No. |
|---|---|---|---|---|---|---|
| | Gamma-Proteobacteria | 543.4623<br>544.4634<br>Aeromonadales<br>Cardiobacteriales<br>648.4603<br>649.4623<br>650.4653<br>793.4792<br>794.4802 | Aeromonadaceae<br>Cardiobacteriaceae | *Aeromonas*<br>*Cardiobacterium* | *Aeromonas hydrophila*<br>*Cardiobacterium hominis* | 1<br>4 |
| | | Enterobacteriales<br>702.5083<br>703.5092<br>993.7282<br>994.7272 | Enterobacteriaceae | *Citrobacter* | *Citrobacter amalonaticus*<br>*Citrobacter braakii*<br>*Citrobacter freundii*<br>*Citrobacter koseri* | 1<br>3<br>4<br>4 |
| | | | | *Enterobacter* | *Enterobacter absuriae*<br>*Enterobacter aerogenes*<br>*Enterobacter amnigenus*<br>*Enterobacter cloacae*<br>*Enterobacter gergoviae* | 2<br>3<br>1<br>3<br>1 |
| | | | | *Escherichia* | *Escherichia coli* | 7 |
| | | | | *Hafnia* | *Hafnia alvei*<br>*Hafnia paralvei*<br>*Hafnia* sp | 3<br>2<br>1 |
| | | | | *Klebsiella* | *Klebsiella oxytoca*<br>*Klebsiella pneumoniae* | 5<br>5 |
| | | | | *Morganella* | *Morganella morganii* | 7 |
| | | | | *Panthoea* | *Panthoea* sp | 1 |
| | | | | *Proteus* | *Proteus mirabilis*<br>*Proteus vulgaris* | 5<br>5 |
| | | | | *Provedencia* | *Provedencia rettgeri*<br>*Provedencia stuartii* | 2<br>2 |
| | | | | *Raoultella* | *Raoultella ornithololytica*<br>*Raoultella planticola* | 1<br>1 |
| | | | | *Salmonella* | *Salmonella poona* | 1 |
| | | | | *Serratia* | *Serratia liquifaciens*<br>*Serratia marcescens* | 3<br>5 |
| | | | | *Shigella* | *Shigella sonnei* | 1 |
| | | Pasteurellales<br>690.4983<br>746.4503<br>823.5453<br>898.6921<br>915.6902<br>977.7282 | Pasteurellaceae | *Aggregatibacter* | *Aggregatibacter aphrophilus* | 5 |
| | | | | *Haemophilus* | *Haemophilus influenzae*<br>*Haemophilus parahaemolyticus*<br>*Haemophilus parainfluenzae* | 5<br>2<br>1 |
| | | | | *Pasteurella* | *Pasteurella multocida* | 2 |
| | | Pseudomonadales | Moraxellaceae | *Acinetobacter* | *Acinetobacter baumanii*<br>*Acinetobacter iwoffii*<br>*Acinetobacter johnsonii*<br>*Acinetobacter junii* | 5<br>5<br>2<br>1 |
| | | | | *Moraxella* | *Moraxella catarrhalis*<br>*Moraxella osloensis* | 5<br>2 |
| | | | Pseudomonadaceae<br>286.1805<br>490.3304<br>514.3294 | *Pseudomonas* | *Pseudomonas aearuginosa*<br>*Pseudomonas luteola*<br>*Pseudomonas monteilii*<br>*Pseudomonas oryzihabitans*<br>*Pseudomonas putida*<br>*Pseudomonas stutzeri* | 7<br>1<br>2<br>2<br>1<br>5 |
| | | Vibrionales<br>605.3823<br>607.3983<br>608.4013<br>633.4134 | Vibrionaceae | *Vibrio* | *Vibrio alginolyticus*<br>*Vibrio cholerae*<br>*Vibrio furnissii* | 1<br>1<br>1 |
| | | Xanthomonadales<br>377.2105<br>562.3504<br>619.4353<br>620.4384<br>705.4713<br>706.4743<br>929.6852<br>930.6892<br>942.6912<br>943.7012<br>944.7052 | Xanthomonadaceae | *Stenotrophomonas* | *Stenotrophomonas maltophilia* | 7 |

TABLE 14-continued

Table of biomarkers: microbial taxon-specific biomarkers
Taxon-specific markers obtained for various microbes. No markers were calculated where the size of sample set was insufficient.

| | Phylum | Class | Order | Family | Genus | Species | No. |
|---|---|---|---|---|---|---|---|
| Gram - positive | Actinobacteria | Actinobacteria | Actinomycetales | Actinomycetaceae 757.5403 879.6112 | *Actinobaculum* *Actinomyces* | *Actinobaculum schaalii* | 2 |
| | | | | | | *Actinomyces graevenitzii* | 1 |
| | | | | | | *Actinomyces israelii* | 1 |
| | | | | | | *Actinomyces odontolyticus* | 2 |
| | | | | | | *Actinomyces oris* | 5 |
| | | | | | | *Actinomyces* sp | 1 |
| | | | | | | *Actinomyces turicensis* | 1 |
| | | | | | | *Actinomyces viscosis* | 2 |
| | | | | Corynebacteriaceae 493.4624 495.4784 497.4845 521.4934 535.4734 537.4904 538.4934 | *Corynebacterium* | *Corynebacterium afermentans* | 2 |
| | | | | | | *Corynebacterium amycolatum* | 3 |
| | | | | | | *Corynebacterium diphtheriae* | 2 |
| | | | | | | *Corynebacterium imitans* | 3 |
| | | | | | | *Corynebacterium minutissimum* | 1 |
| | | | | | | *Corynebacterium* sp | 5 |
| | | | | | | *Corynebacterium striatum* | 3 |
| | | | | Microbacteriaceae | *Microbacterium* | *Microbacterium* sp | 1 |
| | | | | Mycobacteriaceae 391.3684 427.0965 724.8873 817.4152 850.5592 851.5662 852.5672 | *Mycobacterium* | *Mycobacterium avium* | 2 |
| | | | | | | *Mycobacterium fortuitum* | 1 |
| | | | | | | *Mycobacterium peregrium* | 1 |
| | | | | Nocardiaceae 321.2915 743.7273 771.7592 797.7762 798.7762 800.7962 827.8162 828.8222 970.7871 | *Nocardia* *Rhodococcus* | *Nocardia* sp | 1 |
| | | | | | | *Rhodococcus equi* | 1 |
| | | | | | | *Rhodococcus* sp | 2 |
| | | | | Propionibacteriaceae 361.2155 617.4564 713.4752 714.4812 779.5072 877.5592 906.5872 | *Propionibacterium* | *Propionibacterium acnes* | 7 |
| | | | Bifidobacteriales 789.5293 792.5502 819.5783 830.5622 855.5272 884.6092 885.6142 | Bifidobacteriaceae | *Bifidobacterium* | *Bifidobacterium adolescentis* | 1 |
| | | | | | | *Bifidobacterium bifidum* | 2 |
| | | | | | | *Bifidobacterium breve* | 3 |
| | | | | | | *Bifidobacterium infantis* | 1 |
| | | | | | | *Bifidobacterium longum* | 3 |
| | | | | | | *Bifidobacterium pseudocatenulatum* | 2 |
| | | | | | *Gardnerella* | *Gardnerella vaginalis* | 2 |
| | | | Micrococcales 913.5682 | Micrococcaceae 913.5682 914.5711 915.5671 | *Arthrobacter* | *Arthrobacter creatinolyticus* | 1 |
| | | | | | | *Arthrobacter* sp | 1 |
| | | | | | *Kokuria* | *Kokuria kristina* | 2 |
| | | | | | | *Kokuria rhizophila* | 2 |
| | | | | | | *Kokuria varians* | 1 |
| | | | | | *Micrococcus* | *Micrococcus luteus* | 5 |
| | | | | | | *Micrococcus lylae* | 2 |
| | | | | | *Rothia* | *Rothia aeria* | 3 |
| | | | | | | *Rothia amarne* | 1 |
| | | | | | | *Rothia dentocariosa* | 5 |
| | | | | | | *Rothia mucilaginosa* | 5 |
| | | | | | | *Rothia* sp | 1 |
| | | | | Micrococcineae | *Brevibacterium* | *Brevibacterium paucivorans* | 1 |
| | | | | | | *Brevibacterium* sp | 3 |
| | | | | | *Dermabacter* | *Dermabacter hominis* | 2 |
| | | | | | | *Dermobacter* sp | 1 |

TABLE 14-continued

Table of biomarkers: microbial taxon-specific biomarkers
Taxon-specific markers obtained for various microbes. No markers were calculated where the size of sample set was insufficient.

| Phylum | Class | Order | Family | Genus | Species | No. |
|---|---|---|---|---|---|---|
| Firmicutes | Bacilli | Bacillales | Bacillaceae | *Bacillus* | *Bacillus cereus* | 3 |
| | | | | | *Bacillus clausii* | 3 |
| | | | | | *Bacillus lichenformis* | 3 |
| | | | | | *Bacillus pumilus* | 1 |
| | | | | | *Bacillus sonorensis* | 1 |
| | | | | | *Bacillus* sp | 3 |
| | | | | | *Bacillus subtilis* | 3 |
| | | | Listeriaceae 675.9793 832.5352 | *Listeria* | *Listeria monocytogenes* | 7 |
| | | | Paenibacillaceae 871.5892 903.7221 914.7282 915.7282 916.7282 | *Paenibacillus* | *Paenibacillus* sp | 5 |
| | | | | | *Paenibacillus unalis* | 1 |
| | | | Staphylococcaceae 763.5512 765.5482 | *Staphylococcus* | *Staphylococcus aureus* | 3 |
| | | | | | *Staphylococcus capitis* | 3 |
| | | | | | *Staphylococcus caprae* | 1 |
| | | | | | *Staphylococcus cohnii* | 4 |
| | | | | | *Staphylococcus epidermis* | 3 |
| | | | | | *Staphylococcus haemolyticus* | 3 |
| | | | | | *Staphylococcus hominis* | 3 |
| | | | | | *Staphylococcus lugdunensis* | 3 |
| | | | | | *Staphylococcus pasteuri* | 3 |
| | | | | | *Staphylococcus pettenkoferi* | 3 |
| | | | | | *Staphylococcus saprophyticus* | 3 |
| | | | | | *Staphylococcus warneri* | 3 |
| | | Lactobacillales 898.5391 923.5512 925.5671 926.5701 928.5952 949.5672 950.5692 951.5832 952.5861 953.5981 954.6011 955.5971 956.5971 979.6111 990.6001 | Aerococcaceae 163.0506 | *Abiotrophia* | *Abiotrophia defectiva* | 1 |
| | | | | *Aerococcus* | *Aerococcus* sp | 1 |
| | | | | | *Aerococcus viridans* | 2 |
| | | | Carnobacteriaceae | *Granulicatella* | *Granulicatella adiacens* | 1 |
| | | | Enterococcaceae | *Enterococcus* | *Enterococcus avium* | 3 |
| | | | | | *Enterococcus casseliflavus* | 2 |
| | | | | | *Enterococcus cecorum* | 1 |
| | | | | | *Enterococcus faecalis* | 3 |
| | | | | | *Enterococcus faecium* | 3 |
| | | | | | *Enterococcus gallinarum* | 3 |
| | | | | | *Enterococcus raffinosus* | 3 |
| | | | Lactobacillaceae | *Lactococcus* | *Lactococcus lactis* | 1 |
| | | | | | *Lactococcus* spp | 2 |
| | | | Leuconostocaceae | *Leuconostoc* | *Leuconostoc* sp | 1 |
| | | | Streptococcaceae 897.5351 | *Lactobacillus* | *Lactobacillus gasseri* | 2 |
| | | | | | *Lactobacillus rhamnosus* | 3 |
| | | | | *Streptococcus* | *Streptococcus agalactiae* | 3 |
| | | | | | *Streptococcus anginosus* | 3 |
| | | | | | *Streptococcus bovis* | 3 |
| | | | | | *Streptococcus canis* | 1 |
| | | | | | *Streptococcus constellatus* | 2 |
| | | | | | *Streptococcus cristatus* | 2 |
| | | | | | *Streptococcus dysagalactiae* | 3 |
| | | | | | *Streptococcus gallolyticus* | 3 |
| | | | | | *Streptococcus gordonii* | 3 |

TABLE 14-continued

Table of biomarkers: microbial taxon-specific biomarkers
Taxon-specific markers obtained for various microbes. No markers were calculated where the size of sample set was insufficient.

| Phylum | Class | Order | Family | Genus | Species | No. |
|---|---|---|---|---|---|---|
| | | | | | *Streptococcus intermedius* | 3 |
| | | | | | *Streptococcus lutetiensis* | 3 |
| | | | | | *Streptococcus milleri* | 3 |
| | | | | | *Streptococcus mitis* | 3 |
| | | | | | *Streptococcus mutans* | 3 |
| | | | | | *Streptococcus oralis* | 3 |
| | | | | | *Streptococcus parasanguinus* | 3 |
| | | | | | *Streptococcus pneumoniae* | 3 |
| | | | | | *Streptococcus povas* | 1 |
| | | | | | *Streptococcus pseudoporcinus* | 2 |
| | | | | | *Streptococcus pyogenes* | 3 |
| | | | | | *Streptococcus salivarius* | 3 |
| | | | | | *Streptococcus sanguinis* | 3 |
| | | | | | *Streptococcus vestibularis* | 1 |
| | | | | | *Streptococcus viridans* | 3 |
| | Clostridia 449.2685 703.4923 704.4953 731.5253 732.5283 925.7262 | Clostridiales | Clostridiaceae 649.4453 731.5253 897.6951 925.7262 969.7481 970.7541 | *Clostridium* | *Clostridium celerecrescens* | 1 |
| | | | | | *Clostridium difficile* | 4 |
| | | | | | *Clostridium histolyticum* | 2 |
| | | | | | *Clostridium innocuum* | 3 |
| | | | | | *Clostridium paraputrificum* | 2 |
| | | | | | *Clostridium perfringens* | 3 |
| | | | | | *Clostridium ramosum* | 3 |
| | | | | | *Clostridium septicum* | 2 |
| | | | | | *Clostridium sporogenes* | 2 |
| | | | | | *Clostridium tertium* | 3 |
| | | | Peptostreptococcaceae 496.4124 497.4214 498.4244 635.3944 645.4133 646.4173 681.3923 | *Parvinomas* | *Parvinomas micra* | 1 |
| | | | | *Peptoniphilus* | *Peptoniphilus harei* | 5 |
| | Negativicutes 423.3505 425.3644 426.3674 461.3394 560.4194 851.7352 | Selenomonadales | Acidaminococcaceae 627.4403 643.4343 644.4383 730.4652 734.5933 831.5902 977.6971 978.6931 | *Acidaminococcus* | *Acidaminococcus fermentans* | 2 |
| | | | Veillonellaceae 218.1855 229.1815 358.2145 364.2495 655.4713 | *Dialister* | *Dialister* sp | 1 |
| | | | | *Veillonella* | *Veillonella atypica* | 1 |
| | | | | | *Veillonella dispar* | 1 |
| | | | | | *Veillonella parvula* | 1 |
| | | | | | *Veillonella ratti* | 1 |

TABLE 16

Taxon-specific markers as determined on phylum-level.

| Phylogenetic information | Taxonomic level | m/z value | Compound ID |
|---|---|---|---|
| Gram-negatives | Bacteroidetes (Phylum) | 381.2765 | spingolipid |
| | | 653.5113 | Isotope m/z = 653 |
| | | 654.5143 | CerP(d34:1)) |
| | | 623.5024 | isotope m/z = 623 |
| | | 640.4993 | isotope m/z = 635 |
| | | 639.4954 | isotope m/z = 590 |
| | | 393.2764 | Cer(d18:0/h17:0) |
| | | 616.4724 | isotope m/z = 604 |
| | | 624.5054 | isotope m/z = 604 |
| | | 637.5044 | Cer(d34:0(2OH) |
| | | 592.4883 | isotope m/z = 590 |
| | | 604.5083 | PE—DHC |
| | | 605.5113 | PE—DHC |
| | | 606.5033 | PE—DHC |
| | | 590.4923 | |
| | | 591.4963 | |
| | | 705.5562 | |
| | | 691.5395 | |
| | | 677.5238 | |

TABLE 16-continued

Taxon-specific markers as determined on phylum-level.

| Phylogenetic information | Taxonomic level | m/z value | Compound ID |
|---|---|---|---|
| | Fusobacteria (Phylum) | 646.4833 | PE plasmalogen |
| | | 227.2015 | PE plasmalogen combinatorial marker with m/z = 227 |
| | | 648.4832 | |
| | | 856.6782 | |
| | | 865.6632 | |
| | | 696.4953 | |
| | | 714.5492 | |
| | | 673.4443 | |
| | | 644.4652 | |
| | | 884.7083 | |
| | | 645.4633 | |
| | | 647.4812 | |
| | Proteobacteria | 768.5182 | |
| | | 782.5342 | |
| | | 783.5293 | |
| Gram-positives | Actinobacteria | — | |
| | Firmicutes | — | |

TABLE 17

Taxon-specific markers as determined on class-level.

| Phylogenetic information | Taxonomic level | m/z value | Compound ID |
|---|---|---|---|
| Gram-negatives ˡBacteroidetes | Bacteroidetes | 635.5004 | sphingolipid |
| | | 616.5094 | Cer(d36:1(2OH)) |
| | | 628.4913 | PE-Cer(33:1) |
| | | 636.5044 | CerP(d36:1) |
| | | 627.4883 | Cer(d36:0(2OH)) |
| | | 644.5033 | isotope 618 |
| | | 711.5902 | DG(42:5) |
| | | 618.5233 | isotope m/z = 616 |
| | | 712.5933 | |
| | | 619.5273 | |
| | | 697.5743 | |
| | | 620.5184 | |
| | | 698.5763 | |
| | | 648.5003 | |
| | | 637.5044 | |
| | | 617.5124 | |
| | Flavobacteria | 333.2084 | |
| | | 390.2324 | |
| | | 566.4794 | |
| | | 567.4834 | |
| | | 568.4864 | |
| | | 556.4034 | |
| | | 600.4664 | |
| | | 565.4654 | |
| | | 553.4674 | |
| | | 392.2484 | |
| | | 651.4953 | |
| | | 618.4773 | |
| | | 619.4813 | |
| | | 324.2545 | |
| | | 620.4883 | |
| | | 393.2504 | |
| | | 891.7411 | |
| | | 554.4714 | |
| | | 552.4643 | |
| | | 553.4674 | |
| | | 651.4953 | |
| | | 601.4723 | |
| Gram-negatives ˡFusobacteria | Fusobacteria (class) | | |
| Gram-negatives ˡProteobacteria | Alpha-Proteobacteria | | |
| | Beta-Proteobacteria | — | |
| | Epsilon-Proteobacteria | 993.8381 | |
| | | 867.6582 | |
| | | 731.5452 | |
| | | 730.5422 | |

TABLE 17-continued

Taxon-specific markers as determined on class-level.

| Phylogenetic information | Taxonomic level | m/z value | Compound ID |
|---|---|---|---|
| | Gamma-Proteobacteria | — | |
| Gram-positives ˡActinobacteria | Actinobacteria (class) | — | |
| Gram-positives ˡFirmicutes | Bacilli | — | |
| | Clostridia | 731.5253 | PG plasmalogen |
| | | 732.5283 | Isotope m/z = 731 |
| | | 449.2685 | PG plasmalogen |
| | | 703.4923 | Isotope m/z = 703 |
| | | 925.7262 | |
| | | 704.4953 | |
| | Negativicutes | 560.4194 | Isotope m/z = 425 |
| | | 426.3674 | |
| | | 425.3644 | |
| | | 423.3505 | |
| | | 461.3394 | |
| | | 851.7352 | |

TABLE 18

Taxon-specific markers as determined on order-level.

| Phylogenetic information | Taxonomic level | m/z value | Compound ID |
|---|---|---|---|
| Gram-negatives Bacteroidales ˡBacteroidetes | | | |
| Gram-negatives ˡBacteroidetes ˡFlavobacteria | Flavobacteriales | | |
| Gram-negatives ˡFusobacteria ˡFusobacteria | Fusobacteriales | | |
| Gram-negatives ˡProteobacteria ˡAlpha-Proteobacteria | Caulobacterales | 795.5572 | |
| | | 797.5723 | |
| | | 769.5502 | |
| | | 770.5562 | |
| | | 957.6261 | |
| | | 771.5582 | |
| | | 818.5673 | |
| | Rhizobiales | 739.5313 | Isotope m/z = 784 |
| | | 784.5902 | |
| | | 785.5932 | Isotope m/z = 439 |
| | | 439.4155 | |
| | | 440.4195 | |
| | | 799.5/32 | |
| | Rhodospiralles | 733.5752 | |
| | | 734.5753 | |
| | | 729.5813 | |
| | | 733.6173 | |
| | | 722.5753 | |
| | | 662.5393 | |
| | | 747.6283 | |
| | | 757.6173 | |
| Gram-negatives ˡProteobacteria ˡBeta-Proteobacteria | Burkholderiales | — | |
| | Neisseriales | 526.3673 | Isotope m/z = 526 |
| | | 527.3704 | |
| | | 502.3674 | |
| | | 544.3774 | |
| | | 494.3855 | |
| | | 528.3653 | |
| Gram-negatives ˡProteobacteria ˡEpsilon-Proteobacteria | Campylobacterales | — | |
| Gram-negatives ˡProteobacteria ˡGamma-Proteobacteria | Aeromonadales | | |
| | Cardiobacterales | 648.4603 | Isotope m/z = 648 |
| | | 649.4623 | |
| | | 793.4792 | |
| | | 650.4653 | |
| | | 794.4802 | |
| | Enterobacterales | 703.5092 | Isotope m/z = 702 |
| | | 702.5083 | |

TABLE 18-continued

Taxon-specific markers as determined on order-level.

| Phylogenetic information | Taxonomic level | m/z value | Compound ID |
|---|---|---|---|
| | | 993.7282 | |
| | | 994.7272 | |
| | Pasteurellales | 746.4503 | |
| | | 915.6902 | |
| | | 823.5453 | |
| | | 898.6921 | |
| | | 690.4983 | |
| | | 977.7282 | |
| | Pseudomonadales | — | |
| | Vibrionales | 607.3983 | Isotope m/z = 607 |
| | | 608.4013 | |
| | | 633.4134 | |
| | | 605.3823 | |
| | Xanthomonadales | 562.3504 | Isotope m/z = 619 |
| | | 377.2105 | |
| | | 619.4353 | Isotope m/z = 629 |
| | | 620.4384 | |
| | | 930.6892 | Isotope m/z = 643 |
| | | 929.6852 | |
| | | 944.7052 | Isotope m/z = 705 |
| | | 943.7012 | |
| | | 942.6912 | PG(31:1) |
| | | 706.4743 | |
| | | 705.4713 | |
| Gram-positives | Actinomycetales | — | |
| ˡActinobacteria | Bifidobacteriales | 792.5502 | |
| ˡActinobacteria | | 819.5783 | |
| | | 884.6092 | |
| | | 885.6142 | |
| | | 789.5293 | |
| | | 830.5622 | |
| | | 855.5272 | |
| | Micrococcales | 913.5682 | |
| Gram-positives | Bacillales | | |
| ˡFirmicutes | Lactobacillales | 951.5832 | |
| ˡBacilli | | 954.6011 | |
| | | 952.5861 | |
| | | 953.5981 | |
| | | 925.5671 | |
| | | 956.5971 | |
| | | 955.5971 | |
| | | 926.5701 | |
| | | 950.5692 | |
| | | 949.5672 | |
| | | 928.5952 | |
| | | 990.6001 | |
| | | 923.5512 | |
| | | 898.5391 | |
| | | 979.6111 | |
| | Clostridiales | | |
| | Selemonadales | | |

TABLE 19

Taxon-specific markers as determined on family-level

| Phylogenetic information | Taxonomic level | m/z value | Compound ID |
|---|---|---|---|
| Gram-negatives | Bacteroidaceae | 820.7522 | |
| ˡBacteroidetes | Porphyro- | 841.6942 | isotope m/z = 840 |
| ˡBacteroidetes | monadaceae | 840.6842 | isotope m/z = 946 |
| ˡBacteroidales | | 948.7562 | isotope m/z = 946 |
| | | 949.7592 | isotope m/z = 946 |
| | | 947.7502 | SubPG DHC |
| | | 946.7472 | isotope m/z = 944 |
| | | 945.7372 | SubPG DHC |
| | | 944.7342 | isotope m/z = 932 |
| | | 933.7362 | SubPG DHC |
| | | 932.7332 | isotope m/z = 814 |
| | | 872.7072 | isotope m/z = 960 |
| | | 815.7112 | SubPG DHC |
| | | 814.7063 | isotope m/z = 960 |
| | | 858.6972 | isotope m/z = 828 |
| | | 934.7422 | isotope m/z = 958 |
| | | 962.7691 | |
| | | 960.7611 | |
| | | 961.7661 | |
| | | 828.7232 | |
| | | 829.7262 | |
| | | 854.7022 | |
| | | 959.7501 | |
| | | 958.7461 | |
| | | 921.7912 | |
| | | 918.7191 | |
| | | 843.7432 | |
| | | 910.7471 | |
| | | 908.7401 | |
| | | 909.7431 | |
| | Prevotellaceae | 661.5283 | |
| | | 908.7401 | |
| | | 675.5453 | |
| | | 922.7552 | |
| | | 923.7612 | |
| | | 676.5503 | |
| | | 870.8002 | |
| | Rikenellaceae | | |
| Gram-negatives | Flavo- | | |
| ˡBacteroidetes | bacteriaceae | | |
| ˡFlavobacteria | | | |
| ˡFlavobacteriales | | | |
| Gram-negatives | Fusobacteriaceae | | |
| ˡFusobacteria | | | |
| ˡFusobacteria | | | |
| ˡFusobacteriales | | | |
| Gram-negatives | Caulobacteraceae | | |
| ˡProteobacteria | | | |
| ˡAlpha-Proteobacteria | | | |
| ˡCaulobacterales | | | |
| Gram-negatives | Rhizobiaceae | | |
| ˡProteobacteria | | | |
| ˡAlpha-Proteobacteria | | | |
| ˡRhizobiales | | | |
| Gram-negatives | Acetobacteraceae | | |
| ˡProteobacteria | | | |
| ˡAlpha-Proteobacteria | | | |
| ˡRhodospirales | | | |
| Gram-negatives | Alcaligenaceae | | |
| ˡProteobacteria | Burkholderiaceae | 589.4013 | Isotope m/z = 589 |
| ˡBeta-Proteobacteria | | 591.4184 | Isotope m/z = 591 |
| ˡBurkholderiales | | 590.4083 | |
| | | 592.4214 | |
| | Comamonadaceae | 520.3044 | |
| | Sutterellaceae | — | |
| Gram-negatives | Neisseriaceae | | |
| ˡProteobacteria | | | |
| ˡBeta-Proteobacteria | | | |
| ˡNeisseriales | | | |
| Gram-negatives | Campylo- | 993.8381 | |
| ˡProteobacteria | bacteraceae | 867.6582 | |
| ˡEpsilon- | Helico- | 299.2595 | C18:0(+O) |
| Proteobacteria | bacteraceae | 300.2625 | Isotope m/z = 299 |
| ˡCampylobacterales | | 272.2305 | Isotope m/z = 271 |
| | | 271.2284 | C16:0(+O) |
| | | 543.4623 | |
| | | 400.2644 | |
| | | 544.4634 | |
| Gram-negatives | Cardio- | | |
| ˡProteobacteria | bacteriaceae | | |
| ˡGamma- | | | |
| Proteobacteria | | | |
| ˡCardiobacterales | | | |
| Gram-negatives | Entero- | | |
| ˡProteobacteria | bacteriaceae | | |
| ˡGamma- | | | |
| Proteobacteria | | | |
| ˡEnterobacterales | | | |

TABLE 19-continued

Taxon-specific markers as determined on family-level

| Phylogenetic information | Taxonomic level | m/z value | Compound ID |
|---|---|---|---|
| Gram-negatives ˡProteobacteria ˡGamma-Proteobacteria ˡPasteurellales | Pasteurellaceae | | |
| Gram-negatives ˡProteobacteria ˡGamma-Proteobacteria ˡPseudomonadales | Moraxellaceae Pseudomonadaceae | — 514.3294 490.3304 286.1805 | |
| Gram-negatives ˡProteobacteria ˡGamma-Proteobacteria ˡVibrionales | Vibrionaceae | | |
| Gram-negatives ˡProteobacteria ˡGamma-Proteobacteria ˡXanthomonadales | Xanthomonadaceae | | |
| Gram-positives ˡActinobacteria ˡActinobacteria ˡActinomycetales | Actinomyceteae Corynebacteriaceae | 757.5403 879.6112 537.4904 538.4934 535.4734 493.4624 495.4784 497.4845 521.4934 | Combinatorial markers Mycolic acid C35:0 Isotope m/z = 537 Mycolic acid C35:1 Mycolic acid C32:1 Mycolic acid C32:0 Isotope m/z = 495 Mycolic acid C34:1 |
| | Microbacteriaceae Mycobacteriaceae | 851.5662 852.5672 850.5592 391.3684 724.8873 427.0965 817.4152 | PI(35:0) Isotope m/z = 851 |
| | Nocardiaceae | 798.7762 797.7762 828.8222 970.7871 321.2915 827.8162 800.7962 743.7273 771.7592 | Isotope m/z = 797 Mycolic acid C54:3 Isotope m/z = 827 combinatorial Mycolic acid C56:2 Isotope Mycolic acid C54:2 Mycolic acid C50:2 Mycolic acid C52:2 |
| | Propionibacteriaceae | 617.4564 906.5872 779.5072 714.4812 361.2155 713.4752 877.5592 | |
| Gram-positives ˡActinobacteria ˡActinobacteria ˡBifidobacteriales | Bifidobacteriaceae | 792.5502 819.5783 | |
| Gram-positives ˡActinobacteria ˡActinobacteria ˡMicrococcales | Micrococcaceae Micrococcineae | 913.5682 914.5711 915.5671 | Isotope m/z = 913 |
| Gram-positives ˡFirmicutes ˡBacilli ⌊Bacillales | Bacillaceae Listeriaceae Paenibacillaceae | 675.9793 832.5352 915.7282 916.7282 914.7282 871.5892 903.7221 | |
| | Staphylococcaceae | 765.5482 763.5512 163.0506 | Isotope m/z = 763 PG(35:0) |
| Gram-positives ˡFirmicutes ˡBacilli ˡLactoacillales | Aerococcaceae Carnobacteriaceae Enterococcaceae Lactobacillaceae Leuconostocaceae Streptococcaceae | — — 897.5351 | |
| Gram-positives ˡFirmicutes ˡClostridia ˡClostridiales | Clostridiaceae | 731.5253 970.7541 649.4453 897.6951 969.7481 925.7262 | |
| | Peptostreptococcaceae | 497.4214 498.4244 681.3923 635.3944 496.4124 645.4133 646.4173 | Isotope m/z = 497 Isotope m/z = 645 |
| Gram-positives ˡFirmicutes ˡNegativicutes ˡSelemonadales | Acidaminococcaceae | 730.4652 627.4403 831.5902 977.6971 978.6931 643.4343 644.4383 734.5933 | |
| | Veillonellaceae | 229.1815 218.1855 364.2495 655.4713 358.2145 | |

TABLE 20

| m/z | IDs | CD | ANOVA pVal | ANOVA qVal | Healthy EC (Mean) | HO (Mean) | SC (Mean) | SA (Mean) | MedFC-HO-SC | MeanFC-HO-SA |
|---|---|---|---|---|---|---|---|---|---|---|
| 756.5955 | PE(P-38:1) | SC | 0.0335362 | 1 | 0 | 0.001 | 2.9186 | 0.6746 | 11.51106078 | 9.397888508 |
| 865.5746 | PI(36:0) | SC | 8.99775E-06 | 0.000181998 | 4.2331 | 0.2857 | 16.469 | 3.3348 | 5.849108111 | 3.545027299 |
| 747.4995 | PA(40:6) | SC | 0.000029587 | 0.000487705 | 0 | 0.8051 | 33.1513 | 23.0009 | 5.363755646 | 4.836378514 |
| 882.5255 | PS(44:10) | SC | 2.09342E-06 | 4.83105E-05 | 1.2377 | 0.7999 | 17.5562 | 3.0372 | 4.456017148 | 1.924850356 |
| 729.5466 | PA(38:1) | SC | 0.00018847 | 0.00232043 | 0 | 0.6001 | 7.3836 | 2.2515 | 3.621049563 | 1.907761643 |
| 836.5385 | PI(40:5) | SC | 0.000227757 | 0.002766326 | 11.8159 | 4.1195 | 50.29 | 12.0226 | 3.609730406 | 1.545207779 |
| 907.5386 | PI(40:7) | SC | 0.001565923 | 0.01540735 | 0 | 0.2976 | 3.3043 | 0.5694 | 3.472898245 | 0.936067967 |
| 721.5045 | PG(32:0) | SC | 2.591E-07 | 7.14918E-06 | 6.4138 | 1.2772 | 13.6359 | 2.3595 | 3.416335561 | 0.885496713 |
| 725.5165 | PA(38:3) | SC | 0.001014647 | 0.01044902 | 8.9208 | 5.875 | 53.9985 | 45.8083 | 3.200258575 | 2.962948267 |
| 890.5915 | PS(44:6) | SC | 8.93408E-05 | 0.001229222 | 0.7119 | 1.1554 | 10.2085 | 1.4504 | 3.143306593 | 0.32805843 |
| 889.5745 | TG(P-58:20)/PI(38:2) | SC | 2.89892E-07 | 7.87048E-06 | 5.4933 | 5.5739 | 48.3826 | 17.6337 | 3.117729275 | 1.661576196 |
| 720.5005 | PE(P-36:5) | SC | 3.9936E-05 | 0.000627725 | 9.821 | 3.4014 | 27.6954 | 6.804 | 3.025445795 | 1.000254466 |
| 798.6055 | PE(40:2) | SC | 4.95954E-07 | 1.28467E-05 | 0 | 0.9016 | 7.193 | 1.6266 | 2.996034183 | 0.851300098 |
| 864.3816 | RE(40:2) | SC | 8.48139E-07 | 2.07019E-05 | 62.7448 | 11.6176 | 91.8789 | 28.7887 | 2.983421521 | 1.3091058 |
| 816.5585 | PS(42:5) | SC | 1.52034E-10 | 4.83105E-09 | 0 | 1.6337 | 12.8847 | 4.1834 | 2.979443959 | 1.356532867 |
| 881.5234 | PE(42:7) | SC | 3.06222E-07 | 8.22587E-06 | 20.1924 | 5.8436 | 44.2926 | 10.5851 | 2.922136354 | 0.857105566 |
| 909.5536 | PI(38:6) | SC | 2.24965E-12 | 1.70469E-10 | 49.0519 | 15.9328 | 114.7333 | 36.869 | 2.848212447 | 1.210408461 |
| 762.5125 | PE(38:6) | SC | 8.97872E-10 | 0.001232026 | 52.1501 | 10.1699 | 70.944 | 40.8521 | 2.802375182 | 2.006104749 |
| 796.5915 | PE(40:3) | SC | 3.79122E-06 | 8.22564E-05 | 5.1935 | 4.9805 | 33.6477 | 20.3448 | 2.756145403 | 2.030297609 |
| 818.5755 | PE(42:6) | SC | 0.000301686 | 0.003521058 | 0.3887 | 2.2777 | 14.9853 | 7.765 | 2.717898322 | 1.769408185 |
| 688.5255 | PE(32:1) | SC | 0.000342958 | 0.03875409 | 0 | 1.5169 | 9.7615 | 1.7478 | 2.685976876 | 0.204414127 |
| 698.5165 | PE(P-34:2) | SC | 2.68247E-05 | 0.000443613 | 15.976 | 10.0868 | 60.439 | 12.0642 | 2.583011233 | 0.258263694 |
| 730.5425 | PE(35:1) | SC | 9.22832E-07 | 2.22048E-05 | 3.0568 | 3.4431 | 18.7517 | 6.1662 | 2.445241406 | 0.840673601 |
| 863.5705 | PI(36:1) | SC | 7.6787E-07 | 1.89247E-05 | 176.9816 | 37.4607 | 200.7699 | 75.9336 | 2.422093229 | 1.019360549 |
| 671.4685 | PA(34:2) | SC | 0.005222022 | 0.04586887 | 1.5406 | 1.0287 | 5.4109 | 2.2209 | 2.395046269 | 1.110322124 |
| 860.5435 | PE(42:7) | SC | 3.60408E-07 | 1.01514E-08 | 11.4123 | 9.893 | 48.7253 | 18.1579 | 2.300191086 | 0.876117379 |
| 862.5576 | PS(42:6) | SC | 1.20052E-07 | 2.93214E-09 | 65.6885 | 24.024 | 111.5443 | 49.95 | 2.215068508 | 1.056008298 |
| 888.5735 | PS(44:7) | SC | 1.12386E-07 | 2.70063E-09 | 135.8857 | 64.5795 | 280.929 | 113.4454 | 2.121057384 | 0.812849935 |
| 859.5395 | PI(36:3) | SC | 4.51393E-07 | 1.31586E-08 | 77.7761 | 26.7501 | 109.2902 | 47.0364 | 2.030547851 | 0.814233361 |
| 752.5645 | PE(P-38:3) | SC | 0.000105486 | 0.001401967 | 9.7931 | 17.5824 | 70.3579 | 40.0642 | 2.000580411 | 1.188181657 |
| 699.5004 | PA(36:2) | SC | 2.16751E-06 | 4.93473E-05 | 21.1742 | 21.3245 | 83.9542 | 57.5307 | 1.977090586 | 1.431820109 |
| 697.4845 | PA(36:3) | SC | 0.003052866 | 0.02802785 | 2.6456 | 1.9677 | 7.6299 | 2.813 | 1.955153868 | 0.515599272 |
| 807.5075 | PI(32:1) | SC | 0.0015283 | 0.01506637 | 1.2143 | 3.5478 | 13.544 | 2.8181 | 1.93265729 | -0.332201876 |
| 724.5235 | PE(P-36:3) | SC | 3.34117E-08 | 1.07361E-06 | 13.3679 | 24.4632 | 90.6672 | 36.2425 | 1.889967599 | 0.567069342 |
| 728.5635 | PE(P-36:1) | SC | 5.35704E-08 | 1.6893E-06 | 75.1233 | 24.7786 | 90.3378 | 34.6904 | 1.866235103 | 0.485441799 |
| 772.5896 | PE(38:1) | SC | 5.81536E-05 | 0.001008793 | 79.1078 | 42.7078 | 147.5674 | 109.7266 | 1.788802554 | 1.36134182 |
| 861.5535 | PE(36:2) | SC | 1.11286E-08 | 3.86985E-07 | 116.1198 | 72.7123 | 249.9238 | 138.848 | 1.781216958 | 0.93323506 |
| 788.5254 | PE(40:7) | SC | 2.13379E-06 | 4.87984E-05 | 19.5351 | 17.2225 | 52.4945 | 26.0242 | 1.607871697 | 0.595559237 |
| 820.5906 | PE(42:5) | SC | 0.000846836 | 0.008446474 | 0 | 4.7141 | 13.8708 | 7.9687 | 1.55699673 | 0.757362022 |
| 726.5476 | PE(P-36:2) | SC | 2.57574E-07 | 7.14592E-06 | 85.965 | 33.5187 | 95.8155 | 34.6192 | 1.515292862 | 0.04660619 |

TABLE 20-continued

| | | | | | | | |
|---|---|---|---|---|---|---|---|
| 770.5735 | PE(38:2) | SA | 2.30565E-06 | 5.20258E-05 | 152.3456 | 128.0562 | 325.133 | 327.1652 | 1.344252888 | 1.353242195 |
| 690.5105 | PE(32:0) | SC | 0.004089558 | 0.03681327 | 1.8308 | 9.2329 | 23.0854 | 13.957 | 1.322124964 | 0.596133107 |
| 740.5284 | PE(36:3) | SC | 9.15878E-07 | 2.21424E-05 | 56.0117 | 58.7099 | 143.5809 | 71.9384 | 1.290188141 | 0.293158273 |
| 768.5585 | PE(38:3) | SC | 1.58943E-05 | 0.000287172 | 191.6569 | 129.141 | 290.4791 | 253.9433 | 1.169487262 | 0.975559307 |
| 911.5704 | PI(40:5) | SC | 7.21238E-08 | 2.24646E-06 | 52.6973 | 40.8993 | 85.8625 | 42.5665 | 1.069952028 | 0.057642319 |
| 723.4995 | PA(38:4) | SA | 0.00037395 | 0.004275998 | 7.4888 | 20.0312 | 41.4992 | 62.2382 | 1.050834675 | 1.635551486 |
| 742.5424 | PE(36:2) | SA | 2.87707E-06 | 6.29608E-05 | 395.1418 | 345.5038 | 692.7696 | 581.6404 | 1.003674045 | 0.751425902 |
| 701.5155 | PA(36:1) | SA | 1.406E-05 | 0.000272453 | 104.0595 | 173.6574 | 343.5916 | 393.7826 | 0.984450877 | 1.181155475 |
| 714.5105 | PE(34:2) | SC | 2.38041E-06 | 5.3475E-05 | 21.3764 | 38.1989 | 75.3044 | 29.4042 | 0.979203069 | -0.377508854 |
| 744.5575 | PE(36:1) | SC | 0.000434216 | 0.004834464 | 782.4336 | 603.4562 | 1019.6619 | 1009.0828 | 0.756769896 | 0.741723593 |
| 872.6425 | PS(42:1) | SC | 0.001341361 | 0.01337935 | 2.6642 | 9.756 | 16.3726 | 4.596 | 0.746921779 | -1.08591096 |
| 746.5755 | PE(36:0) | SC | 0.000407838 | 0.004601323 | 37.397 | 47.869 | 79.349 | 55.9679 | 0.729120374 | 0.225507949 |
| 819.5536 | PG(P-41:6) | HO | 3.34792E-05 | 0.000543048 | 41.2026 | 48.6631 | 23.5767 | 17.1004 | -1.045466427 | -1.508798156 |
| 816.5805 | PE(38:2)/PS(38:1) | HO | 1.26476E-08 | 4.36814E-07 | 71.9373 | 73.9657 | 35.4711 | 22.4157 | -1.060212336 | -1.722346854 |
| 788.5475 | PS(36:1) | HO | 1.24345E-14 | 1.34319E-12 | 1310.7695 | 1946.6457 | 887.8471 | 1068.1457 | -1.132607179 | -0.865881879 |
| 749.5355 | PG(34:0) | HO | 2.26439E-11 | 1.40199E-09 | 246.3929 | 344.2116 | 150.2673 | 151.2288 | -1.195764622 | -1.186562805 |
| 748.5325 | PE(P-38:5) | HO | 3.12647E-11 | 1.84571E-09 | 511.038 | 745.9556 | 301.8235 | 364.2202 | -1.305384624 | -1.034278825 |
| 868.6124 | PS(42:3) | HO | 0.000341653 | 0.003960214 | 0 | 4.6648 | 1.713 | 0.4246 | -1.445290076 | -3.457638952 |
| 814.5655 | PE(38:3)/PS(38:2) | HO | 3.33067E-16 | 4.57022E-14 | 45.6966 | 106.7905 | 25.2074 | 25.4809 | -2.082864087 | -2.067295171 |
| 847.5665 | PI(P-36:1) | HO | 1.09395E-07 | 3.30593E-06 | 6.2006 | 13.3224 | 3.044 | 2.4174 | -2.12981374 | -2.462325888 |
| 846.5635 | PS(P-42:6) | HO | 5.18541E-12 | 3.60634E-10 | 24.6104 | 30.5856 | 4.4186 | 7.6053 | -2.791191338 | -2.007775515 |
| 724.5325 | PE(P-36:3) | HO | 9.14935E-13 | 7.25801E-11 | 32.8176 | 65.1551 | 7.4891 | 8.0302 | -3.121013851 | -3.020370285 |
| 818.5316 | PS(P-40:6) | HO | 2.22045E-16 | 3.22092E-14 | 37.1244 | 38.8126 | 4.0168 | 5.1328 | -3.272406545 | -2.918707128 |

SC = Serous carcinoma;
HO = Healthy ovary;
SA = StromaA;
CD = Class Diff

| | Number of lipids | Class Diff | |
|---|---|---|---|
| PA | 4 | HealthyEC (Mean) | class where the p value is significant |
| PE | 14 | HealthyOv (Mean) | mean intensity of epithelial cells from Fallopian tube |
| PI | 4 | SerousCarcinoma (Mean) | mean intensity of healthy stroma |
| PS | 9 | StromaA (Mean) | mean intensity of cancer cells from Serous adenocarcinomas |
| PG | 3 | MeanFC-HealthyOv-SerousCarcinoma | mean intensity of cancer associated stroma |
| | | MeanFC-HealthyOv-StromaA | fold change of mean - log(SerousCarcinoma/HealthyOv) |
| | | | fold change of mean - log(StromaA/HealthyOv) |

The invention claimed is:

1. A method of analysis using mass spectrometry and/or ion mobility spectrometry comprising:
   (a) using a first device to generate smoke, aerosol or vapour from a target in vitro or ex vivo cell population and/or culture medium derived therefrom;
   (b) adding a matrix to said aerosol, smoke or vapour, wherein said matrix comprises isopropanol;
   (c) mass analysing and/or ion mobility analysing said smoke, aerosol or vapour, or ions derived therefrom, in order to obtain spectrometric data; and
   (d) analysing said spectrometric data in order to identify and/or characterise said target in vitro or ex vivo cell population or one or more cells and/or compounds present in said target in vitro or ex vivo cell population and/or culture medium derived therefrom,
   wherein the step of analysing comprises analysing said spectrometric data in order to:
   analyse whether there is an infection of said in vitro or ex vivo cell population; or
   analyse the genotype and/or phenotype of said in vitro or ex vivo cell population or one or more cell types present therein; or
   analyse the effect of manipulating the genotype and/or phenotype of said in vitro or ex vivo cell population or one or more cell types present therein.

2. A method as claimed in claim 1, further comprising causing said aerosol, smoke or vapour, or analyte therein, to impact upon a collision surface located within a vacuum chamber of a spectrometer so as to generate a plurality of analyte ions.

3. A method as claimed in claim 2, comprising the step of transferring said analyte ions to an analysis region and then mass analysing and/or ion mobility analysing said smoke, aerosol or vapour, or ions derived therefrom, in order to obtain spectrometric data.

4. A method as claimed in claim 1, wherein said step of using said first device to generate aerosol, smoke or vapour from one or more regions of the target further comprises irradiating said target with a laser.

5. A method as claimed in claim 1, wherein said first device comprises or forms part of an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electroflow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a hybrid CUSA-diathermy device; (xxii) a focussed or unfocussed ultrasonic ablation device; (xxiii) a hybrid focussed or unfocussed ultrasonic ablation and diathermy device; (xxiv) a microwave resonance device; (xxv) a pulsed plasma RF dissection device; (xxvi) an argon plasma coagulation device; (xxvii) a hybrid pulsed plasma RF dissection and argon plasma coagulation device; (xxviii) a hybrid pulsed plasma RF dissection and JeDI device; (xxix) a surgical water/saline jet device; (xxx) a hybrid electrosurgery and argon plasma coagulation device; and (xxxi) a hybrid argon plasma coagulation and water/saline jet device.

6. A method as claimed in claim 1, wherein said cell population is identified, confirmed or authenticated as comprising or consisting of mutant and/or transgenic cells on the basis of said spectrometric data.

7. A method as claimed in claim 1, wherein said method is performed on an in vitro or ex vivo cell population in need of authentication, and the method comprises analysing said spectrometric data in order to: (i) confirm the authenticity of the in vitro or ex vivo cell population; (ii) detect a mutation in said in vitro or ex vivo cell population; or (iii) to detect an undesired variation in said in vitro or ex vivo cell population.

8. A method as claimed in claim 1, wherein said method comprises analysing said spectrometric data in order: (i) to determine whether or not said in vitro or ex vivo cell population suffers from an infection; (ii) to determine whether or not said in vitro or ex vivo cell population is infection free; (iii) to determine whether or not said in vitro or ex vivo cell population has been cured of an infection; (iv) to determine the progression or stage of an infection of an in vitro or ex vivo cell population; and/or (v) to determine the progression or stage of a treatment for an infection of an in vitro or ex vivo cell population.

9. A method as claimed in claim 1 wherein said infection is or comprises a bacterial infection, a *mycoplasma* infection or a viral infection.

10. A method as claimed in claim 1, wherein said method comprises analysing said spectrometric data in order to analyse the effect of a genotype and/or phenotype manipulation on a cellular process, a disease, drug production by an in vitro or ex vivo cell population, and/or the response of an in vitro or ex vivo cell population to a substance and/or environmental condition.

11. A method as claimed in claim 1, wherein said method comprises a screening method, or wherein said method is used for drug discovery and/or drug analysis.

12. A method as claimed in claim 1, wherein said target is a first target sample comprising a first population of cells and said spectrometric data is first spectrometric data and wherein the method further comprises:
   generating aerosol, smoke or vapour from a second different target sample comprising a second population of cells;
   mass analysing and/or ion mobility analysing aerosol, smoke or vapour generated from the second target sample, or ions derived therefrom, so as to obtain second spectrometric data; and
   comparing said first and second spectrometric data to determine differences between said first and the second target samples.

13. A method as claimed in claim 12, wherein said first cell population comprises a first genetic modification and said second cell population does not comprise said first genetic modification, and said method comprises analysing said first and second spectrometric data to analyse the effect of said first genetic modification.

14. A method as claimed in claim 12, wherein said first cell population comprises a first genetic modification and said second cell population comprises a second genetic modification, and said method comprises analysing said first and second spectrometric data to analyse the effect of said second genetic modification.

15. A method as claimed in claim 1, wherein said method comprises manipulating the genotype and/or phenotype of the in vitro or ex vivo target cell population prior to step (a) of claim 1.

16. A method according to claim 1, wherein said genotype and/or phenotype manipulation or mutagenesis is random or targeted mutagenesis.

17. Apparatus comprising:
  a first device for generating smoke, aerosol or vapour from a target in vitro or ex vivo cell population and/or culture medium derived therefrom;
  a second device configured to add a matrix to said aerosol, smoke or vapour, wherein said matrix comprises isopropanol;
  a mass spectrometer and/or ion mobility spectrometer for analysing said smoke, aerosol or vapour, or ions derived therefrom, in order to obtain spectrometric data; and
  a processor adapted to analyse said spectrometric data in order to identify and/or characterise said target in vitro or ex vivo cell population or one or more cells and/or compounds present in said target in vitro or ex vivo cell population and/or culture medium derived therefrom; wherein said analysis comprises analysing said spectrometric data in order to:
    analyse whether there is an infection of said in vitro or ex vivo cell population; or
    analyse the genotype and/or phenotype of said in vitro or ex vivo cell population or one or more cell types present therein; or
    analyse the effect of manipulating the genotype and/or phenotype of said in vitro or ex vivo cell population or one or more cell types present therein.

* * * * *